US007304056B2

(12) United States Patent
Olson et al.

(10) Patent No.: US 7,304,056 B2
(45) Date of Patent: *Dec. 4, 2007

(54) SUCCINOYLAMINO LACTAMS AS INHIBITORS OF Aβ PROTEIN PRODUCTION

(75) Inventors: Richard E. Olson, Wilmington, DE (US); Thomas P. Maduskuie, Wilmington, DE (US); Lorin Andrew Thompson, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/493,156

(22) Filed: Jul. 26, 2006

(65) Prior Publication Data

US 2006/0264417 A1    Nov. 23, 2006

Related U.S. Application Data

(60) Continuation of application No. 11/175,644, filed on Jul. 6, 2005, now Pat. No. 7,101,870, which is a division of application No. 10/285,776, filed on Nov. 1, 2002, now Pat. No. 6,962,913, which is a division of application No. 09/506,360, filed on Feb. 17, 2000, now Pat. No. 6,794,381, which is a continuation-in-part of application No. 09/370,089, filed on Aug. 6, 1999, now abandoned.

(60) Provisional application No. 60/120,227, filed on Feb. 15, 1999, provisional application No. 60/113,558, filed on Dec. 23, 1998, provisional application No. 60/095,698, filed on Aug. 7, 1998.

(51) Int. Cl.
 C07D 243/12    (2006.01)
 A61K 31/55    (2006.01)
 A61P 25/28    (2006.01)

(52) U.S. Cl. .................................. 514/221; 540/517
(58) Field of Classification Search ................ 514/221; 540/517
 See application file for complete search history.

(56) References Cited

U.S. PATENT DOCUMENTS

| | | | |
|---|---|---|---|
| 4,666,829 A | 5/1987 | Glenner et al. |
| 4,929,614 A | 5/1990 | Calvet et al. |
| 5,175,159 A | 12/1992 | Bock et al. |
| 5,283,241 A | 2/1994 | Bochis et al. |
| 5,506,242 A | 4/1996 | MacPherson et al. |
| 5,532,359 A | 7/1996 | Marsters et al. |
| 5,538,845 A | 7/1996 | Knops et al. |
| 5,545,735 A | 8/1996 | Bochis et al. |
| 5,550,126 A | 8/1996 | Horwell et al. |
| 5,552,419 A | 9/1996 | MacPherson et al. |
| 5,578,629 A | 11/1996 | Ciccarone et al. |
| 5,590,851 A | 1/1997 | Ackerman |
| 5,593,846 A | 1/1997 | Schenk et al. |
| 5,594,006 A | 1/1997 | Sakamoto et al. |
| 5,595,990 A | 1/1997 | Baldwin et al. |
| 5,602,145 A | 2/1997 | Samanen |
| 5,602,156 A | 2/1997 | Kohn et al. |
| 5,618,812 A | 4/1997 | Pineiro et al. |
| 5,639,746 A | 6/1997 | Yelm |
| 5,672,596 A | 9/1997 | Wyvratt et al. |
| 5,672,598 A | 9/1997 | De et al. |
| 5,703,129 A | 12/1997 | Felsenstein et al. |
| 5,710,153 A | 1/1998 | Ohmoto et al. |
| 5,710,171 A | 1/1998 | Dinsmore et al. |
| 5,734,054 A | 3/1998 | Dolle, III et al. |
| 5,756,528 A | 5/1998 | Anthony et al. |
| 5,763,437 A | 6/1998 | Sato et al. |
| 5,770,573 A | 6/1998 | Arrhenius et al. |
| 5,840,939 A | 11/1998 | Beckett et al. |
| 5,852,010 A | 12/1998 | Graham et al. |
| 5,856,326 A | 1/1999 | Anthony et al. |
| 5,859,012 A | 1/1999 | Dinsmore et al. |
| 5,869,682 A | 2/1999 | DeSolms |
| 5,872,135 A | 2/1999 | DeSolms |
| 5,885,995 A | 3/1999 | Dinsmore |
| 5,891,889 A | 4/1999 | Anthony et al. |
| 5,905,077 A | 5/1999 | Jungheim et al. |
| 5,919,785 A | 7/1999 | Dinsmore et al. |
| 5,936,089 A | 8/1999 | Carpino et al. |
| 5,965,578 A | 10/1999 | Graham et al. |
| 5,968,924 A | 10/1999 | Wyvratt et al. |
| 5,968,965 A | 10/1999 | Dinsmore et al. |
| 5,985,900 A | 11/1999 | Abreo et al. |
| 5,998,447 A | 12/1999 | Stilz et al. |
| 6,001,835 A | 12/1999 | Dinsmore et al. |
| 6,057,660 A | 5/2000 | Meier et al. |
| 6,060,038 A | 5/2000 | Burns et al. |
| 6,066,738 A | 5/2000 | Dinsmore et al. |
| 6,093,737 A | 7/2000 | Anthony et al. |

(Continued)

FOREIGN PATENT DOCUMENTS

EP    0276436    12/1987

(Continued)

OTHER PUBLICATIONS

Achour et al., *Synth. Commun.* 1994, 24 (20), pp. 2899-2905.

(Continued)

*Primary Examiner*—Bruck Kifle
(74) *Attorney, Agent, or Firm*—Aldo A. Algieri; Kelley Drye & Warren LLP

(57) ABSTRACT

This invention relates to novel lactams having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

9 Claims, No Drawings

U.S. PATENT DOCUMENTS

| | | | |
|---|---|---|---|
| 6,117,910 | A | 9/2000 | Callahan et al. |
| 6,127,427 | A | 10/2000 | Martin et al. |
| 6,228,854 | B1 | 5/2001 | Scarborough et al. |
| 6,242,455 | B1 | 6/2001 | Grams et al. |
| 6,262,047 | B1 | 7/2001 | Zhu et al. |
| 6,271,262 | B1 | 8/2001 | Beckett et al. |
| 6,297,239 | B1 | 10/2001 | DeSolms et al. |
| 6,329,373 | B1 | 12/2001 | Martin et al. |
| 6,333,321 | B1 | 12/2001 | Scarborough |
| 6,358,987 | B1 | 3/2002 | Beckett et al. |
| 6,432,947 | B1 | 8/2002 | Arnaiz et al. |
| 6,440,965 | B1 | 8/2002 | Kelley et al. |

FOREIGN PATENT DOCUMENTS

| | | |
|---|---|---|
| EP | 0421802 | 4/1991 |
| EP | 0434380 | 6/1991 |
| EP | 0606046 | 12/1993 |
| EP | 0652009 | 5/1995 |
| EP | 0842944 | 5/1998 |
| WO | WO 92/00374 | 1/1992 |
| WO | WO 92/06966 | 4/1992 |
| WO | WO 9217460 | 10/1992 |
| WO | WO 9403437 | 2/1994 |
| WO | WO 9405634 | 3/1994 |
| WO | WO 9414776 | 7/1994 |
| WO | WO 9509633 | 4/1995 |
| WO | WO 95/22966 | 8/1995 |
| WO | WO 9617833 | 6/1996 |
| WO | WO 9618602 | 6/1996 |
| WO | WO 9620918 | 7/1996 |
| WO | WO 9629313 | 9/1996 |
| WO | WO 9633165 | 10/1996 |
| WO | WO 9639137 | 12/1996 |
| WO | WO 9712861 | 4/1997 |
| WO | WO 97/18207 | 5/1997 |
| WO | WO 9719053 | 5/1997 |
| WO | WO 9727852 | 8/1997 |
| WO | WO 9736877 | 10/1997 |
| WO | WO 9736879 | 10/1997 |
| WO | WO 9736900 | 10/1997 |
| WO | WO 9738664 | 10/1997 |
| WO | WO 9745412 | 12/1997 |
| WO | WO 98/15828 | 4/1998 |
| WO | WO 9816523 | 4/1998 |
| WO | WO 9822430 | 5/1998 |
| WO | WO 9822433 | 5/1998 |
| WO | WO 9822441 | 5/1998 |
| WO | WO 9822493 | 5/1998 |
| WO | WO 9827053 | 6/1998 |
| WO | WO 9828268 | 7/1998 |
| WO | WO 9828980 | 7/1998 |
| WO | WO 9837079 | 8/1998 |
| WO | WO 9841510 | 9/1998 |
| WO | WO 9844797 | 10/1998 |
| WO | WO 98/51665 | 11/1998 |
| WO | WO 9858915 | 12/1998 |
| WO | WO 9900654 | 1/1999 |
| WO | WO 9903826 | 1/1999 |
| WO | WO 9907730 | 2/1999 |
| WO | WO 9907731 | 2/1999 |
| WO | WO 9917777 | 4/1999 |
| WO | WO 9918951 | 4/1999 |
| WO | WO 9919305 | 4/1999 |
| WO | WO 9932453 | 7/1999 |
| WO | WO 9942889 | 8/1999 |
| WO | WO 9967219 | 12/1999 |
| WO | WO 9967220 | 12/1999 |
| WO | WO 9967221 | 12/1999 |
| WO | WO 9968934 | 12/1999 |
| WO | WO 0002903 | 1/2000 |
| WO | WO 0007995 | 2/2000 |
| WO | WO 0028331 | 5/2000 |
| WO | WO 0038618 | 7/2000 |
| WO | WO 0160826 | 8/2001 |

OTHER PUBLICATIONS

A. Ahmed et al., *FEBS Letters*, (1984), vol. 174, pp. 76-79.
P. Becket, M. J. Crimmin, M. H. Davis, and Z. Spavold, *Synlett* (1993), pp. 137-138.
Bioorg. Med. Chem. Lett., vol. 8, No. 16, pp. 2077-2080.
Bock et al., *J. Med. Chem. 1993*, 36, pp. 4276-4292.
Bock et al., *J. Org. Chem 1987*, 52, pp. 3232-3239.
Bodine et al., *Synth. Commun. 1982*, 12, p. 787.
Buege et al., *Arch. Pharm. 1994*, 327 (2), pp. 99-103.
F. A. Carey and R. J. Sundberg, "Advanced Organic Chemistry, Part A," *New York: Plenum Press*, 1990, pp. 304-305, 342-347, 475-479, 695-698.
Duhammel et al.,Tetrahedron Asymmetry 1991,2(3),pp. 203-206.
D. A. Evans et al., *Org. Synth 1990*, 68, pp. 83-91.
Glenner and Wong, *Biochem. Biophys. Res. Commun.*, 120: pp. 885-890.
J. Higaki, D. Quon, Z. Zhong, B. Cordell, "Inhibition of beta-amyloid Formation identifies Proteolytic Precursors and Subcellular Site of Catabolism", *Neuron 14*, pp. 651-659, 1995.
Jacobson and Reddy, Tetrahedron Letters, vol. 37, No. 46, pp. 8263-8266 (1996).
McClure and Axt, *Bioorganic & Medicinal Chemistry Letters*, 8 (1998), pp. 143-146.
M. G. Natchus et al., "Design and synthesis of conformationally constrained MMP inhibitors," Chemical Abstracts, vol. 129, No. 22, Nov. 30, 1998, abstract No. 290051p.
C. F. Nutaitis and M. W. Ledeboer, *Org.Prep. Proced. Int.* (1992), 24(2), pp. 143-146.
Pratt et al., *Synlett*, May 1998, p. 531.
" Remington's Pharmaceutical Sciences," 17th ed. Mack Publishing Company, Easton, PA, 1985, p. 1418.
D. J. Selkoe, "Cell Biology of the amyloid (beta)-protein precursor and the mechanism of Alzheimer's disease," *Annu. Rev. Cell. Biol.*, 1994, 10: pp. 373-403.
Schwartz et al., *Tetrahedron*, 1997, 53 (26), pp. 8795-8806.
Sherrill and Sugg, *J. Org. Chem. 1995*, 60, pp. 730-734.
Iaylor et al., *Bioorg. Med. Chem. Lett. 1997*, 7 (4), pp. 453-456.
D. A. Walsh, *Synthesis*, Sep. 1980, p. 677.
T.W. Green and Wuts Protective Groups in Organic Synthesis Willey 1991.
Levai et al., Arch.Pharm. 1992(325)(11) pp. 721-726.
U.K Laemmli. Cleavage of Structural Proptains during the assembly of the head of bacteriophage T4, Nature 227,pp. 680-685, (1970).
C. Dingwall, "Spotlight on BACE: The secretase as targets for treatment in Alzheimer disease" The Journal of Clinical Investigation, Vo. 108,No. 9 Nov. 2001,pp. 1243-1246.
R.E. Tanzani et al."Decoding Darkness, The search fro the Genetic Causes of Alzheimer's Disease" Perseus Publishing, 2000, pp. xvii-xviii.
D.J. Selkoe, "Alzhimer's Disease results from the cerebral accumulation and cytotoxicity of amyloid Beta-protein" Journal of Alzhimer's Disease, 3, 2001, pp. 75-81.
R.E. Olson et al, Progress towards testing the amyloid hypothesis: inhibitors of APP processing, Current Opinion in Drug Discovery and Development, 4,2001,pp. 390-401.
Wagner,S.L et al. J.Clinical Invest,104 1999 1329-1332.
Olson, R.E. et al."Annul Rports Mod. Chem" 35, 2000,31-40.
Chemical Abstracts(126:8011).
Su San Mok et al, A Novel Metalloprotease in Rat rain cleaves..
Biochemistry, vol. 36, No. 1, 1997, pp. 156-163 XP002177252.
Bioorg. Med. Chem. Lett., vol. 8, No. 16, pp. 2077-2080, 1998.
Glenner and Wong, *Biochem. Biophys. Res. Commun.*, 120: pp. 885-890, 1990.
Olson, R.E. et al."Annul Rports Mod. Chem" 35, 2000,31-40, 1991.
Chemical Abstracts(126:8011), 1986.

SUCCINOYLAMINO LACTAMS AS INHIBITORS OF Aβ PROTEIN PRODUCTION

RELATED CROSS-REFERENCES

This application is a continuation of U.S. patent application Ser. No. 11/175,644, filed Jul. 6, 2005, now U.S. Pat. No. 7,101,870, which is a divisional of U.S. patent application Ser. No. 10/285,776, filed Nov. 1, 2002, now U.S. Pat. No. 6,962,913, which is a divisional of U.S. patent application Ser. No. 09/506,360, filed Feb. 17, 2000, now U.S. Pat. No. 6,794,381, issued Sep. 21, 2004, which is a continuation-in-part of U.S. patent application Ser. No. 09/370,089, filed Aug. 6, 1999, now abandoned, Provisional Application Ser. No. 60/095,698, filed Aug. 7, 1998 (expired), and Provisional U.S. Patent Application Ser. No. 60/120,227, filed Feb. 15, 1999 (expired), and Provisional Application Ser. No. 60/113,558, filed Dec. 23, 1998 (expired); the disclosures of which are hereby incorporated by reference in their entirety.

FIELD OF THE INVENTION

This invention relates to novel lactams having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

BACKGROUND OF THE INVENTION

Alzheimer's disease (AD) is a degenerative brain disorder characterized clinically by progressive loss of memory, temporal and local orientation, cognition, reasoning, judgment and emotional stability. AD is a common cause of progressive dementia in humans and is one of the major causes of death in the United States. AD has been observed in all races and ethnic groups worldwide, and is a major present and future health problem. No treatment that effectively prevents AD or reverses the clinical symptoms and underlying pathophysiology is currently available (for review, Dennis J. Selkoe; Cell Biology of the amyloid (beta)-protein precursor and the mechanism of Alzheimer's disease, Annu Rev Cell Biol, 1994, 10: 373-403).

Histopathological examination of brain tissue derived upon autopsy or from neurosurgical specimens in effected individuals revealed the occurrence of amyloid plaques and neurofibrillar tangles in the cerebral cortex of such patients. Similar alterations were observed in patients with Trisomy 21 (Down's Syndrome) and hereditary cerebral hemorrhage with amyloidosis of the Dutch-type. Neurofibrillar tangles are nonmembrane-bound bundles of abnormal proteinaceous filaments and biochemical and immunochemical studies led to the conclusion that their principle protein subunit is an altered phosphorylated form of the tau protein (reviewed in Selkoe, 1994).

Biochemical and immunological studies revealed that the dominant proteinaceous component of the amyloid plague is an approximately 4.2 kilodalton (kD) protein of about 39 to 43 amino acids. This protein was designated Aβ, β-amyloid peptide, and sometimes β/A4; referred to herein as Aβ. In addition to deposition of Aβ in amyloid plaques, Aβ is also found in the walls of meningeal and parenchymal arterioles, small arteries, capillaries, and sometimes, venules. Aβ was first purified, and a partial amino acid reported, in 1984 (Glenner and Wong, Biochem. Biophys. Res. Commun. 120: 885-890). The isolation and sequence data for the first 28 amino acids are described in U.S. Pat. No. 4,666,829.

Compelling evidence accumulated during the last decade revealed that Aβ is an internal polypeptide derived from a type 1 integral membrane protein, termed β amyloid precursor protein (APP). β APP is normally produced by many cells both in vivo and in cultured cells, derived from various animals and humans. Aβ is derived from cleavage of β APP by as yet unknown enzyme (protease) system(s), collectively termed secretases.

The existence of at least four proteolytic activities has been postulated. They include β secretase(s), generating the N-terminus of Aβ, a secretase(s) cleaving around the 16/17 peptide bond in Aβ, and γ secretases, generating C-terminal Aβ fragments ending at position 38, 39, 40, 42, and 43 or generating C-terminal extended precursors which are subsequently truncated to the above polypeptides.

Several lines of evidence suggest that abnormal accumulation of Aβ plays a key role in the pathogenesis of AD. Firstly, Aβ is the major protein found in amyloid plaques. Secondly, Aβ is neurotoxic and may be causally related to neuronal death observed in AD patients. Thirdly, missense DNA mutations at position 717 in the 770 isoform of β APP can be found in effected members but not unaffected members of several families with a genetically determined (familiar) form of AD. In addition, several other β APP mutations have been described in familiar forms of AD. Fourthly, similar neuropathological changes have been observed in transgenic animals overexpressing mutant forms of human β APP. Fifthly, individuals with Down's syndrome have an increased gene dosage of β APP and develop early-onset AD. Taken together, these observations strongly suggest that Aβ depositions may be causally related to the AD.

It is hypothesized that inhibiting the production of Aβ will prevent and reduce neurological degeneration, by controlling the formation of amyloid plaques, reducing neurotoxicity and, generally, mediating the pathology associated with Aβ production. One method of treatment methods would therefore be based on drugs that inhibit the formation of Aβ in vivo.

Methods of treatment could target the formation of Aβ through the enzymes involved in the proteolytic processing of b amyloid precursor protein. Compounds that inhibit b or g secretase activity, either directly or indirectly, could control the production of Aβ. Advantageously, compounds that specifically target g secretases, could control the production of Aβ. Such inhibition of β or γ secretases could thereby reduce production of Aβ, which, thereby, could reduce or prevent the neurological disorders associated with Aβ protein.

PCT publication number WO 96/29313 discloses the general formula:

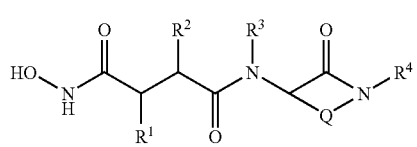

covering metalloprotease inhibiting compounds useful for the treatment of diseases associated with excess and/or unwanted matrix metalloprotease activity, particularly collagenase and or stromelysin activity.

Compounds of general formula:

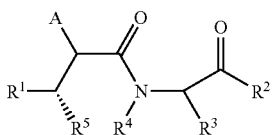

are disclosed in PCT publication number WO 95/22966 relating to matrix metalloprotease inhibitors. The compounds of the invention are useful for the treatment of conditions associated with the destruction of cartilage, including corneal ulceration, osteoporosis, periodontitis and cancer.

European Patent Application number EP 0652009A1 relates to the general formula:

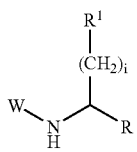

and discloses compounds that are protease inhibitors that inhibit Aβ production.

U.S. Pat. No. 5,703,129 discloses the general formula:

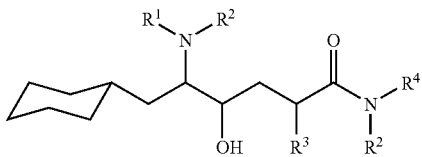

which covers 5-amino-6-cyclohexyl-4-hydroxy-hexanamide derivatives that inhibit Aβ production and are useful in the treatment of Alzheimer's disease.

None of the above references teaches or suggests the compounds of the present invention which are described in detail below.

SUMMARY OF THE INVENTION

One object of the present invention is to provide novel compounds which are useful as inhibitors of the production of Aβ protein or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating degenerative neurological disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of Formula (I):

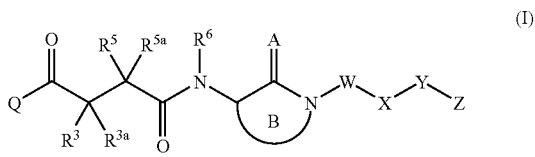

or pharmaceutically acceptable salt or prodrug forms thereof, wherein $R^3$, $R^{3a}$, $R^5$, $R^{5a}$, $R^6$, A, Q, B, W, X, Y, and Z are defined below, are effective inhibitors of the production of Aβ.

DETAILED DESCRIPTION OF PREFERRED EMBODIMENTS

Thus, in a first embodiment, the present invention provides a novel compound of Formula (I):

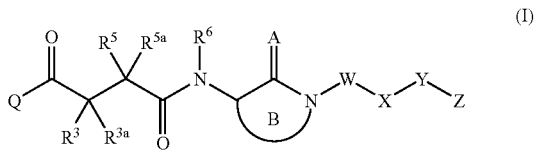

or a pharmaceutically acceptable salt or prodrug thereof, wherein:

A is O or S;

Q is —$OR^1$ or —$NR^1R^2$;

$R^1$, at each occurrence, is independently selected from:
H;
$C_1$-$C_6$ alkyl substituted with 0-3 $R^{1a}$;
$C_2$-$C_6$ alkenyl substituted with 0-3 $R^{1a}$;
$C_3$-$C_{10}$ carbocycle substituted with 0-3 $R^{1b}$;
$C_6$-$C_{10}$ aryl substituted with 0-3 $R^{1b}$; and
5 to 10 membered heterocycle substituted with 0-3 $R^{1b}$;

$R^{1a}$ at each occurrence, is independently selected from H, $C_1$-$C_6$ alkyl, $OR^{14}$, Cl, F, Br, I, =O, CN, $NO_2$, $NR^{15}R^{16}$, $CF_3$;
$C_3$-$C_{10}$ carbocycle substituted with 0-3 $R^{1b}$;
$C_6$-$C_{10}$ aryl substituted with 0-3 $R^{1b}$; and
5 to 6 membered heterocycle substituted with 0-3 $R^{1b}$;

$R^{1b}$, at each occurrence, is independently selected from H, OH, Cl, F, Br, I, CN, $NO_2$, $NR^{15}R^{16}$, $CF_3$, $C_1$-$C_6$ alkyl, $C_1$-$C_4$ alkoxy, $C_1$-$C_4$ haloalkyl, and $C_1$-$C_4$ haloalkoxy;

$R^2$ is independently selected from H, $NH_2$, OH, $C_1$-$C_6$ alkyl, $C_1$-$C_6$ alkoxy, phenoxy, benzyloxy, $C_3$-$C_{10}$ carbocycle, $C_6$-$C_{10}$ aryl and 5 to 10 membered heterocycle;

$R^3$ is —$(CR^7R^{7a})_n$—$R^4$,
—$(CR^7R^{7a})_n$—S—$(CR^7R^{7a})_m$—$R^4$,
—$(CR^7R^{7a})_n$—O—$(CR^7R^{7a})_m$—$R^4$,
—$(CR^7R^{7a})_n$—$N(R^{7b})$—$(CR^7R^{7a})_m$—$R^4$,
—$(CR^7R^{7a})_n$—S(=O)—$(CR^7R^{7a})_m$—$R^4$,
—$(CR^7R^{7a})_n$—S(=O)$_2$—$(CR^7R^{7a})_m$—$R^4$,
—$(CR^7R^{7a})_n$—C(=O)—$(CR^7R^{7a})_m$—$R^4$,
—$(CR^7R^{7a})_n$—$N(R^{7b})C(=O)$—$(CR^7R^{7a})_m$—$R^4$,
—$(CR^7R^{7a})_n$—C(=O)$N(R^{7b})$—$(CR^7R^{7a})_m$—$R^4$,

—(CR$^7$R$^{7a}$)$_n$—N(R$^{7b}$)S(=O)$_2$—(CR$^7$R$^{7a}$)$_m$—R$^4$, or
—(CR$^7$R$^{7a}$)$_n$—S(=O)$_2$N(R$^{7b}$)—(CR$^7$R$^{7a}$)$_m$—R$^4$;

n is 0, 1, 2, or 3;
m is 0, 1, 2, or 3;
R$^{3a}$ is H, OH, C$_1$-C$_4$ alkyl, C$_1$-C$_4$ alkoxy, or C$_2$-C$_4$ alkenyloxy;
R$^4$ is H, OH, OR$^{14a}$,
  C$_1$-C$_6$ alkyl substituted with 0-3 R$^{4a}$,
  C$_2$-C$_6$ alkenyl substituted with 0-3 R$^{4a}$,
  C$_2$-C$_6$ alkynyl substituted with 0-3 R$^{4a}$,
  C$_3$-C$_{10}$ carbocycle substituted with 0-3 R$^{4b}$,
  C$_6$-C$_{10}$ aryl substituted with 0-3 R$^{4b}$, or
  5 to 10 membered heterocycle substituted with 0-3 R$^{4b}$;
R$^{4a}$, at each occurrence, is independently selected from is H,
  F, Cl, Br, I, CF$_3$,
  C$_3$-C$_{10}$ carbocycle substituted with 0-3 R$^{4b}$,
  C$_6$-C$_{10}$ aryl substituted with 0-3 R$^{4b}$, or
  5 to 10 membered heterocycle substituted with 0-3 R$^{4b}$;
R$^{4b}$, at each occurrence, is independently selected from H,
  OH, Cl, F, Br, I, CN, NO$_2$, NR$^{15}$R$^{16}$, CF$_3$, acetyl, SCH$_3$,
  S(=O)CH$_3$, S(=O)$_2$CH$_3$, C$_1$-C$_6$ alkyl, C$_1$-C$_4$ alkoxy,
  C$_1$-C$_4$ haloalkyl, C$_1$-C$_4$ haloalkoxy, and C$_1$-C$_4$ halothioalkoxy;
R$^5$ is H, OR$^{14}$;
  C$_1$-C$_6$ alkyl substituted with 0-3 R$^{5b}$;
  C$_1$-C$_6$ alkoxy substituted with 0-3 R$^{5b}$;
  C$_2$-C$_6$ alkenyl substituted with 0-3 R$^{5b}$;
  C$_2$-C$_6$ alkynyl substituted with 0-3 R$^{5b}$;
  C$_3$-C$_{10}$ carbocycle substituted with 0-3 R$^{5c}$;
  C$_6$-C$_{10}$ aryl substituted with 0-3 R$^{5c}$; or
  5 to 10 membered heterocycle substituted with 0-3 R$^{5c}$;
R$^{5a}$ is H, OH, C$_1$-C$_4$ alkyl, C$_1$-C$_4$ alkoxy, C$_2$-C$_4$ alkenyl, or
  C$_2$-C$_4$ alkenyloxy;
R$^{5b}$, at each occurrence, is independently selected from:
  H, C$_1$-C$_6$ alkyl, CF$_3$, OR$^{14}$, Cl, F, Br, I, =O, CN, NO$_2$,
  NR$^{15}$R$^{16}$;
  C$_3$-C$_{10}$ carbocycle substituted with 0-3 R$^{5c}$;
  C$_6$-C$_{10}$ aryl substituted with 0-3 R$^{5c}$; or
  5 to 10 membered heterocycle substituted with 0-3 R$^{5c}$;
R$^{5c}$, at each occurrence, is independently selected from H,
  OH, Cl, F, Br, I, CN, NO$_2$, NR$^{15}$R$^{16}$, CF$_3$, acetyl, SCH$_3$,
  S(=O)CH$_3$, S(=O)$_2$CH$_3$, C$_1$-C$_6$ alkyl, C$_1$-C$_4$ alkoxy,
  C$_1$-C$_4$ haloalkyl, C$_1$-C$_4$ haloalkoxy, and C$_1$-C$_4$ halothioalkoxy;
R$^6$ is H;
  C$_1$-C$_6$ alkyl substituted with 0-3 R$^{6a}$;
  C$_3$-C$_{10}$ carbocycle substituted with 0-3 R$^{6b}$; or
  C$_6$-C$_{10}$ aryl substituted with 0-3 R$^{6b}$;
R$^{6a}$, at each occurrence, is independently selected from H,
  C$_1$-C$_6$ alkyl, OR$^{14}$, Cl, F, Br, I, =O, CN, NO$_2$, NR$^{15}$R$^{16}$,
  phenyl or CF$_3$;
R$^{6b}$, at each occurrence, is independently selected from H,
  OH, Cl, F, Br, I, CN, NO$_2$, NR$^{15}$R$^{16}$, CF$_3$, C$_1$-C$_6$ alkyl,
  C$_1$-C$_4$ alkoxy, C$_1$-C$_4$ haloalkyl, and C$_1$-C$_4$ haloalkoxy;
R$^7$, at each occurrence, is independently selected from H,
  OH, Cl, F, Br, I, CN, NO$_2$, CF$_3$, and C$_1$-C$_4$ alkyl;
R$^{7a}$, at each occurrence, is independently selected from H,
  OH, Cl, F, Br, I, CN, NO$_2$, CF$_3$, aryl and C$_1$-C$_4$ alkyl;
R$^{7b}$ is independently selected from H and C$_1$-C$_4$ alkyl;
W is —(CR$^8$R$^{8a}$)$_p$—;
p is 0, 1, 2, 3, or 4;
R$^8$ and R$^{8a}$, at each occurrence, are independently selected
  from H, F, C$_1$-C$_4$ alkyl, C$_2$-C$_4$ alkenyl, C$_2$-C$_4$ alkynyl and
  C$_3$-C$_8$ cycloalkyl;

X is a bond;
  C$_6$-C$_{10}$ aryl substituted with 0-3 R$^{Xb}$;
  C$_3$-C$_{10}$ carbocycle substituted with 0-3 R$^{Xb}$; or
  5 to 10 membered heterocycle substituted with 0-2 R$^{Xb}$;
R$^{Xb}$, at each occurrence, is independently selected from H,
  OH, Cl, F, Br, I, CN, NO$_2$, NR$^{15}$R$^{16}$, CF$_3$, acetyl, SCH$_3$,
  S(=O)CH$_3$, S(=O)$_2$CH$_3$, C$_1$-C$_6$ alkyl, C$_1$-C$_4$ alkoxy,
  C$_1$-C$_4$ haloalkyl, C$_1$-C$_4$ haloalkoxy, and C$_1$-C$_4$ halothioalkoxy;
Y is a bond or —(CR$^9$R$^{9a}$)$_t$—V—(CR$^9$R$^{9a}$)$_u$—;
t is 0, 1, 2, or 3;
u is 0, 1, 2, or 3;
R$^9$ and R$^{9a}$, at each occurrence, are independently selected
  from H, F, C$_1$-C$_6$ alkyl or C$_3$-C$_8$ cycloalkyl;
V is a bond, —C(=O)—, —O—, —S—, —S(=O)—,
  —S(=O)$_2$—, —N(R$^{19}$)—, —C(=O)NR$^{19b}$—,
  —NR$^{19b}$C(=O)—, —NR$^{19b}$S(=O)$_2$—,
  —S(=O)$_2$NR$^{19b}$—, —NR$^{19b}$S(=O)—, —S(=O)
  NR$^{19b}$—, —C(=O)O—, or —OC(=O)—;
Z is C$_1$-C$_4$ alkyl substituted with 0-3 R$^{12b}$;
  C$_1$-C$_3$ alkyl substituted with 1-2 R$^{12}$;
  C$_6$-C$_{10}$ aryl substituted with 0-4 R$^{12b}$;
  C$_3$-C$_{10}$ carbocycle substituted with 0-4 R$^{12b}$; or
  5 to 10 membered heterocycle substituted with 0-3 R$^{12b}$;
R$^{12}$ is C$_6$-C$_{10}$ aryl substituted with 0-4 R$^{12b}$;
  C$_3$-C$_{10}$ carbocycle substituted with 0-4 R$^{12b}$; or
  5 to 10 membered heterocycle substituted with 0-3 R$^{12b}$;
R$^{12b}$, at each occurrence, is independently selected from H,
  OH, Cl, F, Br, I, CN, NO$_2$, NR$^{15}$R$^{16}$, CF$_3$, acetyl, SCH$_3$,
  S(=O)CH$_3$, S(=O)$_2$CH$_3$, C$_1$-C$_6$ alkyl, C$_1$-C$_4$ alkoxy,
  C$_1$-C$_4$ haloalkyl, C$_1$-C$_4$ haloalkoxy, and C$_1$-C$_4$ halothioalkoxy;
B is a 5 to 10 membered lactam or thiolactam,
  wherein the lactam or thiolactam is saturated, partially
    saturated or unsaturated;
  wherein each additional lactam carbon or thiolactam
    carbon is substituted with 0-2 R$^{11}$; and,
  optionally, the lactam or thiolactam contains a heteroatom
    selected from —O—, —S—, —S(=O)—,
    —S(=O)$_2$—, and —N(R$^{10}$)—;
R$^{10}$ is H, C(=O)R$^{17}$, C(=O)OR$^{17}$, C(=O)NR$^{18}$R$^{19}$,
  S(=O)$_2$NR$^{18}$R$^{19}$, S(=O)$_2$R$^{17}$;
  C$_1$-C$_6$ alkyl substituted with 0-2 R$^{10a}$;
  C$_6$-C$_{10}$ aryl substituted with 0-4 R$^{10b}$;
  C$_3$-C$_{10}$ carbocycle substituted with 0-3 R$^{10b}$; or
  5 to 10 membered heterocycle optionally substituted with
    0-3 R$^{10b}$;
R$^{10a}$, at each occurrence, is independently selected from H,
  C$_1$-C$_6$ alkyl, OR$^{14}$, Cl, F, Br, I, =O, CN, NO$_2$, NR$^{15}$R$^{16}$,
  CF$_3$, or aryl substituted with 0-4 R$^{10b}$;
R$^{10b}$, at each occurrence, is independently selected from H,
  OH, C$_1$-C$_6$ alkyl, C$_1$-C$_4$ alkoxy, Cl, F, Br, I, CN, NO$_2$,
  NR$^{15}$R$^{16}$, CF$_3$, acetyl, SCH$_3$, S(=O)CH$_3$, S(=O)$_2$CH$_3$,
  C$_1$-C$_6$ alkyl, C$_1$-C$_4$ alkoxy, C$_1$-C$_4$ haloalkyl, C$_1$-C$_4$
  haloalkoxy, and C$_1$-C$_4$ halothioalkoxy;
R$^{11}$, at each occurrence, is independently selected from
  C$_1$-C$_4$ alkoxy, Cl, F, Br, I, =O, CN, NO$_2$, NR$^{18}$R$^{19}$,
  C(=O)R$^{17}$, C(=O)OR$^{17}$, C(=O)NR$^{18}$R$^{19}$,
  S(=O)$_2$NR$^{18}$R$^{19}$, CF$_3$;
  C$_1$-C$_6$ alkyl substituted with 0-1 R$^{11a}$;
  C$_6$-C$_{10}$ aryl substituted with 0-3 R$^{11b}$;
  C$_3$-C$_{10}$ carbocycle substituted with 0-3 R$^{11b}$; or
  5 to 10 membered heterocycle substituted with 0-3 R$^{11b}$;
alternatively, two R$^{11}$ substituents on the same or adjacent
  carbon atoms may be combined to form a C$_3$-C$_6$ carbocycle or a benzo fused radical;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or phenyl substituted with 0-3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ halothioalkyl;

$R^{14}$, at each occurrence, is independently selected from H, phenyl, benzyl, $C_1$-$C_6$ alkyl, or $C_2$-$C_6$ alkoxyalkyl;

$R^{14a}$ is H, phenyl, benzyl, or $C_1$-$C_4$ alkyl;

$R^{15}$, at each occurrence, is independently selected from H, $C_1$-$C_6$ alkyl, benzyl, phenethyl, —C(=O)—($C_1$-$C_6$ alkyl) and —S(=O)$_2$—($C_1$-$C_6$ alkyl);

$R^{16}$, at each occurrence, is independently selected from H, OH, $C_1$-$C_6$ alkyl, benzyl, phenethyl, —C(=O)—($C_1$-$C_6$ alkyl) and —S(=O)$_2$—($C_1$-$C_6$ alkyl);

$R^{17}$ is H, aryl, aryl-$CH_2$—, $C_1$-$C_6$ alkyl, or $C_2$-$C_6$ alkoxyalkyl;

$R^{18}$, at each occurrence, is independently selected from H, $C_1$-$C_6$ alkyl, benzyl, phenethyl, —C(=O)—($C_1$-$C_6$ alkyl) and —S(=O)$_2$—($C_1$-$C_6$ alkyl); and $R^{19}$, at each occurrence, is independently selected from H, OH, $C_1$-$C_6$ alkyl, phenyl, benzyl, phenethyl, —C(=O)—($C_1$-$C_6$ alkyl) and —S(=O)$_2$—($C_1$-$C_6$ alkyl); and $R^{19b}$ is H, $C_1$-$C_6$ alkyl, $C_3$-$C_8$ cycloalkyl, phenyl, benzyl or phenethyl.

[2] In a preferred embodiment the present provides

A is 0;

Q is —$NR^1R^2$;

$R^1$, at each occurrence, is independently selected from:
H;
$C_1$-$C_6$ alkyl substituted with 0-3 $R^{1a}$;
$C_2$-$C_6$ alkenyl substituted with 0-3 $R^{1a}$;

$R^{1a}$, at each occurrence, is independently selected from H, $OR^{14}$, F, =O, $NR^{15}R^{16}$, $CF_3$;
$C_3$-$C_6$ cycloalkyl substituted with 0-3 $R^{1b}$;
phenyl substituted with 0-3 $R^{1b}$; and
5 to 6 membered heterocycle substituted with 0-3 $R^{1b}$;

$R^{1b}$, at each occurrence, is independently selected from H, OH, Cl, F, Br, I, CN, $NO_2$, $NR^{15}R^{16}$, $CF_3$, $C_1$-$C_4$ alkyl, $C_1$-$C_4$ alkoxy, $C_1$-$C_4$ haloalkyl, and $C_1$-$C_4$ haloalkoxy;

$R^2$ is independently selected from H, $NH_2$, OH, $C_1$-$C_6$ alkyl, $C_1$-$C_6$ alkoxy, phenoxy, and benzyloxy;

$R^3$ is —$(CR^7R^{7a})_n$—$R^4$,
—$(CR^7R^{7a})_n$—S—$(CR^7R^{7a})_m$—$R^4$,
—$(CR^7R^{7a})_n$—O$(CR^7R^{7a})_m$—$R^4$,
—$(CR^7R^{7a})_n$—N($R^{7b}$)—$(CR^7R^{7a})_m$—$R^4$,
—$(CR^7R^{7a})_n$—S(=O)—$(CR^7R^{7a})_m$—$R^4$,
—$(CR^7R^{7a})_n$—S(=O)$_2$—$(CR^7R^{7a})_m$—$R^4$,
—$(CR^7R^{7a})_n$—C(=O)—$(CR^7R^{7a})_m$—$R^4$,
—$(CR^7R^{7a})_n$—NHC(=O)—$(CR^7R^{7a})_m$—$R^4$,
—$(CR^7R^{7a})_n$—C(=O)NH—$(CR^7R^{7a})_m$—$R^4$,
—$(CR^7R^{7a})_n$—NHS(=O)$_2$—$(CR^7R^{7a})_m$—$R^4$, or
—$(CR^7R^{7a})_n$—S(=O)$_2$NH—$(CR^7R^{7a})_m$—$R^4$;

n is 0, 1, 2, or 3;

m is 0, 1, 2, or 3;

$R^{3a}$ is H, OH, $C_1$-$C_4$ alkyl, $C_1$-$C_4$ alkoxy, or $C_2$-$C_4$ alkenyloxy;

$R^4$ is H, OH, $OR^{14a}$,
$C_1$-$C_6$ alkyl substituted with 0-3 $R^{4a}$,
$C_2$-$C_6$ alkenyl substituted with 0-3 $R^{4a}$,
$C_2$-$C_6$ alkynyl substituted with 0-3 $R^{4a}$,
$C_3$-$C_{10}$ carbocycle substituted with 0-3 $R^{4b}$,
$C_6$-$C_{10}$ aryl substituted with 0-3 $R^{4b}$, or
5 to 10 membered heterocycle substituted with 0-3 $R^{4b}$;

$R^{4a}$, at each occurrence, is independently selected from is H, F, Cl, Br, I, $CF_3$,
$C_3$-$C_{10}$ carbocycle substituted with 0-3 $R^{4b}$,
$C_6$-$C_{10}$ aryl substituted with 0-3 $R^{4b}$, or
5 to 10 membered heterocycle substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

$R^5$ is H, $OR^{14}$;
$C_1$-$C_6$ alkyl substituted with 0-3 $R^{5b}$;
$C_1$-$C_6$ alkoxy substituted with 0-3 $R^{5b}$;
$C_2$-$C_6$ alkenyl substituted with 0-3 $R^{5b}$;
$C_2$-$C_6$ alkynyl substituted with 0-3 $R^{5b}$;
$C_3$-$C_{10}$ carbocycle substituted with 0-3 $R^{5c}$;
$C_6$-$C_{10}$ aryl substituted with 0-3 $R^{5c}$; or
5 to 10 membered heterocycle substituted with 0-3 $R^{5c}$;

$R^{5a}$ is H, OH, $C_1$-$C_4$ alkyl, $C_1$-$C_4$ alkoxy, $C_2$-$C_4$ alkenyl, or $C_2$-$C_4$ alkenyloxy;

$R^{5b}$, at each occurrence, is independently selected from:
H, $C_1$-$C_6$ alkyl, $CF_3$, $OR^{14}$, Cl, F, Br, I, =O, CN, $NO_2$, $NR^{15}R^{16}$;
$C_3$-$C_{10}$ carbocycle substituted with 0-3 $R^{5c}$;
$C_6$-$C_{10}$ aryl substituted with 0-3 $R^{5c}$; or
5 to 10 membered heterocycle substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

$R^6$ is H;
$C_1$-$C_6$ alkyl substituted with 0-3 $R^{6a}$;
$C_3$-$C_6$ carbocycle substituted with 0-3 $R^{6b}$; or
$C_6$-$C_{10}$ aryl substituted with 0-3 $R^{6b}$;

$R^{6a}$, at each occurrence, is independently selected from H, $C_1$-$C_6$ alkyl, $OR^{14}$, Cl, F, Br, I, =O, CN, $NO_2$, $NR^{15}R^{16}$, phenyl or $CF_3$;

$R^{6b}$, at each occurrence, is independently selected from H, OH, Cl, F, Br, I, CN, $NO_2$, $NR^{15}R^{16}$, $CF_3$, $C_1$-$C_6$ alkyl, $C_1$-$C_4$ alkoxy, $C_1$-$C_4$ haloalkyl, and $C_1$-$C_4$ haloalkoxy;

$R^7$, at each occurrence, is independently selected from H, OH, Cl, F, Br, I, CN, $NO_2$, $CF_3$, and $C_1$-$C_4$ alkyl;

$R^{7a}$, at each occurrence, is independently selected from H, OH, Cl, F, Br, I, CN, $NO_2$, $CF_3$, aryl and $C_1$-$C_4$ alkyl;

$R^{7b}$ is independently selected from H and $C_1$-$C_4$ alkyl;

W is —$(CR^8R^{8a})_p$—;

p is 0, 1, 2, 3, or 4;

$R^8$ and $R^{8a}$, at each occurrence, are independently selected from H, F, $C_1$-$C_4$ alkyl, $C_2$-$C_4$ alkenyl, $C_2$-$C_4$ alkynyl and $C_3$-$C_8$ cycloalkyl;

X is a bond;
$C_6$-$C_{10}$ aryl substituted with 0-3 $R^{Xb}$;
$C_3$-$C_{10}$ carbocycle substituted with 0-3 $R^{Xb}$; or
5 to 10 membered heterocycle substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

Y is a bond or —$(CR^9R^{9a})_t$—V—$(CR^9R^{9a})_u$—;

t is 0, 1, 2, or 3;

u is 0, 1, 2, or 3;

$R^9$ and $R^{9a}$, at each occurrence, are independently selected from H, F, $C_1$-$C_6$ alkyl or $C_3$-$C_8$ cycloalkyl;

V is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)$_2$—, —S(=O)$_2NR^{19b}$—, —$NR^{19b}$S(=O)—, —S(=O)$NR^{19b}$—, —C(=O)O—, or —OC(=O)—;

9

Z is $C_1$-$C_3$ alkyl substituted with 1-2 $R^{12}$;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle substituted with 0-3 $R^{12b}$;

$R^{12}$ is $C_6$-$C_{10}$ aryl substituted with 0-4 $R^{12b}$;
$C_3$-$C_{10}$ carbocycle substituted with 0-4 $R^{12b}$; or
5 to 10 membered heterocycle substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

B is a 6, 7, or 8 membered lactam,
  wherein the lactam is saturated, partially saturated or unsaturated;
  wherein each additional lactam carbon is substituted with 0-2 $R^{11}$; and,
  optionally, the lactam contains a heteroatom selected from —O—, —S—, —S(=O)—, —S(=O)$_2$—, and —N($R^{10}$)—;

$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;
$C_1$-$C_6$ alkyl substituted with 0-1 $R^{10a}$;
$C_6$-$C_{10}$ aryl substituted with 0-4 $R^{10b}$;
$C_3$-$C_{10}$ carbocycle substituted with 0-3 $R^{10b}$; or
5 to 10 membered heterocycle optionally substituted with 0-3 $R^{10b}$;

$R^{10a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or phenyl substituted with 0-4 $R^{10b}$;

$R^{10b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, or $CF_3$;

$R^{11}$, at each occurrence, is independently selected from $C_1$-$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$-$C_6$ alkyl substituted with 0-1 $R^{11a}$;
$C_6$-$C_{10}$ aryl substituted with 0-3 $R^{11b}$;
$C_3$-$C_{10}$ carbocycle substituted with 0-3 $R^{11b}$; or
5 to 10 membered heterocycle substituted with 0-3 $R^{11b}$;
alternatively, two $R^{11}$ substituents on the same or adjacent carbon atoms may be combined to form a $C_3$-$C_6$ carbocycle or a benzo fused radical;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or phenyl substituted with 0-3 $R^{11b}$;

$R^{11b}$, at each occurrence, is independently selected from H, OH, Cl, F, Br, I, CN, $NO_2$, $NR^{15}R^{16}$, $CF_3$, $C_1$-$C_6$ alkyl, $C_1$-$C_4$ alkoxy, $C_1$-$C_4$ haloalkyl, and $C_1$-$C_4$ haloalkoxy;

$R^{14}$ is H, phenyl, benzyl, $C_1$-$C_6$ alkyl, or $C_2$-$C_6$ alkoxyalkyl;

$R^{15}$, at each occurrence, is independently selected from H, $C_1$-$C_6$ alkyl, benzyl, phenethyl, —C(=O)—($C_1$-$C_6$ alkyl) and —S(=O)$_2$—($C_1$-$C_6$ alkyl);

$R^{16}$, at each occurrence, is independently selected from H, OH, $C_1$-$C_6$ alkyl, benzyl, phenethyl, —C(=O)—($C_1$-$C_6$ alkyl) and —S(=O)$_2$—($C_1$-$C_6$ alkyl);

$R^{17}$ is H, aryl, (aryl)$CH_2$—, $C_1$-$C_6$ alkyl, or $C_2$-$C_6$ alkoxyalkyl;

$R^{18}$, at each occurrence, is independently selected from H, $C_1$-$C_6$ alkyl, benzyl, phenethyl, —C(=O)—($C_1$-$C_6$ alkyl) and —S(=O)$_2$—($C_1$-$C_6$ alkyl); and $R^{19}$, at each occurrence, is independently selected from H, OH, $C_1$-$C_6$ alkyl, phenyl, benzyl, phenethyl, —C(=O)—($C_1$-$C_6$ alkyl) and —S(=O)$_2$—($C_1$-$C_6$ alkyl); and $R^{19b}$ is H, $C_1$-$C_6$ alkyl, $C_3$-$C_8$ cycloalkyl, phenyl, benzyl or phenethyl.

10

[3] In a further preferred embodiment the present invention provides

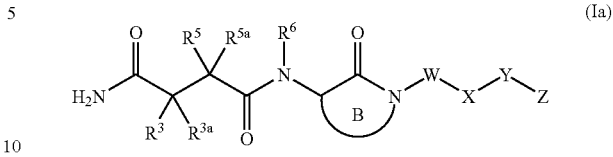

(Ia)

or a pharmaceutically acceptable salt or prodrug thereof, wherein:

$R^3$ is —($CR^7R^{7a}$)$_n$—$R^4$,
  —($CR^7R^{7a}$)$_n$—S—($CR^7R^{7a}$)$_m$—$R^4$,
  —($CR^7R^{7a}$)$_n$—O—($CR^7R^{7a}$)$_m$—$R^4$, or
  —($CR^7R^{7a}$)$_n$—N($R^{7b}$)—($CR^7R^{7a}$)$_m$—$R^4$;

n is 0, 1, or 2;

m is 0, 1, or 2;

$R^{3a}$ is H, OH, methyl, ethyl, propyl, butyl, methoxy, ethoxy, propoxy, or butoxy;

$R^4$ is H, OH, $OR^{14a}$,
  $C_1$-$C_4$ alkyl substituted with 0-2 $R^{4a}$,
  $C_2$-$C_4$ alkenyl substituted with 0-2 $R^{4a}$,
  $C_2$-$C_4$ alkynyl substituted with 0-2 $R^{4a}$,
  $C_3$-$C_6$ cycloalkyl substituted with 0-3 $R^{4b}$,
  $C_6$-$C_{10}$ aryl substituted with 0-3 $R^{4b}$, or
  5 to 10 membered heterocycle substituted with 0-3 $R^{4b}$;

$R^{4a}$, at each occurrence, is independently selected from is H, F, Cl, Br, I $CF_3$,
  $C_3$-$C_{10}$ carbocycle substituted with 0-3 $R^{4b}$,
  $C_6$-$C_{10}$ aryl substituted with 0-3 $R^{4b}$, or
  5 to 10 membered heterocycle substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

$R^5$ is H, $OR^{14}$;
  $C_1$-$C_6$ alkyl substituted with 0-3 $R^{5b}$;
  $C_2$-$C_6$ alkenyl substituted with 0-3 $R^{5b}$;
  $C_2$-$C_6$ alkynyl substituted with 0-3 $R^{5b}$;
  $C_3$-$C_{10}$ carbocycle substituted with 0-3 $R^{5c}$;
  $C_6$-$C_{10}$ aryl substituted with 0-3 $R^{5c}$; or
  5 to 10 membered heterocycle substituted with 0-3 $R^{5c}$;

$R^{5a}$ is H, OH, $C_1$-$C_4$ alkyl, $C_1$-$C_4$ alkoxy, $C_2$-$C_4$ alkenyl, or $C_2$-$C_4$ alkenyloxy;

$R^{5b}$, at each occurrence, is independently selected from:
  H, $C_1$-$C_6$ alkyl, $CF_3$, $OR^{14}$, Cl, F, Br, I, =O, CN, $NO_2$, $NR^{15}R^{16}$;
  $C_3$-$C_{10}$ carbocycle substituted with 0-3 $R^{5c}$;
  $C_6$-$C_{10}$ aryl substituted with 0-3 $R^{5c}$; or
  5 to 10 membered heterocycle substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

$R^6$ is H, methyl, or ethyl;

$R^7$, at each occurrence, is independently selected from H, OH, Cl, F, Br, I, CN, $NO_2$, $CF_3$, and $C_1$-$C_4$ alkyl;

$R^{7a}$, at each occurrence, is independently selected from H, OH, Cl, F, Br, I, CN, $NO_2$, $CF_3$, phenyl and $C_1$-$C_4$ alkyl;

$R^{7b}$ is independently selected from H, methyl, ethyl, propyl, and butyl;

W is —($CR^8R^{8a}$)$_p$—;

p is 0, 1, or 2;

$R^8$ and $R^{8a}$, at each occurrence, are independently selected from H, F, $C_1$-$C_3$ alkyl, $C_2$-$C_3$ alkenyl, $C_2$-$C_3$ alkynyl and $C_3$-$C_6$ cycloalkyl;

X is a bond;
  $C_6$-$C_{10}$ aryl substituted with 0-3 $R^{Xb}$;
  $C_3$-$C_{10}$ carbocycle substituted with 0-2 $R^{Xb}$; or
  5 to 10 membered heterocycle substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

Y is a bond or $-(CR^9R^{9a})_t-V-(CR^9R^{9a})_u-$;

t is 0, 1, or 2;

u is 0, 1, or 2;

$R^9$ and $R^{9a}$, at each occurrence, are independently selected from H, F, $C_1$-$C_4$ alkyl or $C_3$-$C_6$ cycloalkyl;

V is a bond, $-C(=O)-$, $-O-$, $-S-$, $-S(=O)-$, $-S(=O)_2-$, $-N(R^{19})-$, $-C(=O)NR^{19b}-$, $-NR^{19b}C(=O)-$, $-NR^{19b}S(=O)_2-$, $-S(=O)_2NR^{19b}-$, $-NR^{19b}S(=O)-$, or $-S(=O)NR^{19b}-$;

Z is $C_1$-$C_3$ alkyl substituted with 1-2 $R^{12}$;
  $C_6$-$C_{10}$ aryl substituted with 0-4 $R^{12b}$;
  $C_3$-$C_{10}$ carbocycle substituted with 0-4 $R^{12b}$; or
  5 to 10 membered heterocycle substituted with 0-3 $R^{12b}$;

$R^{12}$ is $C_6$-$C_{10}$ aryl substituted with 0-4 $R^{12b}$;
  $C_3$-$C_{10}$ carbocycle substituted with 0-4 $R^{12b}$; or
  5 to 10 membered heterocycle substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

B is a seven membered lactam,
  wherein the lactam is saturated, partially saturated or unsaturated;
  wherein each additional lactam carbon is substituted with 0-2 $R^{11}$; and,
  optionally, the lactam contains a heteroatom selected from $-O-$, $-S-$, $-S(=O)-$, $-S(=O)_2-$, and $-N(R^{10})-$;

$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;
  $C_1$-$C_6$ alkyl substituted with 0-1 $R^{10a}$;
  $C_6$-$C_{10}$ aryl substituted with 0-4 $R^{10b}$;
  $C_3$-$C_{10}$ carbocycle substituted with 0-3 $R^{10b}$; or
  5 to 10 membered heterocycle optionally substituted with 0-3 $R^{10b}$;

$R^{10a}$, at each occurrence, is independently selected from H, $C_1$-$C_6$ alkyl, $OR^{14}$, Cl, F, Br, I, $=O$, CN, $NO_2$, $NR^{15}R^{16}$, $CF_3$, or phenyl substituted with 0-4 $R^{10b}$;

$R^{10b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, or $CF_3$;

$R^{11}$, at each occurrence, is independently selected from $C_1$-$C_4$ alkoxy, Cl, F, $=O$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
  $C_1$-$C_6$ alkyl substituted with 0-1 $R^{11a}$;
  $C_6$-$C_{10}$ aryl substituted with 0-3 $R^{11b}$;
  $C_3$-$C_{10}$ carbocycle substituted with 0-3 $R^{11b}$; or
  5 to 10 membered heterocycle substituted with 0-3 $R^{11b}$;

alternatively, two $R^{11}$ substituents on the same or adjacent carbon atoms may be combined to form a $C_3$-$C_6$ carbocycle or a benzo fused radical;

$R^{11a}$, at each occurrence, is independently selected from H, $C_1$-$C_6$ alkyl, $OR^{14}$, Cl, F, Br, I, $=O$, CN, $NO_2$, $NR^{15}R^{16}$, $CF_3$, or phenyl substituted with 0-3 $R^{11b}$;

$R^{11b}$, at each occurrence, is independently selected from H, OH, Cl, F, Br, I, CN, $NO_2$, $NR^{15}R^{16}$, $CF_3$, $C_1$-$C_6$ alkyl, $C_1$-$C_4$ alkoxy, $C_1$-$C_4$ haloalkyl, and $C_1$-$C_4$ haloalkoxy;

$R^{14}$ is H, phenyl, benzyl, $C_1$-$C_6$ alkyl, or $C_2$-$C_6$ alkoxyalkyl;

$R^{15}$, at each occurrence, is independently selected from H, $C_1$-$C_6$ alkyl, benzyl, phenethyl, $-C(=O)-(C_1$-$C_6$ alkyl) and $-S(=O)_2-(C_1$-$C_6$ alkyl);

$R^{16}$, at each occurrence, is independently selected from H, OH, $C_1$-$C_6$ alkyl, benzyl, phenethyl, $-C(=O)-(C_1$-$C_6$ alkyl) and $-S(=O)_2-(C_1$-$C_6$ alkyl);

$R^{17}$ is H, aryl, (aryl)$CH_2-$, $C_1$-$C_6$ alkyl, or $C_2$-$C_6$ alkoxyalkyl;

$R^{18}$, at each occurrence, is independently selected from H, $C_1$-$C_6$ alkyl, benzyl, phenethyl, $-C(=O)-(C_1$-$C_6$ alkyl) and $-S(=O)_2-(C_1$-$C_6$ alkyl); and $R^{19}$, at each occurrence, is independently selected from H, OH, $C_1$-$C_6$ alkyl, phenyl, benzyl, phenethyl, $-C(=O)-(C_1$-$C_6$ alkyl) and $-S(=O)_2-(C_1$-$C_6$ alkyl); and $R^{19b}$ is H, $C_1$-$C_6$ alkyl, $C_3$-$C_8$ cycloalkyl, phenyl, benzyl or phenethyl.

[4] In a further preferred embodiment the present invention provides $R^3$ is $-(CR^7R^{7a})_n-R^4$,
  $-(CR^7R^{7a})_n-S-(CR^7R^{7a})_m-R^4$,
  $-(CR^7R^{7a})_n-O-(CR^7R^{7a})_m-R^4$, or
  $-(CR^7R^{7a})_n-N(R^{7b})-(CR^7R^{7a})_m-R^4$;

n is 0 or 1;

m is 0 or 1;

$R^{3a}$ is H, OH, methyl, ethyl, propyl, butyl, methoxy, ethoxy, propoxy, or butoxy;

$R^4$ is H, OH,
  $C_1$-$C_4$ alkyl substituted with 0-2 $R^{4a}$,
  $C_2$-$C_4$ alkenyl substituted with 0-2 $R^{4a}$,
  $C_2$-$C_4$ alkynyl substituted with 0-1 $R^{4a}$,
  $C_3$-$C_6$ cycloalkyl substituted with 0-3 $R^{4b}$,
  $C_6$-$C_{10}$ aryl substituted with 0-3 $R^{4b}$, or
  5 to 10 membered heterocycle substituted with 0-3 $R^{4b}$;

$R^{4a}$, at each occurrence, is independently selected from is H, F, Cl, $CF_3$,
  $C_3$-$C_6$ cycloalkyl substituted with 0-3 $R^{4b}$,
  phenyl substituted with 0-3 $R^{4b}$, or
  5 to 6 membered heterocycle substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_4$ alkyl, $C_1$-$C_3$ alkoxy, $C_1$-$C_2$ haloalkyl, and $C_1$-$C_2$ haloalkoxy;

$R^5$ is H, $OR^{14}$;
  $C_1$-$C_4$ alkyl substituted with 0-3 $R^{5b}$;
  $C_2$-$C_4$ alkenyl substituted with 0-2 $R^{5b}$; or
  $C_2$-$C_4$ alkynyl substituted with 0-2 $R^{5b}$;

$R^{5a}$ is H, OH, methyl, ethyl, propyl, butyl, methoxy, ethoxy, propoxy, butoxy, or allyl;

$R^{5b}$, at each occurrence, is independently selected from:
  H, methyl, ethyl, propyl, butyl, $CF_3$, $OR^{14}$, $=O$;
  $C_3$-$C_6$ cycloalkyl substituted with 0-2 $R^{5c}$;
  phenyl substituted with 0-3 $R^{5c}$; or
  5 to 6 membered heterocycle substituted with 0-2 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_4$ alkyl, $C_1$-$C_3$ alkoxy, $C_1$-$C_2$ haloalkyl, and $C_1$-$C_2$ haloalkoxy;

$R^6$ is H;

$R^7$, at each occurrence, is independently selected from H, F, $CF_3$, methyl, and ethyl;

$R^{7a}$, at each occurrence, is independently selected from H, F, $CF_3$, methyl, and ethyl;

$R^{7b}$ is independently selected from H, methyl, and ethyl;

W is a bond, —CH$_2$—, —CH(CH$_3$)—, —CH$_2$CH$_2$— or —CH(CH$_3$)CH$_2$—;

X is a bond;
  phenyl substituted with 0-2 R$^{Xb}$;
  C$_3$-C$_6$ cycloalkyl substituted with 0-2 R$^{Xb}$; or
  5 to 6 membered heterocycle substituted with 0-2 R$^{Xb}$;

R$^{Xb}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, C$_1$-C$_4$ alkyl, C$_1$-C$_3$ alkoxy, C$_1$-C$_2$ haloalkyl, and C$_1$-C$_2$ haloalkoxy;

Y is a bond, —CH$_2$—V—, —V—, or —V—CH$_2$—;

V is a bond, —C(=O)—, —O—, —S—, —S(=O)—, —S(=O)$_2$—, —NH—, —N(CH$_3$)—, or —N(CH$_2$CH$_3$)—;

Z is C$_1$-C$_2$ alkyl substituted with 1-2 R$^{12}$;
  C$_6$-C$_{10}$ aryl substituted with 0-4 R$^{12b}$;
  C$_3$-C$_6$ carbocycle substituted with 0-3 R$^{12b}$; or
  5 to 10 membered heterocycle substituted with 0-3 R$^{12b}$;

R$^{12}$ is C$_6$-C$_{10}$ aryl substituted with 0-4 R$^{12b}$;
  C$_3$-C$_6$ carbocycle substituted with 0-3 R$^{12b}$; or
  5 to 10 membered heterocycle substituted with 0-3 R$^{12b}$;

R$^{12b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, C$_1$-C$_4$ alkyl, C$_1$-C$_3$ alkoxy, C$_1$-C$_2$ haloalkyl, and C$_1$-C$_2$ haloalkoxy;

B is a seven membered lactam,
  wherein the lactam is saturated, partially saturated or unsaturated;
  wherein each additional lactam carbon is substituted with 0-2 R$^{11}$; and,
  optionally, the lactam contains a heteroatom selected from —O—, —S—, —S(=O)—, —S(=O)$_2$—, and —N(R$^{10}$)—;

R$^{10}$ is H, C(=O)R$^{17}$, C(=O)OR$^{17}$;
  C$_1$-C$_4$ alkyl substituted with 0-1 R$^{10a}$;
  phenyl substituted with 0-4 R$^{10b}$;
  C$_3$-C$_6$ carbocycle substituted with 0-3 R$^{10b}$; or
  5 to 6 membered heterocycle optionally substituted with 0-3 R$^{10b}$;

R$^{10a}$, at each occurrence, is independently selected from H, C$_1$-C$_4$ alkyl, OR$^{14}$, Cl, F, Br, I, =O, CN, NO$_2$, NR$^{15}$R$^{16}$, CF$_3$, or phenyl substituted with 0-4 R$^{10b}$;

R$^{10b}$, at each occurrence, is independently selected from H, OH, C$_1$-C$_4$ alkyl, C$_1$-C$_3$ alkoxy, Cl, F, Br, I, CN, NO$_2$, NR$^{15}$R$^{16}$, or CF$_3$;

R$^{11}$, at each occurrence, is independently selected from
  C$_1$-C$_4$ alkoxy, Cl, F, =O, NR$^{18}$R$^{19}$, C(=O)R$^{17}$, C(=O)OR$^{17}$, CF$_3$;
  C$_1$-C$_4$ alkyl substituted with 0-1 R$^{11a}$;
  phenyl substituted with 0-3 R$^{11b}$;
  C$_3$-C$_6$ carbocycle substituted with 0-3 R$^{11b}$; or
  5 to 6 membered heterocycle substituted with 0-3 R$^{11b}$;
alternatively, two R$^{11}$ substituents on the same or adjacent carbon atoms may be combined to form a cyclopropyl, cyclobutyl, cyclopentyl, cyclohexyl, or a benzo fused radical;

R$^{11a}$, at each occurrence, is independently selected from H, C$_1$-C$_4$ alkyl, OR$^{14}$, F, =O, NR$^{15}$R$^{16}$, CF$_3$, or phenyl substituted with 0-3 R$^{11b}$;

R$^{11b}$, at each occurrence, is independently selected from H, OH, Cl, F, NR$^{15}$R$^{16}$, CF$_3$, C$_1$-C$_4$ alkyl, C$_1$-C$_3$ alkoxy, C$_1$-C$_2$ haloalkyl, and C$_1$-C$_2$ haloalkoxy;

R$^{14}$ is H, phenyl, benzyl, C$_1$-C$_4$ alkyl, or C$_2$-C$_4$ alkoxyalkyl;

R$^{15}$, at each occurrence, is independently selected from H, C$_1$-C$_4$ alkyl, benzyl, phenethyl, —C(=O)—(C$_1$-C$_4$ alkyl) and —S(=O)$_2$—(C$_1$-C$_4$ alkyl);

R$^{16}$, at each occurrence, is independently selected from H, OH, C$_1$-C$_4$ alkyl, benzyl, phenethyl, —C(=O)—(C$_1$-C$_4$ alkyl) and —S(=O)$_2$—(C$_1$-C$_4$ alkyl);

R$^{17}$ is H, phenyl, 4-fluorophenyl, 4-chlorophenyl, 4-methylphenyl, 4-trifluorophenyl, (4-fluorophenyl)methyl, (4-chlorophenyl)methyl, (4-methylphenyl)methyl, (4-trifluorophenyl)methyl, methyl, ethyl, propyl, butyl, methoxymethyl, methyoxyethyl, ethoxymethyl, or ethoxyethyl;

R$^{18}$, at each occurrence, is independently selected from H, methyl, ethyl, propyl, butyl, phenyl, benzyl, and phenethyl; and R$^{19}$, at each occurrence, is independently selected from H, methyl, and ethyl.

[5] In a more preferred embodiment the present invention provides (Ib)

or a pharmaceutically acceptable salt or prodrug thereof, wherein:

R$^3$ is —CH$_3$, —CH$_2$CH$_3$, —CH$_2$CH$_2$CH$_3$, —CH$_2$CH$_2$CH$_2$CH$_3$,
  —CH$_2$(CH$_3$)$_2$, —CH(CH$_3$)CH$_2$CH$_3$, —CH$_2$CH(CH$_3$)$_2$, —CH$_2$C(CH$_3$)$_3$,
  —CF$_3$, —CH$_2$CF$_3$, —CH$_2$CH$_2$CF$_3$, —CH$_2$CH$_2$CH$_2$CF$_3$,
  —CH=CH$_2$, —CH$_2$CH=CH$_2$, —CH$_2$C(CH$_3$)=CH$_2$, —CH$_2$CH=C(CH$_3$)$_2$, —CH$_2$CH=CH$_2$, —CH$_2$CH$_2$C(CH$_3$)=CH$_2$, —CH$_2$CH$_2$CH=C(CH$_3$)$_2$, cis-CH$_2$CH=CH(CH$_3$), cis-CH$_2$CH$_2$CH=CH(CH$_3$), trans-CH$_2$CH=CH(CH$_3$), trans-CH$_2$CH$_2$CH=CH(CH$_3$);
  —C≡CH, —CH$_2$C≡CH, —CH$_2$C≡C(CH$_3$),
  cyclopropyl-CH$_2$—, cyclobutyl-CH$_2$—, cyclopentyl-CH$_2$—, cyclohexyl-CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—,
  phenyl-CH$_2$—,
  (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—,
  (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—,
  phenyl-CH$_2$CH$_2$—,
  (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, or $R^5$ is —CH₃, —CH₂CH₃, —CH₂CH₂CH₃, —CH₂(CH₃)₂, —CH₂CH₂CH₂CH₃, —CH(CH₃)CH₂CH₃, —CH₂CH(CH₃)₂, —CH₂C(CH₃)₃, —CH₂CH₂CH₂CH₂CH₃, —CH(CH₃)CH₂CH₂CH₃, —CH₂CH(CH₃)CH₂CH₃, —CH₂CH₂CH(CH₃)₂, —CH(CH₂CH₃)₂, —CF₃, —CH₂CF₃, —CH₂CH₂CF₃, —CH₂CH₂CH₂CF₃, —CH₂CH₂CH₂CH₂CF₃, —CH=CH₂, —CH₂CH=CH₂, —CH=CHCH₃, cis-CH₂CH=CH(CH₃), trans-CH₂CH=CH(CH₃), trans-CH₂CH=CH(C₆H₅), —CH₂CH=C(CH₃)₂, cis-CH₂CH=CHCH₂CH₃, trans-CH₂CH=CHCH₂CH₃, cis-CH₂CH₂CH=CH(CH₃), trans-CH₂CH₂CH=CH(CH₃), trans-CH₂CH=CHCH₂ (C₆H₅), —C≡CH, —CH₂C₂≡CH, —CH₂C≡C(CH₃), —CH₂C≡C(C₆H₅) —CH₂CH₂C≡CH, —CH₂CH₂C≡C(CH₃), —CH₂CH₂C≡C(C₆H₅) —CH₂CH₂CH₂C≡CH, —CH₂CH₂CH₂C≡C(CH₃), —CH₂CH₂CH₂C≡C(C₆H₅)

cyclopropyl-CH₂—, cyclobutyl-CH₂—, cyclopentyl-CH₂—, cyclohexyl-CH₂—, (2-CH₃-cyclopropyl)CH₂—, (3-CH₃-cyclobutyl)CH₂—, cyclopropyl-CH₂CH₂—, cyclobutyl-CH₂CH₂—, cyclopentyl-CH₂CH₂—, cyclohexyl-CH₂CH₂—, (2-CH₃-cyclopropyl)CH₂CH₂—, (3-CH₃-cyclobutyl)CH₂CH₂—, phenyl-CH₂—, (2-F-phenyl)CH₂—, (3-F-phenyl)CH₂—, (4-F-phenyl)CH₂—, furanyl-CH₂—, thienyl-CH₂—, pyridyl-CH₂—, 1-imidazolyl-CH₂—, oxazolyl-CH₂—, isoxazolyl-CH₂—, phenyl-CH₂CH₂—, (2-F-phenyl)CH₂CH₂—, (3-F-phenyl)CH₂CH₂—, (4-F-phenyl)CH₂CH₂—, furanyl-CH₂CH₂—, thienyl-CH₂CH₂—, pyridyl-CH₂CH₂—, 1-imidazolyl-CH₂CH₂—, oxazolyl-CH₂CH₂—, isoxazolyl-CH₂CH₂—, W is a bond, —CH₂—, or —CH(CH₃)—;

X is a bond;

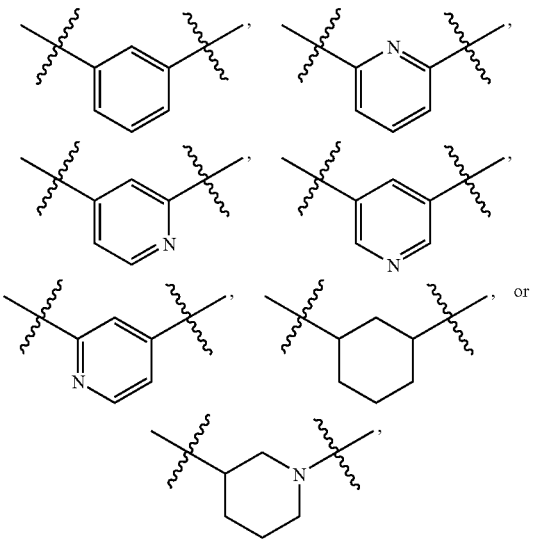

Y is a bond, —CH₂—V—, —V—, or —V—CH₂—;

V is a bond, —C(=O)—, —O—, —S—, —S(=O)—, —S(=O)₂—, —NH—, or —N(CH₃)—,

Z is phenyl 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂—, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, (2-MeO-phenyl)CH₂—, (3-MeO-phenyl)CH₂—, (4-MeO-phenyl)CH₂—, (2-Me-phenyl)CH₂—, (3-Me-phenyl)CH₂—, (4-Me-phenyl)CH₂—, (2-MeS-phenyl)CH₂—, (3-MeS-phenyl)CH₂—, 4-MeS-phenyl)CH₂—, (2-CF₃O-phenyl)CH₂—, (3-CF₃O-phenyl)CH₂—, (4-CF₃O-phenyl)CH₂—, (furanyl)CH₂—, (thienyl)CH₂—, (pyridyl)CH₂—, (2-Me-pyridyl)CH₂—, (3-Me-pyridyl)CH₂—, (4-Me-pyridyl)CH₂—, (1-imidazolyl)CH₂—, (oxazolyl)CH₂—, (isoxazolyl)CH₂—, (1-benzimidazolyl)CH₂—, (cyclopropyl)CH₂—, (cyclobutyl)CH₂—, (cyclopentyl)CH₂—, (cyclohexyl)CH₂—, (morpholino)CH₂—, (N-pipridinyl)CH₂—, phenyl-CH₂CH₂—, (phenyl)₂CHCH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, (3-Cl-4-F-phenyl)CH₂CH₂—, (2-MeO-phenyl)CH₂CH₂—, (3-MeO-phenyl)CH₂CH₂—, (4-MeO-phenyl)CH₂CH₂—, (2-Me-phenyl)CH₂CH₂—, (3-Me-phenyl)CH₂CH₂—, (4-Me-phenyl)CH₂CH₂—, (2-MeS-phenyl)CH₂CH₂—, (3-MeS-phenyl)CH₂CH₂—, (4-MeS-phenyl)CH₂CH₂—, (2-CF₃O-phenyl)CH₂CH₂—, (3-CF₃O-phenyl)CH₂CH₂—, (4-CF₃O-phenyl)CH₂CH₂—, (furanyl)CH₂CH₂—,(thienyl)CH₂CH₂—, (pyridyl)CH₂CH₂—, (2-Me-pyridyl)CH₂CH₂—, (3-Me-pyridyl)CH₂CH₂—, (4-Me-pyridyl)CH₂CH₂—, (imidazolyl)CH₂CH₂—, (oxazolyl)CH₂CH₂—, (isoxazolyl)CH₂CH₂—, (benzimidazolyl)CH₂CH₂—,(cyclopropyl)CH₂CH₂—, (cyclobutyl)CH₂CH₂—,(cyclopentyl)CH₂CH₂—, (cyclohexyl)CH₂CH₂—,(morpholino)CH₂CH₂—, (N-pipridinyl)CH₂CH₂—, B is a seven membered lactam, wherein the lactam is saturated, partially saturated or unsaturated;

wherein each additional lactam carbon is substituted with 0-2 $R^{11}$; and, optionally, the lactam contains a heteroatom selected from —O—, —S—, —S(=O)—, —S(=O)$_2$—, and —N(R$^{10}$)—;

R$^{10}$ is H, methyl, ethyl, phenyl, benzyl, phenethyl, 4-F-phenyl, (4-F-phenyl)CH$_2$—, (4-F-phenyl)CH$_2$CH$_2$—, 4-Cl-phenyl, (4-Cl-phenyl)CH$_2$—, (4-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 4-CF$_3$-phenyl, (4-CF$_3$-phenyl)CH$_2$—, or (4-CF$_3$-phenyl)CH$_2$CH$_2$—;

R$^{11}$, at each occurrence, is independently selected from H, =O, methyl, ethyl, phenyl, benzyl, phenethyl, 4-F-phenyl, (4-F-phenyl)CH$_2$—, (4-F-phenyl)CH$_2$CH$_2$—, 4-Cl-phenyl, (4-Cl-phenyl)CH$_2$—, (4-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 4-CF$_3$-phenyl, (4-CF$_3$-phenyl)CH$_2$—, or (4-CF$_3$-phenyl)CH$_2$CH$_2$—; and alternatively, two R$^{11}$ substituents on the same or adjacent carbon atoms may be combined to form a cyclopropyl, cyclobutyl, cyclopentyl, cyclohexyl, or a benzo fused radical.

[6] In a further more preferred embodiment the present invention provides

B is

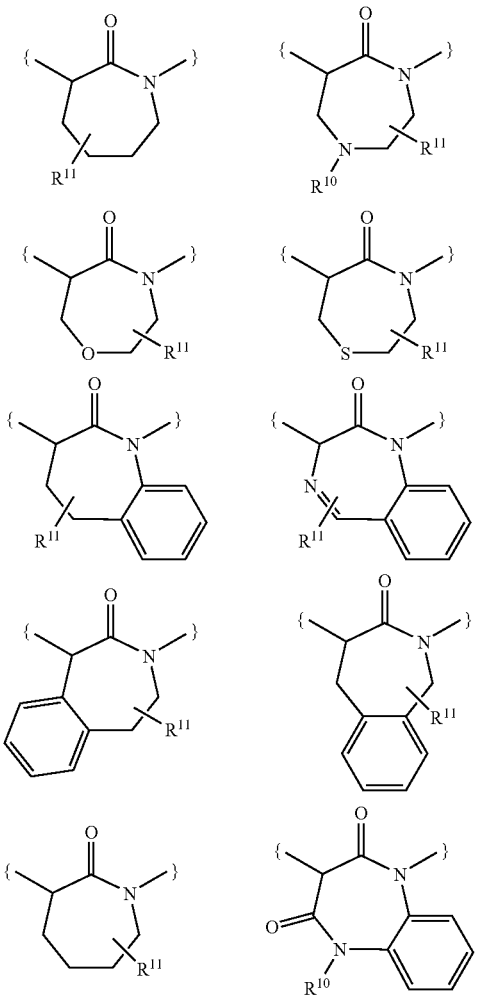

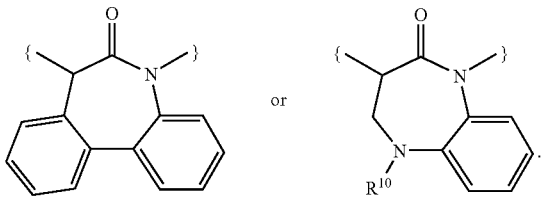

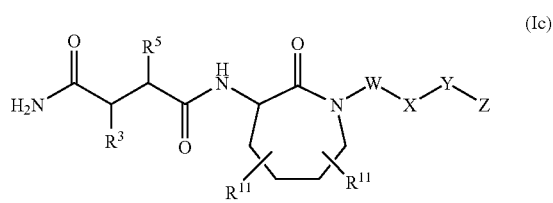

[7] In an even more preferred embodiment the present invention provides $$\text{(Ic)}$$

or a pharmaceutically acceptable salt or prodrug thereof, wherein:

R$^3$ is R$^4$,

R$^4$ is C$_1$-C$_4$ alkyl substituted with 0-2 R$^{4a}$,
C$_2$-C$_4$ alkenyl substituted with 0-2 R$^{4a}$,
C$_2$-C$_4$ alkynyl substituted with 0-2 R$^{4a}$, R$^{4a}$, at each occurrence, is independently selected from is H, F, CF$_3$,
C$_3$-C$_6$ cycloalkyl substituted with 0-3 R$^{4b}$,
phenyl substituted with 0-3 R$^{4b}$, or
5 to 6 membered heterocycle substituted with 0-3 R$^{4b}$;

R$^{4b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$-C$_2$ haloalkyl, and C$_1$-C$_2$ haloalkoxy;

R$^5$ is C$_1$-C$_4$ alkyl substituted with 0-3 R$^{5b}$;
C$_2$-C$_4$ alkenyl substituted with 0-2 R$^{5b}$; or
C$_2$-C$_4$ alkynyl substituted with 0-2 R$^{5b}$;

R$^{5b}$, at each occurrence, is independently selected from:
H, methyl, ethyl, propyl, butyl, CF$_3$, OR$^{14}$, =O;
C$_3$-C$_6$ cycloalkyl substituted with 0-2 R$^{5C}$;
phenyl substituted with 0-3 R$^{5c}$; or
5 to 6 membered heterocycle substituted with 0-2 R$^{5c}$;

R$^{5c}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$-C$_2$ haloalkyl, and C$_1$-C$_2$ haloalkoxy;

W is —CH$_2$—, or —CH(CH$_3$)—;

X is a bond;
phenyl substituted with 0-2 R$^{Xb}$;
C$_3$-C$_6$ cycloalkyl substituted with 0-2 R$^{Xb}$; or
5 to 6 membered heterocycle substituted with 0-2 R$^{Xb}$;

R$^{Xb}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$-C$_2$ haloalkyl, and C$_1$-C$_2$ haloalkoxy;

Y is a bond, —CH$_2$—V—, —V—, or —V—CH$_2$—;

V is a bond, —C(=O)—, —O—, —S—, —S(=O)—, —S(=O)$_2$—, —NH—, —N(CH$_3$)—, or —N(CH$_2$CH$_3$)—, Z is $C_1$-$C_2$ alkyl substituted with 1-2 $R^{12}$;
$C_6$-$C_{10}$ aryl substituted with 0-4 $R^{12b}$;
$C_3$-$C_6$ carbocycle substituted with 0-3 $R^{12b}$; or
5 to 10 membered heterocycle substituted with 0-3 $R^{12b}$;
$R^{12}$ is $C_6$-$C_{10}$ aryl substituted with 0-4 $R^{12b}$;
$C_3$-$C_6$ carbocycle substituted with 0-3 $R^{12b}$; or
5 to 10 membered heterocycle substituted with 0-3 $R^{12b}$;
$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
$R^{11}$ is methoxy, ethoxy, propoxy, butoxy, Cl, F, =O, $NR^{18}R^{19}$, $CF_3$;
$C_1$-$C_4$ alkyl substituted with 0-1 $R^{11a}$;
phenyl substituted with 0-3 $R^{11b}$;
$C_3$-$C_6$ carbocycle substituted with 0-3 $R^{11b}$; or
5 to 6 membered heterocycle substituted with 0-3 $R^{11b}$;
alternatively, two $R^{11}$ substituents on the same or adjacent carbon atoms may be combined to form a cyclopropyl, cyclobutyl, cyclopentyl, cyclohexyl, or a benzo fused radical;
$R^{11a}$, at each occurrence, is independently selected from H, $C_1$-$C_4$ alkyl, $OR^{14}$, F, =O, $NR^{15}R^{16}$, $CF_3$, or phenyl substituted with 0-3 $R^{11b}$;
$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;
$R^{14}$ is H, phenyl, benzyl, methyl, ethyl, propyl, butyl;
$R^{15}$, at each occurrence, is independently selected from H, methyl, ethyl, propyl, and butyl;
$R^{16}$, at each occurrence, is independently selected from H, OH, $C_1$-$C_4$ alkyl, benzyl, phenethyl, —C(=O)—($C_1$-$C_4$ alkyl) and —S(=O)$_2$—($C_1$-$C_4$ alkyl);
$R^{18}$, at each occurrence, is independently selected from H, methyl, ethyl, propyl, butyl, phenyl, benzyl, and phenethyl; and
$R^{19}$, at each occurrence, is independently selected from H, methyl, and ethyl.

[8] In another even more preferred embodiment the present invention provides

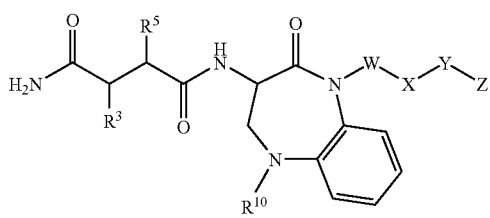

(Id)

or a pharmaceutically acceptable salt or prodrug thereof, wherein:
$R^3$ is $R^4$,
$R^4$ is $C_1$-$C_4$ alkyl substituted with 0-2 $R^{4a}$,
$C_2$-$C_4$ alkenyl substituted with 0-2 $R^{4a}$,
$C_2$-$C_4$ alkynyl substituted with 0-2 $R^{4a}$,
$R^{4a}$, at each occurrence, is independently selected from is H, F, $CF_3$,
$C_3$-$C_6$ cycloalkyl substituted with 0-3 $R^{4b}$,
phenyl substituted with 0-3 $R^{4b}$, or
5 to 6 membered heterocycle substituted with 0-3 $R^{4b}$;
$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
$R^5$ is $C_1$-$C_4$ alkyl substituted with 0-3 $R^{5b}$;
$C_2$-$C_4$ alkenyl substituted with 0-2 $R^{5b}$; or
$C_2$-$C_4$ alkynyl substituted with 0-2 $R^{5b}$;
$R^{5b}$, at each occurrence, is independently selected from:
H, methyl, ethyl, propyl, butyl, $CF_3$, $OR^{14}$, =O;
$C_3$-$C_6$ cycloalkyl substituted with 0-2 $R^{5c}$;
phenyl substituted with 0-3 $R^{5c}$; or
5 to 6 membered heterocycle substituted with 0-2 $R^{5c}$;
$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
W is —$CH_2$—, or —$CH(CH_3)$—;
X is a bond;
phenyl substituted with 0-2 $R^{Xb}$;
$C_3$-$C_6$ cycloalkyl substituted with 0-2 $R^{Xb}$; or
5 to 6 membered heterocycle substituted with 0-2 $R^{Xb}$;
$R^{Xb}$ at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
Y is a bond, —$CH_2$—V—, —V—, or —V—$CH_2$—;
V is a bond, —C(=O)—, —O—, —S—, —S(=O)—, —S(=O)$_2$—, —NH—, —N($CH_3$)—, or —N($CH_2CH_3$)—,
Z is $C_1$-$C_2$ alkyl substituted with 1-2 $R^{12}$;
$C_6$-$C_{10}$ aryl substituted with 0-4 $R^{12b}$;
$C_3$-$C_6$ carbocycle substituted with 0-3 $R^{12b}$; or
5 to 10 membered heterocycle substituted with 0-3 $R^{12b}$;
$R^{12}$ is $C_6$-$C_{10}$ aryl substituted with 0-4 $R^{12b}$;
$C_3$-$C_6$ carbocycle substituted with 0-3 $R^{12b}$; or
5 to 10 membered heterocycle substituted with 0-3 $R^{12b}$;
$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
$R^{10}$ is H, C(=O)$R^{17}$, C(=O)$OR^{17}$;
$C_1$-$C_4$ alkyl substituted with 0-1 $R^{10a}$;
phenyl substituted with 0-4 $R^{10b}$;
$C_3$-$C_6$ carbocycle substituted with 0-3 $R^{10b}$; or
5 to 6 membered heterocycle optionally substituted with 0-3 $R^{10b}$;
$R^{10a}$, at each occurrence, is independently selected from H, $C_1$-$C_4$ alkyl, $OR^{14}$, Cl, F, Br, I, =O, CN, $NO_2$, $NR^{15}R^{16}$, $CF_3$, or phenyl substituted with 0-4 $R^{10b}$;
$R^{10b}$, at each occurrence, is independently selected from H, OH, methyl, ethyl, propyl, butyl, methoxy, ethoxy, propoxy, Cl, F, Br, I, CN, $NO_2$, $NR^{15}R^{16}$, or $CF_3$;
$R^{14}$ is H, phenyl, benzyl, methyl, ethyl, propyl, butyl;
$R^{15}$, at each occurrence, is independently selected from H, methyl, ethyl, propyl, and butyl;
$R^{16}$, at each occurrence, is independently selected from H, OH, $C_1$-$C_4$ alkyl, benzyl, phenethyl, —C(=O)—($C_1$-$C_4$ alkyl) and —S(=O)$_2$—($C_1$-$C_4$ alkyl); and
$R^{17}$ is H, phenyl, 4-fluorophenyl, 4-chlorophenyl, 4-methylphenyl, 4-trifluorophenyl, (4-fluorophenyl)methyl, (4-chlorophenyl)methyl, (4-methylphenyl)methyl, (4-trifluorophenyl)methyl, methyl, ethyl, propyl, butyl, methoxymethyl, methyoxyethyl, ethoxymethyl, or ethoxyethyl.

[9] In another even more preferred embodiment the present invention provides (Ie)

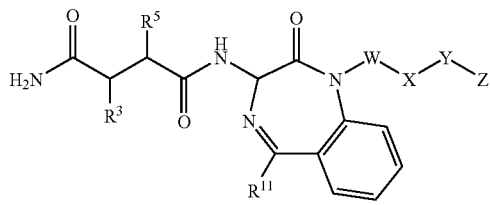

or a pharmaceutically acceptable salt or prodrug thereof, wherein:
$R^3$ is $R^4$,
$R^4$ is $C_1$-$C_4$ alkyl substituted with 0-2 $R^{4a}$,
  $C_2$-$C_4$ alkenyl substituted with 0-2 $R^{4a}$,
  $C_2$-$C_4$ alkynyl substituted with 0-2 $R^{4a}$,
$R^{4a}$, at each occurrence, is independently selected from is H, F, $CF_3$,
  $C_3$-$C_6$ cycloalkyl substituted with 0-3 $R^{4b}$,
  phenyl substituted with 0-3 $R^{4b}$, or
  5 to 6 membered heterocycle substituted with 0-3 $R^{4b}$;
$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
$R^5$ is $C_1$-$C_4$ alkyl substituted with 0-3 $R^{5b}$;
  $C_2$-$C_4$ alkenyl substituted with 0-2 $R^{5b}$; or
  $C_2$-$C_4$ alkynyl substituted with 0-2 $R^{5b}$;
$R^{5b}$, at each occurrence, is independently selected from:
  H, methyl, ethyl, propyl, butyl, $CF_3$, $OR^{14}$, =O;
  $C_3$-$C_6$ cycloalkyl substituted with 0-2 $R^{5c}$;
  phenyl substituted with 0-3 $R^{5c}$; or
  5 to 6 membered heterocycle substituted with 0-2 $R^{5c}$;
$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
W is —$CH_2$—, or —$CH(CH_3)$—;
X is a bond;
  phenyl substituted with 0-2 $R^{Xb}$;
  $C_3$-$C_6$ cycloalkyl substituted with 0-2 $R^{Xb}$; or
  5 to 6 membered heterocycle substituted with 0-2 $R^{Xb}$;
$R^{Xb}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
Y is a bond, —$CH_2$—V—, —V—, or —V—$CH_2$—;
V is a bond, —C(=O)—, —O—, —S—, —S(=O)—, —S(=O)_2—, —NH—, —N($CH_3$)—, or —N($CH_2CH_3$)—,
Z is $C_1$-$C_2$ alkyl substituted with 1-2 $R^{12}$;
  $C_6$-$C_{10}$ aryl substituted with 0-4 $R^{12b}$;
  $C_3$-$C_6$ carbocycle substituted with 0-3 $R^{12b}$; or
  5 to 10 membered heterocycle substituted with 0-3 $R^{12b}$;
$R^{12}$ is $C_6$-$C_{10}$ aryl substituted with 0-4 $R^{12b}$;
  $C_3$-$C_6$ carbocycle substituted with 0-3 $R^{12b}$; or
  5 to 10 membered heterocycle substituted with 0-3 $R^{12b}$;
$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
$R^{11}$ is methoxy, ethoxy, propoxy, butoxy, Cl, F, =O, $NR^{18}R^{19}$, $CF_3$;
  $C_1$-$C_4$ alkyl substituted with 0-1 $R^{11a}$;
  phenyl substituted with 0-3 $R^{11b}$;

$C_3$-$C_6$ carbocycle substituted with 0-3 $R^{11b}$; or
5 to 6 membered heterocycle substituted with 0-3 $R^{11b}$;
$R^{11a}$, at each occurrence, is independently selected from H, $C_1$-$C_4$ alkyl, $OR^{14}$, F, =O, $NR^{15}R^{16}$, $CF_3$, or phenyl substituted with 0-3 $R^{11b}$;
$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;
$R^{14}$ is H, phenyl, benzyl, methyl, ethyl, propyl, butyl;
$R^{15}$, at each occurrence, is independently selected from H, methyl, ethyl, propyl, and butyl;
$R^{16}$, at each occurrence, is independently selected from H, OH, $C_1$-$C_4$ alkyl, benzyl, phenethyl, —C(=O)—($C_1$-$C_4$ alkyl) and —S(=O)_2—($C_1$-$C_4$ alkyl);
$R^{18}$, at each occurrence, is independently selected from H, methyl, ethyl, propyl, butyl, phenyl, benzyl, and phenethyl; and
$R^{19}$, at each occurrence, is independently selected from H, methyl, and ethyl.

[10] In another even more preferred embodiment the present invention provides

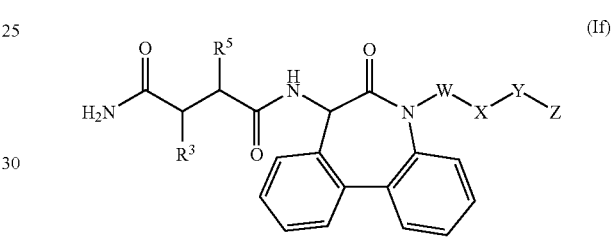

(If)

or a pharmaceutically acceptable salt or prodrug thereof, wherein:
$R^3$ is $R^4$,
$R^4$ is $C_1$-$C_4$ alkyl substituted with 0-2 $R^{4a}$,
  $C_2$-$C_4$ alkenyl substituted with 0-2 $R^{4a}$,
  $C_2$-$C_4$ alkynyl substituted with 0-1 $R^{4a}$,
$R^{4a}$, at each occurrence, is independently selected from is H, F, $CF_3$,
  $C_3$-$C_6$ cycloalkyl substituted with 0-3 $R^{4b}$,
  phenyl substituted with 0-3 $R^{4b}$, or
  5 to 6 membered heterocycle substituted with 0-3 $R^{4b}$;
$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
$R^5$ is $C_1$-$C_4$ alkyl substituted with 0-3 $R^{5b}$;
  $C_2$-$C_4$ alkenyl substituted with 0-2 $R^{5b}$; or
  $C_2$-$C_4$ alkynyl substituted with 0-2 $R^{5b}$;
$R^{5b}$, at each occurrence, is independently selected from:
  H, methyl, ethyl, propyl, butyl, $CF_3$, $OR^{14}$, =O;
  $C_3$-$C_6$ cycloalkyl substituted with 0-2 $R^{5c}$;
  phenyl substituted with 0-3 $R^5C$; or
  5 to 6 membered heterocycle substituted with 0-2 $R^{5c}$;
$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
W is —$CH_2$—, or —$CH(CH_3)$—;
X is a bond;
  phenyl substituted with 0-2 $R^{Xb}$;
  $C_3$-$C_6$ cycloalkyl substituted with 0-2 $R^{Xb}$; or
  5 to 6 membered heterocycle substituted with 0-2 $R^{Xb}$;

$R^{Xb}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

Y is a bond, —$CH_2$—V—, —V—, or —V—$CH_2$—;

V is a bond, —C(=O)—, —O—, —S—, —S(=O)—, —S(=O)$_2$—, —NH—, —N(CH$_3$)—, or —N(CH$_2$CH$_3$)—, Z is $C_1$-$C_2$ alkyl substituted with 1-2 $R^{12}$;
$C_6$-$C_{10}$ aryl substituted with 0-4 $R^{12b}$;
$C_3$-$C_6$ carbocycle substituted with 0-3 $R^{12b}$; or
5 to 10 membered heterocycle substituted with 0-3 $R^{12b}$;

$R^{12}$ is $C_6$-$C_{10}$ aryl substituted with 0-4 $R^{12b}$;
$C_3$-$C_6$ carbocycle substituted with 0-3 $R^{12b}$; or
5 to 10 membered heterocycle substituted with 0-3 $R^{12b}$;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

$R^{14}$ is H, phenyl, benzyl, methyl, ethyl, propyl, butyl;

$R^{15}$, at each occurrence, is independently selected from H, methyl, ethyl, propyl, and butyl; and $R^{16}$, at each occurrence, is independently selected from H, OH, $C_1$-$C_4$ alkyl, benzyl, phenethyl, —C(=O)—($C_1$-$C_4$ alkyl) and —S(=O)$_2$—($C_1$-$C_4$ alkyl).

[11] In another preferred embodiment the present invention provides

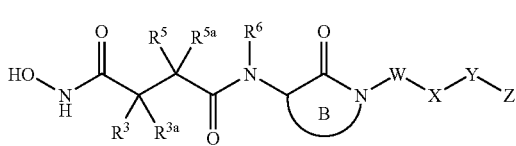

(IIa)

or a pharmaceutically acceptable salt or prodrug thereof, wherein:

$R^3$ is —$(CR^7R^{7a})_n$—$R^4$,
—$(CR^7R^{7a})_n$—S—$(CR^7R^{7a})_m$—$R^4$,
—$(CR^7R^{7a})_n$—O—$(CR^7R^{7a})_m$—$R^4$, or
—$(CR^7R^{7a})_n$—$N(R^{7b})$—$(CR^7R^{7a})_m$—$R^4$;

n is 0, 1, or 2;
m is 0, 1, or 2;

$R^{3a}$ is H, OH, methyl, ethyl, propyl, butyl, methoxy, ethoxy, propoxy, or butoxy;

$R^4$ is H, OH, $OR^{14a}$,
$C_1$-$C_4$ alkyl substituted with 0-2 $R^{4a}$,
$C_2$-$C_4$ alkenyl substituted with 0-2 $R^{4a}$,
$C_2$-$C_4$ alkynyl substituted with 0-2 $R^{4a}$,
$C_3$-$C_6$ cycloalkyl substituted with 0-3 $R^{4b}$,
$C_6$-$C_{10}$ aryl substituted with 0-3 $R^{4b}$, or
5 to 10 membered heterocycle substituted with 0-3 $R^{4b}$;

$R^{4a}$, at each occurrence, is independently selected from is H, F, Cl, Br, I $CF_3$,
$C_3$-$C_{10}$ carbocycle substituted with 0-3 $R^{4b}$,
$C_6$-$C_{10}$ aryl substituted with 0-3 $R^{4b}$, or
5 to 10 membered heterocycle substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

$R^5$ is H, $OR^{14}$;
$C_1$-$C_6$ alkyl substituted with 0-3 $R^{5b}$;
$C_2$-$C_6$ alkenyl substituted with 0-3 $R^{5b}$;
$C_2$-$C_6$ alkynyl substituted with 0-3 $R^{5b}$;
$C_3$-$C_{10}$ carbocycle substituted with 0-3 $R^{5c}$;
$C_6$-$C_{10}$ aryl substituted with 0-3 $R^{5c}$; or
5 to 10 membered heterocycle substituted with 0-3 $R^{5c}$;

$R^{5a}$ is H, OH, $C_1$-$C_4$ alkyl, $C_1$-$C_4$ alkoxy, $C_2$-$C_4$ alkenyl, or $C_2$-$C_4$ alkenyloxy;

$R^{5b}$, at each occurrence, is independently selected from:
H, $C_1$-$C_6$ alkyl, $CF_3$, $OR^{14}$, Cl, F, Br, I, =O, CN, $NO_2$, $NR^{15}R^{16}$;
$C_3$-$C_{10}$ carbocycle substituted with 0-3 $R^5C$;
$C_6$-$C_{10}$ aryl substituted with 0-3 $R^5C$; or
5 to 10 membered heterocycle substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

$R^6$ is H, methyl, or ethyl;

$R^7$, at each occurrence, is independently selected from H, OH, Cl, F, Br, I, CN, $NO_2$, $CF_3$, and $C_1$-$C_4$ alkyl;

$R^{7a}$, at each occurrence, is independently selected from H, OH, Cl, F, Br, I, CN, $NO_2$, $CF_3$, phenyl and $C_1$-$C_4$ alkyl;

$R^{7b}$ is independently selected from H, methyl, ethyl, propyl, and butyl;

w is —$(CR^8R^{8a})_p$—;

p is 0, 1, or 2;

$R^8$ and $R^{8a}$, at each occurrence, are independently selected from H, F, $C_1$-$C_3$ alkyl, $C_2$-$C_3$ alkenyl, $C_2$-$C_3$ alkynyl and $C_3$-$C_6$ cycloalkyl;

X is a bond;
$C_6$-$C_{10}$ aryl substituted with 0-3 $R^{Xb}$;
$C_3$-$C_{10}$ carbocycle substituted with 0-2 $R^{Xb}$; or
5 to 10 membered heterocycle substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

Y is a bond or —$(CR^9R^{9a})_t$—V—$(CR^9R^{9a})_u$—;

t is 0, 1, or 2;
u is 0, 1, or 2;

$R^9$ and $R^{9a}$, at each occurrence, are independently selected from H, F, $C_1$-$C_4$ alkyl or $C_3$-$C_6$ cycloalkyl;

V is a bond, —C(=O)—, —O—, —S—, —S(=O)—, —S(=O)$_2$—, —$N(R^{19})$—, —C(=O)$NR^{19b}$—, —$NR^{19b}$C(=O)—, —$NR^{19b}$S(=O)$_2$—, —S(=O)$_2NR^{19b}$—, —$NR^{19b}$S(=O)—, or —S(=O)$NR^{19b}$—;

Z is $C_1$-$C_3$ alkyl substituted with 1-2 $R^{12}$;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle substituted with 0-3 $R^{12b}$;

$R^{12}$ is $C_6$-$C_{10}$ aryl substituted with 0-4 $R^{12b}$;
$C_3$-$C_{10}$ carbocycle substituted with 0-4 $R^{12b}$; or
5 to 10 membered heterocycle substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

B is a seven membered lactam,
wherein the lactam is saturated, partially saturated or unsaturated;
wherein each additional lactam carbon is substituted with 0-2 $R^{11}$; and,
optionally, the lactam contains a heteroatom selected from —O—, —S—, —S(=O)—, —S(=O)$_2$—, and —$N(R^{10})$—;

$R^{10}$ is H, C(=O)$R^{17}$, C(=O)$OR^{17}$, C(=O)$NR^{18}R^{19}$, $S(=O)_2NR^{18}R^{19}$, $S(=O)_2R^{17}$,
$C_1$-$C_6$ alkyl substituted with 0-1 $R^{10a}$;

$C_6$-$C_{10}$ aryl substituted with 0-4 $R^{10b}$;
$C_3$-$C_{10}$ carbocycle substituted with 0-3 $R^{10b}$; or
5 to 10 membered heterocycle optionally substituted with 0-3 $R^{10b}$;

$R^{10a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or phenyl substituted with 0-4 $R^{10b}$;

$R^{10b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, or $CF_3$;

$R^{11}$, at each occurrence, is independently selected from
$C_1$-$C_4$ alkoxy, Cl, F, =O, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$-$C_6$ alkyl substituted with 0-1 $R^{11a}$;
$C_6$-$C_{10}$ aryl substituted with 0-3 $R^{11b}$;
$C_3$-$C_{10}$ carbocycle substituted with 0-3 $R^{11b}$; or
5 to 10 membered heterocycle substituted with 0-3 $R^{11b}$;
alternatively, two $R^{11}$ substituents on the same or adjacent carbon atoms may be combined to form a $C_3$-$C_6$ carbocycle or a benzo fused radical;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or phenyl substituted with 0-3 $R^{11b}$;

$R^{11b}$, at each occurrence, is independently selected from H, OH, Cl, F, Br, I, CN, $NO_2$, $NR^{15}R^{16}$, $CF_3$, $C_1$-$C_6$ alkyl, $C_1$-$C_4$ alkoxy, $C_1$-$C_4$ haloalkyl, and $C_1$-$C_4$ haloalkoxy;

$R^{14}$ is H, phenyl, benzyl, $C_1$-$C_6$ alkyl, or $C_2$-$C_6$ alkoxyalkyl;

$R^{15}$, at each occurrence, is independently selected from H, $C_1$-$C_6$ alkyl, benzyl, phenethyl, —C(=O)—($C_1$-$C_6$ alkyl) and —S(=O)$_2$—($C_1$-$C_6$ alkyl);

$R^{16}$, at each occurrence, is independently selected from H, OH, $C_1$-$C_6$ alkyl, benzyl, phenethyl, —C(=O)—($C_1$-$C_6$ alkyl) and —S(=O)$_2$—($C_1$-$C_6$ alkyl);

$R^{17}$ is H, aryl, (aryl)$CH_2$—, $C_1$-$C_6$ alkyl, or $C_2$-$C_6$ alkoxyalkyl;

$R^{18}$, at each occurrence, is independently selected from H, $C_1$-$C_6$ alkyl, benzyl, phenethyl, —C(=O)—($C_1$-$C_6$ alkyl) and —S(=O)$_2$—($C_1$-$C_6$ alkyl); and $R^{19}$, at each occurrence, is independently selected from H, OH, $C_1$-$C_6$ alkyl, phenyl, benzyl, phenethyl, —C(=O)—($C_1$-$C_6$ alkyl) and —S(=O)$_2$—($C_1$-$C_6$ alkyl); and $R^{19b}$ is H, $C_1$-$C_6$ alkyl, $C_3$-$C_8$ cycloalkyl, phenyl, benzyl or phenethyl.

[12] In a more preferred embodiment the present invention provides

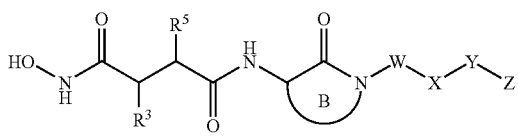

(IIb)

or a pharmaceutically acceptable salt or prodrug thereof, wherein:
$R^3$ is $R^4$,
n is 0 or 1;
m is 0 or 1;
$R^4$ is H, OH,
$C_1$-$C_4$ alkyl substituted with 0-2 $R^{4a}$,
$C_2$-$C_4$ alkenyl substituted with 0-2 $R^{4a}$,
$C_2$-$C_4$ alkynyl substituted with 0-1 $R^{4a}$,
$C_3$-$C_6$ cycloalkyl substituted with 0-3 $R^{4b}$,
$C_6$-$C_{10}$ aryl substituted with 0-3 $R^{4b}$, or
5 to 10 membered heterocycle substituted with 0-3 $R^{4b}$;

$R^{4a}$, at each occurrence, is independently selected from is H, F, Cl, $CF_3$,
$C_3$-$C_6$ cycloalkyl substituted with 0-3 $R^{4b}$,
phenyl substituted with 0-3 $R^{4b}$, or
5 to 6 membered heterocycle substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_4$ alkyl, $C_1$-$C_3$ alkoxy, $C_1$-$C_2$ haloalkyl, and $C_1$-$C_2$ haloalkoxy;

$R^5$ is H, $OR^{14}$;
$C_1$-$C_4$ alkyl substituted with 0-3 $R^{5b}$;
$C_2$-$C_4$ alkenyl substituted with 0-2 $R^{5b}$; or
$C_2$-$C_4$ alkynyl substituted with 0-2 $R^{5b}$;

$R^{5b}$, at each occurrence, is independently selected from:
H, methyl, ethyl, propyl, butyl, $CF_3$, $OR^{14}$, =O;
$C_3$-$C_6$ cycloalkyl substituted with 0-2 $R^{5c}$;
phenyl substituted with 0-3 $R^{5c}$; or
5 to 6 membered heterocycle substituted with 0-2 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_4$ alkyl, $C_1$-$C_3$ alkoxy, $C_1$-$C_2$ haloalkyl, and $C_1$-$C_2$ haloalkoxy;

W is a bond, —$CH_2$—, —$CH(CH_3)$—, —$CH_2CH_2$— or —$CH(CH_3)CH_2$—;

X is a bond;
phenyl substituted with 0-2 $R^{Xb}$;
$C_3$-$C_6$ cycloalkyl substituted with 0-2 $R^{Xb}$; or
5 to 6 membered heterocycle substituted with 0-2 $R^{Xb}$;

$R^{Xb}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$-$C_4$ alkyl, $C_1$-$C_3$ alkoxy, $C_1$-$C_2$ haloalkyl, and $C_1$-$C_2$ haloalkoxy;

Y is a bond, —$CH_2$—V—, —V—, or —V—$CH_2$—;

V is a bond, —C(=O)—, —O—, —S—, —S(=O)—, —S(=O)$_2$—, —NH—, —$N(CH_3)$—, or —$N(CH_2CH_3)$—, Z is $C_1$-$C_2$ alkyl substituted with 1-2 $R^{12}$;
$C_6$-$C_{10}$ aryl substituted with 0-4 $R^{12b}$;
$C_3$-$C_6$ carbocycle substituted with 0-3 $R^{12b}$; or
5 to 10 membered heterocycle substituted with 0-3 $R^{12b}$;

$R^{12}$ is $C_6$-$C_{10}$ aryl substituted with 0-4 $R^{12b}$;
$C_3$-$C_6$ carbocycle substituted with 0-3 $R^{12b}$; or
5 to 10 membered heterocycle substituted with 0-3 $R^{12b}$;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$-$C_4$ alkyl, $C_1$-$C_3$ alkoxy, $C_1$-$C_2$ haloalkyl, and $C_1$-$C_2$ haloalkoxy;

B is a seven membered lactam,
wherein the lactam is saturated, partially saturated or unsaturated;
wherein each additional lactam carbon is substituted with 0-2 $R^{11}$; and,
optionally, the lactam contains a heteroatom selected from —O—, —S—, —S(=O)—, —S(=O)$_2$—, and —$N(R^{10})$—;

$R^{10}$ is H, $C(=O)R^{17}$, $C(=O)OR^{17}$;
$C_1$-$C_4$ alkyl substituted with 0-1 $R^{10a}$;
phenyl substituted with 0-4 $R^{10b}$;
$C_3$-$C_6$ carbocycle substituted with 0-3 $R^{10b}$; or
5 to 6 membered heterocycle optionally substituted with 0-3 $R^{10b}$;

$R^{10a}$, at each occurrence, is independently selected from H, $C_1$-$C_4$ alkyl, $OR^{14}$, Cl, F, Br, I, =O, CN, $NO_2$, $NR^{15}R^{16}$, $CF_3$, or phenyl substituted with 0-4 $R^{10b}$;

$R^{10b}$, at each occurrence, is independently selected from H, OH, $C_1$-$C_4$ alkyl, $C_1$-$C_3$ alkoxy, Cl, F, Br, I, CN, $NO_2$, $NR^{15}R^{16}$, or $CF_3$;

$R^{11}$, at each occurrence, is independently selected from
$C_1$-$C_4$ alkoxy, Cl, F, =O, $NR^{18}R^{19}$, $C(=O)R^{17}$, $C(=O)OR^{17}$, $CF_3$;
$C_1$-$C_4$ alkyl substituted with 0-1 $R^{11a}$;
phenyl substituted with 0-3 $R^{11b}$;
$C_3$-$C_6$ carbocycle substituted with 0-3 $R^{11b}$; or
5 to 6 membered heterocycle substituted with 0-3 $R^{11b}$;

alternatively, two $R^{11}$ substituents on the same or adjacent carbon atoms may be combined to form a cyclopropyl, cyclobutyl, cyclopentyl, cyclohexyl, or a benzo fused radical;

$R^{11a}$, at each occurrence, is independently selected from H, $C_1$-$C_4$ alkyl, $OR^{14}$, F, =O, $NR^{15}R^{16}$, $CF_3$, or phenyl substituted with 0-3 $R^{11b}$;

$R^{11b}$, at each occurrence, is independently selected from H, OH, Cl, F, $NR^{15}R^{16}$, $CF_3$, $C_1$-$C_4$ alkyl, $C_1$-$C_3$ alkoxy, $C_1$-$C_2$ haloalkyl, and $C_1$-$C_2$ haloalkoxy;

$R^{14}$ is H, phenyl, benzyl, $C_1$-$C_4$ alkyl, or $C_2$-$C_4$ alkoxyalkyl;

$R^{15}$, at each occurrence, is independently selected from H, $C_1$-$C_4$ alkyl, benzyl, phenethyl, —C(=O)—($C_1$-$C_4$ alkyl) and —S(=O)$_2$—($C_1$-$C_4$ alkyl);

$R^{16}$, at each occurrence, is independently selected from H, OH, $C_1$-$C_4$ alkyl, benzyl, phenethyl, —C(=O)—($C_1$-$C_4$ alkyl) and —S(=O)$_2$—($C_1$-$C_4$ alkyl);

$R^{17}$ is H, phenyl, 4-fluorophenyl, 4-chlorophenyl, 4-methylphenyl, 4-trifluorophenyl, (4-fluorophenyl)methyl, (4-chlorophenyl)methyl, (4-methylphenyl)methyl, (4-trifluorophenyl)methyl, methyl, ethyl, propyl, butyl, methoxymethyl, methyoxyethyl, ethoxymethyl, or ethoxyethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl.

[13] In an even more preferred embodiment the present invention provides

B is

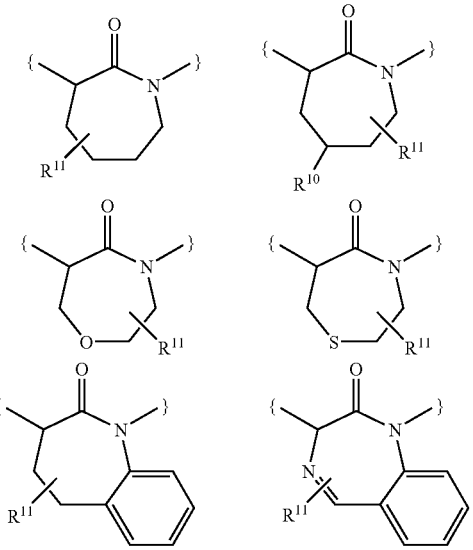

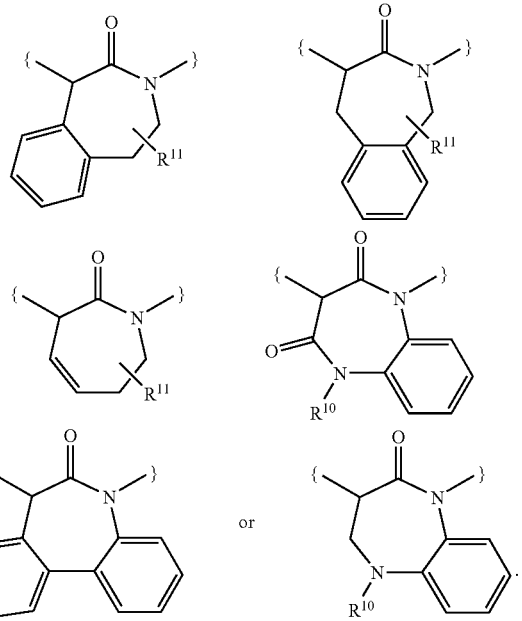

[14] In a preferred embodiment the present provides
A is S;
Q is —$NR^1R^2$;
$R^1$, at each occurrence, is independently selected from:
H;
$C_1$-$C_6$ alkyl substituted with 0-3 $R^{1a}$;
$C_2$-$C_6$ alkenyl substituted with 0-3 $R^{1a}$;

$R^{1a}$, at each occurrence, is independently selected from H, $OR^{14}$, F, =O, $NR^{15}R^{16}$, $CF_3$;
$C_3$-$C_6$ cycloalkyl substituted with 0-3 $R^{1b}$;
phenyl substituted with 0-3 $R^{1b}$; and
5 to 6 membered heterocycle substituted with 0-3 $R^{1b}$;

$R^{1b}$, at each occurrence, is independently selected from H, OH, Cl, F, Br, I, CN, $NO_2$, $NR^{15}R^{16}$, $CF_3$, $C_1$-$C_4$ alkyl, $C_1$-$C_4$ alkoxy, $C_1$-$C_4$ haloalkyl, and $C_1$-$C_4$ haloalkoxy;

$R^2$ is independently selected from H, $NH_2$, OH, $C_1$-$C_6$ alkyl, $C_1$-$C_6$ alkoxy, phenoxy, and benzyloxy;

$R^3$ is —$(CR^7R^{7a})_n$—$R^4$,
—$(CR^7R^{7a})_n$—S—$(CR^7R^{7a})_m$—$R^4$,
—$(CR^7R^{7a})_n$—O—$(CR^7R^{7a})_m$—$R^4$,
—$(CR^7R^{7a})_n$—N($R^{7b}$)—$(CR^7R^{7a})_m$—$R^4$,
—$(CR^7R^{7a})_n$—S(=O)—$(CR^7R^{7a})_m$—$R^4$,
—$(CR^7R^{7a})_n$—S(=O)$_2$—$(CR^7R^{7a})_m$—$R^4$,
—$(CR^7R^{7a})_n$—C(=O)—$(CR^7R^{7a})_m$—$R^4$,
—$(CR^7R^{7a})_n$—NHC(=O)—$(CR^7R^{7a})_m$—$R^4$,
—$(CR^7R^{7a})_n$—C(=O)NH—$(CR^7R^{7a})_m$—$R^4$,
—$(CR^7R^{7a})_n$—NHS(=O)$_2$—$(CR^7R^{7a})_m$—$R^4$, or
—$(CR^7R^{7a})_n$—S(=O)$_2$NH—$(CR^7R^{7a})_m$—$R^4$;
n is 0, 1, 2, or 3;
m is 0, 1, 2, or 3;
$R^{3a}$ is H, OH, $C_1$-$C_4$ alkyl, $C_1$-$C_4$ alkoxy, or $C_2$-$C_4$ alkenyloxy;
$R^4$ is H, OH, $OR^{14a}$,
$C_1$-$C_6$ alkyl substituted with 0-3 $R^{4a}$,
$C_2$-$C_6$ alkenyl substituted with 0-3 $R^{4a}$,
$C_2$-$C_6$ alkynyl substituted with 0-3 $R^{4a}$,
$C_3$-$C_{10}$ carbocycle substituted with 0-3 $R^{4b}$,
$C_6$-$C_{10}$ aryl substituted with 0-3 $R^{4b}$, or
5 to 10 membered heterocycle substituted with 0-3 $R^{4b}$;

$R^{4a}$, at each occurrence, is independently selected from is H, F, Cl, Br, I, $CF_3$,
   $C_3$-$C_{10}$ carbocycle substituted with 0-3 $R^{4b}$,
   $C_6$-$C_{10}$ aryl substituted with 0-3 $R^{4b}$, or
   5 to 10 membered heterocycle substituted with 0-3 $R^{4b}$;
$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;
$R^5$ is H, $OR^{14}$;
   $C_1$-$C_6$ alkyl substituted with 0-3 $R^{5b}$;
   $C_1$-$C_6$ alkoxy substituted with 0-3 $R^{5b}$;
   $C_2$-$C_6$ alkenyl substituted with 0-3 $R^{5b}$;
   $C_2$-$C_6$ alkynyl substituted with 0-3 $R^{5b}$;
   $C_3$-$C_{10}$ carbocycle substituted with 0-3 $R^{5c}$;
   $C_6$-$C_{10}$ aryl substituted with 0-3 $R^{5c}$; or
   5 to 10 membered heterocycle substituted with 0-3 $R^{5c}$;
$R^{5a}$ is H, OH, $C_1$-$C_4$ alkyl, $C_1$-$C_4$ alkoxy, $C_2$-$C_4$ alkenyl, or $C_2$-$C_4$ alkenyloxy;
$R^{5b}$, at each occurrence, is independently selected from:
   H, $C_1$-$C_6$ alkyl, $CF_3$, $OR^{14}$, Cl, F, Br, I, =O, CN, $NO_2$, $NR^{15}R^{16}$;
   $C_3$-$C_{10}$ carbocycle substituted with 0-3 $R^{5c}$;
   $C_6$-$C_{10}$ aryl substituted with 0-3 $R^{5c}$; or
   5 to 10 membered heterocycle substituted with 0-3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;
$R^6$ is H;
   $C_1$-$C_6$ alkyl substituted with 0-3 $R^{6a}$;
   $C_3$-$C_6$ carbocycle substituted with 0-3 $R^{6b}$; or
   $C_6$-$C_{10}$ aryl substituted with 0-3 $R^{6b}$;
$R^{6a}$, at each occurrence, is independently selected from H, $C_1$-$C_6$ alkyl, $OR^{14}$, Cl, F, Br, I, =O, CN, $NO_2$, $NR^{15}R^{16}$, phenyl or $CF_3$;
$R^{6b}$, at each occurrence, is independently selected from H, OH, Cl, F, Br, I, CN, $NO_2$, $NR^{15}R^{16}$, $CF_3$, $C_1$-$C_6$ alkyl, $C_1$-$C_4$ alkoxy, $C_1$-$C_4$ haloalkyl, and $C_1$-$C_4$ haloalkoxy;
$R^7$, at each occurrence, is independently selected from H, OH, Cl, F, Br, I, CN, $NO_2$, $CF_3$, and $C_1$-$C_4$ alkyl;
$R^{7a}$, at each occurrence, is independently selected from OH, Cl, F, Br, I, CN, $NO_2$, $CF_3$, aryl and $C_1$-$C_4$ alkyl;
$R^{7b}$ is independently selected from H and $C_1$-$C_4$ alkyl;
W is $(CR^8R^{8a})_p$—;
p is 0, 1, 2, 3, or 4;
$R^8$ and $R^{8a}$, at each occurrence, are independently selected from H, F, $C_1$-$C_4$ alkyl, $C_2$-$C_4$ alkenyl, $C_2$-$C_4$ alkynyl and $C_3$-$C_8$ cycloalkyl;
X is a bond;
   $C_6$-$C_{10}$ aryl substituted with 0-3 $R^{Xb}$;
   $C_3$-$C_{10}$ carbocycle substituted with 0-3 $R^{Xb}$; or
   5 to 10 membered heterocycle substituted with 0-2 $R^{Xb}$;
$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;
Y is a bond or —$(CR^9R^{9a})_t$—V—$(CR^9R^{9a})_u$—;
t is 0, 1, 2, or 3;
u is 0, 1, 2, or 3;
$R^9$ and $R^{9a}$, at each occurrence, are independently selected from H, F, $C_1$-$C_6$ alkyl or $C_3$-$C_8$ cycloalkyl;
V is a bond, —C(=O)—, —O—, —S—, —S(=O)—, —S(=O)_2—, —N($R^{19}$)—, C(=O)$NR^{19b}$—, $NR^{19b}$C(=O)—, —$NR^{19b}$S(=O)_2—, —S(=O)_2$NR^{19b}$—, —$NR^{19b}$S(=O)—, —S(=O)$NR^{19b}$—, —C(=O)O—, or —OC(=O)—;

Z is $C_1$-$C_3$ alkyl substituted with 1-2 $R^{12}$;
   $C_6$-$C_{10}$ aryl substituted with 0-4 $R^{12b}$;
   $C_3$-$C_{10}$ carbocycle substituted with 0-4 $R^{12b}$; or
   5 to 10 membered heterocycle substituted with 0-3 $R^{12b}$;
$R^{12}$ is $C_6$-$C_{10}$ aryl substituted with 0-4 $R^{12b}$;
   $C_3$-$C_{10}$ carbocycle substituted with 0-4 $R^{12b}$; or
   5 to 10 membered heterocycle substituted with 0-3 $R^{12b}$;
$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;
B is a 6, 7, or 8 membered thiolactam,
   wherein the thiolactam is saturated, partially saturated or unsaturated;
   wherein each additional thiolactam carbon is substituted with 0-2 $R^{11}$; and,
   optionally, the thiolactam contains a heteroatom selected from —O—, —S—, —S(=O)—, —S(=O)_2—, and —N($R^{10}$)—;
$R^{10}$ is H, C(=O)$R^{17}$, C(=O)O$R^{17}$, C(=O)$NR^{18}R^{19}$, S(=O)_2$NR^{18}R^{19}$, S(=O)_2$R^{17}$;
   $C_1$-$C_6$ alkyl substituted with 0-1 $R^{10a}$; $C_6$-$C_{10}$ aryl substituted with 0-4 $R^{10b}$;
   $C_3$-$C_{10}$ carbocycle substituted with 0-3 $R^{10b}$; or
   5 to 10 membered heterocycle optionally substituted with 0-3 $R^{10b}$;
$R^{10a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or phenyl substituted with 0-4 $R^{10b}$;
$R^{10b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, or $CF_3$;
$R^{11}$, at each occurrence, is independently selected from $C_1$-$C_4$ alkoxy, Cl, F, Br, I, =O, CN, $NO_2$, $NR^{18}R^{19}$, C(=O)$R^{17}$, C(=O)O$R^{17}$, C(=O)$NR^{18}R^{19}$, S(=O)_2$NR^{18}R^{19}$, $CF_3$;
   $C_1$-$C_6$ alkyl substituted with 0-1 $R^{11a}$;
   $C_6$-$C_{10}$ aryl substituted with 0-3 $R^{11b}$;
   $C_3$-$C_{10}$ carbocycle substituted with 0-3 $R^{11b}$; or
   5 to 10 membered heterocycle substituted with 0-3 $R^{11b}$;
alternatively, two $R^{11}$ substituents on the same or adjacent carbon atoms may be combined to form a $C_3$-$C_6$ carbocycle or a benzo fused radical;
$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or phenyl substituted with 0-3 $R^{11b}$;
$R^{11b}$, at each occurrence, is independently selected from H, OH, Cl, F, Br, I, CN, $NO_2$, $NR^{15}R^{16}$, $CF_3$, $C_1$-$C_6$ alkyl, $C_1$-$C_4$ alkoxy, $C_1$-$C_4$ haloalkyl, and $C_1$-$C_4$ haloalkoxy;
$R^{14}$ is H, phenyl, benzyl, $C_1$-$C_6$ alkyl, or $C_2$-$C_6$ alkoxyalkyl;
$R^{15}$, at each occurrence, is independently selected from H, $C_1$-$C_6$ alkyl, benzyl, phenethyl, —C(=O)—($C_1$-$C_6$ alkyl) and —S(=O)_2—($C_1$-$C_6$ alkyl);
$R^{16}$, at each occurrence, is independently selected from H, OH, $C_1$-$C_6$ alkyl, benzyl, phenethyl, —C(=O)—($C_1$-$C_6$ alkyl) and —S(=O)_2—($C_1$-$C_6$ alkyl);
$R^{17}$ is H, aryl, (aryl)$CH_2$—, $C_1$-$C_6$ alkyl, or $C_2$-$C_6$ alkoxyalkyl;
$R^{18}$, at each occurrence, is independently selected from H, $C_1$-$C_6$ alkyl, benzyl, phenethyl, —C(=O)—($C_1$-$C_6$ alkyl) and —S(=O)_2—($C_1$-$C_6$ alkyl); and
$R^{19}$, at each occurrence, is independently selected from H, OH, $C_1$-$C_6$ alkyl, phenyl, benzyl, phenethyl, —C(=O)—($C_1$-$C_6$ alkyl) and —S(=O)_2—($C_1$-$C_6$ alkyl); and
$R^{19b}$ is H, $C_1$-$C_6$ alkyl, $C_3$-$C_8$ cycloalkyl, phenyl, benzyl or phenethyl.

[15] In a further preferred embodiment the present invention provides

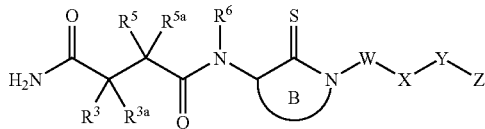

(Ig)

or a pharmaceutically acceptable salt or prodrug thereof, wherein:

$R^3$ is —$(CR^7R^{7a})_n$—$R^4$,
—$(CR^7R^{7a})_n$—S—$(CR^7R^{7a})_m$—$R^4$,
—$(CR^7R^{7a})_n$—O—$(CR^7R^{7a})_m$—$R^4$, or
—$(CR^7R^{7a})_n$—N($R^{7b}$)—$(CR^7R^{7a})_m$—$R^4$;

n is 0, 1, or 2;

m is 0, 1, or 2;

$R^{3a}$ is H, OH, methyl, ethyl, propyl, butyl, methoxy, ethoxy, propoxy, or butoxy;

$R^4$ is H, OH, $OR^{14a}$,
$C_1$-$C_4$ alkyl substituted with 0-2 $R^{4a}$,
$C_2$-$C_4$ alkenyl substituted with 0-2 $R^{4a}$,
$C_2$-$C_4$ alkynyl substituted with 0-2 $R^{4a}$,
$C_3$-$C_6$ cycloalkyl substituted with 0-3 $R^{4b}$,
$C_6$-$C_{10}$ aryl substituted with 0-3 $R^{4b}$, or
5 to 10 membered heterocycle substituted with 0-3 $R^{4b}$;

$R^{4a}$, at each occurrence, is independently selected from is H, F, Cl, Br, I $CF_3$,
$C_3$-$C_{10}$ carbocycle substituted with 0-3 $R^{4b}$,
$C_6$-$C_{10}$ aryl substituted with 0-3 $R^{4b}$, or
5 to 10 membered heterocycle substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

$R^5$ is H, $OR^{14}$;
$C_1$-$C_6$ alkyl substituted with 0-3 $R^{5b}$;
$C_2$-$C_6$ alkenyl substituted with 0-3 $R^{5b}$;
$C_2$-$C_6$ alkynyl substituted with 0-3 $R^{5b}$;
$C_3$-$C_{10}$ carbocycle substituted with 0-3 $R^{5c}$;
$C_6$-$C_{10}$ aryl substituted with 0-3 $R^{5c}$; or
5 to 10 membered heterocycle substituted with 0-3 $R^{5c}$;

$R^{5a}$ is H, OH, $C_1$-$C_4$ alkyl, $C_1$-$C_4$ alkoxy, $C_2$-$C_4$ alkenyl, or $C_2$-$C_4$ alkenyloxy;

$R^{5b}$, at each occurrence, is independently selected from:
H, $C_1$-$C_6$ alkyl, $CF_3$, $OR^{14}$, Cl, F, Br, I, =O, CN, $NO_2$, $NR^{15}R^{16}$;
$C_3$-$C_{10}$ carbocycle substituted with 0-3 $R^{5c}$;
$C_6$-$C_{10}$ aryl substituted with 0-3 $R^{5c}$; or
5 to 10 membered heterocycle substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

$R^6$ is H, methyl, or ethyl;

$R^7$, at each occurrence, is independently selected from H, OH, Cl, F, Br, I, CN, $NO_2$, $CF_3$, and $C_1$-$C_4$ alkyl;

$R^{7a}$, at each occurrence, is independently selected from H, OH, Cl, F, Br, I, CN, $NO_2$, $CF_3$, phenyl and $C_1$-$C_4$ alkyl;

$R^{7b}$ is independently selected from H, methyl, ethyl, propyl, and butyl;

W is —$(CR^8R^{8a})_p$—;

p is 0, 1, or 2;

$R^8$ and $R^{8a}$, at each occurrence, are independently selected from H, F, $C_1$-$C_3$ alkyl, $C_2$-$C_3$ alkenyl, $C_2$-$C_3$ alkynyl and $C_3$-$C_6$ cycloalkyl;

X is a bond;
$C_6$-$C_{10}$ aryl substituted with 0-3 $R^{Xb}$;
$C_3$-$C_{10}$ carbocycle substituted with 0-2 $R^{Xb}$; or
5 to 10 membered heterocycle substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

Y is a bond or —$(CR^9R^{9a})_t$—V—$(CR^9R^{9a})_u$—;

t is 0, 1, or 2;

u is 0, 1, or 2;

$R^9$ and $R^{9a}$, at each occurrence, are independently selected from H, F, $C_1$-$C_4$ alkyl or $C_3$-$C_6$ cycloalkyl;

V is a bond, —C(=O)—, —O—, —S—, —S(=O)—, —S(=O)$_2$—, —N($R^{19}$)—C(=O)$NR^{19b}$—, $NR^{19b}$C(=O)—, —$NR^{19b}$S(=O)$_2$—, —S(=O)$_2NR^{19b}$—, —$NR^{19b}$S(=O)—, or —S(=O)$NR^{19b}$—;

Z is $C_1$-$C_3$ alkyl substituted with 1-2 $R^{12}$;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle substituted with 0-3 $R^{12b}$;

$R^{12}$ is $C_6$-$C_{10}$ aryl substituted with 0-4 $R^{12b}$;
$C_3$-$C_{10}$ carbocycle substituted with 0-4 $R^{12b}$; or
5 to 10 membered heterocycle substituted with 0-3 $R^{12b}$;

$R^{12b}$ at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, and $C_1$-$C_4$ haloalkoxy;

B is a seven membered thiolactam,
wherein the thiolactam is saturated, partially saturated or unsaturated;
wherein each additional thiolactam carbon is substituted with 0-2 $R^{11}$; and,
optionally, the thiolactam contains a heteroatom selected from —O—, —S—, —S(=O)—, —S(=O)$_2$—, and —N($R^{10}$)—;

$R^{10}$ is H, C(=O)$R^{17}$, C(=O)$OR^{17}$, C(=O)$NR^{18}R^{19}$, S(=O)$_2NR^{18}R^{19}$, S(=O)$_2R^{17}$;
$C_1$-$C_6$ alkyl substituted with 0-1 $R^{10a}$;
$C_6$-$C_{10}$ aryl substituted with 0-4 $R^{10b}$;
$C_3$-$C_{10}$ carbocycle substituted with 0-3 $R^{10b}$; or
5 to 10 membered heterocycle optionally substituted with 0-3 $R^{10b}$;

$R^{10a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or phenyl substituted with 0-4 $R^{10b}$;

$R^{10b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, or $CF_3$;

$R^{11}$, at each occurrence, is independently selected from $C_1$-$C_4$ alkoxy, Cl, F, =O, $NR^{18}R^{19}$, C(=O)$R^{17}$, C(=O)$OR^{17}$, C(=O)$NR^{18}R^{19}$, S(=O)$_2NR^{18}R^{19}$, $CF_3$;
$C_1$-$C_6$ alkyl substituted with 0-1 $R^{11a}$;
$C_6$-$C_{10}$ aryl substituted with 0-3 $R^{11b}$;
$C_3$-$C_{10}$ carbocycle substituted with 0-3 $R^{11b}$; or
5 to 10 membered heterocycle substituted with 0-3 $R^{11b}$;

alternatively, two $R^{11}$ substituents on the same or adjacent carbon atoms may be combined to form a $C_3$-$C_6$ carbocycle or a benzo fused radical;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or phenyl substituted with 0-3 $R^{11b}$;

$R^{11b}$, at each occurrence, is independently selected from H, OH, Cl, F, Br, I, CN, NO$_2$, NR$^{15}$R$^{16}$, CF$_3$, C$_1$-C$_6$ alkyl, C$_1$-C$_4$ alkoxy, C$_1$-C$_4$ haloalkyl, and C$_1$-C$_4$ haloalkoxy;

$R^{14}$ is H, phenyl, benzyl, C$_1$-C$_6$ alkyl, or C$_2$-C$_6$alkoxyalkyl;

$R^{15}$, at each occurrence, is independently selected from H, C$_1$-C$_6$ alkyl, benzyl, phenethyl, —C(=O)—(C$_1$-C$_6$ alkyl) and —S(=O)$_2$—(C$_1$-C$_6$ alkyl);

$R^{16}$, at each occurrence, is independently selected from H, OH, C$_1$-C$_6$ alkyl, benzyl, phenethyl, —C(=O)—(C$_1$-C$_6$ alkyl) and —S(=O)$_2$—(C$_1$-C$_6$ alkyl);

$R^{17}$ is H, aryl, (aryl)CH$_2$—, C$_1$-C$_6$ alkyl, or C$_2$-C$_6$ alkoxyalkyl;

$R^{18}$, at each occurrence, is independently selected from H, C$_1$-C$_6$ alkyl, benzyl, phenethyl, —C(=O)—(C$_1$-C$_6$ alkyl) and —S(=O)$_2$—(C$_1$-C$_6$ alkyl); and $R^{19}$, at each occurrence, is independently selected from H, OH, C$_1$-C$_6$ alkyl, phenyl, benzyl, phenethyl, —C(=O)—(C$_1$-C$_6$ alkyl) and —S(=O)$_2$—(C$_1$-C$_6$ alkyl); and $R^{19b}$ is H, C$_1$-C$_6$ alkyl, C$_3$-C$_8$ cycloalkyl, phenyl, benzyl or phenethyl.

[16] In a further preferred embodiment the present invention provides $R^3$ is —(CR$^7$R$^{7a}$)$_n$—R$^4$,
—(CR$^7$R$^{7a}$)$_n$—S—(CR$^7$R$^{7a}$)$_m$—R$^4$,
—(CR$^7$R$^{7a}$)$_n$—O—(CR$^7$R$^{7a}$)$_m$—R$^4$, or
—(CR$^7$R$^{7a}$)$_n$—N(R$^{7b}$)—(CR$^7$R$^{7a}$)$_m$—R$^4$;

n is 0 or 1;
m is 0 or 1;

$R^{3a}$ is H, OH, methyl, ethyl, propyl, butyl, methoxy, ethoxy, propoxy, or butoxy;

$R^4$ is H, OH,
C$_1$-C$_4$ alkyl substituted with 0-2 R$^{4a}$,
C$_2$-C$_4$ alkenyl substituted with 0-2 R$^{4a}$,
C$_2$-C$_4$ alkynyl substituted with 0-1 R$^{4a}$,
C$_3$-C$_6$ cycloalkyl substituted with 0-3 R$^{4b}$,
C$_6$-C$_{10}$ aryl substituted with 0-3 R$^{4b}$, or
5 to 10 membered heterocycle substituted with 0-3 R$^{4b}$;

$R^{4a}$, at each occurrence, is independently selected from is H, F, Cl, CF$_3$,
C$_3$-C$_6$ cycloalkyl substituted with 0-3 R$^{4b}$,
phenyl substituted with 0-3 R$^{4b}$, or
5 to 6 membered heterocycle substituted with 0-3 R$^{4b}$;

$R^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_4$ alkyl, C$_1$-C$_3$ alkoxy, C$_1$-C$_2$ haloalkyl, and C$_1$-C$_2$ haloalkoxy;

$R^5$ is H, OR$^{14}$;
C$_1$-C$_4$ alkyl substituted with 0-3 R$^{5b}$;
C$_2$-C$_4$ alkenyl substituted with 0-2 R$^{5b}$; or
C$_2$-C$_4$ alkynyl substituted with 0-2 R$^{5b}$;

$R^{5a}$ is H, OH, methyl, ethyl, propyl, butyl, methoxy, ethoxy, propoxy, butoxy, or allyl;

$R^{5b}$, at each occurrence, is independently selected from:
H, methyl, ethyl, propyl, butyl, CF$_3$, OR$^{14}$, =O;
C$_3$-C$_6$ cycloalkyl substituted with 0-2 R$^{5c}$;
phenyl substituted with 0-3 R$^{5c}$; or
5 to 6 membered heterocycle substituted with 0-2 R$^{5c}$;

$R^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_4$ alkyl, C$_1$-C$_3$ alkoxy, C$_1$-C$_2$ haloalkyl, and C$_1$-C$_2$ haloalkoxy;

$R^6$ is H;

$R^7$, at each occurrence, is independently selected from H, F, CF$_3$, methyl, and ethyl;

$R^{7a}$, at each occurrence, is independently selected from H, F, CF$_3$, methyl, and ethyl;

$R^{7b}$ is independently selected from H, methyl, and ethyl;

W is a bond, —CH$_2$—, —CH(CH$_3$)—, —CH$_2$CH$_2$— or —CH(CH$_3$)CH$_2$—;

X is a bond;
phenyl substituted with 0-2 R$^{Xb}$;
C$_3$-C$_6$ cycloalkyl substituted with 0-2 R$^{Xb}$; or
5 to 6 membered heterocycle substituted with 0-2 R$^{Xb}$;

$R^{Xb}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, C$_1$-C$_4$ alkyl, C$_1$-C$_3$ alkoxy, C$_1$-C$_2$ haloalkyl, and C$_1$-C$_2$ haloalkoxy;

Y is a bond, —CH$_2$—V—, —V—, or —V—CH$_2$—;

V is a bond, —C(=O)—, —O—, —S—, —S(=O)—, —S(=O)$_2$—, —NH—, —N(CH$_3$)—, or —N(CH$_2$CH$_3$)—, Z is C$_1$-C$_2$ alkyl substituted with 1-2 R$^{12}$;
C$_6$-C$_{10}$ aryl substituted with 0-4 R$^{12b}$;
C$_3$-C$_6$ carbocycle substituted with 0-3 R$^{12b}$; or
5 to 10 membered heterocycle substituted with 0-3 R$^{12b}$;

$R^{12}$ is C$_6$-C$_{10}$ aryl substituted with 0-4 R$^{12b}$;
C$_3$-C$_6$ carbocycle substituted with 0-3 R$^{12b}$; or
5 to 10 membered heterocycle substituted with 0-3 R$^{12b}$;

$R^{12b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, C$_1$-C$_4$ alkyl, C$_1$-C$_3$ alkoxy, C$_1$-C$_2$ haloalkyl, and C$_1$-C$_2$ haloalkoxy;

B is a seven membered thiolactam,
wherein the thiolactam is saturated, partially saturated or unsaturated;
wherein each additional thiolactam carbon is substituted with 0-2 R$^{11}$; and,
optionally, the thiolactam contains a heteroatom selected from —O—, —S—, —S(=O)—, —S(=O)$_2$—, and —N(R$^{10}$)—;

$R^{10}$ is H, C(=O)R$^{17}$, C(=O)OR$^{17}$;
C$_1$-C$_4$ alkyl substituted with 0-1 R$^{10a}$;
phenyl substituted with 0-4 R$^{10b}$;
C$_3$-C$_6$ carbocycle substituted with 0-3 R$^{10b}$; or
5 to 6 membered heterocycle optionally substituted with 0-3 R$^{10b}$;

$R^{10a}$, at each occurrence, is independently selected from H, C$_1$-C$_4$ alkyl, OR$^{14}$, Cl, F, Br, I, =O, CN, NO$_2$, NR$^{15}$R$^{16}$, CF$_3$, or phenyl substituted with 0-4 R$^{10b}$;

$R^{10b}$, at each occurrence, is independently selected from H, OH, C$_1$-C$_4$ alkyl, C$_1$-C$_3$ alkoxy, Cl, F, Br, I, CN, NO$_2$, NR$^{15}$R$^{16}$, or CF$_3$;

$R^{11}$, at each occurrence, is independently selected from
C$_1$-C$_4$ alkoxy, Cl, F, =O, NR$^{18}$R$^{19}$, C(=O)R$^{17}$, C(=O)OR$^{17}$, CF$_3$;
C$_1$-C$_4$ alkyl substituted with 0-1 R$^{11a}$;
phenyl substituted with 0-3 R$^{11b}$;
C$_3$-C$_6$ carbocycle substituted with 0-3 R$^{11b}$; or
5 to 6 membered heterocycle substituted with 0-3 R$^{11b}$;

alternatively, two R$^{11}$ substituents on the same or adjacent carbon atoms may be combined to form a cyclopropyl, cyclobutyl, cyclopentyl, cyclohexyl, or a benzo fused radical;

$R^{11a}$, at each occurrence, is independently selected from H, C$_1$-C$_4$ alkyl, OR$^{14}$, F, =O, NR$^{15}$R$^{16}$, CF$_3$, or phenyl substituted with 0-3 R$^{11b}$;

$R^{11b}$, at each occurrence, is independently selected from H, OH, Cl, F, NR$^{15}$R$^{16}$, CF$_3$, C$_1$-C$_4$ alkyl, C$_1$-C$_3$ alkoxy, C$_1$-C$_2$ haloalkyl, and C$_1$-C$_2$ haloalkoxy;

$R^{14}$ is H, phenyl, benzyl, C$_1$-C$_4$ alkyl, or C$_2$-C$_4$ alkoxyalkyl;

$R^{15}$, at each occurrence, is independently selected from H, C$_1$-C$_4$ alkyl, benzyl, phenethyl, —C(=O)—(C$_1$-C$_4$ alkyl) and —S(=O)$_2$—(C$_1$-C$_4$ alkyl);

$R^{16}$, at each occurrence, is independently selected from H, OH, $C_1$-$C_4$ alkyl, benzyl, phenethyl, —C(=O)—($C_1$-$C_4$ alkyl) and —S(=O)$_2$—($C_1$-$C_4$ alkyl);

$R^{17}$ is H, phenyl, 4-fluorophenyl, 4-chlorophenyl, 4-methylphenyl, 4-trifluorphenyl, (4-fluorophenyl)methyl, (4-chlorophenyl)methyl, (4-methylphenyl)methyl, (4-trifluorophenyl)methyl, methyl, ethyl, propyl, butyl, methoxymethyl, methyoxyethyl, ethoxymethyl, or ethoxyethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl.

[17] In a more preferred embodiment the present invention provides

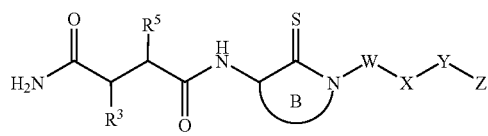

(Ih)

or a pharmaceutically acceptable salt or prodrug thereof, wherein:

$R^3$ is —$CH_3$, —$CH_2CH_3$, —$CH_2CH_2CH_3$, —$CH_2CH_2CH_2CH_3$, —$CH_2(CH_3)_2$, —$CH(CH_3)CH_2CH_3$, —$CH_2CH(CH_3)_2$, —$CH_2C(CH_3)_3$, —$CF_3$, —$CH_2CF_3$, —$CH_2CH_2CF_3$, —$CH_2CH_2CH_2CF_3$, —CH=$CH_2$, —$CH_2$CH=$CH_2$, —$CH_2$C($CH_3$)=$CH_2$, —$CH_2$CH=C($CH_3$)$_2$, —$CH_2CH_2$CH=$CH_2$, —$CH_2CH_2$C($CH_3$)=$CH_2$, —$CH_2CH_2$CH=C($CH_3$)$_2$, cis-$CH_2$CH=CH($CH_3$), cis-$CH_2CH_2$CH=CH($CH_3$), trans-$CH_2$CH=CH($CH_3$), trans-$CH_2CH_2$CH=CH($CH_3$);

—C≡CH, —$CH_2$C≡CH, —$CH_2$C≡C($CH_3$), cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-$CH_2CH_2$—, cyclohexyl-$CH_2CH_2$—, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$—, (4-Cl-phenyl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl)$CH_2$—, (3-Cl-4-F-phenyl)$CH_2$—, phenyl-$CH_2CH_2$—, (2-F-phenyl)$CH_2CH_2$—, (3-F-phenyl)$CH_2CH_2$—, (4-F-phenyl)$CH_2CH_2$—, (2-Cl-phenyl)$CH_2CH_2$—, (3-Cl-phenyl)$CH_2CH_2$—, (4-Cl-phenyl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2CH_2$—, (2,5-diCl-phenyl)$CH_2CH_2$—, (2,6-diCl-phenyl)$CH_2CH_2$—, (3,4-diCl-phenyl)$CH_2CH_2$—, (3,5-diCl-phenyl)$CH_2CH_2$—, (3-F-4-Cl-phenyl)$CH_2CH_2$—, (3-F-5-Cl-phenyl)$CH_2CH_2$—, or $R^5$ is —$CH_3$, —$CH_2CH_3$, —$CH_2CH_2CH_3$, —$CH_2(CH_3)_2$, —$CH_2CH_2CH_2CH_3$, —$CH(CH_3)CH_2CH_3$, —$CH_2$CH($CH_3$)$_2$, —$CH_2$C($CH_3$)$_3$, —$CH_2CH_2CH_2CH_2CH_3$, —CH($CH_3$)$CH_2CH_2CH_3$, —$CH_2$CH($CH_3$)$CH_2CH_3$, —$CH_2CH_2$CH($CH_3$)$_2$, —CH($CH_2CH_3$)$_2$, —$CF_3$, —$CH_2CF_3$, —$CH_2CH_2CF_3$, —$CH_2CH_2CH_2CF_3$, —$CH_2CH_2CH_2CH_2CF_3$, —CH=$CH_2$, —$CH_2$CH=$CH_2$, —CH=CH$CH_3$, cis-$CH_2$CH=CH($CH_3$), trans-$CH_2$CH=CH($CH_3$), trans-$CH_2$CH=CH($C_6H_5$), —$CH_2$CH=C($CH_3$)$_2$, cis-$CH_2CH_2$CH=CH$CH_2CH_3$, trans-$CH_2CH_2$CH=CH$CH_2CH_3$, cis-$CH_2CH_2$CH=CH($CH_3$), trans-$CH_2CH_2$CH=CH($CH_3$), trans-$CH_2CH_2$CH=CH$CH_2$($C_6H_5$), —C≡CH, —$CH_2$C≡CH, —$CH_2$C≡C($CH_3$), —$CH_2$C≡C($C_6H_5$) —$CH_2CH_2$C≡CH, —$CH_2$C≡C($CH_3$), —$CH_2CH_2$C≡C($C_6H_5$) —$CH_2CH_2CH_2$C≡CH, —$CH_2CH_2CH_2$C≡C($CH_3$), —$CH_2CH_2CH_2$C≡C($C_6H_5$)

cyclopropyl-$CH_2$—, cyclobutyl-$CH_2$—, cyclopentyl-$CH_2$—, cyclohexyl-$CH_2$—, (2-$CH_3$-cyclopropyl)$CH_2$—, (3-$CH_3$-cyclobutyl)$CH_2$—, cyclopropyl-$CH_2CH_2$—, cyclobutyl-$CH_2CH_2$—, cyclopentyl-$CH_2CH_2$—, cyclohexyl-$CH_2CH_2$—, (2-$CH_3$-cyclopropyl)$CH_2CH_2$—, (3-$CH_3$-cyclobutyl)$CH_2CH_2$—, phenyl-$CH_2$—, (2-F-phenyl)$CH_2$—, (3-F-phenyl)$CH_2$—, (4-F-phenyl)$CH_2$—, furanyl-$CH_2$—, thienyl-$CH_2$—, pyridyl-$CH_2$—, 1-imidazolyl-$CH_2$—, oxazolyl-$CH_2$—, isoxazolyl-$CH_2$—, phenyl-$CH_2CH_2$—, (2-F-phenyl)$CH_2CH_2$—, (3-F-phenyl)$CH_2CH_2$—, (4-F-phenyl)$CH_2CH_2$—, furanyl-$CH_2CH_2$—, thienyl-$CH_2CH_2$—, pyridyl-$CH_2CH_2$—, 1-imidazolyl-$CH_2CH_2$—, oxazolyl-$CH_2CH_2$—, isoxazolyl-$CH_2CH_2$—, W is a bond, —$CH_2$—, or —CH($CH_3$)—;

X is a bond;

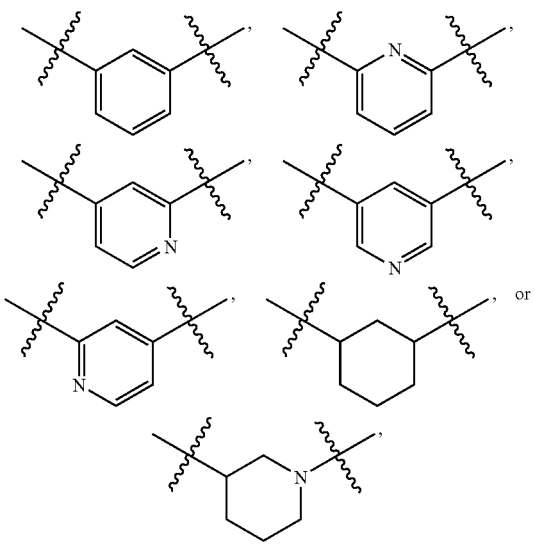

Y is a bond, —$CH_2$—V—, —V—, or —V—$CH_2$—;

V is a bond, —C(=O)—, —O—, —S—, —S(=O)—, —S(=O)$_2$—, —NH—, or —N($CH_3$)—,

Z is phenyl 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-$CF_3$O-phenyl, 3-$CF_3$O-phenyl, 4-$CF_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$—, (4-Cl-phenyl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl)$CH_2$—, (3-Cl-4-F-phenyl)$CH_2$—, (2-MeO-phenyl)$CH_2$—, (3-MeO-phenyl)$CH_2$—, (4-MeO-phenyl)$CH_2$—, (2-Me-phenyl)$CH_2$—, (3-Me-phenyl)$CH_2$—, (4-Me-phenyl)$CH_2$—, (2-MeS-phenyl)$CH_2$—, (3-MeS-phenyl)$CH_2$—, 4-MeS-phenyl)$CH_2$—, (2-$CF_3$O-phenyl)$CH_2$—, (3-$CF_3$O-phenyl)$CH_2$—, (4-$CF_3$O-phenyl)$CH_2$—, (furanyl)$CH_2$—,(thienyl)$CH_2$—, (pyridyl)$CH_2$—, (2-Me-pyridyl)$CH_2$—, (3-Me-pyridyl)$CH_2$—, (4-Me-pyridyl)$CH_2$—, (1-imidazolyl)$CH_2$—, (oxazolyl)$CH_2$—, (isoxazolyl)$CH_2$—, (1-benzimidazolyl)$CH_2$—, (cyclopropyl)$CH_2$—, (cyclobutyl)$CH_2$—, (cyclopentyl)$CH_2$—, (cyclohexyl)$CH_2$—, (morpholino)$CH_2$—, (N-pipridinyl)$CH_2$—, phenyl-$CH_2CH_2$—, (phenyl)$_2$CH$CH_2$—, (2-F-phenyl)$CH_2CH_2$—, (3-F-phenyl)$CH_2CH_2$—, (4-F-phenyl)$CH_2CH_2$—, (2-Cl-phenyl)$CH_2CH_2$—, (3-Cl-phenyl)$CH_2CH_2$—, (4-Cl-phenyl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2CH_2$—, (2,5-diCl-phenyl)$CH_2CH_2$—, (2,6-diCl-phenyl)$CH_2CH_2$—, (3,4-diCl-phenyl)$CH_2CH_2$—, (3,5-diCl-phenyl)$CH_2CH_2$—, (3-F-4-Cl-phenyl)$CH_2CH_2$—, (3-F-5-Cl-phenyl)$CH_2CH_2$—, (3-Cl-4-F-phenyl)$CH_2CH_2$—, (2-MeO-phenyl)$CH_2CH_2$—, (3-MeO-phenyl)$CH_2CH_2$—, (4-MeO-phenyl)$CH_2CH_2$—, (2-Me-phenyl)$CH_2CH_2$—, (3-Me-phenyl)$CH_2CH_2$—, (4-Me-phenyl)$CH_2CH_2$—, (2-MeS-phenyl)$CH_2CH_2$—, (3-MeS-phenyl)$CH_2CH_2$—, (4-MeS-phenyl)$CH_2CH_2$—, (2-$CF_3$O-phenyl)$CH_2CH_2$—, (3-$CF_3$O-phenyl)$CH_2CH_2$—, (4-$CF_3$O-phenyl)$CH_2CH_2$—, (furanyl)$CH_2CH_2$—,(thienyl)$CH_2CH_2$—, (pyridyl)$CH_2CH_2$—, (2-Me-pyridyl)$CH_2CH_2$—, (3-Me-pyridyl)$CH_2CH_2$—, (4-Me-pyridyl)$CH_2CH_2$—, (imidazolyl)$CH_2CH_2$—, (oxazolyl)$CH_2CH_2$—, (isoxazolyl)$CH_2CH_2$—, (benzimidazolyl)$CH_2CH_2$—,(cyclopropyl)$CH_2CH_2$—, (cyclobutyl)$CH_2CH_2$—,(cyclopentyl)$CH_2CH_2$—, (cyclohexyl)$CH_2CH_2$—,(morpholino)$CH_2CH_2$—, (N-pipridinyl)$CH_2CH_2$—, B is a seven membered thiolactam,
  wherein the thiolactam is saturated, partially saturated or unsaturated;
  wherein each additional thiolactam carbon is substituted with 0-2 $R^{11}$; and,
  optionally, the thiolactam contains a heteroatom selected from —O—, —S—, —S(=O)—, —S(=O)$_2$—, and —N($R^{10}$)—;

$R^{10}$ is H, methyl, ethyl, phenyl, benzyl, phenethyl, 4-F-phenyl, (4-F-phenyl)$CH_2$—, (4-F-phenyl)$CH_2CH_2$—, 4-Cl-phenyl, (4-Cl-phenyl)$CH_2$—, (4-Cl-phenyl)$CH_2CH_2$—, 4-$CH_3$-phenyl, (4-$CH_3$-phenyl)$CH_2$—, (4-$CH_3$-phenyl)$CH_2CH_2$—, 4-$CF_3$-phenyl, (4-$CF_3$-phenyl)$CH_2$—, or (4-$CF_3$-phenyl)$CH_2CH_2$—;

$R^{11}$, at each occurrence, is independently selected from H, =O, methyl, ethyl, phenyl, benzyl, phenethyl, 4-F-phenyl, (4-F-phenyl)$CH_2$—, (4-F-phenyl)$CH_2CH_2$—, 4-Cl-phenyl, (4-Cl-phenyl)$CH_2$—, (4-Cl-phenyl)$CH_2CH_2$—, 4-$CH_3$-phenyl, (4-$CH_3$-phenyl)$CH_2$—, (4-$CH_3$-phenyl)$CH_2CH_2$—, 4-$CF_3$-phenyl, (4-$CF_3$-phenyl)$CH_2$—, or (4-$CF_3$-phenyl)$CH_2CH_2$—; and alternatively, two $R^{11}$ substituents on the same or adjacent carbon atoms may be combined to form a cyclopropyl, cyclobutyl, cyclopentyl, cyclohexyl, or a benzo fused radical.

[18] In a further more preferred embodiment the present invention provides

B is

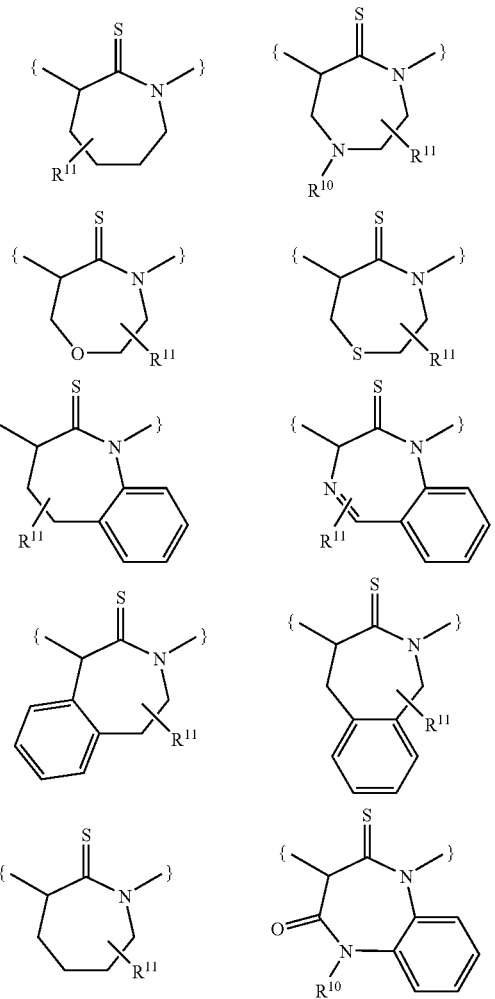

-continued

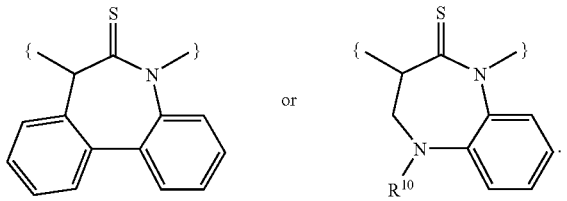

[19] In another even more preferred embodiment the present invention provides compounds of Formula (I) selected from:

(2R,3S)N1-[(3S)-hexahydro-1-(3-phenoxybenzyl)-2-oxo-1H-azepin-3-yl]-2-(2-methylpropyl)-3-(propyl)-butanediamide;

(2R,3S)N1-[(3S)-hexahydro-1-(3-(4-methoxyphenyl)benzyl)-2-oxo-1H-azepin-3-yl]-2-(2-methylpropyl)-3-(propyl)-butanediamide;

(2R,3S)N1-[(3S)-hexahydro-1-(3-(4-trifluoromethylphenyl)benzyl)-2-oxo-1H-azepin-3-yl]-2-(2-methylpropyl)-3-(propyl)-butanediamide;

(2R,3S)N1-[(3S)-hexahydro-1-(3-(4-methylphenyl)benzyl)-2-oxo-1H-azepin-3-yl]-2-(2-methylpropyl)-3-(propyl)-butanediamide;

(2R,3S)N1-[(3S)-hexahydro-1-(3-(2,4-dichlorophenyl)benzyl)-2-oxo-1H-azepin-3-yl]-2-(2-methylpropyl)-3-(propyl)-butanediamide;

(2R,3S)N1-[(3S)-hexahydro-1-(3-(3-chloro-4-fluorophenyl)benzyl)-2-oxo-1H-azepin-3-yl]-2-(2-methylpropyl)-3-(propyl)-butanediamide;

(2R,3S)N1-[(3S)-hexahydro-1-(benzophenon-3-yl)-2-oxo-1H-azepin-3-yl]-2-(2-methylpropyl)-3-(propyl)-butanediamide;

(2R,3S)N1-[(3S)-hexahydro-1-(3-(2-naphthyl)benzyl)-2-oxo-1H-azepin-3-yl]-2-(2-methylpropyl)-3-(propyl)-butanediamide;

(2R,3S)N1-[(3S)-hexahydro-1-(3-(3-fluorophenyl)benzyl)-2-oxo-1H-azepin-3-yl]-2-(2-methylpropyl)-3-(propyl)-butanediamide;

(2R,3S)N1-[(3S)-hexahydro-1-(3-(3-methoxyphenyl)benzyl)-2-oxo-1H-azepin-3-yl]-2-(2-methylpropyl)-3-(propyl)-butanediamide;

(2R,3S)N1-[(3S)-hexahydro-1-(3-(2-methoxyphenyl)benzyl)-2-oxo-1H-azepin-3-yl]-2-(2-methylpropyl)-3-(propyl)-butanediamide;

(2R,3S)N1-[(3S)-hexahydro-1-(3-(4-methoxyphenyl)pyrid-5-ylmethyl)-2-oxo-1H-azepin-3-yl]-2-(2-methylpropyl)-3-(propyl)-butanediamide;

(2R,3S)N1-[(3S)-hexahydro-1-(3-(4-trifluoromethylphenyl)pyrid-5-ylmethyl)-2-oxo-1H-azepin-3-yl]-2-(2-methylpropyl)-3-(propyl)-butanediamide;

(2R,3S)N1-[(3S)-hexahydro-1-(3-(3-chloro-4-fluorophenyl)pyrid-5-ylmethyl)-2-oxo-1H-azepin-3-yl]-2-(2-methylpropyl)-3-(propyl)-butanediamide;

(2R,3S)N1-[(3S)-hexahydro-1-(4-(4-trifluoromethylphenyl)benzyl)-2-oxo-1H-azepin-3-yl]-2-(2-methylpropyl)-3-(propyl)-butanediamide;

(2S,3R)N1-[(3S)-hexahydro-1-(3-(2-tetrazolylphenyl)benzyl)-2-oxo-1H-azepin-3-yl]-2-(propyl)-3-(2-methylpropyl)-butanediamide;

(2S,3R)N1-[(3S)-hexahydro-1-(3-phenoxybenzyl)-2-oxo-1H-azepin-3-yl]-2-(propyl)-3-(2-methylpropyl)-butanediamide;

(2R,3S)N1-[(3S)-hexahydro-1-(3-phenoxybenzyl)-2-oxo-1H-azepin-3-yl]-2-(2-methylpropyl)-3-(allyl)-butanediamide;

(2R,3S)N1-[(3S)-hexahydro-1-(benzophenon-3-yl)-2-oxo-1H-azepin-3-yl]-2-(2-methylpropyl)-3-(allyl)-butanediamide;

(2R)N1-[(3S)-hexahydro-1-(3-phenoxybenzyl)-2-oxo-1H-azepin-3-yl]-2-(2-methylpropyl)-butanediamide;

(2R,3S)N1-[(3S)-hexahydro-1-(3-(4-methoxyphenyl)benzyl)-2-oxo-1H-azepin-3-yl]-2-(2-methylpropyl)-3-(allyl)-butanediamide;

(2R,3S)N1-[(3S)-hexahydro-1-(3-(4-trifluoromethylphenyl)benzyl)-2-oxo-1H-azepin-3-yl]-2-(2-methylpropyl)-3-(allyl)-butanediamide;

(2R,3S)N1-[(3S)-hexahydro-1-(3-(4-methylphenyl)benzyl)-2-oxo-1H-azepin-3-yl]-2-(2-methylpropyl)-3-(allyl)-butanediamide;

(2R,3S)N1-[(3S)-hexahydro-1-(3-(2,4-dichlorophenyl)benzyl)-2-oxo-1H-azepin-3-yl]-2-(2-methylpropyl)-3-(allyl)-butanediamide;

(2R,3S)N1-[(3S)-hexahydro-1-(3-(3-chloro-4-fluorophenyl)benzyl)-2-oxo-1H-azepin-3-yl]-2-(2-methylpropyl)-3-(allyl)-butanediamide;

(2R,3S)N1-[(3S)-hexahydro-1-(3-(2-naphthyl)benzyl)-2-oxo-1H-azepin-3-yl]-2-(2-methylpropyl)-3-(allyl)-butanediamide;

(2R,3S)N1-[(3S)-hexahydro-1-(3-phenoxybenzyl)-2-oxo-1H-azepin-3-yl]-2-(2-methylpropyl)-3-(butyl)-butanediamide;

(2R,3S)N1-[(3S)-hexahydro-1-(3-(4-methoxyphenyl)benzyl)-2-oxo-1H-azepin-3-yl]-2-(2-methylpropyl)-3-(butyl)-butanediamide;

(2R,3S)N1-[(3S)-hexahydro-1-(3-(4-trifluoromethylphenyl)benzyl)-2-oxo-1H-azepin-3-yl]-2-(2-methylpropyl)-3-(butyl)-butanediamide;

(2R,3S)N1-[(3S)-hexahydro-1-(3-(4-methylphenyl)benzyl)-2-oxo-1H-azepin-3-yl]-2-(2-methylpropyl)-3-(butyl)-butanediamide;

(2R,3S)N1-[(3S)-hexahydro-1-(3-(2,4-dichlorophenyl)benzyl)-2-oxo-1H-azepin-3-yl]-2-(2-methylpropyl)-3-(butyl)-butanediamide;

(2R,3S)N1-[(3S)-hexahydro-1-(3-(3-chloro-4-fluorophenyl)benzyl)-2-oxo-1H-azepin-3-yl]-2-(2-methylpropyl)-3-(butyl)-butanediamide;

(2R,3S)N1-[(3S)-hexahydro-1-(benzophenon-3-yl)-2-oxo-1H-azepin-3-yl]-2-(2-methylpropyl)-3-(butyl)-butanediamide;

(2R,3S)N1-[(3S)-hexahydro-1-(3-(2-naphthyl)benzyl)-2-oxo-1H-azepin-3-yl]-2-(2-methylpropyl)-3-(butyl)-butanediamide;

(2R,3S)N1-[(3S)-hexahydro-1-(3-phenoxybenzyl)-2-oxo-1H-azepin-3-yl]-2-(cyclopropylmethyl)-3-(propyl)-butanediamide;

(2R,3S)N1-[(3S)-hexahydro-1-(3-(4-methoxyphenyl)benzyl)-2-oxo-1H-azepin-3-yl]-2-(cyclopropylmethyl)-3-(propyl)-butanediamide;

(2R,3S)N1-[(3S)-hexahydro-1-(3-(4-trifluoromethylphenyl)benzyl)-2-oxo-1H-azepin-3-yl]-2-(cyclopropylmethyl)-3-(propyl)-butanediamide;

(2R,3S)N1-[(3S)-hexahydro-1-(3-(4-methylphenyl)benzyl)-2-oxo-1H-azepin-3-yl]-2-(cyclopropylmethyl)-3-(propyl)-butanediamide;

(2R,3S)N1-[(3S)-hexahydro-1-(3-(2,4-dichlorophenyl)benzyl)-2-oxo-1H-azepin-3-yl]-2-(cyclopropylmethyl)-3-(propyl)-butanediamide;

(2R,3S)N1-[(3S)-hexahydro-1-(3-(3-chloro-4-fluorophenyl)benzyl)-2-oxo-1H-azepin-3-yl]-2-(cyclopropylmethyl)-3-(propyl)-butanediamide;

(2R,3S)N1-[(3S)-hexahydro-1-(benzophenon-3-yl)-2-oxo-1H-azepin-3-yl]-2-(cyclopropylmethyl)-3-(propyl)-butanediamide;

(2R,3S)N1-[(3S)-hexahydro-1-(3-(2-naphthyl)benzyl)-2-oxo-1H-azepin-3-yl]-2-(cyclopropylmethyl)-3-(propyl)-butanediamide;

(2R,3S)N1-[(3S)-hexahydro-1-(3-phenoxybenzyl)-2-oxo-1H-azepin-3-yl]-2-(cyclopropylmethyl)-3-(allyl)-butanediamide;

(2R,3S)N1-[(3S)-hexahydro-1-(3-(4-methoxyphenyl)benzyl)-2-oxo-1H-azepin-3-yl]-2-(cyclopropylmethyl)-3-(allyl)-butanediamide;

(2R,3S)N1-[(3S)-hexahydro-1-(3-(4-trifluoromethylphenyl)benzyl)-2-oxo-1H-azepin-3-yl]-2-(cyclopropylmethyl)-3-(allyl)-butanediamide;

(2R,3S)N1-[(3S)-hexahydro-1-(3-(4-methylphenyl)benzyl)-2-oxo-1H-azepin-3-yl]-2-(cyclopropylmethyl)-3-(allyl)-butanediamide;

(2R,3S)N1-[(3S)-hexahydro-1-(3-(2,4-dichlorophenyl)benzyl)-2-oxo-1H-azepin-3-yl]-2-(cyclopropylmethyl)-3-(allyl)-butanediamide;

(2R,3S)N1-[(3S)-hexahydro-1-(3-(3-chloro-4-fluorophenyl)benzyl)-2-oxo-1H-azepin-3-yl]-2-(cyclopropylmethyl)-3-(allyl)-butanediamide;

(2R,3S)N1-[(3S)-hexahydro-1-(benzophenon-3-yl)-2-oxo-1H-azepin-3-yl]-2-(cyclopropylmethyl)-3-(allyl)-butanediamide;

(2R,3S)N1-[(3S)-hexahydro-1-(3-(2-naphthyl)benzyl)-2-oxo-1H-azepin-3-yl]-2-(cyclopropylmethyl)-3-(allyl)-butanediamide;

(2R,3S)N1-[(3S)-hexahydro-1-(3-phenoxybenzyl)-2-oxo-1H-azepin-3-yl]-2-(cyclopropylmethyl)-3-(butyl)-butanediamide;

(2R,3S)N1-[(3S)-hexahydro-1-(3-(4-methoxyphenyl)benzyl)-2-oxo-1H-azepin-3-yl]-2-(cyclopropylmethyl)-3-(butyl)-butanediamide;

(2R,3S)N1-[(3S)-hexahydro-1-(3-(4-trifluoromethylphenyl)benzyl)-2-oxo-1H-azepin-3-yl]-2-(cyclopropylmethyl)-3-(butyl)-butanediamide;

(2R,3S)N1-[(3S)-hexahydro-1-(3-(4-methylphenyl)benzyl)-2-oxo-1H-azepin-3-yl]-2-(cyclopropylmethyl)-3-(butyl)-butanediamide;

(2R,3S)N1-[(3S)-hexahydro-1-(3-(2,4-dichlorophenyl)benzyl)-2-oxo-1H-azepin-3-yl]-2-(cyclopropylmethyl)-3-(butyl)-butanediamide;

(2R,3S)N1-[(3S)-hexahydro-1-(3-(3-chloro-4-fluorophenyl)benzyl)-2-oxo-1H-azepin-3-yl]-2-(cyclopropylmethyl)-3-(butyl)-butanediamide;

(2R,3S)N1-[(3S)-hexahydro-1-(benzophenon-3-yl)-2-oxo-1H-azepin-3-yl]-2-(cyclopropylmethyl)-3-(butyl)-butanediamide;

(2R,3S)N1-[(3S)-hexahydro-1-(3-(2-naphthyl)benzyl)-2-oxo-1H-azepin-3-yl]-2-(cyclopropylmethyl)-3-(butyl)-butanediamide;

(2R,3S)N1-[(3S)-hexahydro-1-(3-phenoxybenzyl)-2-oxo-1H-azepin-3-yl]-2-(cyclobutylmethyl)-3-(propyl)-butanediamide;

(2R,3S)N1-[(3S)-hexahydro-1-(3-(4-methoxyphenyl)benzyl)-2-oxo-1H-azepin-3-yl]-2-(cyclobutylmethyl)-3-(propyl)-butanediamide;

(2R,3S)N1-[(3S)-hexahydro-1-(3-(4-trifluoromethylphenyl)benzyl)-2-oxo-1H-azepin-3-yl]-2-(cyclobutylmethyl)-3-(propyl)-butanediamide;

(2R,3S)N1-[(3S)-hexahydro-1-(3-(4-methylphenyl)benzyl)-2-oxo-1H-azepin-3-yl]-2-(cyclobutylmethyl)-3-(propyl)-butanediamide;

(2R,3S)N1-[(3S)-hexahydro-1-(3-(2,4-dichlorophenyl)benzyl)-2-oxo-1H-azepin-3-yl]-2-(cyclobutylmethyl)-3-(propyl)-butanediamide;

(2R,3S)N1-[(3S)-hexahydro-1-(3-(3-chloro-4-fluorophenyl)benzyl)-2-oxo-1H-azepin-3-yl]-2-(cyclobutylmethyl)-3-(propyl)-butanediamide;

(2R,3S)N1-[(3S)-hexahydro-1-(benzophenon-3-yl)-2-oxo-1H-azepin-3-yl]-2-(cyclobutylmethyl)-3-(propyl)-butanediamide;

(2R,3S)N1-[(3S)-hexahydro-1-(3-(2-naphthyl)benzyl)-2-oxo-1H-azepin-3-yl]-2-(cyclobutylmethyl)-3-(propyl)-butanediamide;

(2R,3S)N1-[(3S)-hexahydro-1-(3-phenoxybenzyl)-2-oxo-1H-azepin-3-yl]-2-(cyclobutylmethyl)-3-(allyl)-butanediamide;

(2R,3S)N1-[(3S)-hexahydro-1-(3-(4-methoxyphenyl)benzyl)-2-oxo-1H-azepin-3-yl]-2-(cyclobutylmethyl)-3-(allyl)-butanediamide;

(2R,3S)N1-[(3S)-hexahydro-1-(3-(4-trifluoromethylphenyl)benzyl)-2-oxo-1H-azepin-3-yl]-2-(cyclobutylmethyl)-3-(allyl)-butanediamide;

(2R,3S)N1-[(3S)-hexahydro-1-(3-(4-methylphenyl)benzyl)-2-oxo-1H-azepin-3-yl]-2-(cyclobutylmethyl)-3-(allyl)-butanediamide;

(2R,3S)N1-[(3S)-hexahydro-1-(3-(2,4-dichlorophenyl)benzyl)-2-oxo-1H-azepin-3-yl]-2-(cyclobutylmethyl)-3-(allyl)-butanediamide;

(2R,3S)N1-[(3S)-hexahydro-1-(3-(3-chloro-4-fluorophenyl)benzyl)-2-oxo-1H-azepin-3-yl]-2-(cyclobutylmethyl)-3-(allyl)-butanediamide;

(2R,3S)N1-[(3S)-hexahydro-1-(benzophenon-3-yl)-2-oxo-1H-azepin-3-yl]-2-(cyclobutylmethyl)-3-(allyl)-butanediamide;

(2R,3S)N1-[(3S)-hexahydro-1-(3-(2-naphthyl)benzyl)-2-oxo-1H-azepin-3-yl]-2-(cyclobutylmethyl)-3-(allyl)-butanediamide;

(2R,3S)N1-[(3S)-hexahydro-1-(3-phenoxybenzyl)-2-oxo-1H-azepin-3-yl]-2-(cyclobutylmethyl)-3-(butyl)-butanediamide;

(2R,3S)N1-[(3S)-hexahydro-1-(3-(4-methoxyphenyl)benzyl)-2-oxo-1H-azepin-3-yl]-2-(cyclobutylmethyl)-3-(butyl)-butanediamide;

(2R,3S)N1-[(3S)-hexahydro-1-(3-(4-trifluoromethylphenyl)benzyl)-2-oxo-1H-azepin-3-yl]-2-(cyclobutylmethyl)-3-(butyl)-butanediamide;

(2R,3S)N1-[(3S)-hexahydro-1-(3-(4-methylphenyl)benzyl)-2-oxo-1H-azepin-3-yl]-2-(cyclobutylmethyl)-3-(butyl)-butanediamide;

(2R,3S)N1-[(3S)-hexahydro-1-(3-(2,4-dichlorophenyl)benzyl)-2-oxo-1H-azepin-3-yl]-2-(cyclobutylmethyl)-3-(butyl)-butanediamide;

(2R,3S)N1-[(3S)-hexahydro-1-(3-(3-chloro-4-fluorophenyl)benzyl)-2-oxo-1H-azepin-3-yl]-2-(cyclobutylmethyl)-3-(butyl)-butanediamide;

(2R,3S)N1-[(3S)-hexahydro-1-(benzophenon-3-yl)-2-oxo-1H-azepin-3-yl]-2-(cyclobutylmethyl)-3-(butyl)-butanediamide;

(2R,3S)N1-[(3S)-hexahydro-1-(3-(2-naphthyl)benzyl)-2-oxo-1H-azepin-3-yl]-2-(cyclobutylmethyl)-3-(butyl)-butanediamide;

(2R,3S)N1-[(3S)-hexahydro-1-(3-phenoxybenzyl)-2-oxo-1H-azepin-3-yl]-2-(cyclopentylmethyl)-3-(propyl)-butanediamide;

(2R,3S)N1-[(3S)-hexahydro-1-(3-(4-methoxyphenyl)benzyl)-2-oxo-1H-azepin-3-yl]-2-(cyclopentylmethyl)-3-(propyl)-butanediamide;

(2R,3S)N1-[(3S)-hexahydro-1-(3-(4-trifluoromethylphenyl)benzyl)-2-oxo-1H-azepin-3-yl]-2-(cyclopentylmethyl)-3-(propyl)-butanediamide;

(2R,3S)N1-[(3S)-hexahydro-1-(3-(4-methylphenyl)benzyl)-2-oxo-1H-azepin-3-yl]-2-(cyclopentylmethyl)-3-(propyl)-butanediamide;

(2R,3S)N1-[(3S)-hexahydro-1-(3-(2,4-dichlorophenyl)benzyl)-2-oxo-1H-azepin-3-yl]-2-(cyclopentylmethyl)-3-(propyl)-butanediamide;

(2R,3S)N1-[(3S)-hexahydro-1-(3-(3-chloro-4-fluorophenyl)benzyl)-2-oxo-1H-azepin-3-yl]-2-(cyclopentylmethyl)-3-(propyl)-butanediamide;

(2R,3S)N1-[(3S)-hexahydro-1-(benzophenon-3-yl)-2-oxo-1H-azepin-3-yl]-2-(cyclopentylmethyl)-3-(propyl)-butanediamide;

(2R,3S)N1-[(3S)-hexahydro-1-(3-(2-naphthyl)benzyl)-2-oxo-1H-azepin-3-yl]-2-(cyclopentylmethyl)-3-(propyl)-butanediamide;

(2R,3S)N1-[(3S)-hexahydro-1-(3-phenoxybenzyl)-2-oxo-1H-azepin-3-yl]-2-(cyclopentylmethyl)-3-(allyl)-butanediamide;

(2R,3S)N1-[(3S)-hexahydro-1-(3-(4-methoxyphenyl)benzyl)-2-oxo-1H-azepin-3-yl]-2-(cyclopentylmethyl)-3-(allyl)-butanediamide;

(2R,3S)N1-[(3S)-hexahydro-1-(3-(4-trifluoromethylphenyl)benzyl)-2-oxo-1H-azepin-3-yl]-2-(cyclopentylmethyl)-3-(allyl)-butanediamide;

(2R,3S)N1-[(3S)-hexahydro-1-(3-(4-methylphenyl)benzyl)-2-oxo-1H-azepin-3-yl]-2-(cyclopentylmethyl)-3-(allyl)-butanediamide;

(2R,3S)N1-[(3S)-hexahydro-1-(3-(2,4-dichlorophenyl)benzyl)-2-oxo-1H-azepin-3-yl]-2-(cyclopentylmethyl)-3-(allyl)-butanediamide;

(2R,3S)N1-[(3S)-hexahydro-1-(3-(3-chloro-4-fluorophenyl)benzyl)-2-oxo-1H-azepin-3-yl]-2-(cyclopentylmethyl)-3-(allyl)-butanediamide;

(2R,3S)N1-[(3S)-hexahydro-1-(benzophenon-3-yl)-2-oxo-1H-azepin-3-yl]-2-(cyclopentylmethyl)-3-(allyl)-butanediamide;

(2R,3S)N1-[(3S)-hexahydro-1-(3-(2-naphthyl)benzyl)-2-oxo-1H-azepin-3-yl]-2-(cyclopentylmethyl)-3-(allyl)-butanediamide;

(2R,3S)N1-[(3S)-hexahydro-1-(3-phenoxybenzyl)-2-oxo-1H-azepin-3-yl]-2-(cyclopentylmethyl)-3-(butyl)-butanediamide;

(2R,3S)N1-[(3S)-hexahydro-1-(3-(4-methoxyphenyl)benzyl)-2-oxo-1H-azepin-3-yl]-2-(cyclopentylmethyl)-3-(butyl)-butanediamide;

(2R,3S)N1-[(3S)-hexahydro-1-(3-(4-trifluoromethylphenyl)benzyl)-2-oxo-1H-azepin-3-yl]-2-(cyclopentylmethyl)-3-(butyl)-butanediamide;

(2R,3S)N1-[(3S)-hexahydro-1-(3-(4-methylphenyl)benzyl)-2-oxo-1H-azepin-3-yl]-2-(cyclopentylmethyl)-3-(butyl)-butanediamide;

(2R,3S)N1-[(3S)-hexahydro-1-(3-(2,4-dichlorophenyl)benzyl)-2-oxo-1H-azepin-3-yl]-2-(cyclopentylmethyl)-3-(butyl)-butanediamide;

(2R,3S)N1-[(3S)-hexahydro-1-(3-(3-chloro-4-fluorophenyl)benzyl)-2-oxo-1H-azepin-3-yl]-2-(cyclopentylmethyl)-3-(butyl)-butanediamide;

(2R,3S)N1-[(3S)-hexahydro-1-(benzophenon-3-yl)-2-oxo-1H-azepin-3-yl]-2-(cyclopentylmethyl)-3-(butyl)-butanediamide; and (2R,3S)N1-[(3S)-hexahydro-1-(3-(2-naphthyl)benzyl)-2-oxo-1H-azepin-3-yl]-2-(cyclopentylmethyl)-3-(butyl)-butanediamide;

(2R,3S)N1-[(3S)-hexahydro-1-(benzyl)-2-oxo-1H-azepin-3-yl]-2-(2-methylpropyl)-3-(propyl)-butanediamide, (2R,3S)N1-[(3S)-hexahydro-1-(phenethyl)-2-oxo-1H-azepin-3-yl]-2-(2-methylpropyl)-3-(propyl)-butanediamide;

(2R,3S)N1-[(3S)-hexahydro-1-((4-fluorophenyl)methyl)-2-oxo-1H-azepin-3-yl]-2-(2-methylpropyl)-3-(propyl)-butanediamide;

(2R,3S)N1-[(3S)-hexahydro-1-(cyclopropylmethyl)-2-oxo-1H-azepin-3-yl]-2-(2-methylpropyl)-3-(propyl)-butanediamide;

(2R,3S)N1-[(3S)-hexahydro-1-(cyclobutylmethyl)-2-oxo-1H-azepin-3-yl]-2-(2-methylpropyl)-3-(propyl)-butanediamide;

(2R,3S)N1-[(3S)-hexahydro-1-(cyclopentylmethyl)-2-oxo-1H-azepin-3-yl]-2-(2-methylpropyl)-3-(propyl)-butanediamide;

(2R,3S)N1-[(3S)-hexahydro-1-(cyclohexylmethyl)-2-oxo-1H-azepin-3-yl]-2-(2-methylpropyl)-3-(propyl)-butanediamide;

(2R,3S)N1-[(3S)-hexahydro-1-(cyclopropylethyl)-2-oxo-1H-azepin-3-yl]-2-(2-methylpropyl)-3-(propyl)-butanediamide;

(2R,3S)N1-[(3S)-hexahydro-1-(cyclobutylethyl)-2-oxo-1H-azepin-3-yl]-2-(2-methylpropyl)-3-(propyl)-butanediamide;

(2R,3S)N1-[(3S)-hexahydro-1-(cyclopentylethyl)-2-oxo-1H-azepin-3-yl]-2-(2-methylpropyl)-3-(propyl)-butanediamide;

(2R,3S)N1-[(3S)-hexahydro-1-(cyclohexylethyl)-2-oxo-1H-azepin-3-yl]-2-(2-methylpropyl)-3-(propyl)-butanediamide;

(2R,3S)N1-[(3S)-hexahydro-1-(benzyl)-2-oxo-1H-azepin-3-yl]-2-(2-methylpropyl)-3-(allyl)-butanediamide;

(2R,3S)N1-[(3S)-hexahydro-1-(phenethyl)-2-oxo-1H-azepin-3-yl]-2-(2-methylpropyl)-3-(allyl)-butanediamide;

(2R,3S)N1-[(3S)-hexahydro-1-((4-fluorophenyl)methyl)-2-oxo-1H-azepin-3-yl]-2-(2-methylpropyl)-3-(allyl)-butanediamide;

(2R,3S)N1-[(3S)-hexahydro-1-(cyclopropylmethyl)-2-oxo-1H-azepin-3-yl]-2-(2-methylpropyl)-3-(allyl)-butanediamide;

(2R,3S)N1-[(3S)-hexahydro-1-(cyclobutylmethyl)-2-oxo-1H-azepin-3-yl]-2-(2-methylpropyl)-3-(allyl)-butanediamide;

(2R,3S)N1-[(3S)-hexahydro-1-(cyclopentylmethyl)-2-oxo-1H-azepin-3-yl]-2-(2-methylpropyl)-3-(allyl)-butanediamide;

(2R,3S)N1-[(3S)-hexahydro-1-(cyclohexylmethyl)-2-oxo-1H-azepin-3-yl]-2-(2-methylpropyl)-3-(allyl)-butanediamide;

(2R,3S)N1-[(3S)-hexahydro-1-(cyclopropylethyl)-2-oxo-1H-azepin-3-yl]-2-(2-methylpropyl)-3-(allyl)-butanediamide;

(2R,3S)N1-[(3S)-hexahydro-1-(cyclobutylethyl)-2-oxo-1H-azepin-3-yl]-2-(2-methylpropyl)-3-(allyl)-butanediamide;

(2R,3S)N1-[(3S)-hexahydro-1-(cyclopentylethyl)-2-oxo-1H-azepin-3-yl]-2-(2-methylpropyl)-3-(allyl)-butanediamide;

(2R,3S)N1-[(3S)-hexahydro-1-(cyclohexylethyl)-2-oxo-1H-azepin-3-yl]-2-(2-methylpropyl)-3-(allyl)-butanediamide;

(2R,3S)N1-[(3S)-hexahydro-1-(benzyl)-2-oxo-1H-azepin-3-yl]-2-(2-methylpropyl)-3-(butyl)-butanediamide;

(2R,3S)N1-[(3S)-hexahydro-1-(phenethyl)-2-oxo-1H-azepin-3-yl]-2-(2-methylpropyl)-3-(butyl)-butanediamide;

(2R,3S)N1-[(3S)-hexahydro-1-((4-fluorophenyl)methyl)-2-oxo-1H-azepin-3-yl]-2-(2-methylpropyl)-3-(butyl)-butanediamide;

(2R,3S)N1-[(3S)-hexahydro-1-(cyclopropylmethyl)-2-oxo-1H-azepin-3-yl]-2-(2-methylpropyl)-3-(butyl)-butanediamide;

(2R,3S)N1-[(3S)-hexahydro-1-(cyclobutylmethyl)-2-oxo-1H-azepin-3-yl]-2-(2-methylpropyl)-3-(butyl)-butanediamide;

(2R,3S)N1-[(3S)-hexahydro-1-(cyclopentylmethyl)-2-oxo-1H-azepin-3-yl]-2-(2-methylpropyl)-3-(butyl)-butanediamide;

(2R,3S)N1-[(3S)-hexahydro-1-(cyclohexylmethyl)-2-oxo-1H-azepin-3-yl]-2-(2-methylpropyl)-3-(butyl)-butanediamide;

(2R,3S)N1-[(3S)-hexahydro-1-(cyclopropylethyl)-2-oxo-1H-azepin-3-yl]-2-(2-methylpropyl)-3-(butyl)-butanediamide;

(2R,3S)N1-[(3S)-hexahydro-1-(cyclobutylethyl)-2-oxo-1H-azepin-3-yl]-2-(2-methylpropyl)-3-(butyl)-butanediamide;

(2R,3S)N1-[(3S)-hexahydro-1-(cyclopentylethyl)-2-oxo-1H-azepin-3-yl]-2-(2-methylpropyl)-3-(butyl)-butanediamide; and (2R,3S)N1-[(3S)-hexahydro-1-(cyclohexylethyl)-2-oxo-1H-azepin-3-yl]-2-(2-methylpropyl)-3-(butyl)-butanediamide.

[20] In another even more preferred embodiment the present invention provides compounds of Formula (I) selected from:

(2R,3S)N1-[1,3-dihydro-1-(3-phenoxybenzyl)-2-oxo-5-(phenyl)-2H-1,4-benzodiazepin-3-yl]-2-(2-methylpropyl)-3-(allyl)-butanediamide;

(2R,3S)N1-[1,3-dihydro-1-(3-phenoxybenzyl)-2-oxo-5-(phenyl)-2H-1,4-benzodiazepin-3-yl]-2-(2-methylpropyl)-3-(propyl)-butanediamide;

(2R,3S)N1-[1,3-dihydro-1-(3-(4-methoxyphenyl)benzyl)-2-oxo-5-(phenyl)-2H-1,4-benzodiazepin-3-yl]-2-(2-methylpropyl)-3-(propyl)-butanediamide;

(2R,3S)N1-[1,3-dihydro-1-(3-(4-trifluoromethylphenyl)benzyl)-2-oxo-5-(phenyl)-2H-1,4-benzodiazepin-3-yl]-2-(2-methylpropyl)-3-(propyl)-butanediamide;

(2R,3S)N1-[1,3-dihydro-1-(3-(4-methylphenyl)benzyl)-2-oxo-5-(phenyl)-2H-1,4-benzodiazepin-3-yl]-2-(2-methylpropyl)-3-(propyl)-butanediamide;

(2R,3S)N1-[1,3-dihydro-1-(3-(2,4-dichlorophenyl)benzyl)-2-oxo-5-(phenyl)-2H-1,4-benzodiazepin-3-yl]-2-(2-methylpropyl)-3-(propyl)-butanediamide;

(2R,3S)N1-[1,3-dihydro-1-(3-(3-chloro-4-fluorophenyl)benzyl)-2-oxo-5-(phenyl)-2H-1,4-benzodiazepin-3-yl]-2-(2-methylpropyl)-3-(propyl)-butanediamide;

(2R,3S)N1-[1,3-dihydro-1-(benzophenon-3-yl)-2-oxo-5-(phenyl)-2H-1,4-benzodiazepin-3-yl]-2-(2-methylpropyl)-3-(propyl)-butanediamide;

(2R,3S)N1-[1,3-dihydro-1-(3-(2-naphthyl)benzyl)-2-oxo-5-(phenyl)-2H-1,4-benzodiazepin-3-yl]-2-(2-methylpropyl)-3-(propyl)-butanediamide;

(2R,3S)N1-[1,3-dihydro-1-(3-(4-methoxyphenyl)benzyl)-2-oxo-5-(phenyl)-2H-1,4-benzodiazepin-3-yl]-2-(2-methylpropyl)-3-(allyl)-butanediamide;

(2R,3S)N1-[1,3-dihydro-1-(3-(4-trifluoromethylphenyl)benzyl)-2-oxo-5-(phenyl)-2H-1,4-benzodiazepin-3-yl]-2-(2-methylpropyl)-3-(allyl)-butanediamide;

(2R,3S)N1-[1,3-dihydro-1-(3-(4-methylphenyl)benzyl)-2-oxo-5-(phenyl)-2H-1,4-benzodiazepin-3-yl]-2-(2-methylpropyl)-3-(allyl)-butanediamide;

(2R,3S)N1-[1,3-dihydro-1-(3-(2,4-dichlorophenyl)benzyl)-2-oxo-5-(phenyl)-2H-1,4-benzodiazepin-3-yl]-2-(2-methylpropyl)-3-(allyl)-butanediamide;

(2R,3S)N1-[1,3-dihydro-1-(3-(3-chloro-4-fluorophenyl)benzyl)-2-oxo-5-(phenyl)-2H-1,4-benzodiazepin-3-yl]-2-(2-methylpropyl)-3-(allyl)-butanediamide;

(2R,3S)N1-[1,3-dihydro-1-(3-(2-naphthyl)benzyl)-2-oxo-5-(phenyl)-2H-1,4-benzodiazepin-3-yl]-2-(2-methylpropyl)-3-(allyl)-butanediamide;

(2R,3S)N1-[1,3-dihydro-1-(3-phenoxybenzyl)-2-oxo-5-(phenyl)-2H-1,4-benzodiazepin-3-yl]-2-(2-methylpropyl)-3-(butyl)-butanediamide;

(2R,3S)N1-[1,3-dihydro-1-(3-(4-methoxyphenyl)benzyl)-2-oxo-5-(phenyl)-2H-1,4-benzodiazepin-3-yl]-2-(2-methylpropyl)-3-(butyl)-butanediamide;

(2R,3S)N1-[1,3-dihydro-1-(3-(4-trifluoromethylphenyl)benzyl)-2-oxo-5-(phenyl)-2H-1,4-benzodiazepin-3-yl]-2-(2-methylpropyl)-3-(butyl)-butanediamide;

(2R,3S)N1-[1,3-dihydro-1-(3-(4-methylphenyl)benzyl)-2-oxo-5-(phenyl)-2H-1,4-benzodiazepin-3-yl]-2-(2-methylpropyl)-3-(butyl)-butanediamide;

(2R,3S)N1-[1,3-dihydro-1-(3-(2,4-dichlorophenyl)benzyl)-2-oxo-5-(phenyl)-2H-1,4-benzodiazepin-3-yl]-2-(2-methylpropyl)-3-(butyl)-butanediamide;

(2R,3S)N1-[1,3-dihydro-1-(3-(3-chloro-4-fluorophenyl)benzyl)-2-oxo-5-(phenyl)-2H-1,4-benzodiazepin-3-yl]-2-(2-methylpropyl)-3-(butyl)-butanediamide;

(2R,3S)N1-[1,3-dihydro-1-(benzophenon-3-yl)-2-oxo-5-(phenyl)-2H-1,4-benzodiazepin-3-yl]-2-(2-methylpropyl)-3-(butyl)-butanediamide;

(2R,3S)N1-[1,3-dihydro-1-(3-(2-naphthyl)benzyl)-2-oxo-5-(phenyl)-2H-1,4-benzodiazepin-3-yl]-2-(2-methylpropyl)-3-(butyl)-butanediamide;

(2R,3S)N1-[1,3-dihydro-1-(3-phenoxybenzyl)-2-oxo-5-(phenyl)-2H-1,4-benzodiazepin-3-yl]-2-(cyclopropylmethyl)-3-(propyl)-butanediamide;

(2R,3S)N1-[1,3-dihydro-1-(3-(4-methoxyphenyl)benzyl)-2-oxo-5-(phenyl)-2H-1,4-benzodiazepin-3-yl]-2-(cyclopropylmethyl)-3-(propyl)-butanediamide;

(2R,3S)N1-[1,3-dihydro-1-(3-(4-trifluoromethylphenyl)benzyl)-2-oxo-5-(phenyl)-2H-1,4-benzodiazepin-3-yl]-2-(cyclopropylmethyl)-3-(propyl)-butanediamide;

(2R,3S)N1-[1,3-dihydro-1-(3-(4-methylphenyl)benzyl)-2-oxo-5-(phenyl)-2H-1,4-benzodiazepin-3-yl]-2-(cyclopropylmethyl)-3-(propyl)-butanediamide;

(2R,3S)N1-[1,3-dihydro-1-(3-(2,4-dichlorophenyl)benzyl)-2-oxo-5-(phenyl)-2H-1,4-benzodiazepin-3-yl]-2-(cyclopropylmethyl)-3-(propyl)-butanediamide;

(2R,3S)N1-[1,3-dihydro-1-(3-(3-chloro-4-fluorophenyl)benzyl)-2-oxo-5-(phenyl)-2H-1,4-benzodiazepin-3-yl]-2-(cyclopropylmethyl)-3-(propyl)-butanediamide;

(2R,3S)N1-[1,3-dihydro-1-(benzophenon-3-yl)-2-oxo-5-(phenyl)-2H-1,4-benzodiazepin-3-yl]-2-(cyclopropylmethyl)-3-(propyl)-butanediamide;

(2R,3S)N1-[1,3-dihydro-1-(3-(2-naphthyl)benzyl)-2-oxo-5-(phenyl)-2H-1,4-benzodiazepin-3-yl]-2-(cyclopropylmethyl)-3-(propyl)-butanediamide;

(2R,3S)N1-[1,3-dihydro-1-(3-phenoxybenzyl)-2-oxo-5-(phenyl)-2H-1,4-benzodiazepin-3-yl]-2-(cyclopropylmethyl)-3-(allyl)-butanediamide;

(2R,3S)N1-[1,3-dihydro-1-(3-(4-methoxyphenyl)benzyl)-2-oxo-5-(phenyl)-2H-1,4-benzodiazepin-3-yl]-2-(cyclopropylmethyl)-3-(allyl)-butanediamide;

(2R,3S)N1-[1,3-dihydro-1-(3-(4-trifluoromethylphenyl)benzyl)-2-oxo-5-(phenyl)-2H-1,4-benzodiazepin-3-yl]-2-(cyclopropylmethyl)-3-(allyl)-butanediamide;

(2R,3S)N1-[1,3-dihydro-1-(3-(4-methylphenyl)benzyl)-2-oxo-5-(phenyl)-2H-1,4-benzodiazepin-3-yl]-2-(cyclopropylmethyl)-3-(allyl)-butanediamide;

(2R,3S)N1-[1,3-dihydro-1-(3-(2,4-dichlorophenyl)benzyl)-2-oxo-5-(phenyl)-2H-1,4-benzodiazepin-3-yl]-2-(cyclopropylmethyl)-3-(allyl)-butanediamide;

(2R,3S)N1-[1,3-dihydro-1-(3-(3-chloro-4-fluorophenyl)benzyl)-2-oxo-5-(phenyl)-2H-1,4-benzodiazepin-3-yl]-2-(cyclopropylmethyl)-3-(allyl)-butanediamide;

(2R,3S)N1-[1,3-dihydro-1-(benzophenon-3-yl)-2-oxo-5-(phenyl)-2H-1,4-benzodiazepin-3-yl]-2-(cyclopropylmethyl)-3-(allyl)-butanediamide;

(2R,3S)N1-[1,3-dihydro-1-(3-(2-naphthyl)benzyl)-2-oxo-5-(phenyl)-2H-1,4-benzodiazepin-3-yl]-2-(cyclopropylmethyl)-3-(allyl)-butanediamide;

(2R,3S)N1-[1,3-dihydro-1-(3-phenoxybenzyl)-2-oxo-5-(phenyl)-2H-1,4-benzodiazepin-3-yl]-2-(cyclopropylmethyl)-3-(butyl)-butanediamide;

(2R,3S)N1-[1,3-dihydro-1-(3-(4-methoxyphenyl)benzyl)-2-oxo-5-(phenyl)-2H-1,4-benzodiazepin-3-yl]-2-(cyclopropylmethyl)-3-(butyl)-butanediamide;

(2R,3S)N1-[1,3-dihydro-1-(3-(4-trifluoromethylphenyl)benzyl)-2-oxo-5-(phenyl)-2H-1,4-benzodiazepin-3-yl]-2-(cyclopropylmethyl)-3-(butyl)-butanediamide;

(2R,3S)N1-[1,3-dihydro-1-(3-(4-methylphenyl)benzyl)-2-oxo-5-(phenyl)-2H-1,4-benzodiazepin-3-yl]-2-(cyclopropylmethyl)-3-(butyl)-butanediamide;

(2R,3S)N1-[1,3-dihydro-1-(3-(2,4-dichlorophenyl)benzyl)-2-oxo-5-(phenyl)-2H-1,4-benzodiazepin-3-yl]-2-(cyclopropylmethyl)-3-(butyl)-butanediamide;

(2R,3S)N1-[1,3-dihydro-1-(3-(3-chloro-4-fluorophenyl)benzyl)-2-oxo-5-(phenyl)-2H-1,4-benzodiazepin-3-yl]-2-(cyclopropylmethyl)-3-(butyl)-butanediamide;

(2R,3S)N1-[1,3-dihydro-1-(benzophenon-3-yl)-2-oxo-5-(phenyl)-2H-1,4-benzodiazepin-3-yl]-2-(cyclopropylmethyl)-3-(butyl)-butanediamide;

(2R,3S)N1-[1,3-dihydro-1-(3-(2-naphthyl)benzyl)-2-oxo-5-(phenyl)-2H-1,4-benzodiazepin-3-yl]-2-(cyclopropylmethyl)-3-(butyl)-butanediamide;

(2R,3S)N1-[1,3-dihydro-1-(3-phenoxybenzyl)-2-oxo-5-(phenyl)-2H-1,4-benzodiazepin-3-yl]-2-(cyclobutylmethyl)-3-(propyl)-butanediamide;

(2R,3S)N1-[1,3-dihydro-1-(3-(4-methoxyphenyl)benzyl)-2-oxo-5-(phenyl)-2H-1,4-benzodiazepin-3-yl]-2-(cyclobutylmethyl)-3-(propyl)-butanediamide;

(2R,3S)N1-[1,3-dihydro-1-(3-(4-trifluoromethylphenyl)benzyl)-2-oxo-5-(phenyl)-2H-1,4-benzodiazepin-3-yl]-2-(cyclobutylmethyl)-3-(propyl)-butanediamide;

(2R,3S)N1-[1,3-dihydro-1-(3-(4-methylphenyl)benzyl)-2-oxo-5-(phenyl)-2H-1,4-benzodiazepin-3-yl]-2-(cyclobutylmethyl)-3-(propyl)-butanediamide;

(2R,3S)N1-[1,3-dihydro-1-(3-(2,4-dichlorophenyl)benzyl)-2-oxo-5-(phenyl)-2H-1,4-benzodiazepin-3-yl]-2-(cyclobutylmethyl)-3-(propyl)-butanediamide;

(2R,3S)N1-[1,3-dihydro-1-(3-(3-chloro-4-fluorophenyl)benzyl)-2-oxo-5-(phenyl)-2H-1,4-benzodiazepin-3-yl]-2-(cyclobutylmethyl)-3-(propyl)-butanediamide;

(2R,3S)N1-[1,3-dihydro-1-(benzophenon-3-yl)-2-oxo-5-(phenyl)-2H-1,4-benzodiazepin-3-yl]-2-(cyclobutylmethyl)-3-(propyl)-butanediamide;

(2R,3S)N1-[1,3-dihydro-1-(3-(2-naphthyl)benzyl)-2-oxo-5-(phenyl)-2H-1,4-benzodiazepin-3-yl]-2-(cyclobutylmethyl)-3-(propyl)-butanediamide;

(2R,3S)N1-[1,3-dihydro-1-(3-phenoxybenzyl)-2-oxo-5-(phenyl)-2H-1,4-benzodiazepin-3-yl]-2-(cyclobutylmethyl)-3-(allyl)-butanediamide;

(2R,3S)N1-[1,3-dihydro-1-(3-(4-methoxyphenyl)benzyl)-2-oxo-5-(phenyl)-2H-1,4-benzodiazepin-3-yl]-2-(cyclobutylmethyl)-3-(allyl)-butanediamide;

(2R,3S)N1-[1,3-dihydro-1-(3-(4-trifluoromethylphenyl)benzyl)-2-oxo-5-(phenyl)-2H-1,4-benzodiazepin-3-yl]-2-(cyclobutylmethyl)-3-(allyl)-butanediamide;

(2R,3S)N1-[1,3-dihydro-1-(3-(4-methylphenyl)benzyl)-2-oxo-5-(phenyl)-2H-1,4-benzodiazepin-3-yl]-2-(cyclobutylmethyl)-3-(allyl)-butanediamide;

(2R,3S)N1-[1,3-dihydro-1-(3-(2,4-dichlorophenyl)benzyl)-2-oxo-5-(phenyl)-2H-1,4-benzodiazepin-3-yl]-2-(cyclobutylmethyl)-3-(allyl)-butanediamide;

(2R,3S)N1-[1,3-dihydro-1-(3-(3-chloro-4-fluorophenyl)benzyl)-2-oxo-5-(phenyl)-2H-1,4-benzodiazepin-3-yl]-2-(cyclobutylmethyl)-3-(allyl)-butanediamide;

(2R,3S)N1-[1,3-dihydro-1-(benzophenon-3-yl)-2-oxo-5-(phenyl)-2H-1,4-benzodiazepin-3-yl]-2-(cyclobutylmethyl)-3-(allyl)-butanediamide;

(2R,3S)N1-[1,3-dihydro-1-(3-(2-naphthyl)benzyl)-2-oxo-5-(phenyl)-2H-1,4-benzodiazepin-3-yl]-2-(cyclobutylmethyl)-3-(allyl)-butanediamide;

(2R,3S)N1-[1,3-dihydro-1-(3-phenoxybenzyl)-2-oxo-5-(phenyl)-2H-1,4-benzodiazepin-3-yl]-2-(cyclobutylmethyl)-3-(butyl)-butanediamide;

(2R,3S)N1-[1,3-dihydro-1-(3-(4-methoxyphenyl)benzyl)-2-oxo-5-(phenyl)-2H-1,4-benzodiazepin-3-yl]-2-(cyclobutylmethyl)-3-(butyl)-butanediamide;

(2R,3S)N1-[1,3-dihydro-1-(3-(4-trifluoromethylphenyl)benzyl)-2-oxo-5-(phenyl)-2H-1,4-benzodiazepin-3-yl]-2-(cyclobutylmethyl)-3-(butyl)-butanediamide;

(2R,3S)N1-[1,3-dihydro-1-(3-(4-methylphenyl)benzyl)-2-oxo-5-(phenyl)-2H-1,4-benzodiazepin-3-yl]-2-(cyclobutylmethyl)-3-(butyl)-butanediamide;

(2R,3S)N1-[1,3-dihydro-1-(3-(2,4-dichlorophenyl)benzyl)-2-oxo-5-(phenyl)-2H-1,4-benzodiazepin-3-yl]-2-(cyclobutylmethyl)-3-(butyl)-butanediamide;

(2R,3S)N1-[1,3-dihydro-1-(3-(3-chloro-4-fluorophenyl)benzyl)-2-oxo-5-(phenyl)-2H-1,4-benzodiazepin-3-yl]-2-(cyclobutylmethyl)-3-(butyl)-butanediamide;

(2R,3S)N1-[1,3-dihydro-1-(benzophenon-3-yl)-2-oxo-5-(phenyl)-2H-1,4-benzodiazepin-3-yl]-2-(cyclobutylmethyl)-3-(butyl)-butanediamide;

(2R,3S)N1-[1,3-dihydro-1-(3-(2-naphthyl)benzyl)-2-oxo-5-(phenyl)-2H-1,4-benzodiazepin-3-yl]-2-(cyclobutylmethyl)-3-(butyl)-butanediamide;

(2R,3S)N1-[1,3-dihydro-1-(3-phenoxybenzyl)-2-oxo-5-(phenyl)-2H-1,4-benzodiazepin-3-yl]-2-(cyclopentylmethyl)-3-(propyl)-butanediamide;

(2R,3S)N1-[1,3-dihydro-1-(3-(4-methoxyphenyl)benzyl)-2-oxo-5-(phenyl)-2H-1,4-benzodiazepin-3-yl]-2-(cyclopentylmethyl)-3-(propyl)-butanediamide;

(2R,3S)N1-[1,3-dihydro-1-(3-(4-trifluoromethylphenyl)benzyl)-2-oxo-5-(phenyl)-2H-1,4-benzodiazepin-3-yl]-2-(cyclopentylmethyl)-3-(propyl)-butanediamide;

(2R,3S)N1-[1,3-dihydro-1-(3-(4-methylphenyl)benzyl)-2-oxo-5-(phenyl)-2H-1,4-benzodiazepin-3-yl]-2-(cyclopentylmethyl)-3-(propyl)-butanediamide;

(2R,3S)N1-[1,3-dihydro-1-(3-(2,4-dichlorophenyl)benzyl)-2-oxo-5-(phenyl)-2H-1,4-benzodiazepin-3-yl]-2-(cyclopentylmethyl)-3-(propyl)-butanediamide;

(2R,3S)N1-[1,3-dihydro-1-(3-(3-chloro-4-fluorophenyl)
benzyl)-2-oxo-5-(phenyl)-2H-1,4-benzodiazepin-3-yl]-2-
(cyclopentylmethyl)-3-(propyl)-butanediamide;

(2R,3S)N1-[1,3-dihydro-1-(benzophenon-3-yl)-2-oxo-5-
(phenyl)-2H-1,4-benzodiazepin-3-yl]-2-(cyclopentylm-
ethyl)-3-(propyl)-butanediamide;

(2R,3S)N1-[1,3-dihydro-1-(3-(2-naphthyl)benzyl)-2-oxo-5-
(phenyl)-2H-1,4-benzodiazepin-3-yl]-2-(cyclopentylm-
ethyl)-3-(propyl)-butanediamide;

(2R,3S)N1-[1,3-dihydro-1-(3-phenoxybenzyl)-2-oxo-5-
(phenyl)-2H-1,4-benzodiazepin-3-yl]-2-(cyclopentylm-
ethyl)-3-(allyl)-butanediamide;

(2R,3S)N1-[1,3-dihydro-1-(3-(4-methoxyphenyl)benzyl)-2-
oxo-5-(phenyl)-2H-1,4-benzodiazepin-3-yl]-2-(cyclo-
pentylmethyl)-3-(allyl)-butanediamide;

(2R,3S)N1-[1,3-dihydro-1-(3-(4-trifluoromethylphenyl)
benzyl)-2-oxo-5-(phenyl)-2H-1,4-benzodiazepin-3-yl]-2-
(cyclopentylmethyl)-3-(allyl)-butanediamide;

(2R,3S)N1-[1,3-dihydro-1-(3-(4-methylphenyl)benzyl)-2-
oxo-5-(phenyl)-2H-1,4-benzodiazepin-3-yl]-2-(cyclo-
pentylmethyl)-3-(allyl)-butanediamide;

(2R,3S)N1-[1,3-dihydro-1-(3-(2,4-dichlorophenyl)benzyl)-
2-oxo-5-(phenyl)-2H-1,4-benzodiazepin-3-yl]-2-(cyclo-
pentylmethyl)-3-(allyl)-butanediamide;

(2R,3S)N1-[1,3-dihydro-1-(3-(3-chloro-4-fluorophenyl)
benzyl)-2-oxo-5-(phenyl)-2H-1,4-benzodiazepin-3-yl]-2-
(cyclopentylmethyl)-3-(allyl)-butanediamide;

(2R,3S)N1-[1,3-dihydro-1-(benzophenon-3-yl)-2-oxo-5-
(phenyl)-2H-1,4-benzodiazepin-3-yl]-2-(cyclopentylm-
ethyl)-3-(allyl)-butanediamide;

(2R,3S)N1-[1,3-dihydro-1-(3-(2-naphthyl)benzyl)-2-oxo-5-
(phenyl)-2H-1,4-benzodiazepin-3-yl]-2-(cyclopentylm-
ethyl)-3-(allyl)-butanediamide;

(2R,3S)N1-[1,3-dihydro-1-(3-phenoxybenzyl)-2-oxo-5-
(phenyl)-2H-1,4-benzodiazepin-3-yl]-2-(cyclopentylm-
ethyl)-3-(butyl)-butanediamide;

(2R,3S)N1-[1,3-dihydro-1-(3-(4-methoxyphenyl)benzyl)-2-
oxo-5-(phenyl)-2H-1,4-benzodiazepin-3-yl]-2-(cyclo-
pentylmethyl)-3-(butyl)-butanediamide;

(2R,3S)N1-[1,3-dihydro-1-(3-(4-trifluoromethylphenyl)
benzyl)-2-oxo-5-(phenyl)-2H-1,4-benzodiazepin-3-yl]-2-
(cyclopentylmethyl)-3-(butyl)-butanediamide;

(2R,3S)N1-[1,3-dihydro-1-(3-(4-methylphenyl)benzyl)-2-
oxo-5-(phenyl)-2H-1,4-benzodiazepin-3-yl]-2-(cyclo-
pentylmethyl)-3-(butyl)-butanediamide;

(2R,3S)N1-[1,3-dihydro-1-(3-(2,4-dichlorophenyl)benzyl)-
2-oxo-5-(phenyl)-2H-1,4-benzodiazepin-3-yl]-2-(cyclo-
pentylmethyl)-3-(butyl)-butanediamide;

(2R,3S)N1-[1,3-dihydro-1-(3-(3-chloro-4-fluorophenyl)
benzyl)-2-oxo-5-(phenyl)-2H-1,4-benzodiazepin-3-yl]-2-
(cyclopentylmethyl)-3-(butyl)-butanediamide;

(2R,3S)N1-[1,3-dihydro-1-(benzophenon-3-yl)-2-oxo-5-
(phenyl)-2H-1,4-benzodiazepin-3-yl]-2-(cyclopentylm-
ethyl)-3-(butyl)-butanediamide; and (2R,3S)N1-[1,3-dihydro-1-(3-(2-naphthyl)benzyl)-2-oxo-5-
(phenyl)-2H-1,4-benzodiazepin-3-yl]-2-(cyclopentylm-
ethyl)-3-(butyl)-butanediamide;

(2R,3S)N1-[1,3-dihydro-1-(benzyl)-2-oxo-5-(phenyl)-2H-
1,4-benzodiazepin-3-yl]-2-(2-methylpropyl)-3-(propyl)-
butanediamide;

(2R,3S)N1-[1,3-dihydro-1-(phenethyl)-2-oxo-5-(phenyl)-
2H-1,4-benzodiazepin-3-yl]-2-(2-methylpropyl)-3-(pro-
pyl)-butanediamide;

(2R,3S)N1-[1,3-dihydro-1-((4-fluorophenyl)methyl)-2-oxo-
5-(phenyl)-2H-1,4-benzodiazepin-3-yl]-2-(2-methylpro-
pyl)-3-(propyl)-butanediamide;

(2R,3S)N1-[1,3-dihydro-1-(cyclopropylmethyl)-2-oxo-5-
(phenyl)-2H-1,4-benzodiazepin-3-yl]-2-(2-methylpro-
pyl)-3-(propyl)-butanediamide;

(2R,3S)N1-[1,3-dihydro-1-(cyclobutylmethyl)-2-oxo-5-
(phenyl)-2H-1,4-benzodiazepin-3-yl]-2-(2-methylpro-
pyl)-3-(propyl)-butanediamide;

(2R,3S)N1-[1,3-dihydro-1-(cyclopentylmethyl)-2-oxo-5-
(phenyl)-2H-1,4-benzodiazepin-3-yl]-2-(2-methylpro-
pyl)-3-(propyl)-butanediamide;

(2R,3S)N1-[1,3-dihydro-1-(cyclohexylmethyl)-2-oxo-5-
(phenyl)-2H-1,4-benzodiazepin-3-yl]-2-(2-methylpro-
pyl)-3-(propyl)-butanediamide;

(2R,3S)N1-[1,3-dihydro-1-(cyclopropylethyl)-2-oxo-5-
(phenyl)-2H-1,4-benzodiazepin-3-yl]-2-(2-methylpro-
pyl)-3-(propyl)-butanediamide;

(2R,3S)N1-[1,3-dihydro-1-(cyclobutylethyl)-2-oxo-5-(phe-
nyl)-2H-1,4-benzodiazepin-3-yl]-2-(2-methylpropyl)-3-
(propyl)-butanediamide;

(2R,3S)N1-[1,3-dihydro-1-(cyclopentylethyl)-2-oxo-5-
(phenyl)-2H-1,4-benzodiazepin-3-yl]-2-(2-methylpro-
pyl)-3-(propyl)-butanediamide;

(2R,3S)N1-[1,3-dihydro-1-(cyclohexylethyl)-2-oxo-5-(phe-
nyl)-2H-1,4-benzodiazepin-3-yl]-2-(2-methylpropyl)-3-
(propyl)-butanediamide;

(2R,3S)N1-[1,3-dihydro-1-(benzyl)-2-oxo-5-(phenyl)-2H-
1,4-benzodiazepin-3-yl]-2-(2-methylpropyl)-3-(allyl)-bu-
tanediamide;

(2R,3S)N1-[1,3-dihydro-1-(phenethyl)-2-oxo-5-(phenyl)-
2H-1,4-benzodiazepin-3-yl]-2-(2-methylpropyl)-3-(al-
lyl)-butanediamide;

(2R,3S)N1-[1,3-dihydro-1-((4-fluorophenyl)methyl)-2-oxo-
5-(phenyl)-2H-1,4-benzodiazepin-3-yl]-2-(2-methylpro-
pyl)-3-(allyl)-butanediamide;

(2R,3S)N1-[1,3-dihydro-1-(cyclopropylmethyl)-2-oxo-5-
(phenyl)-2H-1,4-benzodiazepin-3-yl]-2-(2-methylpro-
pyl)-3-(allyl)-butanediamide;

(2R,3S)N1-[1,3-dihydro-1-(cyclobutylmethyl)-2-oxo-5-
(phenyl)-2H-1,4-benzodiazepin-3-yl]-2-(2-methylpro-
pyl)-3-(allyl)-butanediamide;

(2R,3S)N1-[1,3-dihydro-1-(cyclopentylmethyl)-2-oxo-5-
(phenyl)-2H-1,4-benzodiazepin-3-yl]-2-(2-methylpro-
pyl)-3-(allyl)-butanediamide;

(2R,3S)N1-[1,3-dihydro-1-(cyclohexylmethyl)-2-oxo-5-
(phenyl)-2H-1,4-benzodiazepin-3-yl]-2-(2-methylpro-
pyl)-3-(allyl)-butanediamide;

(2R,3S)N1-[1,3-dihydro-1-(cyclopropylethyl)-2-oxo-5-
(phenyl)-2H-1,4-benzodiazepin-3-yl]-2-(2-methylpro-
pyl)-3-(allyl)-butanediamide;

(2R,3S)N1-[1,3-dihydro-1-(cyclobutylethyl)-2-oxo-5-(phe-
nyl)-2H-1,4-benzodiazepin-3-yl]-2-(2-methylpropyl)-3-
(allyl)-butanediamide;

(2R,3S)N1-[1,3-dihydro-1-(cyclopentylethyl)-2-oxo-5-
(phenyl)-2H-1,4-benzodiazepin-3-yl]-2-(2-methylpro-
pyl)-3-(allyl)-butanediamide;

(2R,3S)N1-[1,3-dihydro-1-(cyclohexylethyl)-2-oxo-5-(phe-
nyl)-2H-1,4-benzodiazepin-3-yl]-2-(2-methylpropyl)-3-
(allyl)-butanediamide;

(2R,3S)N1-[1,3-dihydro-1-(benzyl)-2-oxo-5-(phenyl)-2H-
1,4-benzodiazepin-3-yl]-2-(2-methylpropyl)-3-(butyl)-
butanediamide;

(2R,3S)N1-[1,3-dihydro-1-(phenethyl)-2-oxo-5-(phenyl)-
2H-1,4-benzodiazepin-3-yl]-2-(2-methylpropyl)-3-(bu-
tyl)-butanediamide;

(2R,3S)N1-[1,3-dihydro-1-((4-fluorophenyl)methyl)-2-oxo-
5-(phenyl)-2H-1,4-benzodiazepin-3-yl]-2-(2-methylpro-
pyl)-3-(butyl)-butanediamide;

(2R,3S)N1-[1,3-dihydro-1-(cyclopropylmethyl)-2-oxo-5-(phenyl)-2H-1,4-benzodiazepin-3-yl]-2-(2-methylpropyl)-3-(butyl)-butanediamide;
(2R,3S)N1-[1,3-dihydro-1-(cyclobutylmethyl)-2-oxo-5-(phenyl)-2H-1,4-benzodiazepin-3-yl]-2-(2-methylpropyl)-3-(butyl)-butanediamide;
(2R,3S)N1-[1,3-dihydro-1-(cyclopentylmethyl)-2-oxo-5-(phenyl)-2H-1,4-benzodiazepin-3-yl]-2-(2-methylpropyl)-3-(butyl)-butanediamide;
(2R,3S)N1-[1,3-dihydro-1-(cyclohexylmethyl)-2-oxo-5-(phenyl)-2H-1,4-benzodiazepin-3-yl]-2-(2-methylpropyl)-3-(butyl)-butanediamide;
(2R,3S)N1-[1,3-dihydro-1-(cyclopropylethyl)-2-oxo-5-(phenyl)-2H-1,4-benzodiazepin-3-yl]-2-(2-methylpropyl)-3-(butyl)-butanediamide;
(2R,3S)N1-[1,3-dihydro-1-(cyclobutylethyl)-2-oxo-5-(phenyl)-2H-1,4-benzodiazepin-3-yl]-2-(2-methylpropyl)-3-(butyl)-butanediamide;
(2R,3S)N1-[1,3-dihydro-1-(cyclopentylethyl)-2-oxo-5-(phenyl)-2H-1,4-benzodiazepin-3-yl]-2-(2-methylpropyl)-3-(butyl)-butanediamide; and
(2R,3S)N1-[1,3-dihydro-1-(cyclohexylethyl)-2-oxo-5-(phenyl)-2H-1,4-benzodiazepin-3-yl]-2-(2-methylpropyl)-3-(butyl)-butanediamide.

[21] In another even more preferred embodiment the present invention provides compounds of Formula (I) selected from:

(2R,3S)N1-[6,7-dihydro-5-(3-phenoxybenzyl)-6-oxo-5H-dibenz[b,d]azepin-7-yl]-2-(2-methylpropyl)-3-(propyl)-butanediamide;
(2R,3S)N1-[6,7-dihydro-5-(3-(4-methoxyphenyl)benzyl)-6-oxo-5H-dibenz[b,d]azepin-7-yl]-2-(2-methylpropyl)-3-(propyl)-butanediamide;
(2R,3S)N1-[6,7-dihydro-5-(3-(4-trifluoromethylphenyl)benzyl)-6-oxo-5H-dibenz[b,d]azepin-7-yl]-2-(2-methylpropyl)-3-(propyl)-butanediamide;
(2R,3S)N1-[6,7-dihydro-5-(3-(4-methylphenyl)benzyl)-6-oxo-5H-dibenz[b,d]azepin-7-yl]-2-(2-methylpropyl)-3-(propyl)-butanediamide;
(2R,3S)N1-[6,7-dihydro-5-(3-(2,4-dichlorophenyl)benzyl)-6-oxo-5H-dibenz[b,d]azepin-7-yl]-2-(2-methylpropyl)-3-(propyl)-butanediamide;
(2R,3S)N1-[6,7-dihydro-5-(3-(3-chloro-4-fluorophenyl)benzyl)-6-oxo-5H-dibenz[b,d]azepin-7-yl]-2-(2-methylpropyl)-3-(propyl)-butanediamide;
(2R,3S)N1-[6,7-dihydro-5-(benzophenon-3-yl)-6-oxo-5H-dibenz[b,d]azepin-7-yl]-2-(2-methylpropyl)-3-(propyl)-butanediamide;
(2R,3S)N1-[6,7-dihydro-5-(3-(2-naphthyl)benzyl)-6-oxo-5H-dibenz[b,d]azepin-7-yl]-2-(2-methylpropyl)-3-(propyl)-butanediamide;
(2R,3S)N1-[6,7-dihydro-5-(3-phenoxybenzyl)-6-oxo-5H-dibenz[b,d]azepin-7-yl]-2-(2-methylpropyl)-3-(allyl)-butanediamide;
(2R,3S)N1-[6,7-dihydro-5-(3-(4-methoxyphenyl)benzyl)-6-oxo-5H-dibenz[b,d]azepin-7-yl]-2-(2-methylpropyl)-3-(allyl)-butanediamide;
(2R,3S)N1-[6,7-dihydro-5-(3-(4-trifluoromethylphenyl)benzyl)-6-oxo-5H-dibenz[b,d]azepin-7-yl]-2-(2-methylpropyl)-3-(allyl)-butanediamide;
(2R,3S)N1-[6,7-dihydro-5-(3-(4-methylphenyl)benzyl)-6-oxo-5H-dibenz[b,d]azepin-7-yl]-2-(2-methylpropyl)-3-(allyl)-butanediamide;
(2R,3S)N1-[6,7-dihydro-5-(3-(2,4-dichlorophenyl)benzyl)-6-oxo-5H-dibenz[b,d]azepin-7-yl]-2-(2-methylpropyl)-3-(allyl)-butanediamide;
(2R,3S)N1-[6,7-dihydro-5-(3-(3-chloro-4-fluorophenyl)benzyl)-6-oxo-5H-dibenz[b,d]azepin-7-yl]-2-(2-methylpropyl)-3-(allyl)-butanediamide;
(2R,3S)N1-[6,7-dihydro-5-(3-(2-naphthyl)benzyl)-6-oxo-5H-dibenz[b,d]azepin-7-yl]-2-(2-methylpropyl)-3-(allyl)-butanediamide;
(2R,3S)N1-[6,7-dihydro-5-(3-phenoxybenzyl)-6-oxo-5H-dibenz[b,d]azepin-7-yl]-2-(2-methylpropyl)-3-(butyl)-butanediamide;
(2R,3S)N1-[6,7-dihydro-S-(3-(4-methoxyphenyl)benzyl)-6-oxo-5H-dibenz[b,d]azepin-7-yl]-2-(2-methylpropyl)-3-(butyl)-butanediamide;
(2R,3S)N1-[6,7-dihydro-5-(3-(4-trifluoromethylphenyl)benzyl)-6-oxo-5H-dibenz[b,d]azepin-7-yl]-2-(2-methylpropyl)-3-(butyl)-butanediamide;
(2R,3S)N1-[6,7-dihydro-5-(3-(4-methylphenyl)benzyl)-6-oxo-5H-dibenz[b,d]azepin-7-yl]-2-(2-methylpropyl)-3-(butyl)-butanediamide;
(2R,3S)N1-[6,7-dihydro-5-(3-(2,4-dichlorophenyl)benzyl)-6-oxo-5H-dibenz[b,d]azepin-7-yl]-2-(2-methylpropyl)-3-(butyl)-butanediamide;
(2R,3S)N1-[6,7-dihydro-5-(3-(3-chloro-4-fluorophenyl)benzyl)-6-oxo-5H-dibenz[b,d]azepin-7-yl]-2-(2-methylpropyl)-3-(butyl)-butanediamide;
(2R,3S)N1-[6,7-dihydro-5-(benzophenon-3-yl)-6-oxo-5H-dibenz[b,d]azepin-7-yl]-2-(2-methylpropyl)-3-(butyl)-butanediamide;
(2R,3S)N1-[6,7-dihydro-5-(3-(2-naphthyl)benzyl)-6-oxo-5H-dibenz[b,d]azepin-7-yl]-2-(2-methylpropyl)-3-(butyl)-butanediamide;
(2R,3S)N1-[6,7-dihydro-5-(3-phenoxybenzyl)-6-oxo-5H-dibenz[b,d]azepin-7-yl]-2-(cyclopropylmethyl)-3-(propyl)-butanediamide;
(2R,3S)N1-[6,7-dihydro-5-(3-(4-methoxyphenyl)benzyl)-6-oxo-5H-dibenz[b,d]azepin-7-yl]-2-(cyclopropylmethyl)-3-(propyl)-butanediamide;
(2R,3S)N1-[6,7-dihydro-5-(3-(4-trifluoromethylphenyl)benzyl)-6-oxo-5H-dibenz[b,d]azepin-7-yl]-2-(cyclopropylmethyl)-3-(propyl)-butanediamide;
(2R,3S)N1-[6,7-dihydro-5-(3-(4-methylphenyl)benzyl)-6-oxo-5H-dibenz[b,d]azepin-7-yl]-2-(cyclopropylmethyl)-3-(propyl)-butanediamide;
(2R,3S)N1-[6,7-dihydro-5-(3-(2,4-dichlorophenyl)benzyl)-6-oxo-5H-dibenz[b,d]azepin-7-yl]-2-(cyclopropylmethyl)-3-(propyl)-butanediamide;
(2R,3S)N1-[6,7-dihydro-5-(3-(3-chloro-4-fluorophenyl)benzyl)-6-oxo-5H-dibenz[b,d]azepin-7-yl]-2-(cyclopropylmethyl)-3-(propyl)-butanediamide;
(2R,3S)N1-[6,7-dihydro-5-(benzophenon-3-yl)-6-oxo-5H-dibenz[b,d]azepin-7-yl]-2-(cyclopropylmethyl)-3-(propyl)-butanediamide;
(2R,3S)N1-[6,7-dihydro-5-(3-(2-naphthyl)benzyl)-6-oxo-5H-dibenz[b,d]azepin-7-yl]-2-(cyclopropylmethyl)-3-(propyl)-butanediamide;
(2R,3S)N1-[6,7-dihydro-5-(3-phenoxybenzyl)-6-oxo-5H-dibenz[b,d]azepin-7-yl]-2-(cyclopropylmethyl)-3-(allyl)-butanediamide;
(2R,3S)N1-[6,7-dihydro-5-(3-(4-methoxyphenyl)benzyl)-6-oxo-5H-dibenz[b,d]azepin-7-yl]-2-(cyclopropylmethyl)-3-(allyl)-butanediamide;
(2R,3S)N1-[6,7-dihydro-5-(3-(4-trifluoromethylphenyl)benzyl)-6-oxo-5H-dibenz[b,d]azepin-7-yl]-2-(cyclopropylmethyl)-3-(allyl)-butanediamide;
(2R,3S)N1-[6,7-dihydro-5-(3-(4-methylphenyl)benzyl)-6-oxo-5H-dibenz[b,d]azepin-7-yl]-2-(cyclopropylmethyl)-3-(allyl)-butanediamide;

(2R,3S)N1-[6,7-dihydro-5-(3-(2,4-dichlorophenyl)benzyl)-6-oxo-5H-dibenz[b,d]azepin-7-yl]-2-(cyclopropylmethyl)-3-(allyl)-butanediamide;

(2R,3S)N1-[6,7-dihydro-5-(3-(3-chloro-4-fluorophenyl)benzyl)-6-oxo-5H-dibenz[b,d]azepin-7-yl]-2-(cyclopropylmethyl)-3-(allyl)-butanediamide;

(2R,3S)N1-[6,7-dihydro-5-(benzophenon-3-yl)-6-oxo-5H-dibenz[b,d]azepin-7-yl]-2-(cyclopropylmethyl)-3-(allyl)-butanediamide;

(2R,3S)N1-[6,7-dihydro-5-(3-(2-naphthyl)benzyl)-6-oxo-5H-dibenz[b,d]azepin-7-yl]-2-(cyclopropylmethyl)-3-(allyl)-butanediamide;

(2R,3S)N1-[6,7-dihydro-5-(3-phenoxybenzyl)-6-oxo-5H-dibenz[b,d]azepin-7-yl]-2-(cyclopropylmethyl)-3-(butyl)-butanediamide;

(2R,3S)N1-[6,7-dihydro-5-(3-(4-methoxyphenyl)benzyl)-6-oxo-5H-dibenz[b,d]azepin-7-yl]-2-(cyclopropylmethyl)-3-(butyl)-butanediamide;

(2R,3S)N1-[6,7-dihydro-5-(3-(4-trifluoromethylphenyl)benzyl)-6-oxo-5H-dibenz[b,d]azepin-7-yl]-2-(cyclopropylmethyl)-3-(butyl)-butanediamide;

(2R,3S)N1-[6,7-dihydro-5-(3-(4-methylphenyl)benzyl)-6-oxo-5H-dibenz[b,d]azepin-7-yl]-2-(cyclopropylmethyl)-3-(butyl)-butanediamide;

(2R,3S)N1-[6,7-dihydro-5-(3-(2,4-dichlorophenyl)benzyl)-6-oxo-5H-dibenz[b,d]azepin-7-yl]-2-(cyclopropylmethyl)-3-(butyl)-butanediamide;

(2R,3S)N1-[6,7-dihydro-5-(3-(3-chloro-4-fluorophenyl)benzyl)-6-oxo-5H-dibenz[b,d]azepin-7-yl]-2-(cyclopropylmethyl)-3-(butyl)-butanediamide;

(2R,3S)N1-[6,7-dihydro-5-(benzophenon-3-yl)-6-oxo-5H-dibenz[b,d]azepin-7-yl]-2-(cyclopropylmethyl)-3-(butyl)-butanediamide;

(2R,3S)N1-[6,7-dihydro-5-(3-(2-naphthyl)benzyl)-6-oxo-5H-dibenz[b,d]azepin-7-yl]-2-(cyclopropylmethyl)-3-(butyl)-butanediamide;

(2R,3S)N1-[6,7-dihydro-5-(3-phenoxybenzyl)-6-oxo-5H-dibenz[b,d]azepin-7-yl]-2-(cyclobutylmethyl)-3-(propyl)-butanediamide;

(2R,3S)N1-[6,7-dihydro-5-(3-(4-methoxyphenyl)benzyl)-6-oxo-5H-dibenz[b,d]azepin-7-yl]-2-(cyclobutylmethyl)-3-(propyl)-butanediamide;

(2R,3S)N1-[6,7-dihydro-5-(3-(4-trifluoromethylphenyl)benzyl)-6-oxo-5H-dibenz[b,d]azepin-7-yl]-2-(cyclobutylmethyl)-3-(propyl)-butanediamide;

(2R,3S)N1-[6,7-dihydro-5-(3-(4-methylphenyl)benzyl)-6-oxo-5H-dibenz[b,d]azepin-7-yl]-2-(cyclobutylmethyl)-3-(propyl)-butanediamide;

(2R,3S)N1-[6,7-dihydro-5-(3-(2,4-dichlorophenyl)benzyl)-6-oxo-5H-dibenz[b,d]azepin-7-yl]-2-(cyclobutylmethyl)-3-(propyl)-butanediamide;

(2R,3S)N1-[6,7-dihydro-5-(3-(3-chloro-4-fluorophenyl)benzyl)-6-oxo-5H-dibenz[b,d]azepin-7-yl]-2-(cyclobutylmethyl)-3-(propyl)-butanediamide;

(2R,3S)N1-[6,7-dihydro-5-(benzophenon-3-yl)-6-oxo-5H-dibenz[b,d]azepin-7-yl]-2-(cyclobutylmethyl)-3-(propyl)-butanediamide;

(2R,3S)N1-[6,7-dihydro-5-(3-(2-naphthyl)benzyl)-6-oxo-5H-dibenz[b,d]azepin-7-yl]-2-(cyclobutylmethyl)-3-(propyl)-butanediamide;

(2R,3S)N1-[6,7-dihydro-5-(3-phenoxybenzyl)-6-oxo-5H-dibenz[b,d]azepin-7-yl]-2-(cyclobutylmethyl)-3-(allyl)-butanediamide;

(2R,3S)N1-[6,7-dihydro-5-(3-(4-methoxyphenyl)benzyl)-6-oxo-5H-dibenz[b,d]azepin-7-yl]-2-(cyclobutylmethyl)-3-(allyl)-butanediamide;

(2R,3S)N1-[6,7-dihydro-5-(3-(4-trifluoromethylphenyl)benzyl)-6-oxo-5H-dibenz[b,d]azepin-7-yl]-2-(cyclobutylmethyl)-3-(allyl)-butanediamide;

(2R,3S)N1-[6,7-dihydro-5-(3-(4-methylphenyl)benzyl)-6-oxo-5H-dibenz[b,d]azepin-7-yl]-2-(cyclobutylmethyl)-3-(allyl)-butanediamide;

(2R,3S)N1-[6,7-dihydro-5-(3-(2,4-dichlorophenyl)benzyl)-6-oxo-5H-dibenz[b,d]azepin-7-yl]-2-(cyclobutylmethyl)-3-(allyl)-butanediamide;

(2R,3S)N1-[6,7-dihydro-5-(3-(3-chloro-4-fluorophenyl)benzyl)-6-oxo-5H-dibenz[b,d]azepin-7-yl]-2-(cyclobutylmethyl)-3-(allyl)-butanediamide;

(2R,3S)N1-[6,7-dihydro-5-(benzophenon-3-yl)-6-oxo-5H-dibenz[b,d]azepin-7-yl]-2-(cyclobutylmethyl)-3-(allyl)-butanediamide;

(2R,3S)N1-[6,7-dihydro-5-(3-(2-naphthyl)benzyl)-6-oxo-5H-dibenz[b,d]azepin-7-yl]-2-(cyclobutylmethyl)-3-(allyl)-butanediamide;

(2R,3S)N1-[6,7-dihydro-5-(3-phenoxybenzyl)-6-oxo-5H-dibenz[b,d]azepin-7-yl]-2-(cyclobutylmethyl)-3-(butyl)-butanediamide;

(2R,3S)N1-[6,7-dihydro-5-(3-(4-methoxyphenyl)benzyl)-6-oxo-5H-dibenz[b,d]azepin-7-yl]-2-(cyclobutylmethyl)-3-(butyl)-butanediamide;

(2R,3S)N1-[6,7-dihydro-5-(3-(4-trifluoromethylphenyl)benzyl)-6-oxo-5H-dibenz[b,d]azepin-7-yl]-2-(cyclobutylmethyl)-3-(butyl)-butanediamide;

(2R,3S)N1-[6,7-dihydro-5-(3-(4-methylphenyl)benzyl)-6-oxo-5H-dibenz[b,d]azepin-7-yl]-2-(cyclobutylmethyl)-3-(butyl)-butanediamide;

(2R,3S)N1-[6,7-dihydro-5-(3-(2,4-dichlorophenyl)benzyl)-6-oxo-5H-dibenz[b,d]azepin-7-yl]-2-(cyclobutylmethyl)-3-(butyl)-butanediamide;

(2R,3S)N1-[6,7-dihydro-5-(3-(3-chloro-4-fluorophenyl)benzyl)-6-oxo-5H-dibenz[b,d]azepin-7-yl]-2-(cyclobutylmethyl)-3-(butyl)-butanediamide;

(2R,3S)N1-[6,7-dihydro-5-(benzophenon-3-yl)-6-oxo-5H-dibenz[b,d]azepin-7-yl]-2-(cyclobutylmethyl)-3-(butyl)-butanediamide;

(2R,3S)N1-[6,7-dihydro-5-(3-(2-naphthyl)benzyl)-6-oxo-5H-dibenz[b,d]azepin-7-yl]-2-(cyclobutylmethyl)-3-(butyl)-butanediamide;

(2R,3S)N1-[6,7-dihydro-5-(3-phenoxybenzyl)-6-oxo-5H-dibenz[b,d]azepin-7-yl]-2-(cyclopentylmethyl)-3-(propyl)-butanediamide;

(2R,3S)N1-[6,7-dihydro-5-(3-(4-methoxyphenyl)benzyl)-6-oxo-5H-dibenz[b,d]azepin-7-yl]-2-(cyclopentylmethyl)-3-(propyl)-butanediamide;

(2R,3S)N1-[6,7-dihydro-5-(3-(4-trifluoromethylphenyl)benzyl)-6-oxo-5H-dibenz[b,d]azepin-7-yl]-2-(cyclopentylmethyl)-3-(propyl)-butanediamide;

(2R,3S)N1-[6,7-dihydro-5-(3-(4-methylphenyl)benzyl)-6-oxo-5H-dibenz[b,d]azepin-7-yl]-2-(cyclopentylmethyl)-3-(propyl)-butanediamide;

(2R,3S)N1-[6,7-dihydro-5-(3-(2,4-dichlorophenyl)benzyl)-6-oxo-5H-dibenz[b,d]azepin-7-yl]-2-(cyclopentylmethyl)-3-(propyl)-butanediamide;

(2R,3S)N1-[6,7-dihydro-5-(3-(3-chloro-4-fluorophenyl)benzyl)-6-oxo-5H-dibenz[b,d]azepin-7-yl]-2-(cyclopentylmethyl)-3-(propyl)-butanediamide;

(2R,3S)N1-[6,7-dihydro-5-(benzophenon-3-yl)-6-oxo-5H-dibenz[b,d]azepin-7-yl]-2-(cyclopentylmethyl)-3-(propyl)-butanediamide;

(2R,3S)N1-[6,7-dihydro-5-(3-(2-naphthyl)benzyl)-6-oxo-5H-dibenz[b,d]azepin-7-yl]-2-(cyclopentylmethyl)-3-(propyl)-butanediamide;

(2R,3S)N1-[6,7-dihydro-5-(3-phenoxybenzyl)-6-oxo-5H-dibenz[b,d]azepin-7-yl]-2-(cyclopentylmethyl)-3-(allyl)-butanediamide;

(2R,3S)N1-[6,7-dihydro-5-(3-(4-methoxyphenyl)benzyl)-6-oxo-5H-dibenz[b,d]azepin-7-yl]-2-(cyclopentylmethyl)-3-(allyl)-butanediamide;

(2R,3S)N1-[6,7-dihydro-5-(3-(4-trifluoromethylphenyl)benzyl)-6-oxo-5H-dibenz[b,d]azepin-7-yl]-2-(cyclopentylmethyl)-3-(allyl)-butanediamide;

(2R,3S)N1-[6,7-dihydro-5-(3-(4-methylphenyl)benzyl)-6-oxo-5H-dibenz[b,d]azepin-7-yl]-2-(cyclopentylmethyl)-3-(allyl)-butanediamide;

(2R,3S)N1-[6,7-dihydro-5-(3-(2,4-dichlorophenyl)benzyl)-6-oxo-5H-dibenz[b,d]azepin-7-yl]-2-(cyclopentylmethyl)-3-(allyl)-butanediamide;

(2R,3S)N1-[6,7-dihydro-5-(3-(3-chloro-4-fluorophenyl)benzyl)-6-oxo-5H-dibenz[b,d]azepin-7-yl]-2-(cyclopentylmethyl)-3-(allyl)-butanediamide;

(2R,3S)N1-[6,7-dihydro-5-(benzophenon-3-yl)-6-oxo-5H-dibenz[b,d]azepin-7-yl]-2-(cyclopentylmethyl)-3-(allyl)-butanediamide;

(2R,3S)N1-[6,7-dihydro-5-(3-(2-naphthyl)benzyl)-6-oxo-5H-dibenz[b,d]azepin-7-yl]-2-(cyclopentylmethyl)-3-(allyl)-butanediamide;

(2R,3S)N1-[6,7-dihydro-5-(3-phenoxybenzyl)-6-oxo-5H-dibenz[b,d]azepin-7-yl]-2-(cyclopentylmethyl)-3-(butyl)-butanediamide;

(2R,3S)N1-[6,7-dihydro-5-(3-(4-methoxyphenyl)benzyl)-6-oxo-5H-dibenz[b,d]azepin-7-yl]-2-(cyclopentylmethyl)-3-(butyl)-butanediamide;

(2R,3S)N1-[6,7-dihydro-5-(3-(4-trifluoromethylphenyl)benzyl)-6-oxo-5H-dibenz[b,d]azepin-7-yl]-2-(cyclopentylmethyl)-3-(butyl)-butanediamide;

(2R,3S)N1-[6,7-dihydro-5-(3-(4-methylphenyl)benzyl)-6-oxo-5H-dibenz[b,d]azepin-7-yl]-2-(cyclopentylmethyl)-3-(butyl)-butanediamide;

(2R,3S)N1-[6,7-dihydro-5-(3-(2,4-dichlorophenyl)benzyl)-6-oxo-5H-dibenz[b,d]azepin-7-yl]-2-(cyclopentylmethyl)-3-(butyl)-butanediamide;

(2R,3S)N1-[6,7-dihydro-5-(3-(3-chloro-4-fluorophenyl)benzyl)-6-oxo-5H-dibenz[b,d]azepin-7-yl]-2-(cyclopentylmethyl)-3-(butyl)-butanediamide;

(2R,3S)N1-[6,7-dihydro-5-(benzophenon-3-yl)-6-oxo-5H-dibenz[b,d]azepin-7-yl]-2-(cyclopentylmethyl)-3-(butyl)-butanediamide; and (2R,3S)N1-[6,7-dihydro-5-(3-(2-naphthyl)benzyl)-6-oxo-5H-dibenz[b,d]azepin-7-yl]-2-(cyclopentylmethyl)-3-(butyl)-butanediamide.

(2R,3S)N1-[6,7-dihydro-5-(benzyl)-6-oxo-5H-dibenz[b,d]azepin-7-yl]-2-(2-methylpropyl)-3-(propyl)-butanediamide;

(2R,3S)N1-[6,7-dihydro-5-(phenethyl)-6-oxo-5H-dibenz[b,d]azepin-7-yl]-2-(2-methylpropyl)-3-(propyl)-butanediamide;

(2R,3S)N1-[6,7-dihydro-5-((4-fluorophenyl)methyl)-6-oxo-5H-dibenz[b,d]azepin-7-yl]-2-(2-methylpropyl)-3-(propyl)-butanediamide;

(2R,3S)N1-[6,7-dihydro-5-(cyclopropylmethyl)-6-oxo-5H-dibenz[b,d]azepin-7-yl]-2-(2-methylpropyl)-3-(propyl)-butanediamide;

(2R,3S)N1-[6,7-dihydro-5-(cyclobutylmethyl)-6-oxo-5H-dibenz[b,d]azepin-7-yl]-2-(2-methylpropyl)-3-(propyl)-butanediamide;

(2R,3S)N1-[6,7-dihydro-5-(cyclopentylmethyl)-6-oxo-5H-dibenz[b,d]azepin-7-yl]-2-(2-methylpropyl)-3-(propyl)-butanediamide;

(2R,3S)N1-[6,7-dihydro-5-(cyclohexylmethyl)-6-oxo-5H-dibenz[b,d]azepin-7-yl]-2-(2-methylpropyl)-3-(propyl)-butanediamide;

(2R,3S)N1-[6,7-dihydro-5-(cyclopropylethyl)-6-oxo-5H-dibenz[b,d]azepin-7-yl]-2-(2-methylpropyl)-3-(propyl)-butanediamide;

(2R,3S)N1-[6,7-dihydro-5-(cyclobutylethyl)-6-oxo-5H-dibenz[b,d]azepin-7-yl]-2-(2-methylpropyl)-3-(propyl)-butanediamide;

(2R,3S)N1-[6,7-dihydro-5-(cyclopentylethyl)-6-oxo-5H-dibenz[b,d]azepin-7-yl]-2-(2-methylpropyl)-3-(propyl)-butanediamide;

(2R,3S)N1-[6,7-dihydro-5-(cyclohexylethyl)-6-oxo-5H-dibenz[b,d]azepin-7-yl]-2-(2-methylpropyl)-3-(propyl)-butanediamide;

(2R,3S)N1-[6,7-dihydro-5-(benzyl)-6-oxo-5H-dibenz[b,d]azepin-7-yl]-2-(2-methylpropyl)-3-(allyl)-butanediamide;

(2R,3S)N1-[6,7-dihydro-5-(phenethyl)-6-oxo-5H-dibenz[b,d]azepin-7-yl]-2-(2-methylpropyl)-3-(allyl)-butanediamide;

(2R,3S)N1-[6,7-dihydro-5-((4-fluorophenyl)methyl)-6-oxo-5H-dibenz[b,d]azepin-7-yl]-2-(2-methylpropyl)-3-(allyl)-butanediamide;

(2R,3S)N1-[6,7-dihydro-5-(cyclopropylmethyl)-6-oxo-5H-dibenz[b,d]azepin-7-yl]-2-(2-methylpropyl)-3-(allyl)-butanediamide;

(2R,3S)N1-[6,7-dihydro-5-(cyclobutylmethyl)-6-oxo-5H-dibenz[b,d]azepin-7-yl]-2-(2-methylpropyl)-3-(allyl)-butanediamide;

(2R,3S)N1-[6,7-dihydro-5-(cyclopentylmethyl)-6-oxo-5H-dibenz[b,d]azepin-7-yl]-2-(2-methylpropyl)-3-(allyl)-butanediamide;

(2R,3S)N1-[6,7-dihydro-5-(cyclohexylmethyl)-6-oxo-5H-dibenz[b,d]azepin-7-yl]-2-(2-methylpropyl)-3-(allyl)-butanediamide;

(2R,3S)N1-[6,7-dihydro-5-(cyclopropylethyl)-6-oxo-5H-dibenz[b,d]azepin-7-yl]-2-(2-methylpropyl)-3-(allyl)-butanediamide;

(2R,3S)N1-[6,7-dihydro-5-(cyclobutylethyl)-6-oxo-5H-dibenz[b,d]azepin-7-yl]-2-(2-methylpropyl)-3-(allyl)-butanediamide;

(2R,3S)N1-[6,7-dihydro-5-(cyclopentylethyl)-6-oxo-5H-dibenz[b,d]azepin-7-yl]-2-(2-methylpropyl)-3-(allyl)-butanediamide;

(2R,3S)N1-[6,7-dihydro-5-(cyclohexylethyl)-6-oxo-5H-dibenz[b,d]azepin-7-yl]-2-(2-methylpropyl)-3-(allyl)-butanediamide;

(2R,3S)N1-[6,7-dihydro-5-(benzyl)-6-oxo-5H-dibenz[b,d]azepin-7-yl]-2-(2-methylpropyl)-3-(butyl)-butanediamide;

(2R,3S)N1-[6,7-dihydro-5-(phenethyl)-6-oxo-5H-dibenz[b,d]azepin-7-yl]-2-(2-methylpropyl)-3-(butyl)-butanediamide;

(2R,3S)N1-[6,7-dihydro-5-((4-fluorophenyl)methyl)-6-oxo-5H-dibenz[b,d]azepin-7-yl]-2-(2-methylpropyl)-3-(butyl)-butanediamide;

(2R,3S)N1-[6,7-dihydro-5-(cyclopropylmethyl)-6-oxo-5H-dibenz[b,d]azepin-7-yl]-2-(2-methylpropyl)-3-(butyl)-butanediamide;

(2R,3S)N1-[6,7-dihydro-5-(cyclobutylmethyl)-6-oxo-5H-dibenz[b,d]azepin-7-yl]-2-(2-methylpropyl)-3-(butyl)-butanediamide;

(2R,3S)N1-[6,7-dihydro-5-(cyclopentylmethyl)-6-oxo-5H-dibenz[b,d]azepin-7-yl]-2-(2-methylpropyl)-3-(butyl)-butanediamide;

(2R,3S)N1-[6,7-dihydro-5-(cyclohexylmethyl)-6-oxo-5H-dibenz[b,d]azepin-7-yl]-2-(2-methylpropyl)-3-(butyl)-butanediamide;

(2R,3S)N1-[6,7-dihydro-5-(cyclopropylethyl)-6-oxo-5H-dibenz[b,d]azepin-7-yl]-2-(2-methylpropyl)-3-(butyl)-butanediamide;

(2R,3S)N1-[6,7-dihydro-5-(cyclobutylethyl)-6-oxo-5H-dibenz[b,d]azepin-7-yl]-2-(2-methylpropyl)-3-(butyl)-butanediamide;

(2R,3S)N1-[6,7-dihydro-5-(cyclopentylethyl)-6-oxo-5H-dibenz[b,d]azepin-7-yl]-2-(2-methylpropyl)-3-(butyl)-butanediamide; and (2R,3S)N1-[6,7-dihydro-5-(cyclohexylethyl)-6-oxo-5H-dibenz[b,d]azepin-7-yl]-2-(2-methylpropyl)-3-(butyl)-butanediamide.

[22] In another even more preferred embodiment the present invention provides compounds of Formula (I) selected from:

(2R,3S)N1-[1,3,4,5-tetrahydro-1-(3-phenoxybenzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclopentylmethyl)-3-(butyl)-butanediamide; and (2R,3S)N1-[1,3,4,5-tetrahydro-1-(3-(2-naphthyl)benzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(phenethyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-((4-fluorophenyl)methyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(cyclopropylmethyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(cyclobutylmethyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(cyclopentylmethyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(cyclohexylmethyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(cyclopropylethyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(cyclobutylethyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(cyclopentylethyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(cyclohexylethyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(phenethyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-((4-fluorophenyl)methyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(cyclopropylmethyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(cyclobutylmethyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(cyclopentylmethyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(cyclohexylmethyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(cyclopropylethyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(cyclobutylethyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(cyclopentylethyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(cyclohexylethyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(phenethyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-((4-fluorophenyl)methyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(cyclopropylmethyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(cyclobutylmethyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(cyclopentylmethyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(cyclohexylmethyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(cyclopropylethyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(cyclobutylethyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(cyclopentylethyl)-2-oxo-5-(phenyl)-2H-1,5-benzodiazepin-3-yl]-2-(2-methylpropyl)-3-(butyl)-butanediamide; and (2R,3S)N1-[1,3,4,5-tetrahydro-1-(cyclohexylethyl)-2-oxo-5-(phenyl)-2H-1,5-benzodiazepin-3-yl]-2-(2-methylpropyl)-3-(butyl)-butanediamide.

[23] In another even more preferred embodiment the present invention provides compounds of Formula (I) selected from:

(2R,3S)N1-[(3S)-hexahydro-1-(3,3-diphenylpropyl)-2-oxo-1H-azepin-3-yl]-N4-(hydroxy)-2-(2-methylpropyl)-3-(propyl)-butanediamide;

(2R,3S)N1-[(3S)-hexahydro-1-(3-phenoxybenzyl)-2-oxo-1H-azepin-3-yl]-N4-(hydroxy)-2-(2-methylpropyl)-3-(propyl)-butanediamide;

(2R,3S)N1-[(3S)-hexahydro-1-(phenyl)-2-oxo-1H-azepin-3-yl]-N4-(hydroxy)-2-(2-methylpropyl)-3-(propyl)-butanediamide;

(2R,3S)N1-[(3S)-hexahydro-1-(3-phenoxybenzyl)-2-oxo-1H-azepin-3-yl]-N4-(methyl)-2-(2-methylpropyl)-3-(propyl)-butanediamide;

(2R,3S)N1-[(3S)-hexahydro-1-(3-phenoxybenzyl)-2-oxo-1H-azepin-3-yl]-N4-(methoxy)-N4-(methyl)-2-(2-methylpropyl)-3-(propyl)-butanediamide;

(2R,3S)N1-[(3S)-hexahydro-1-(3-phenoxybenzyl)-2-oxo-1H-azepin-3-yl]-N4-(methoxy)-2-(2-methylpropyl)-3-(propyl)-butanediamide;

(2R,3S)N1-[(3S)-hexahydro-1-(3-phenoxybenzyl)-2-oxo-1H-azepin-3-yl]-N4-(amino)-2-(2-methylpropyl)-3-(propyl)-butanediamide;

(2R,3S)N1-[(3S)-hexahydro-1-(3-phenoxybenzyl)-2-oxo-1H-azepin-3-yl]-N4-(hydroxy)-2-(2-methylpropyl)-3-(allyl)-butanediamide;

(2R,3S)N1-[(3S)-hexahydro-1-(3-(2,4-dichlorophenyl)benzyl)-2-oxo-1H-azepin-3-yl]-N4-(hydroxy)-2-(2-methylpropyl)-3-(propyl)-butanediamide;

(2R,3S)N1-[(3S)-hexahydro-1-(3-(4-fluorophenyl)benzyl)-2-oxo-1H-azepin-3-yl]-N4-(hydroxy)-2-(2-methylpropyl)-3-(propyl)-butanediamide;

(2R,3S)N1-[(3S)-hexahydro-1-(3-(4-methylphenyl)benzyl)-2-oxo-1H-azepin-3-yl]-N4-(hydroxy)-2-(2-methylpropyl)-3-(propyl)-butanediamide;

(2R,3S)N1-[(3S)-hexahydro-1-(3-(4-methoxyphenyl)benzyl)-2-oxo-1H-azepin-3-yl]-N4-(hydroxy)-2-(2-methylpropyl)-3-(propyl)-butanediamide;

(2R,3S)N1-[(3S)-hexahydro-1-(3-(3-methylphenyl)benzyl)-2-oxo-1H-azepin-3-yl]-N4-(hydroxy)-2-(2-methylpropyl)-3-(propyl)-butanediamide;

(2R,3S)N1-[(3S)-hexahydro-1-(3-(3-chloro-4-fluorophenyl)benzyl)-2-oxo-1H-azepin-3-yl]-N4-(hydroxy)-2-(2-methylpropyl)-3-(propyl)-butanediamide;

(2R,3S)N1-[(3S)-hexahydro-1-(3-(4-trifluoromethylphenyl)benzyl)-2-oxo-1H-azepin-3-yl]-N4-(hydroxy)-2-(2-methylpropyl)-3-(propyl)-butanediamide;

(2R,3S)N1-[(3S)-hexahydro-1-(3-(3-methoxyphenyl)benzyl)-2-oxo-1H-azepin-3-yl]-N4-(hydroxy)-2-(2-methylpropyl)-3-(propyl)-butanediamide;

(2R,3S)N1-[(3S)-hexahydro-1-(3-(3-fluorophenyl)benzyl)-2-oxo-1H-azepin-3-yl]-N4-(hydroxy)-2-(2-methylpropyl)-3-(propyl)-butanediamide;

(2R,3S)N1-[(3S)-hexahydro-1-(3-(2-methoxyphenyl)benzyl)-2-oxo-1H-azepin-3-yl]-N4-(hydroxy)-2-(2-methylpropyl)-3-(propyl)-butanediamide;

(2R,3S)N1-[(3S)-hexahydro-1-(3-(2-naphthyl)benzyl)-2-oxo-1H-azepin-3-yl]-N4-(hydroxy)-2-(2-methylpropyl)-3-(propyl)-butanediamide;

(2R,3S)N1-[(3S)-hexahydro-1-(3-phenoxybenzyl)-2-oxo-1H-azepin-3-yl]-N4-(butyl)-2-(2-methylpropyl)-3-(propyl)-butanediamide;

(2R,3S)N1-[(3S)-hexahydro-1-(3-phenoxybenzyl)-2-oxo-1H-azepin-3-yl]-N4-(2-furylmethyl)-2-(2-methylpropyl)-3-(propyl)-butanediamide;

(2R,3S)N1-[(3S)-hexahydro-1-(3-phenoxybenzyl)-2-oxo-1H-azepin-3-yl]-N4-(cyclopentyl)-2-(2-methylpropyl)-3-(propyl)-butanediamide; and (2R,3S)N1-[(3S)-hexahydro-1-(3-phenoxybenzyl)-2-oxo-1H-azepin-3-yl]-N4-(cinnamyl)-2-(2-methylpropyl)-3-(propyl)-butanediamide.

In another preferred embodiment of the present invention, Q is N(OH)H.

In another preferred embodiment of the present invention, Q is $NH_2$.

In another preferred embodiment
$R^3$ is $R^4$,
$R^{3a}$ is H, methyl, ethyl, propyl, or butyl;
$R^4$ is $C_1$-$C_6$ alkyl, $C_2$-$C_6$ alkenyl, $C_2$-$C_6$ alkynyl
$R^5$ is $C_1$-$C_6$ alkyl, $C_2$-$C_6$ alkenyl, $C_2$-$C_6$ alkynyl
$R^{5a}$ is H, methyl, ethyl, propyl, or butyl; and
the total number of carbon atoms in $R^3$, $R^{3a}$, $R^5$ and $R^{5a}$ equals seven or more.

In another preferred embodiment
$R^3$ is $R^4$;
$R^{3a}$ is H;
$R^4$ is $C_1$-$C_4$ alkyl substituted with 1-2 $R^{4a}$,
$R^{4a}$, at each occurrence, is independently selected from
  $C_3$-$C_6$ cycloalkyl substituted with 0-3 $R^{4b}$,
  phenyl substituted with 0-3 $R^{4b}$, or
  5 to 6 membered heterocycle substituted with 0-3 $R^{4b}$;
$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
$R^5$ is $C_2$-$C_4$ alkyl substituted with 0-3 $R^{5b}$;
  $C_2$-$C_4$ alkenyl substituted with 0-2 $R^{5b}$; or
  $C_2$-$C_4$ alkynyl substituted with 0-2 $R^{5b}$;
$R^{5b}$, at each occurrence, is independently selected from:
  H, methyl, ethyl, propyl, butyl, $CF_3$, $OR^{14}$, =O;
  $C_3$-$C_6$ cycloalkyl substituted with 0-2 $R^{5c}$;
  phenyl substituted with 0-3 $R^{5c}$; or
  5 to 6 membered heterocycle substituted with 0-2 $R^{5c}$; and
$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy.

In another preferred embodiment
$R^3$ is $R^4$;
$R^{3a}$ is H;
$R^4$ is $C_2$-$C_4$ alkyl substituted with 0-2 $R^{4a}$,
  $C_2$-$C_4$ alkenyl substituted with 0-2 $R^{4a}$,
  $C_2$-$C_4$ alkynyl substituted with 0-2 $R^{4a}$,
$R^{4a}$, at each occurrence, is independently selected from is H, F, $CF_3$,
  $C_3$-$C_6$ cycloalkyl substituted with 0-3 $R^{4b}$,
  phenyl substituted with 0-3 $R^{4b}$, or
  5 to 6 membered heterocycle substituted with 0-3 $R^{4b}$;
$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
$R^5$ is $C_1$-$C_4$ alkyl substituted with 1-2 $R^{5b}$;
$R^{5b}$, at each occurrence, is independently selected from:
  $C_3$-$C_6$ cycloalkyl substituted with 0-2 $R^{5c}$;

phenyl substituted with 0-3 $R^{5c}$; or 5 to 6 membered heterocycle substituted with 0-2 $R^{5c}$; and $R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy.

In another preferred embodiment

W is —$(CH_2)_p$—;

p is 1, 2, or 3;

X is a bond;

phenyl substituted with 0-2 $R^{Xb}$;

$C_3$-$C_6$ cycloalkyl substituted with 0-2 $R^{Xb}$; or 5 to 6 membered heterocycle substituted with 0-2 $R^{Xb}$;

wherein the 5 to 6 membered heterocycle does not contain an oxo or imino substitued ring atom; and $R^{Xb}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy.

In another preferred embodiment when $R^1$ is H, $R^2$ is hydroxy, and $R^{11}$ is H, then X is not a bond.

It is understood that any and all embodiments of the present invention may be taken in conjunction with any other embodiment to describe additional even more preferred embodiments of the present invention.

In a second embodiment, the present invention provides a pharmaceutical composition comprising a compound of Formula (I) and a pharmaceutically acceptable carrier.

In a third embodiment, the present invention provides a method for the treatment of neurological disorders associated with β-amyloid production comprising administering to a host in need of such treatment a therapeutically effective amount of a compound of Formula (I).

In a preferred embodiment the neurological disorder associated with β-amyloid production is Alzheimer's Disease.

In a fourth embodiment, the present invention provides a method for the treatment of neurological disorders associated with β-amyloid production comprising administering to a host in need of such treatment a therapeutically effective amount of a metalloprotease inhibitor which inhibits γ-secretase activity.

In a preferred embodiment the neurological disorder associated with β-amyloid production is Alzheimer's Disease.

In a preferred embodiment, the metalloprotease inhibitor is a hydroxamic acid.

In a more preferred embodiment, the metalloprotease inhibitor is a hydroxamic acid with an $IC_{50}$ value of less than 10 μM in the Aβ immunoprecipitation assay.

In a fifth embodiment, the present invention provides a method for inhibiting γ-secretase activity for the treatment of a physiological disorder associated with inhibiting γ-secretase activity comprising administering to a host in need of such inhibition a therapeutically effective amount of a compound of Formula (I) that inhibits γ-secretase activity.

In a preferred embodiment the physiological disorder associated with inhibiting γ-secretase activity is Alzheimer's Disease.

In a sixth embodiment, the present invention provides a compound of Formula (I) for use in therapy.

In a preferred embodiment the present invention provides a compound of Formula (I) for use in therapy of Alzheimer's Disease.

In a seventh embodiment, the present invention provides for the use of a compound of Formula (I) for the manufacture of a medicament for the treatment of Alzheimer's Disease.

Definitions

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is:

1
```
Asp Ala Glu Phe Arg His Asp Ser Gly Tyr
11
Glu Val His His Gln Lys Leu Val Phe Phe
21
Ala Glu Asp Val Gly Ser Asn Lys Gly Ala
31
Ile Ile Gly Leu Met Val Gly Gly Val Val
41
Ile Ala Thr.
```

However, a skilled artisan knows that fragments generated by enzymatic degradation can result in loss of amino acids 1-10 and/or amino acids 39-43. Thus, an amino acid sequence 1-43 represents the maximum sequence of amino acids for Aβ peptide.

The term "APP", as used herein, refers to the protein known in the art as b amyloid precursor protein. This protein is the precursor for Aβ and through the activity of "secretase" enzymes, as used herein, it is processed into Aβ. Differing secretase enzymes, known in the art, have been designated b secretase, generating the N-terminus of Aβ, a secretase cleaving around the 16/17 peptide bond in Aβ, and "γ secretases", as used herein, generating C-terminal Aβ fragments ending at position 38, 39, 40, 41, 42, and 43 or generating C-terminal extended precursors which are subsequently truncated to the above polypeptides.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^{5b}$) occurs more than one time in any constituent or formula for a compound, its definition at each occurrence is independent of its definition at every other occurrence. Thus, for example, if a group is shown to be substituted with 0-2 $R^{5b}$, then said group may optionally be substituted with up to two $R^{5b}$ groups and $R^{5b}$ at each occurrence is selected independently from the definition of $R^{5b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$-$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group, unless otherwise specified, is "$C_1$-$C_4$ alkyl".

As used herein, "alkenyl" or "alkenylene" is intended to include hydrocarbon chains of either a straight or branched configuration and one or more unsaturated carbon-carbon bonds which may occur in any stable point along the chain. Examples of "$C_2$-$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" or "alkynylene" is intended to include hydrocarbon chains of either a straight or branched configuration and one or more carbon-carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" is represents an alkyl group as defined above with the indicated number of carbon atoms attached through a sulphur bridge.

"Halo" or "halogen" as used herein refers to fluoro, chloro, bromo, and iodo. Unless otherwise specified, preferred halo is fluoro and chloro. "Counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

"Cycloalkyl" is intended to include saturated ring groups, having the specified number of carbon atoms. For example, "$C_3$-$C_6$ cycloalkyl" denotes such as cyclopropyl, cyclobutyl, cyclopentyl, or cyclohexyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred "carbocycle" are cyclopropyl, cyclobutyl, cyclopentyl, and cyclohexyl.

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms, preferably 1, 2, or 3 heteroatoms, independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", "$C_6$-$C_{10}$ aryl" or aromatic residue, is intended to mean an aromatic moiety containing the specified number of carbon atoms; for example phenyl, pyridinyl or naphthyl. Unless otherwise specified, "aryl" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The phrase "additional lactam carbons and thiolactam carbons", as used herein, is intended to denote the number of optional carbon atoms in the lactam ring or thiolactam ring B of Formula (I). Formula (I''):

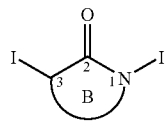
(I'')

represents the lactam ring B of Formula (I). The ring numbering shown for lactams of Formula (I'') applies to analogous thiolactams. Additional lactam carbons are carbons in lactam ring B other than the carbons numbered 2 and 3 in the backbone of the formula. The additional lactam carbons may be optionally replaced by a heteroatom selected from oxygen, nitrogen and sulfur. Lactam ring B contains 1, 2, 3, 4, 5, 6 or 7 optional carbons, wherein one optional carbon may optionally be replaced by a heteroatom, such that the total number of members of lactam ring B, including atoms numbered 1, 2 and 3 in the backbone, does not exceed 10. It is preferred that the total number of atoms of lactam ring B is 6, 7 or 8; it is more preferred that the total number of atoms of lactam ring B is seven. Examples of lactam ring B include:

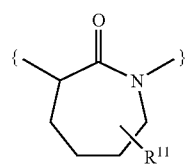
B1

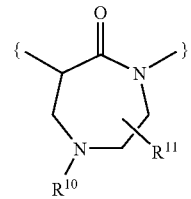
B2

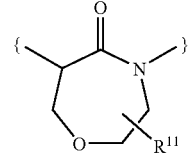
B3

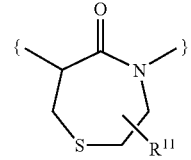
B4

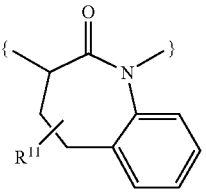
B5

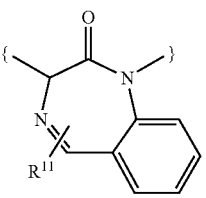
B6

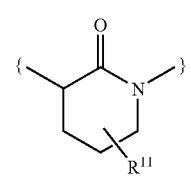
B7

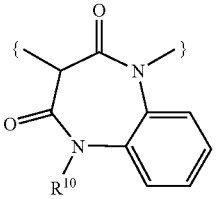
B8

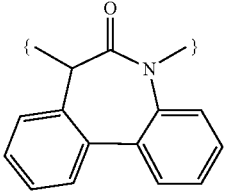
B9

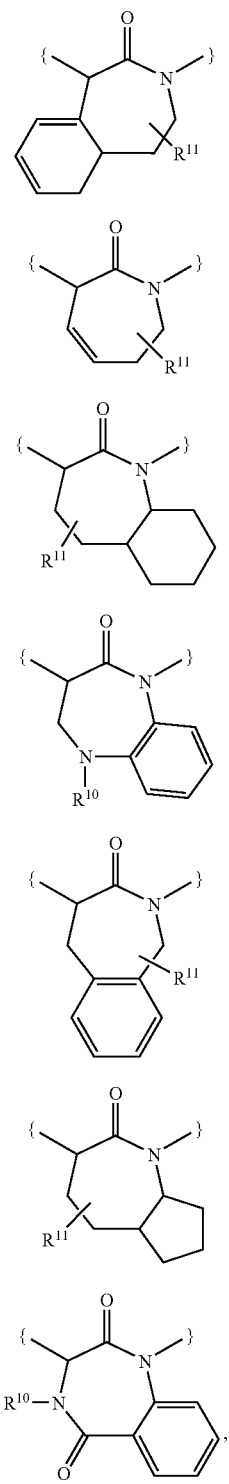

B10

B11

B12

B13

B14

B15

B16 and their thiolactam counterparts. The examples are not intended to limit the invention. Preferred examples of lactam ring B are B1, B2, B5, B6, B8, B9, B13, and B16; more preferred examples of lactam ring B are B1, B6, B8, B9, and B13. Preferred examples of substituent $R^{10}$ or $R^{11}$ on lactam B are methyl, ethyl, phenyl, 4-fluorophenyl, 4-chlorophenyl, 4-trifluorophenyl, (4-fluorophenyl)methyl, (4-chlorophenyl)methyl, and (4-trifluorophenyl)methyl.

The compounds herein described may have asymmetric centers. One enantiomer of a compound of Formula (I) may display superior chemical activity over the opposite enantiomer. For example carbon 3 of lactam ring B Formula (I″) may exist in either an S or R configuration. Thus, an R or S configuration at carbon 3 in Formula (I″) is considered part of the invention. An example of such configuration includes,

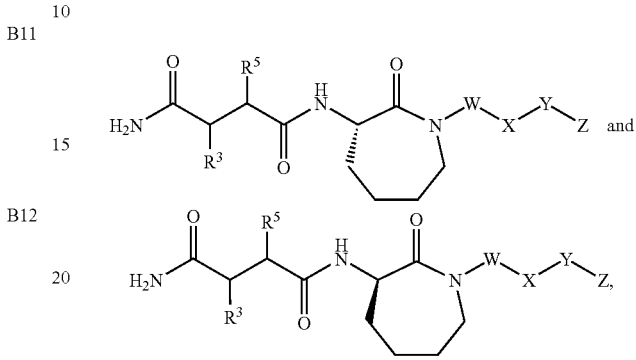

but is not intended to be limited to this example of ring B. When required, separation of the racemic material can be achieved by methods known in the art. Additionally, the carbon atoms to which $R^3$ and $R^5$ are attached may describe chiral carbons which may display superior chemical activity over the opposite enantiomer. For example, where $R^3$ and $R^5$ are not H, then the configuration of the two centers may be described as (2R,3R), (2R,3S), (2S,3R), or (2S,3S). All configurations are considered part of the invention; however, the (2R,3S) and the (2S,3R) are preferred and the (2R,3S) is more preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Methods for the synthesis of succinylamino lactams are known in the art and are disclosed in a number of references including PCT publication number WO 96/29313, which is hereby incorporated by reference.

Disubstituted succinate derivatives can be prepared by a number of known procedures. The procedure of Evans (D. A. Evans et al, *Org. Synth*. 86, p83 (1990)) is outlined in Scheme 1 where acylation of an oxazolidinone with an acylating agent such as an acid chloride provides structures 1. Alkylation to form 2 followed by cleavage of the chiral auxiliary and subsequent alkylation of the dianion of the carboxylic acid 3 provides a variety of disubstituted succinates which can be separated and incorporated into structures of Formula (I) by those skilled in the art. Additional examples are found in P. Becket, M. J. Crimmin, M. H. Davis, Z. Spavold, Synlett, (1993), 137-138, incorporated herein by reference.

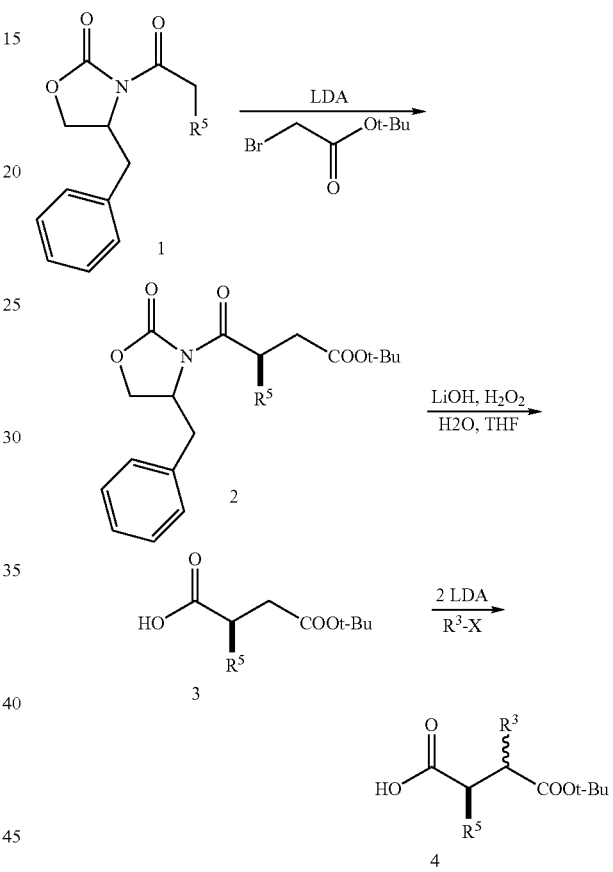

Scheme 1

Diastereomerically pure succinate derivatives can be accessed using the chemistry outlined below, adapted from P. Becket, M. J. Crimmin, M. H. Davis, Z. Spavold, Synlett, (1993), 137-138 incorporated herein by reference. This reference provides the synthesis below to obtain compound 9. Compound 11 is used as an intermediate and is prepared from 9 by hydrogenation of the allyl group followed by coupling of 9-fluorenemethanol under standard conditions using DCC and DMAP in $CH_2Cl_2$. Deprotection of the tert-butyl ester is accomplished by treatment with 50% trifluoroacetic acid.

Additional methods useful for the preparation of succinate derivatives are known by those skilled in the art. Such references include, McClure and Axt, Bioorganic & Medicinal Chemistry Letters, 8 (1998) 143-146; Jacobson and Reddy, Tetrahedron Letters, Vol 37, No. 46, 8263-8266 (1996); Pratt et al., SYNLETT, May 1998, p. 531; WO 97/18207; and WO 98/51665. The synthetic disclosures of WO97/18207 and WO 98/51665 are hereby incorporated by reference.

Scheme 2

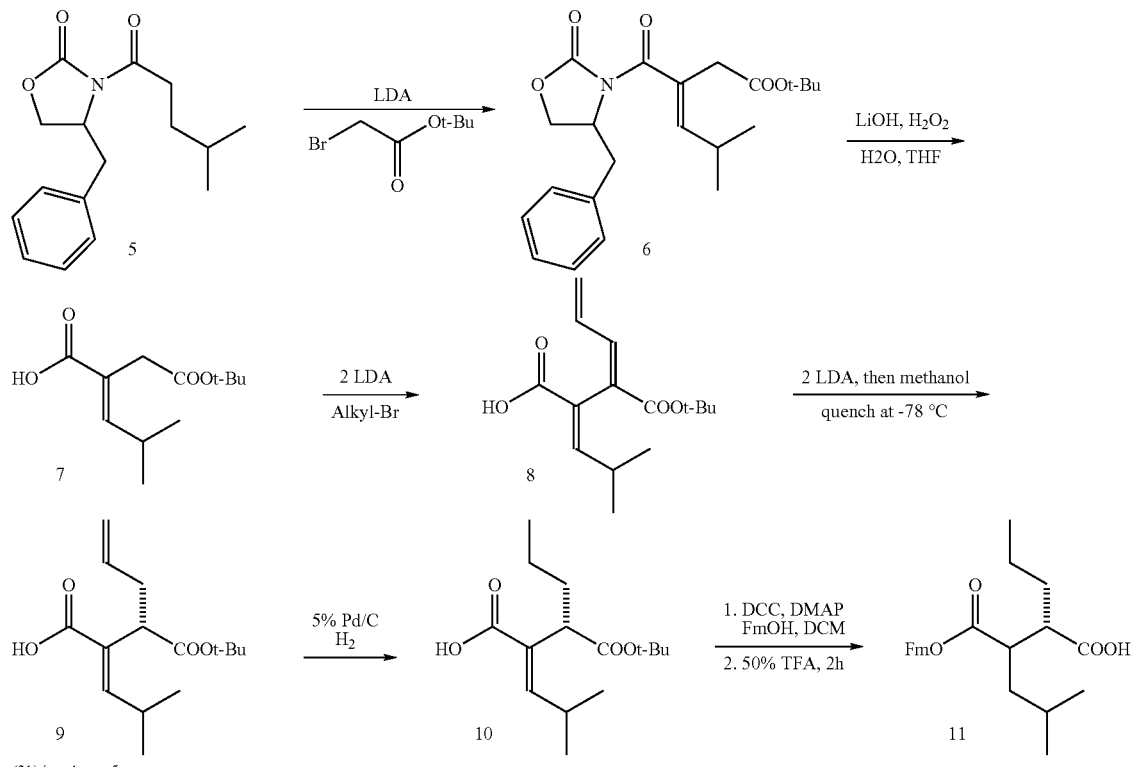

(21) in scheme 5

A variety of compounds of Formula (I) can be prepared by methods described in Scheme 4. The protected α-amine 3 of the α-amino-ε-caprolactam can be prepared by methods well known in the literature for amino protecting groups as discussed in Theodora W. Greene's book "Protective Groups in Organic Synthesis", like N-Boc using di-t-butyldicarbonate in an appropriate solvent like DMSO. A sulfur atom can be introduced into the ring providing L-α-amino-β-thio-ε-caprolactam according to the procedure in S. A. Ahmed et al, FEBS Letters, (1984), vol. 174, pages 76-9 (Scheme 3). One skilled in the art can extend this methodology to the synthesis of β-amino and oxygen containing rings by analogy. The sulfur-containing molecules can also be oxidized to the sulfoxide and sulfone by methods known to one skilled in the art.

Scheme 3

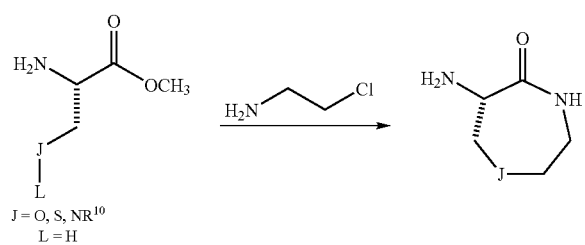

$J = O, S, NR^{10}$
$L = H$

The lactam nitrogen of compound 13 can be alkylated by generating the anion with bases such as LDA, lithium bis(trimethylsilyl)amide or sodium hydride in solvents like THF, with or without cosolvents such as DMPU or HMPA and reacting this with a variety of groups containing leaving groups (X") like bromide, iodide, mesylate or tosylate. Alkylating agents such as α-bromo amides, ketones and acids can be prepared by a number of literature methods including halogenation of amino acids by diazotization or are commercially available. Other suitable alkylating agents such as alkyl, allylic and benzylic halides can be formed form a variety of precursors such as free-radical addition of halides or activation of alcohols, and other chemistries known to those skilled in the art. For discussion of these types of reactions, see Carey, F. A. and Sundberg, R. J., Advanced Organic Chemistry, Part A, New York: Plenum Press, 1990, pages 304-305, 342-347, 695-698.

The N-Boc protecting group can be removed by any number of methods well known in the literature like TFA in methylene chloride to give the compound 15. The amine 15 can be coupled to an appropriately substituted carboxylic acid or acid chloride by methods well described in the literature for making amide bonds, like TBTU in DMF with a base like NMM to give the elaborated compound 16. Compounds 16 can be alkylated using standard bases like LDA, NaH, or NaHMDS to deprotonate the amide followed by addition of an alkylating agent with an appropriate leaving group like halide, mesylate, or triflate in an appropriate solvent to provide compounds 17 with an $R^6$ substituent. The t-butyl ester is then removed by treatment with TFA in methylene chloride to give the carboxylic acid 17.

Scheme 4

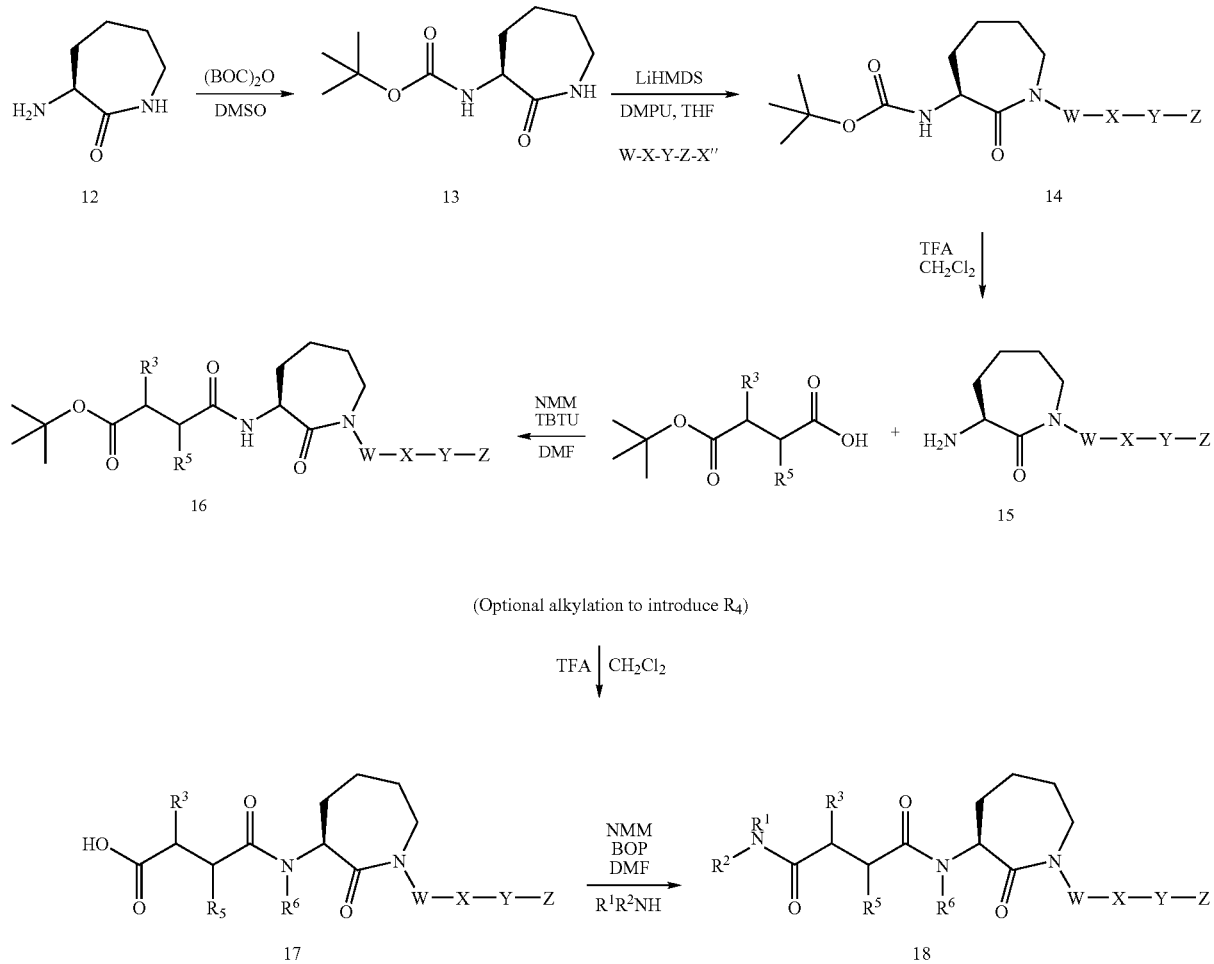

The final compounds 18 were prepared by treating the activated carboxylic acid of 17 with an appropriately substituted amine. For instance, activation of the carboxylic acid with HATU (O-(7-azabenzotriazol-1-yl)-1,1,3,3,-tetramethyluronium hexafluorophosphate) or PyBOP (benzotriazole-1-yl-oxy-tris-pyrrolidino-phosphonium hexafluorophosphate) or other coupling agents known to those skilled in the art allows condensation with ammonia to form primary amides. Similarly, condensation of the activated acid with hydroxylamine hydrochloride provides the hydroxamic acid, or reaction with a primary or secondary amine provides the substituted amine derivative. Activation of the acid with PyBrOP (bromo-tris-pyrrolidino-phosphonium hexafluorophosphate) followed by addition of an alcohol and 4-dimethylaminopyridine allows formation of the ester directly. For additional acylation reactions see for example Carey, F. A. and Sundberg, R. J., Advanced Organic Chemistry, Part A, New York: Plenum Press, 1990, pages 475-479.

Additional Examples of compounds of Formula (I) can be prepared as shown in Scheme 5. A suitable resin for solid phase synthesis such as Fmoc (Fluorenylmethylcarbonyl)- protected hydroxylamine bound to polystyrene beads can be purchased from Novabiochem, Inc. Deprotection of the Fmoc group under standard conditions using 20% piperidine in DMF provides trityl-linked hydroxylamine resin. Coupling of a fluorenylmethyl-protected succinic acid derivative such as 20 with a coupling agent such as HATU in a suitable solvent like DMF or N-methylpyrrolidinone provides the support-bound hydroxamate 21. The Fluorenylmethyl ester can be removed using 20% piperidine in DMF to provide the free carboxylic acid which can be coupled to amines like the caprolactam 22 (which is available using chemistry outlined in Scheme 4) using PyBOP (benzotriazole-1-yl-oxy-tris-pyrrolidino-phosphonium hexafluorophosphate) and a suitable base like DIEA in DMF or NMP. The support-bound intermediate 23 can then be elaborated to biaryl structures of the type 24 using typical Suzuki coupling conditions employing a catalyst such as Palladium complexes like tetrakis(triphenylphosphine)-palladium with 2M aqueous sodium carbonate as a base in a suitable solvent like THF or DME and an excess of a boronic acid. The final compounds are liberated from the support employing dilute (5%) trifluoroacetic acid in $CH_2CL_2$ and purified by conventional chromatography.

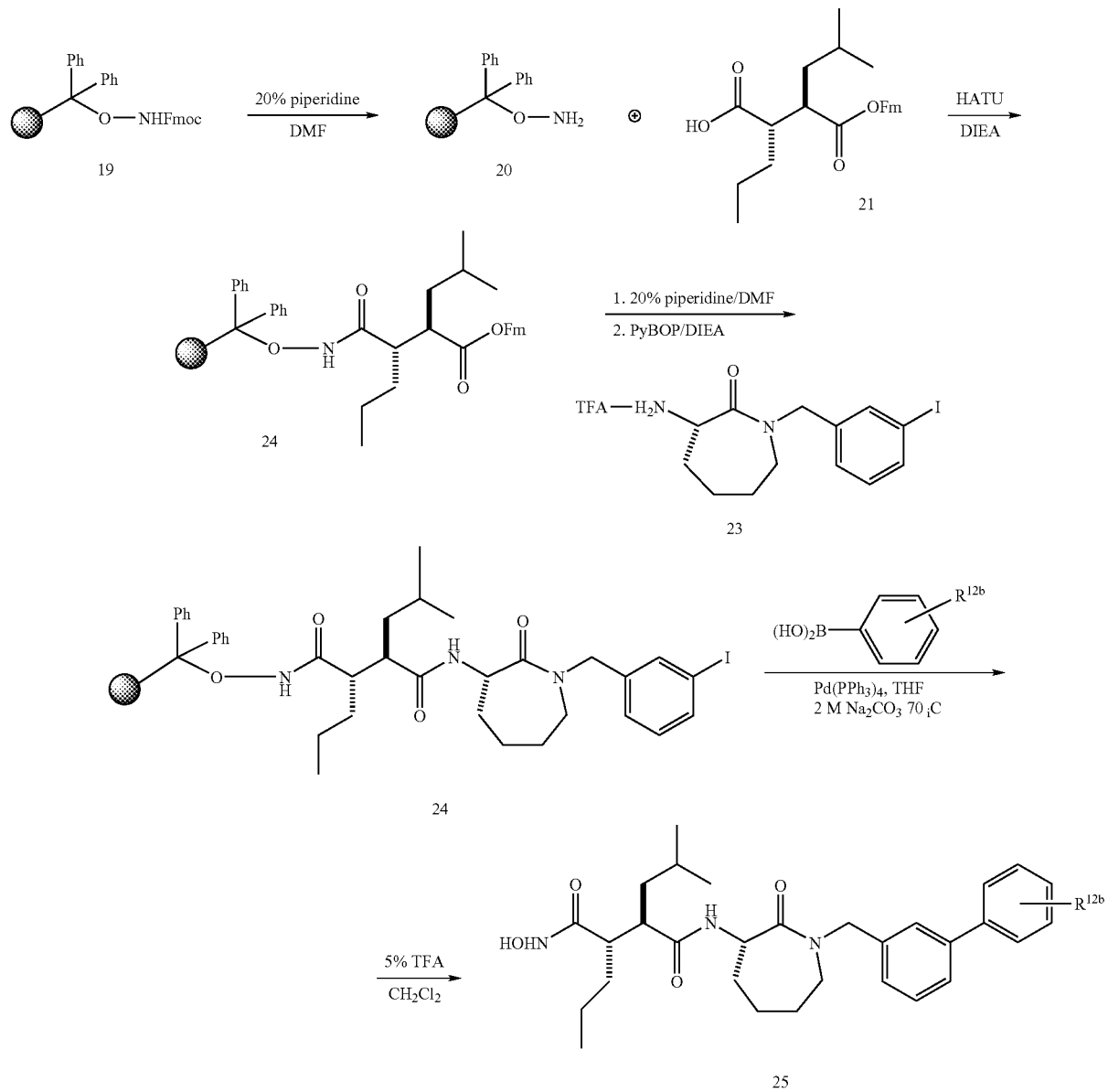

= polystyrene beads

General Procedure for Solid-phase Synthesis According to Scheme 5.

Resin 20 of Scheme 5: Fmoc-protected resin 19 (2.0 g, 0.78 mmol/g, 1.56 mmol) is purchased from Novabiochem and swelled in 20 ml of $CH_2Cl_2$ for 1 hour. The $CH_2Cl_2$ is removed and the resin is then treated with 25% v/v piperidine in DMF (8 mL) and allowed to shake slowly for 16 h. The solvent was removed by filtration and the resin was shaken with an additional 8 mL of 25% v/v piperidine in DMF for 2 h at rt. The solvents were removed by filtration, and the resin 20 was rinsed 3× with 20 mL of DMF, 3× with 20 mL of methanol, and 3× with 20 mL of $CH_2Cl_2$ and dried in vacuo.

Succinate 10 of Scheme 2: Succinate 9 is prepared according to the literature procedure (P. Becket, M. J. Crimmin, M. H. Davis, Z. Spavold, Synlett, (1993), 137-138). Succinate 9 (17.8 g, 66 mmol) is dissolved in 250 mL of ethyl acetate and placed in a Parr shaker bottle. To the solution is added 890 mg of 5% palladium on carbon, and the bottle is pressurized to 40 psi with hydrogen gas and shaken for 2.5 h at rt. The hydrogen is removed and the palladium catalyst is removed by filtration through a pad of celite. Concentration of the ethyl acetate solution provides 17.5 g (98%) of succinate 10. No further purification is necessary. MS $(M-H)^+=271$.

Succinate 21 of Scheme 5: Succinate 10 (6.3 g, 23.1 mmol) is dissolved in 125 mL of $CH_2Cl_2$ and 4.8 g (23.3 mmol) of dicyclohexylcarbodiimide is added. The solution is stirred at rt for 30 min and then 4.6 g (23.4 mmol) of 9-fluorenemethanol is added followed by 122 mg (1 mmol) of 4-dimethylaminopyridine. After 5 h of stirring at rt, the reaction solution was diluted with an additional 100 mL of $CH_2Cl_2$ and filtered through a pad of celite to remove precipitated dicyclohexylurea. The solution was then washed 3× with 50 mL of a 1N HCl solution, 3× with 50 mL of a saturated sodium bicarbonate solution, and 2× with 50 mL of brine. The crude product was dried over $MgSO_4$ and concentrated onto 15 g of silica gel. Chromatography eluting with a gradient of 2.5% to 5% ethyl acetate/hexanes provided 6.4 g (61%) of the diester as an oil. The purified diester (6.4 g 14.2 mmol) is then dissolved in 25 mL of $CH_2Cl_2$, 25 mL of trifluoroacetic acid is added, and the reaction solution is stirred at rt for 2 h. The reaction solution is directly concentrated in vacuo to an oil which is then redissolved in 25 mL of toluene and reconcentrated, followed by drying in vacuo to provide 6.3 g (98%) of the desired succinate 9 as an oil which solidifies on standing. MS $(M+Na)^+=471$, $(M+2Na)^+=439$.

Caprolactam 23 of Scheme 5: Boc-caprolactam 14 (5.0 g, 21.9 mmol) is dissolved in 60 mL of THF and chilled to −78° C. To the chilled solution is added 24 mL of a 1.0 M solution of lithium bis(trimethylsilyl)amide in THF, and the solution was brought to 0° C. and stirred for 15 min. To the anion solution was added 6.5 g (22 mmol) of 3-iodobenzyl bromide (Aldrich) and the solution was allowed to warm to rt and stirred for 18 h. The reaction solution was diluted with 50 mL of water and extracted 3× with ethyl acetate. The combined organic layers were dried over $MgSO_4$ and concentrated in vacuo. The crude product was purified by chromatography eluting with a gradient of 5-20% ethyl acetate/hexanes to afford 7.0 g (72%) of the title compound as a white solid. MS $(M+Na)^+=467$.

Resin 22 of Scheme 5: Resin 22 (2.0 g, 0.78 mmol/g, 1.56 mmol) was swollen in 3 mL of DMF. In a separate flask, 1.85 g (4.68 mmol) of succinate 21 was dissolved in 3 mL of DMF and 2.5 mL of N,N-diisopropylethylamine (14 mmol) was added, followed by 1.81 g (4.68 mmol) of HATU. The solution containing the active ester was added to the slurried resin and the reaction suspension was slowly shaken for 18 h. The resin was then washed 3× with 20 mL of DMF, 3× with 20 mL of methanol, and 3× with 20 mL of $CH_2Cl_2$. Loading of the resin was determined by Fmoc quantitation to be 0.25 mmol/g, see Reddy, M. P.; Voelker, P. J. *Int. J. Pept. Protein Res.* 1998, 31, 345-348.

Resin 24 of Scheme 5: Resin 22 (2.0 g, 0.25 mmol/g, 0.5 mmol) was suspended in 10 mL of 25% piperidine in DMF. The suspended resin was shaken for 30 min at rt, and then the resin was washed 3× with 20 mL of DMF, 3× with 20 mL of methanol, and 3× with 20 mL of $CH_2Cl_2$. Deprotected resin (1.0 g, 0.25 mmol) was swollen in 2 mL of DMF. To the slurry was added 650 mg (1.25 mmol) of PyBOP and 217 mL (1.25 mmol) of DIEA. Separately, 443 mg (0.97 mmol) of caprolactam 23 was dissolved in 2 mL of DMF and 436 mL (2.5 mmol) of DIEA was added. The caprolactam solution was added to the resin slurry and the resin was mixed for 18 h at rt. The solvents were then removed and the coupling was repeated, with shaking at rt for 6 h. The resin was then washed 3× with 10 mL of DMF, 3× with 10 mL of methanol, and 3× with 10 mL of $CH_2Cl_2$.

Products 25 of Scheme 5: A 70 mg (17.5 mmol) portion of resin 24 was suspended in 1 mL of THF in a screw-cap vial. To the slurry was added a boronic acid (0.15 mmol), 150 mL of a 2 M solution of sodium carbonate, and 15 mg (13 mmol) of tetrakis(triphenylphosphine)palladium. The vial was tightly closed and heated to 60° C. for 16 h using a dry heater on a shaker table. The solvents were then removed by filtration and the resin was washed 3× with THF (2 mL), 3× with methanol (2 mL), 3× with water, and 3× with $CH_2Cl_2$. The resins were then placed in a glass vial and cleaved with 1 mL of 5% trifluoroacetic acid in $CH_2Cl_2$ for 30 min. The solution was filtered off and the resin was washed with an additional 2 mL of $CH_2Cl_2$ and the combined filtrates were evaporated to dryness to yield the crude products 25. The products were purified by chromatography eluting with 10-100% ethyl acetate in hexanes to yield 13.0 to 6.0 mg (14-60%) of the final products.

Additional Examples of compounds of Formula (I) can be prepared as shown in Scheme 6. A suitable resin for solid phase synthesis such as Fmoc (Fluorenylmethylcarbonyl)-protected peptide amide linker (PAL)-derivatized polystyrene beads can be purchased from Perkin Elmer Biosystems, Inc. Deprotection of the Fmoc group under standard conditions using 20% piperidine in DMF provides the free benzylamine. Coupling of a succinic acid derivative such as 28 (which is available using chemistry outlined in Scheme 4) with a coupling agent such as HATU in a suitable solvent like DMF or N-methylpyrrolidinone provides the support-bound amide 29. The support-bound intermediate 29 can then be elaborated to biaryl structures of the type 24 using typical Suzuki coupling conditions employing a catalyst such as Palladium complexes like tetrakis(triphenylphosphine)-palladium with 2M aqueous sodium carbonate as a base in a suitable solvent like THF or DME and an excess of a boronic acid. The final compounds are liberated from the support employing 50% trifluoroacetic acid in $CH_2Cl_2$ and can be purified by conventional chromatography or preparative HPLC.

Scheme 6

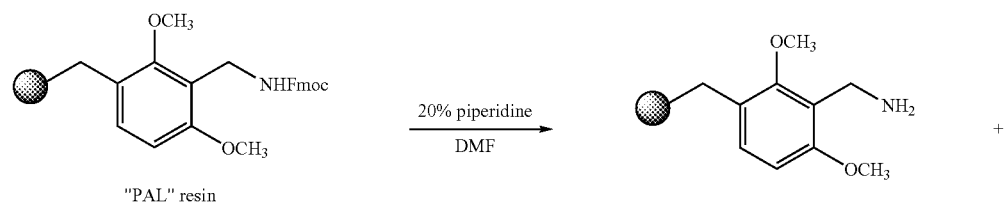

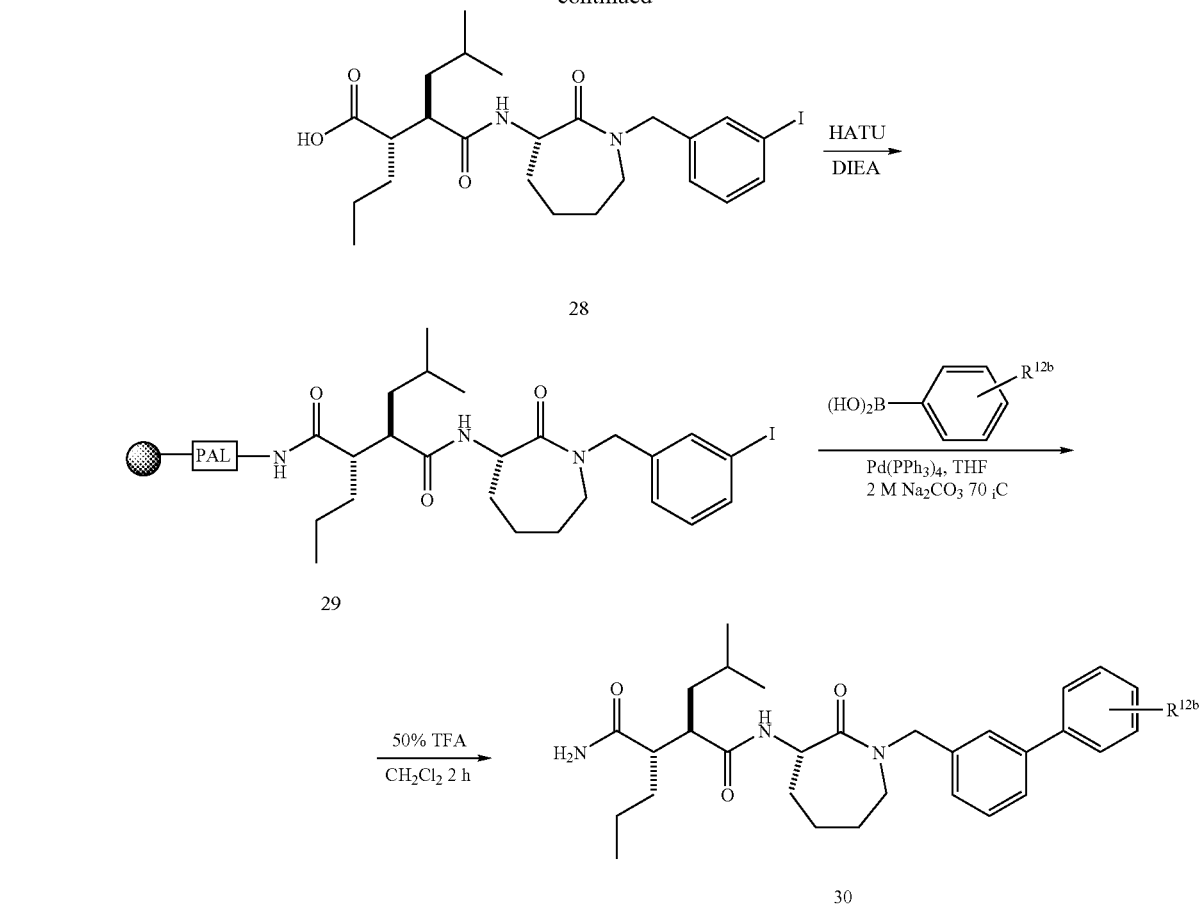

● = polystyrene beads

General Procedure for Solid-phase Synthesis According to Scheme 6

Resin 27 of Scheme 6: Fmoc-protected PAL resin 26 (0.80 g, 0.50 mmol/g, 0.40 mmol) is purchased from Advanced Chemtech and swelled in 20 ml of $CH_2Cl_2$ for 1 hour. The $CH_2Cl_2$ is removed and the resin is then treated with 25% v/v piperidine in DMF (6 mL) and allowed to shake slowly for 1 h. The solvents were removed by filtration, and the resin 27 was rinsed 3× with 20 mL of DMF, 3× with 20 mL of methanol, and 3× with 20 mL of $CH_2Cl_2$. and dried in vacuo.

Acid 28 of Scheme 6: To a solution of 0.100 g (367 mmol) of succinate 10 dissolved in 2.0 mL of dry DMF was added 0.120 mL (1.10 mmol) of N-methylmorpholine. A second solution containing 0.139 g (0.403 mmol) of caprolactam 23 of Scheme 5 dissolved in 2.0 mL of DMF was then added. To the mixed solution was added 229 mg (0.440 mmol) of PyBop and the reaction solution was stirred for 16 h at rt. The reaction solution was diluted with water (20 mL) and extracted 3× with 100 mL of ethyl acetate. The combined organic layers were dried with $Na_2SO_4$ and concentrated under reduced pressure. The resulting oil was purified by chromatography eluting with a gradient of 5-20% ethyl acetate in hexanes to provide 0.195 g (0.360 mmol, 98%) of the tert-butyl ester of Acid 28 (MS M+Na=621). The purified ester (0.195 g, 0.360 mmol) was dissolved in 10 mL of 25% trifluoroacetic acid in $CH_2Cl_2$ and stirred for 2 h at rt. The solvents were removed under reduced pressure and the acid was redissolved in 5 mL of toluene and reconcentrated 2× to remove residual TFA. The crude acid was found to be pure by $^1H$ NMR and was used in Scheme 6 without further purification.

Resin 29 of Scheme 6. Resin 27 (800 mg, 0.40 mmol) was solvated in 4.0 mL of dry DMF and 0.63 mL (3.6 mmol) of diisopropylethylamine was added followed by a solution of Acid 28 dissolved in 4 mL of DMF. To the slurry was then added 0.465 g (1.2 mmol) of HATU and the slurry was shaken for 26 h at rt. The solvents were removed by filtration, and the resin 29 was rinsed 3× with 20 mL of DMF, 3× with 20 mL of methanol, and 3× with 20 mL of $CH_2Cl_2$. and dried in vacuo.

Products 30 of Scheme 6: A 75 mg (0.38 mmol/g, 28.8 mmol) portion of resin 24 was suspended in 1 mL of THF in a screw-cap vial. To the slurry was added a boronic acid (0.33 mmol), 150 mL of a 2 M solution of sodium carbonate, and 15 mg (13 mmol) of tetrakis(triphenylphosphine)palladium. The vial was tightly closed and heated to 60° C. for 16 h using a dry heater on a shaker table. The solvents were then removed by filtration and the resin was washed 3× with THF (2 mL), 3× with methanol (2 mL), 3× with water, and 3× with $CH_2Cl_2$. The resins were then placed in a glass vial and cleaved with 1 mL of 5% trifluoroacetic acid in $CH_2Cl_2$ for 2 h. The solution was filtered off and the resin was washed with an additional 2 mL of $CH_2Cl_2$ and the combined filtrates were evaporated to dryness to yield the crude products 25. The products were purified by chromatography eluting with 10-100% ethyl acetate in hexanes to yield 0.5 to 2.0 mg (14-60%) of the final products.

The internal phenyl ring can be exchanged for a pyridine ring using chemistry outlined in Scheme 7. The chloromethyl pyridine 33 is prepared using a known procedure reported in Nutaitis, Charles F.; Ledeboer, Mark W. Org. Prep. Proced. Int. (1992), 24(2), 143-6 Incorporated herein by reference. After freebasing the pyridine, alkylation with the Boc-caprolactam provides pyridine intermediate 34, which can be elaborated to the protected amide 35 with succinate 10. Substitution can then be introduced using Suzuki methodology employing a palladium source such as tetrakis(triphenylphosphine) palladium(0) or bis(diphenylphosphinoferrocene) palladium(II) dichloride and a suitable base such as sodium carbonate or triethylamine in a solvent such as THF or toluene containing 10% methanol. Stille chemistry is also possible using a suitable palladium source such as tetrakis(triphenylphosphine)palladium(0) and an aryl or vinyl tin derivative in a solvent such as benzene, toluene, or xylenes. The tert-butyl ester is then deprotected under standard acidic conditions using trifluoroacetic acid and the amide is formed under standard conditions to provide products 36.

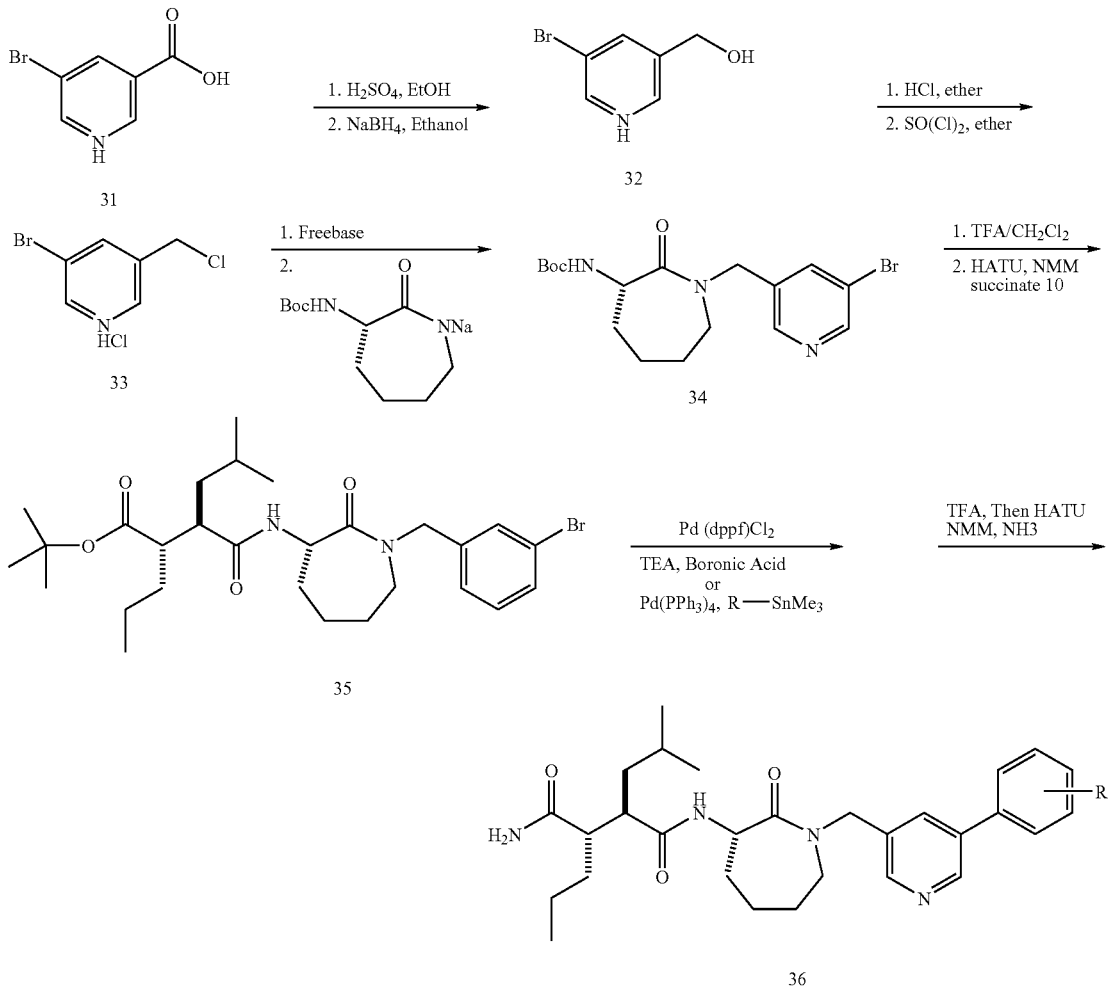

General Procedure for Synthesis According to Scheme 7

The chloromethyl pyridine HCl salt 33 is prepared using a known procedure reported in Nutaitis, Charles F.; Ledeboer, Mark W. Org. Prep. Proced. Int. (1992), 24(2), 143-6.

Caprolactam 34: Pyridine HCl salt 33 (2.0 g, 8.3 mmol) is dissolved in 50 mL of a saturated $NaHCO_3$ solution and the solution is extracted with 30 mL of $CH_2Cl_2$ 3 x followed by concentration of the organic layers to provide the free base. Separately, 1.8 g (7.8 mmol) of caprolactam 13 is dissolved in 40 mL of dry THF and chilled to −78° C. To the solution was added 8.7 mL of a 1M solution of sodium bis(trimethylsilyl) amide. The solution was brought to 0° C. and stirred for 30 min. To the resultant anion was added a solution of 1.7 g (8.3 mmol) of pyridine 33 free base dissolved in 40 mL of THF. The resulting reaction solution was stirred at rt for 18 h and then heated to 50° C. and stirred an additional 3 h. The reaction solution was allowed to cool and then 50 mL of water was added and the aqueous layer was extracted 2× with 100 mL of ethyl acteate. The combined organic layers were dried and concentrated under reduced pressure to provide the crude product which was purified by chromatography eluting with 20 to 100% ethyl acetate in hexanes to provide 1.5 g (51%) of caprolactam 34 as an oil.

cially available aldehyde-derived resin 37 under conditions for reductive amination such as sodium tris(acetoxy)borohydride in $CH_2Cl_2$ containing 1% acetic provides a support-bound amine 38. The carboxylic acid 39 can then be coupled to the support-bound amine generating an amide 40 which can be liberated from the support employing trifluoroacetic acid in $CH_2Cl_2$.

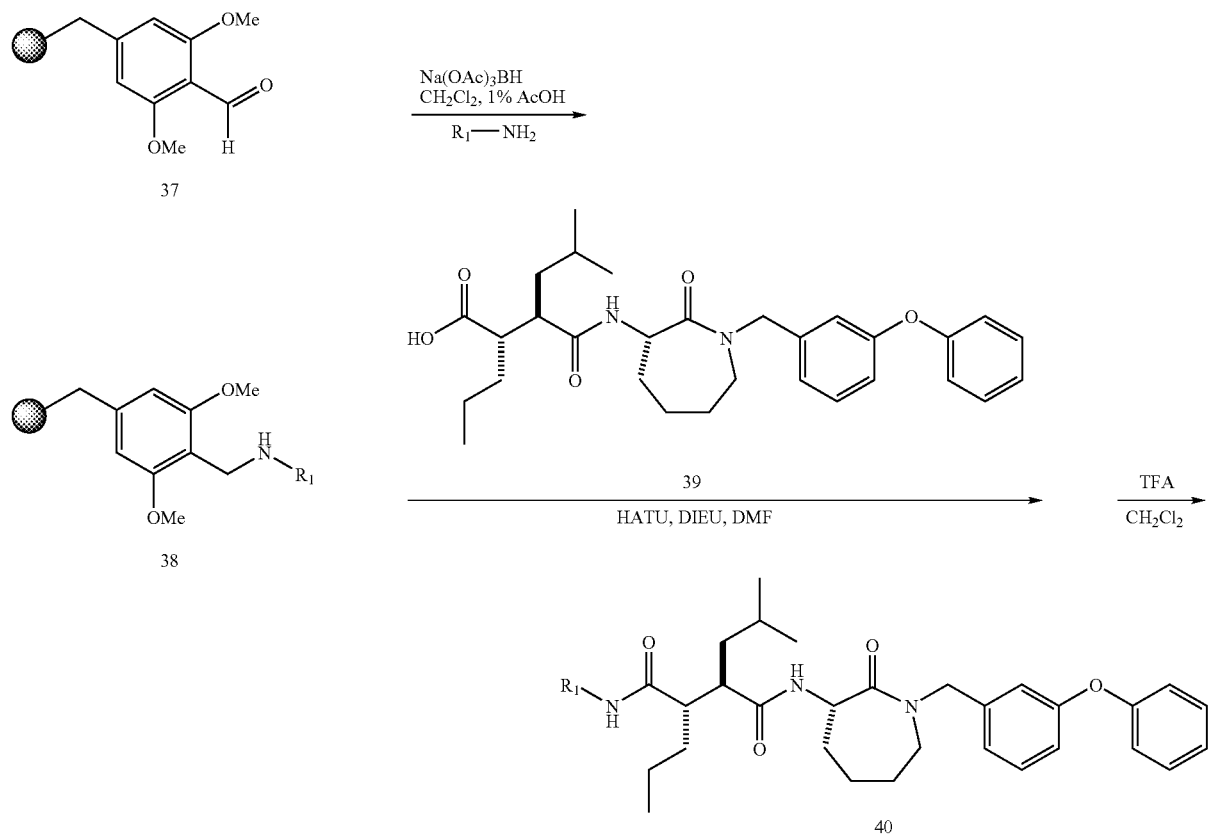

Amide 35: Caprolactam 34 (0.40 g, 1.0 mmol) is dissolved in 20 mL of 50% trifluoroacetic acid in $CH_2Cl_2$ and stirred at rt for 30 min. The solvents were then removed under reduced pressure and the resulting oil was redissolved in 5 mL of toluene and reconcentrated to remove residual TFA. Separately, 0.270 g (1.0 mmol) of succinate 10 was dissolved in 5.0 mL of dry DMF and 0.44 mL (4 mmol) of N-methylmorpholine was added followed by 0.50 g (1.3 mmol) of HATU and the resulting solution was stirred at rt for 30 min. The crude deprotected caprolactam from above was dissolved in 5.0 mL of dry DMF and added to the succinate solution and the resulting solution was heated to 50° C. and stirred for 2 days. The solution was then diluted with 20 mL of water and extracted with 3 50 mL portions of ethyl acetate. The combined organic layers were dried and concentrated under reduced pressure to provide an oil which was purified by chromatography eluting with 20 to 50% ethyl acetate in hexanes to provide 0.40 g (70%) of the Amide 35.

Additional examples can be prepared by the method shown in Scheme 8. Coupling of an amine onto a commer- General Procedure for Solid-phase Synthesis According to Scheme 8

Resin 38 of Scheme 5: Aldehyde-derived resin 37 (200 mg, 0.5 mmol/g, 0.1 mmol) is purchased from Perkin Elmer Biosystems and swelled in 3 ml of $CH_2Cl_2$ for 1 hour. An amine (1.0 mmol), sodium tris(acetoxy)borohydride (106 mg, 0.5 mmol) and acetic acid (30 µL, 1%) are added and the reaction is shaken on a shaker table for 16 h at rt. The solvents were removed by filtration and the resin 38 was rinsed 3× with 20 mL of DMF, 3× with 20 mL of methanol, and 3× with 20 mL of $CH_2Cl_2$. and dried in vacuo.

Products 40 of Scheme 8: Carboxylic acid 39 (23 mg, 0.045 mmol), diisopropylethylamine (13 mL, 0.075 mmol) and HATU (17.1 mg, 0.045 mmol) were mixed in 0.5 mL of DMF for 30 min. Amine-derived resins 38 (30 mg, 0.015 mmol) were then added and the suspension was shaken at rt for 16 h. The solvents were removed by filtration and the resins were rinsed 3× with 20 mL of DMF, 3× with 20 mL of methanol, and 3× with 20 mL of $CH_2Cl_2$. The isolated resins were then cleaved by the addition of 0.50 mL of trifluoroacetic acid. The product solutions were concentrated and redissolved in 0.5 mL of methanol and reconcentrated 2× to remove residual TFA. Product yields ranged from 0-100% based on the structure of the amine.

The compounds of Formula (I) of the present invention can also be prepared from aminolactam or aminothiolactam 42 and succinic acid derivatives 41 using amide bond syntheses known in the art, including methods commonly used in peptide syntheses, such as HATU, TBTU, BOP, pyBOP, EDC, CDI, DCC, hydroxysuccinimide, mixed carboxylic anhydride, and phenyl ester mediated couplings, as illustrated in Scheme 9 for the synthesis of aminolactam or aminothiolactam 43, an embodiment of the present invention.

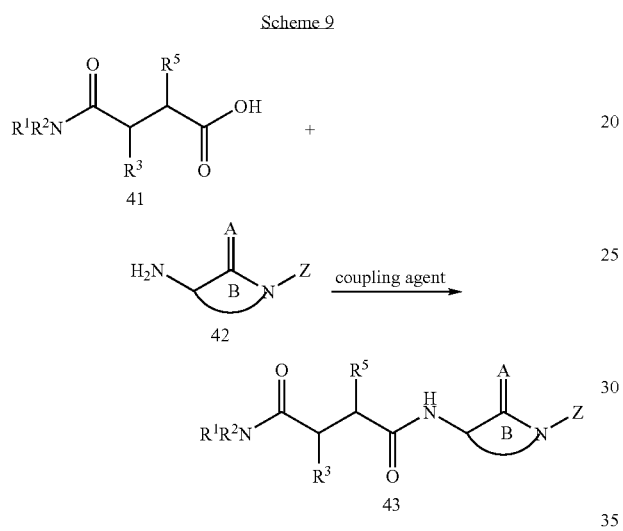

Depending on the structure of the final product, it is appreciated by those skilled in the art that protecting groups or precursor functionality convertable to the desired groups may be desireable. Protecting groups and their use in synthesis are described in Green and Wuts, *Protective Groups in Organic Synthesis*, (Wiley 1991). The use of protecting groups is further illustrated in Scheme 10, in which the succinate half-ester 44 (Becket et al., Synlett 1993, 137-138) is coupled to the aminobenzodiazepine 45 (Sherrill and Sugg, J. Org. Chem. 1995, 60, 730-734; Bock et al., J. Med. Chem., 1993, 36, 4276-4292) to give ester 46, followed by conversion of the ester group to the primary amide 47.

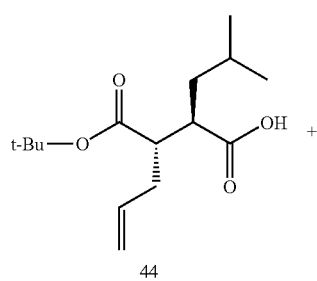

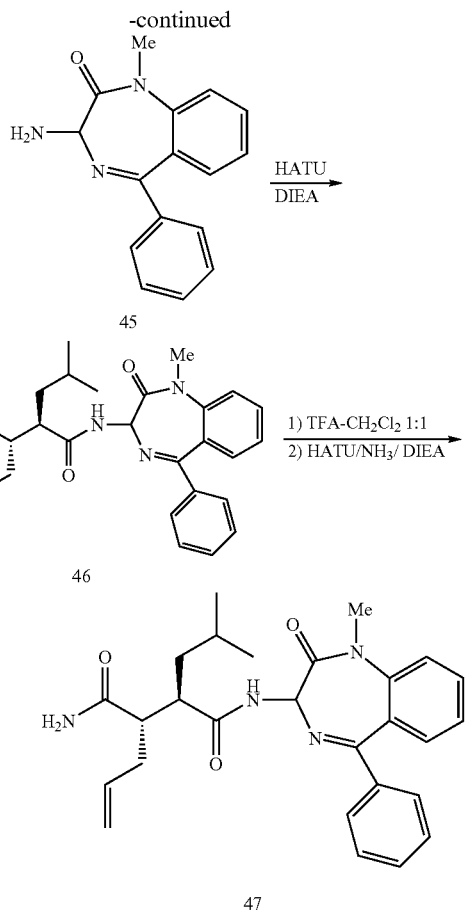

Methods for the synthesis of lactams as contemplated by the present invention in lactam ring B in Formula (I), including amino benzodiazepines, are known in the art and are disclosed in a number of references including PCT publication number WO 98/28268, which is hereby incorporated by reference. Additional references include Bock, et al, J. Org. Chem., 1987, 52, 3232-3239 and Sherrill et al, J. Org. Chem., 1995, 60, 730-734; Walsh, D. A., Synthesis, September 1980, p. 677.

The synthesis of the thiolactams of the present invention (Formula (I), A=S) can be carried out using thiolactam intermediates (42, A=S), using the methods described above. The thiolactam intermediates may be prepared from suitably protected aminolactams employing methods known to those skilled in the art, using, for example, Lawessson's reagent, $P_4S_{10}$, or related methods (see Taylor et al., Bioorg. Med. Chem. Lett. 1997, 7 (4), 453-456; Schwarz et al., Tetrahedron, 1997, 53 (26), 8795-8806; Achour et al., Synth. Commun. 1994, 24 (20), 2899-2905; Buege et al., Arch. Pharm. 1994, 327 (2), 99-103; Levai, et al., Arch. Pharm. 1992 (325 (11), 721-726; Duhammel et al., Tetrahedron Asymmetry 1991, 2 (3), 203-206; Bodine et al., Synth. Commun. 1982, 12, 787). Deprotection of the amine, coupling to an appropriate succinate derivative and elaboration of the distal succinic acid derivative provides the desired thiolactams of the present invention.

EXAMPLES

Chemical abbreviations used in the Examples are defined as follows: "DMPU" for 1,3-dimethyl-3,4,5,6-tetrahydro-2(1H)-pyrimidone, "TBTU" for O-(1H-benzotriazol-1-yl)-N,N,N',N'-tetramethyluronium tetrafluoroborate, and "BOP" for benzotriazol-1-yloxytris-(dimethylamino)phosphonium hexafluorophosphate. It is understood that one skilled in the art can discern compounds used in the synthesis of Examples of the invention may be referred to by structure and number. For example, Resin 20 refers to the resin of structure 20 in Scheme 5; succinate 9 refers to the structure 9 found in Scheme 2 which is a succinate compound.

"HPLC" is an abbreviation used herein for high pressure liquid chromatography. Reverse-phase HPLC was carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid).

Example 1

(2R,3S)N1-[(3S)-hexahydro-1-(3,3-diphenylpropyl)-2-oxo-1H-azepin-3-yl]-N4-(hydroxy)-2-(2-methylpropyl)-3-(propyl)-butanediamide

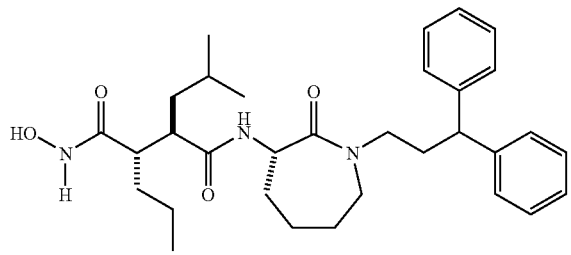

Step (1a): Di-tert-butyldicarbonate (10.2 g, 46.7 mmoles) was added portion wise to a solution of L-(−)-α-amino-ε-caprolactam (5.0 g, 39.0 mmoles) in dimethyl sulfoxide (30 mL). After 5 h at rt, the reaction was partitioned between water (100 mL) and ethyl acetate. The combined organic extracts were washed successively with 1 M HCl (50 mL), brine, and dried (MgSO$_4$) and concentrated in vacuo. The residue was recrystallized in 1:1 v/v ether-hexanes, two crops yielded the desired product (6.26 g, 70%) as white solid. MS (M+H-BOC)$^+$=129.

Step (1b): Triphenylphosphine (3.0 g, 11.4 mmoles) and carbon tetrabromide (3.75 g, 11.7 mmoles) were added successively to a cooled (0° C.) solution of 3,3-biphenyl-1-propanol (1.5 mL, 7.5 mmoles) in dichloromethane (20 mL). After 1.5 hours at rt, the mixture was concentrated in vacuo. The residue was purified by flash chromatography on silica gel (hexanes) to give the desired product (1.93 g, 93% yield) as a clear oil. MS (M−BrC$_2$H$_4$)$^+$=167

Step (1c): A 1.0 M tetrahydrofuran solution of lithium bis(trimethylsilyl)amide (1.3 mL) was added over 15 minutes to compound of Step (1a) (0.29 g, 1.27 mmoles) in tetrahydrofuran (3 mL) and DMPU (2 mL) at −78° C. The iodo compound prepared from compound (1b) (0.85 g, 3.09 mmoles) by typical Finkelstein methodology, in tetrahydrofuran (4 mL) was added and the reaction was allowed to warm to rt slowly. This was stirred for 10 hours at ambient temperature, partitioned between water and ethyl acetate. The combined organic extracts were washed successively with water (20 mL), brine (20 mL), and dried (MgSO$_4$) and concentrated in vacuo. The resulting residue was purified by silica gel column (ethyl acetate:hexanes, 5:95 then ethyl acetate:hexanes, 15:85) to give the desired product (0.16 g, 30%). MS (M-Ot-Bu)$^+$=349.

Step (1d): Trifluoroacetic acid (3 mL) was added to a solution of compound of Step (1c) (0.16 mg, 0.38 mmoles) in dichloromethane (9 mL). After 2 h at rt, the solvent was removed in vacuo. The residual trifluoroacetic acid was removed by azeotrope with dichloromethane (50 mL), toluene (50 mL), and dichloromethane (50 mL) successively to give the desired product (0.17 g, 99%) as a yellow oil. MS (M+H)$^+$=323.

Step (1e): 4-Methylmorpholine (0.6 mL, 5.46 mmoles) and TBTU (0.11 g, 0.34 mmoles) were added to a solution of succinate acid (P. Becket, M. J. Crimmin, M. H. Davis, Z. Spavold, Synlett, (1993), 137-138) (0.085 g, 0.31 mmoles) in N,N-dimethylformamide (3 mL). After 30 minutes at rt, the compound from step (1d) (0.17 g, 0.39 mmoles) was added to the mixture. The reaction was stirred for 16 h at rt, then partitioned between 1 M HCl (20 mL) and ethyl acetate. The combined organic extracts were washed successively with saturated aqueous sodium bicarbonate (20 mL), water (20 mL), brine (20 mL), dried (MgSO$_4$) and concentrated in vacuo. The residue was purified by silica gel chromatography (ethyl acetate:hexanes, 7:93 gradient to ethyl acetate:hexanes 25:75) to give the desired product (120 mg, 67%) as a clear oil. MS (M+NH$_4$-Ot-Bu)$^+$=521.

Step (1f): Trifluoroacetic acid (3 mL) was added to a solution of compound of Step (1e) (120 mg, 0.21 mmoles) in dichloromethane (9 mL). After 3 hours at rt, the mixture was concentrated in vacuo. The residual trifluoroacetic acid was removed by azeotrope with toluene (1×50 mL) and dichloromethane (1×50 mL). The residue was triturated with Et$_2$O:Hexanes 95:5, to give the desired product (75 mg, 70%) as a white solid. MS (M−H)$^-$=519.

Step (1g): 4-Methylmorpholine (0.05 mL, 0.45 mmoles) and BOP (73 mg, 0.17 mmoles) were added to a solution of compound of Step (1f) (60 mg, 0.12 mmoles) in N,N-dimethylformamide (2 mL). Hydroxylamine (33 mg, 0.47 mmoles) was added to the mixture, the reaction was stirred for 16 h at rt, was concentrated in vacuo, was acidified with trifluoroacetic acid, then purified by reverse phase HPLC on a Vydac C-18 column, to give the desired hydroxamic acid as a white solid (45 mg, 75%). MS (M−H)$^-$=534.

Example 2

(2R,3S)N1-[(3S)-hexahydro-1-(3-phenoxybenzyl)-2-oxo-1H-azepin-3-yl]-N4-(hydroxy)-2-(2-methylpropyl)-3-(propyl)-butanediamide

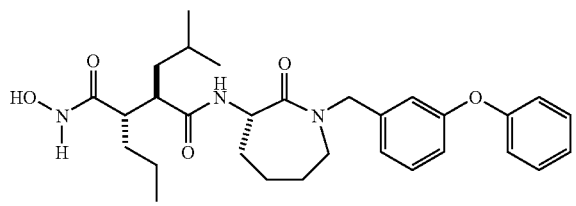

Step (2a): Triphenylphosphine (3.40 g, 13.0 mmoles) and carbontetrabromide (4.20 g, 13.0 mmoles) were added successively to a solution of m-phenoxybenzyl alcohol (1.5 mL, 8.6 mmoles). After 4 h at rt the mixture was concentrated and was purified by silica gel column (hexanes, then ethyl acetate:hexanes, 5:95) to give the desired bromide (1.3 g, 57%) as a yellow oil. MS (M-Br)+=183.

Step (2b): A 1 M solution of lithium bis(trimethylsilyl) amide was added dropwise to a solution of compound of Step (1a) (0.3 g, 1.31 mmoles) in tetrahydrofuran (5 mL) at −78° C. After 30 minutes a solution of compound of Step (2a) (0.43 g, 1.63 mmoles) in tetrahydrofuran (4 mL) was added to the mixture dropwise. The reaction was allowed to come to ambient temperature, stirred for 16 h, then partitioned between water and ethyl acetate. The combined organic extracts were washed successively with water (20 mL), brine (20 mL), dried (MgSO₄) and concentrated in vacuo. The crude residue was purified by silica gel chromatography (ethyl acetate:hexanes, 5:95 then ethyl acetate: hexanes, 15:85) to give the desired product (360 mg, 67%) as a clear oil. MS (M-Ot-Bu)+=337.

Step (2c): Trifluoroacetic acid (5 mL) was added to a solution of compound of Step (2b) in dichloromethane (15 mL). After 3 h at rt the solution was concentrated in vacuo. The residual trifluoroacetic acid was removed from residue by azeotrope with toluene (50 mL) then dichloromethane (30 mL) to yield the desired amine (390 mg, 99%) as a clear oil. MS (M+H)+=311.

Step (2d): Following a procedure analogous to the preparation of Step (1e), but using the compound from of Step (2c) (390 mg, 0.88 mmoles) the amide was prepared, The crude compound was purified by silica gel chromatography to give the desired product (0.38 g, 92%) as a yellow oil. MS (M-Ot-Bu)+=491.

Step (2e): Following a procedure analogous to the preparation of step (1f), but using the compound from Step (2d) (380 mg, 0.67 mmoles), the carboxylic acid was prepared. The product was precipitated from ethyl ether with hexanes, to give the desired acid (227 mg, 66%) as a white solid. MS (M−H)−=507.

Step (2f): Following a procedure analogous to the preparation of compound of Step (1 g), but using the compound from step (2e) (150 mg, 0.29 mmoles) the title compound was prepared. The crude was purified by reverse phase HPLC on a Vydac C-18 column to give the desired product (90 mg, 58%) as a white solid. MS (M−H)−=522.

Example 3

(2R,3S)N1-[(3S)-hexahydro-1-(phenyl)-2-oxo-1H-azepin-3-yl]-N4-(hydroxy)-2-(2-methylpropyl)-3-(propyl)-butanediamide

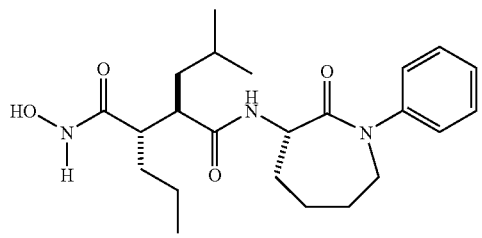

Step (3a): Triethylamine (1.5 mL, 10.8 mmoles), copper (II) acetate (0.95 g, 5.2 mmoles) and phenylboric acid (1.6 g, 13.1 mmoles) were added successively to a solution of compound of Step (1a) (1.0 g, 4.4 mmoles) in dichloromethane (20 mL). After 2.5 h at rt, more phenylboric acid (0.5 g, 4.1 mmoles) was added to the mixture. After an additional 3 hours at rt more phenylboric acid (0.5 g, 4.1 mmoles) was added to the mixture. After 65 h at rt, the mixture was filtered over celite. The filtrate was concentrated in vacuo, and the residue was purified by silica gel chromatography (ethyl acetate:hexanes, 5:95 then 15:85) to give the desired product (250 mg, 19%). MS (M-Ot-Bu)+ =231.

Step (3b): Following a procedure analogous to the preparation of compound of Step (2c), but using compound of Step (3a) (250 mg, 0.82 mmoles), the amine (300 mg, 99%) was prepared as a yellow oil. MS (M+H)+=205.

Step (3c): Following a procedure analogous to the preparation of compound of Step (1e), but using compound from Step (3b) (0.3 g, 0.94 mmoles), the amide was prepared. The residue was purified by silica gel chromatography (ethyl acetate:hexanes, 5:95 to 20:80 in 5% increments, 500 mL each ratio) to give the desired product (210 mg, 60%) as a clear oil. MS (M+H-t-Bu)+=403.

Step (3d): Following a procedure analogous to the preparation of compound of Step (1f), but using compound from Step (3c) (200 mg, 0.44 mmoles) the acid was prepared. The crude oil was triturated with ether:hexanes 1:1 to give the desired acid (114 mg, 65%) as a white solid. MS (M-OH)+ =385.

Step (3e): Following a procedure analogous to the preparation of compound of Step (1g), but using compound from Step (3d) (82 mg, 0.20 mmoles) the title compound was prepared. The crude product was purified by reverse phase HPLC on a Vydac C-18 column to give the desired product (80 mg, 94%). MS (M−H)−=416.

Example 4

(2R,3S)N1-[(3S)-hexahydro-1-(3-phenoxybenzyl)-2-oxo-1H-azepin-3-yl]-N4-(methyl)-2-(2-methylpropyl)-3-(propyl)-butanediamide

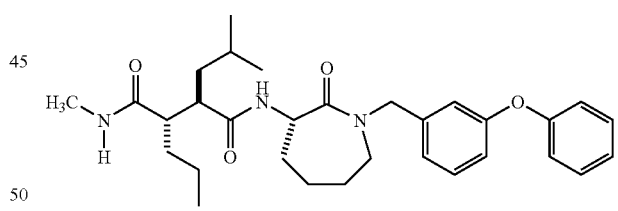

Following a procedure analogous to the preparation of Example 3, compound of Step (2e) (100 mg, 0.20 mmol) was treated with HATU (O-(7-azabenzotriazol-1-yl)-1,1,3,3,-tetramethyluronium hexafluorophosphate) (114 mg, 0.30 mmol) and N-methyl morpholine (66 mL, 0.6 mmol) in 2 mL of DMF for 15 min at rt. A solution of 2.0 M methylamine in THF (0.2 mL, 0.4 mmol) was added and the reaction solution was stirred for 1 h at rt. The reaction solution was diluted with 1N HCl (5 mL) and extracted 3× with 10 mL of ethyl acetate. The combined organic layers were washed with a saturated sodium bicarbonate solution (5 mL) and brine (5 mL), dried over magnesium sulfate, and concentrated in vacou to provide the crude amide. Purification by reverse phase HPLC on a Vydac-18 column provided the desired amide (30 mg, 30%). MS (M+Na)+=544.

Example 5

(2R,3S)N1-[(3S)-hexahydro-1-(3-phenoxybenzyl)-2-oxo-1H-azepin-3-yl]-N4-(methoxy)-N4-(methyl)-2-(2-methylpropyl)-3-(propyl)-butanediamide

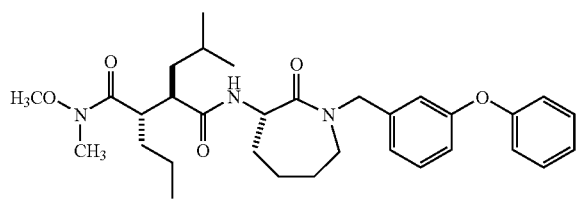

Following a procedure analogous to the preparation of Example 4, compound of Step (2e) (100 mg, 0.20 mmol) was activated and condensed with N,O-dimethylhydroxylamine hydrochloride (40 mg, 0.40 mmol). Purification by reverse phase HPLC on a Vydac-18 column provided the desired amide (30 mg, 30%). MS (M+Na)$^+$=574.

Example 6

(2R,3S)N1-[(3S)-hexahydro-1-(3-phenoxybenzyl)-2-oxo-1H-azepin-3-yl]-N4-(methoxy)-2-(2-methylpropyl)-3-(propyl)-butanediamide

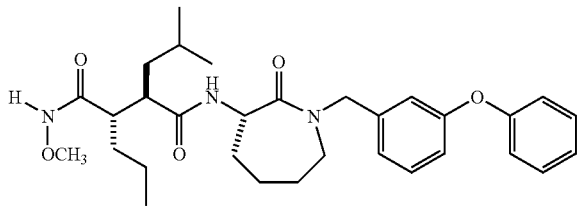

Following a procedure analogous to the preparation of Example 4, compound of Step (2e) (100 mg, 0.20 mmol) was activated and condensed with O-methylhydroxylamine hydrochloride (40 mg, 0.40 mmol). Purification by reverse phase HPLC on a Vydac-18 column provided the desired amide (30 mg, 30%). MS (M+Na)$^+$=560.

Example 7

(2R,3S)N1-[(3S)-hexahydro-1-(3-phenoxybenzyl)-2-oxo-1H-azepin-3-yl]-2-(2-methylpropyl)-3-(propyl)-butanediamide

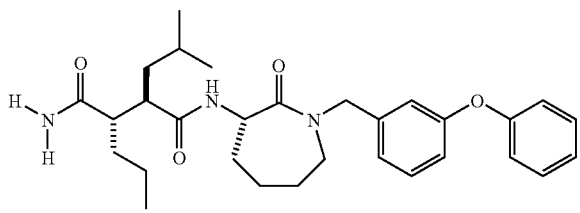

Following a procedure analogous to the preparation of Example 4, compound of Step (2e) (100 mg, 0.20 mmol) was activated and condensed with a 2.0 M solution of ammonia in dioxane (0.2 mL, 0.4 mmol). Purification by reverse phase HPLC on a Vydac-18 column provided the desired amide (30 mg, 30%). MS (M+Na)$^+$=530.

Example 7A (2R,3S)N1-[(3S)-hexahydro-1-(3-phenoxybenzyl)-2-oxo-1H-azepin-3-yl]-N4-(amino)-2-(2-methylpropyl)-3-(propyl)-butanediamide

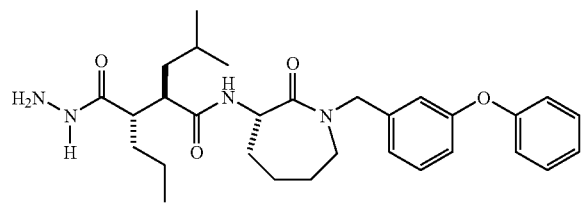

Following a procedure analogous to the preparation of Example 4, compound of Step (2e) (100 mg, 0.20 mmol) was activated and condensed with hydrazine (13 mg, 0.4 mmol). Purification by reverse phase HPLC on a Vydac-18 column provided the desired amide (11.1 mg, 21%). MS (M+Na)$^+$=542.

Example 8

(2R,3S)N1-[(3S)-hexahydro-1-(3-phenoxybenzyl)-2-oxo-1H-azepin-3-yl]-2-(2-methylpropyl)-3-(propyl)-butanediamide

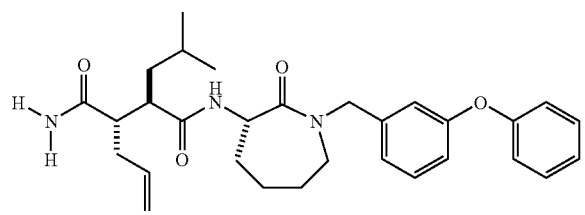

(8a) Compound 8a was synthesized following a procedure analogous to the preparation of the compound 1e, but using the caprolactam 2c (2.5 g, 5.89 mmol), succinate 9 (1.64 g, 6.0 mmol), and HATU instead of TBTU. The compound was purified by chromatogrphy eluting with 5% methanol in CH$_2$Cl$_2$ to afford 1.50 g (45%) of the desired ester.

(8b) The ester from 8a (1.18 g, 2.10 mmol) was dissolved in 10 mL of a 50% solution of trifluoroacetic acid in CH$_2$Cl$_2$ and stirred at rt for 2 h. The solvents were removed by concentration under reduced pressure and the crude product was dissolved in 10 mL of toluene and reconcentrated twice to remove residual TFA. The crude acid was used without further purification or characterization.

Following a procedure analogous to the preparation of Example 7, compound 8b (1.065 g, 2.10 mmol) was activated and condensed with an excess of gaseous ammonia. Purification by reverse phase HPLC on a Vydac-18 column provided 500 mg (47%) of the desired compound of Example 8. MS (M+Na)$^+$=528.

Example 9

(2R,3S)N1-[(3S)-hexahydro-1-(3-phenoxybenzyl)-2-oxo-1H-azepin-3-yl]-N4-(hydroxy)-2-(2-methylpropyl)-3-(allyl)-butanediamide

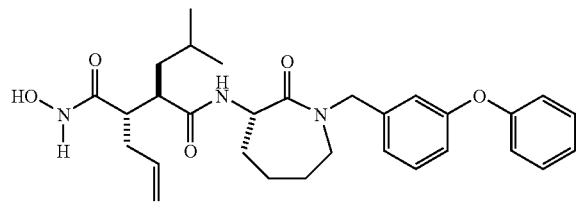

Example 9 was synthesized following a procedure analogous to the preparation of Example 2, but using succinate 9 (Scheme 2). Purification by reverse phase HPLC on a Vydac-18 column provided 150 mg of Example 9. MS (M+Na)$^+$=544.

Example 10

(2R,3S)N1-[(3S)-hexahydro-1-(3-(2,4-dichlorophenyl)benzyl)-2-oxo-1H-azepin-3-yl]-N4-(hydroxy)-2-(2-methylpropyl)-3-(propyl)-butanediamide

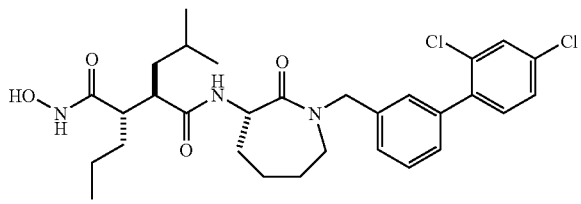

The general procedure reported for Scheme 5 was followed using 2,4-dichlorophenyl boronic acid. Purification afforded 6.0 mg (60%) of the desired product. MS (M+Na)$^+$=598.

Example 11

(2R,3S)N1-[(3S)-hexahydro-1-(3-(4-fluorophenyl)benzyl)-2-oxo-1H-azepin-3-yl]-N4-(hydroxy)-2-(2-methylpropyl)-3-(propyl)-butanediamide

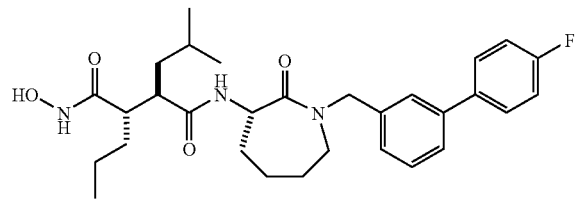

The general procedure reported for Scheme 5 was followed using 4-fluorophenyl boronic acid. Purification afforded 5.0 mg (54%) of the desired product. MS (M+Na)$^+$=548.

Example 12

(2R,3S)N1-[(3S)-hexahydro-1-(3-(4-methylphenyl)benzyl)-2-oxo-1H-azepin-3-yl]-N4-(hydroxy)-2-(2-methylpropyl)-3-(propyl)-butanediamide

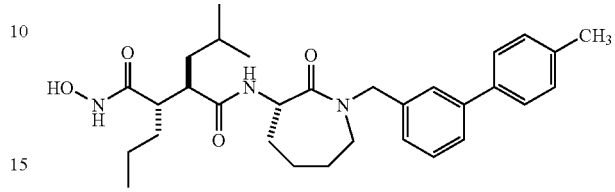

The general procedure reported for Scheme 5 was followed using 4-methylphenyl boronic acid. Purification afforded 3.0 mg (33%) of the desired product. MS (M+Na)$^+$=544.

Example 13

(2R,3S)N1-[(3S)-hexahydro-1-(3-(4-methoxyphenyl)benzyl)-2-oxo-1H-azepin-3-yl]-N4-(hydroxy)-2-(2-methylpropyl)-3-(propyl)-butanediamide

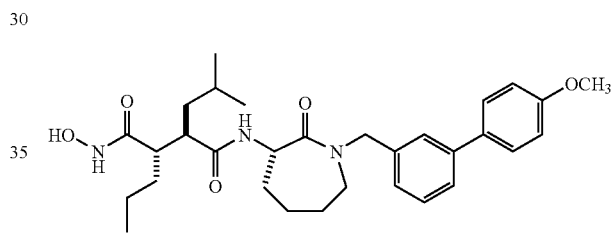

The general procedure reported for Scheme 5 was followed using 4-methoxyphenyl boronic acid. Purification afforded 3.0 mg (32%) of the desired product. MS (M+Na)$^+$=560.

Example 14

(2R,3S)N1-[(3S)-hexahydro-1-(3-(3-methylphenyl)benzyl)-2-oxo-1H-azepin-3-yl]-N4-(hydroxy)-2-(2-methylpropyl)-3-(propyl)-butanediamide

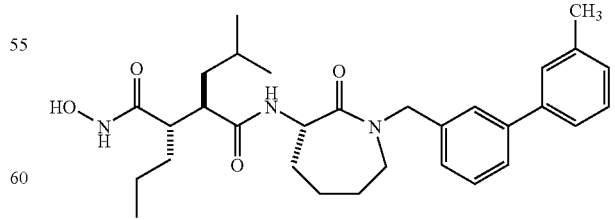

The general procedure reported for Scheme 5 was followed using 3-methylphenyl boronic acid. Purification afforded 3.0 mg (33%) of the desired product. MS (M+Na)$^+$=544.

Example 15

(2R,3S)N1-[(3S)-hexahydro-1-(3-(3-chloro-4-fluorophenyl)benzyl)-2-oxo-1H-azepin-3-yl]-N4-(hydroxy)-2-(2-methylpropyl)-3-(propyl)-butanediamide

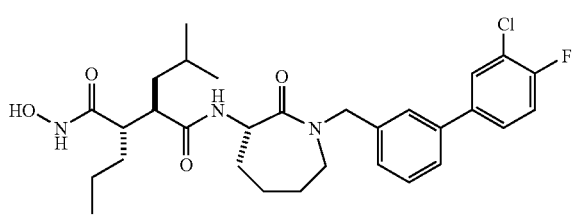

The general procedure reported for Scheme 5 was followed using 3-chloro-4-fluorophenyl boronic acid. Purification afforded 4.0 mg (41%) of the desired product. MS (M+Na)$^+$=582.

Example 16

(2R,3S)N1-[(3S)-hexahydro-1-(3-(4-trifluoromethylphenyl)benzyl)-2-oxo-1H-azepin-3-yl]-N4-(hydroxy)-2-(2-methylpropyl)-3-(propyl)-butanediamide

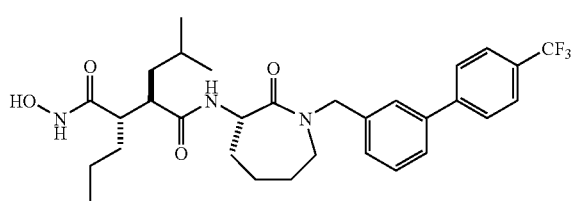

The general procedure reported for Scheme 5 was followed using 4-trifluoromethylphenyl boronic acid. Purification afforded 4.0 mg (40%) of the desired product. MS (M+Na)$^+$=598.

Example 17

(2R,3S)N1-[(3S)-hexahydro-1-(3-(3-methoxyphenyl)benzyl)-2-oxo-1H-azepin-3-yl]-N4-(hydroxy)-2-(2-methylpropyl)-3-(propyl)-butanediamide

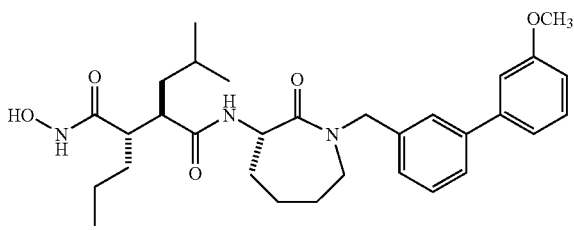

The general procedure reported for Scheme 5 was followed using 3-methoxyphenyl boronic acid. Purification afforded 4.1 mg (44%) of the desired product. MS (M+Na)$^+$=560.

Example 18

(2R,3S)N1-[(3S)-hexahydro-1-(3-(3-fluorophenyl)benzyl)-2-oxo-1H-azepin-3-yl]-N4-(hydroxy)-2-(2-methylpropyl)-3-(propyl)-butanediamide

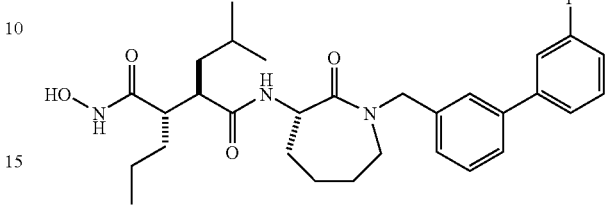

The general procedure reported for Scheme 5 was followed using 3-fluorophenyl boronic acid. Purification afforded 3.5 mg (38%) of the desired product. MS (M+Na)$^+$=548.

Example 19

(2R,3S)N1-[(3S)-hexahydro-1-(3-(2-methoxyphenyl)benzyl)-2-oxo-1H-azepin-3-yl]-N4-(hydroxy)-2-(2-methylpropyl)-3-(propyl)-butanediamide

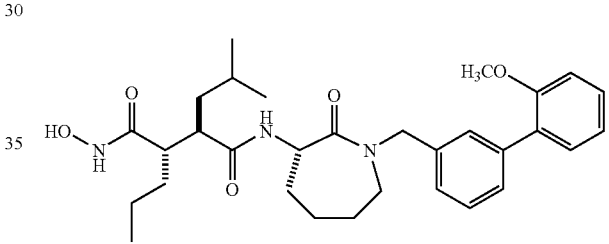

The general procedure reported for Scheme 5 was followed using 2-methoxyphenyl boronic acid. Purification afforded 1.3 mg (14%) of the desired product. MS (M+Na)$^+$=560.

Example 20

(2R,3S)N1-[(3S)-hexahydro-1-(3-(2-naphthyl)benzyl)-2-oxo-1H-azepin-3-yl]-N4-(hydroxy)-2-(2-methylpropyl)-3-(propyl)-butanediamide

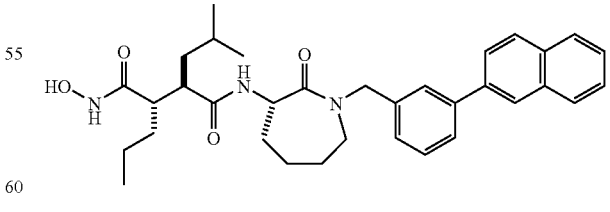

The general procedure reported for Scheme 5 was followed using 2-naphthyl boronic acid. Purification afforded 3.0 mg (31%) of the desired product. MS (M+Na)$^+$=580.

It will be understood by one skilled in the art that Scheme 6 can be followed in a manner analogous to the procedure for Scheme 5.

Example 21

(2R,3S)N1-[(3S)-hexahydro-1-(3-(4-methoxyphenyl)benzyl)-2-oxo-1H-azepin-3-yl]-2-(2-methylpropyl)-3-(propyl)-butanediamide

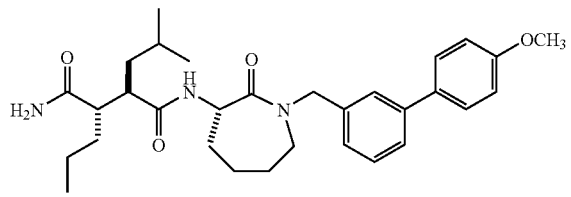

The general procedure reported for Scheme 6 was followed using 4-methoxyphenyl boronic acid. Purification afforded 0.5 mg of the desired product. MS (M+Na)$^+$=544.

Example 22

(2R,3S)N1-[(3S)-hexahydro-1-(3-(3-fluorophenyl)benzyl)-2-oxo-1H-azepin-3-yl]-2-(2-methylpropyl)-3-(propyl)-butanediamide

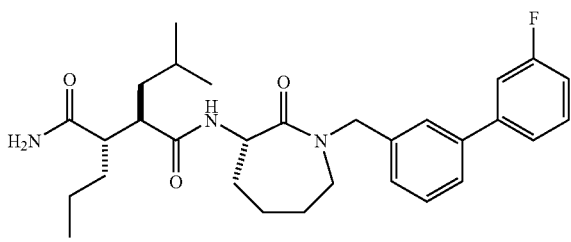

The general procedure reported for Scheme 6 was followed using 3-fluorophenyl boronic acid. Purification afforded 1.6 mg of the desired product. MS (M+Na)$^+$=532.

Example 23

(2R,3S)N1-[(3S)-hexahydro-1-(3-(4-trifluoromethylphenyl)benzyl)-2-oxo-1H-azepin-3-yl]-2-(2-methylpropyl)-3-(propyl)-butanediamide

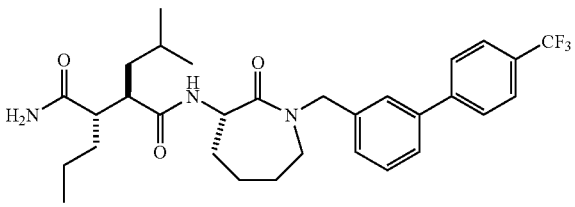

The general procedure reported for Scheme 6 was followed using 4-trifluoromethylphenyl boronic acid. Purification afforded 0.7 mg (4.3%) of the desired product. MS (M+Na)$^+$=582.

Example 24

(2R,3S)N1-[(3S)-hexahydro-1-(3-(2,4-dichlorophenyl)benzyl)-2-oxo-1H-azepin-3-yl]-2-(2-methylpropyl)-3-(propyl)-butanediamide

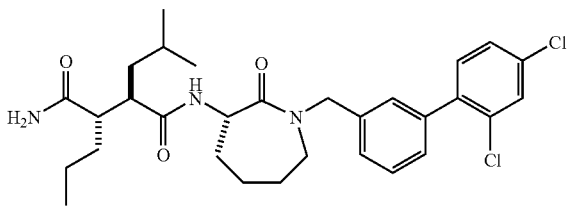

The general procedure reported for Scheme 6 was followed using 2,6-dichlorophenyl boronic acid. Purification afforded 1.8 mg (11%) of the desired product. MS (M+Na)$^+$=582.

Example 25

(2R,3S)N1-[(3S)-hexahydro-1-(3-(4-methylphenyl)benzyl)-2-oxo-1H-azepin-3-yl]-2-(2-methylpropyl)-3-(propyl)-butanediamide

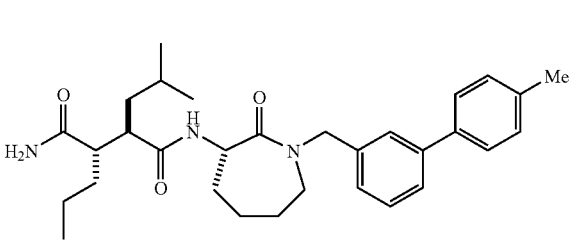

The general procedure reported for Scheme 6 was followed using 4-tolyl boronic acid. Purification afforded 1.8 mg (12%) of the desired product. MS (M+Na)$^+$=528.

Example 26

(2R,3S)N1-[(3S)-hexahydro-1-(3-(4-methoxyphenyl)benzyl)-2-oxo-1H-azepin-3-yl]-2-(2-methylpropyl)-3-(propyl)-butanediamide

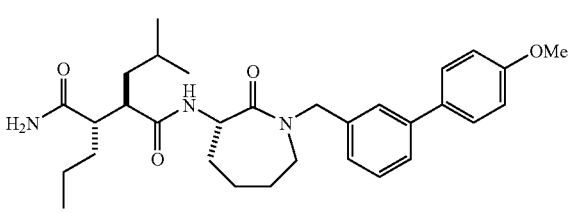

The general procedure reported for Scheme 6 was followed using 4-methoxyphenyl boronic acid. Purification afforded 0.5 mg (3.3%) of the desired product. MS (M+Na)$^+$=544.

Example 27

(2R,3S)N1-[(3S)-hexahydro-1-(3-(3-chloro-4-fluorophenyl)benzyl)-2-oxo-1H-azepin-3-yl]-2-(2-methylpropyl)-3-(propyl)-butanediamide

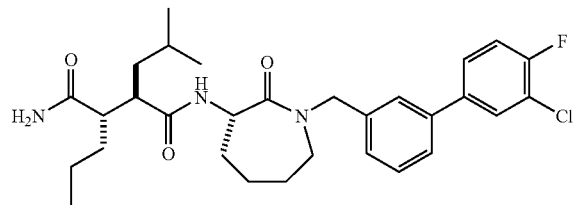

The general procedure reported for Scheme 6 was followed using 4-fluoro-3-chlorophenyl boronic acid. Purification afforded 0.5 mg (3.3%) of the desired product. MS (M+Na)$^+$=567.

Example 28

(2R,3S)N1-[(3S)-hexahydro-1-(3-(3-methoxyphenyl)benzyl)-2-oxo-1H-azepin-3-yl]-2-(2-methylpropyl)-3-(propyl)-butanediamide

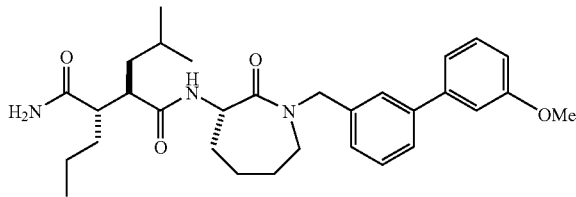

The general procedure reported for Scheme 6 was followed using 2-methoxyphenyl boronic acid. Purification afforded 0.8 mg (5.3%) of the desired product. MS (M+Na)$^+$=544.

Example 29

(2R,3S)N1-[(3S)-hexahydro-1-(3-(2-methoxyphenyl)benzyl)-2-oxo-1H-azepin-3-yl]-2-(2-methylpropyl)-3-(propyl)-butanediamide

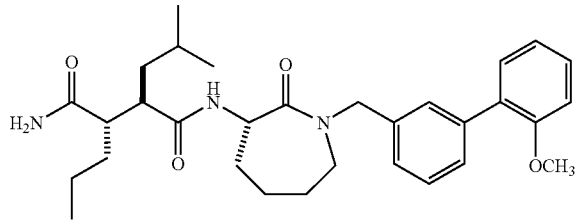

The general procedure reported for Scheme 6 was followed using 2-methoxyphenyl boronic acid. Purification afforded 1.5 mg (10%) of the desired product. MS (M+Na)$^+$=544.

It will be understood by one skilled in the art that Scheme 7 can be followed in a manner analogous to the procedure for Schemes 5 and 6.

Example 30

(2R,3S)N1-[(3S)-hexahydro-1-(3-(4-methoxyphenyl)pyrid-5-ylmethyl)-2-oxo-1H-azepin-3-yl]-2-(2-methylpropyl)-3-(propyl)-butanediamide

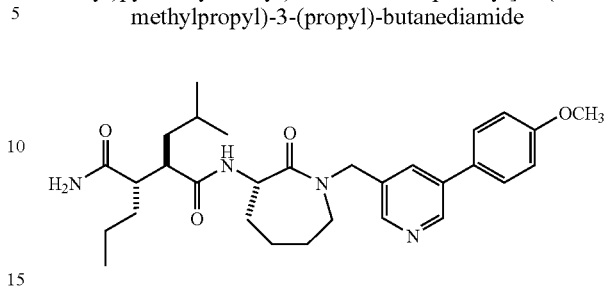

Amide 35 of Scheme 7 (0.10 g, 0.18 mmol) was dissolved in 5 mL of toluene and 41 mg (0.27 mmol) of 4-methoxyphenyl boronic acid was added, followed by 31 mg (0.0147 mmol) of tetrakis(triphenylphosphine)palladium, 0.5 mL of a 2M sodium carbonate solution and 0.5 mL of methanol. The reaction solution was heated to reflux for 16 h and then allowed to cool to rt. The reaction solution was diluted with 10 mL of water and extracted 2× with 50 mL of ethyl acetate. The combined organic layers were dried and concentrated and the resulting oil was purified by chromatography eluting with 30 to 100% ethyl acetate in hexanes as a solvent to provide 30 mg (29%) of biaryl product. MS (M+H)$^+$=580.

The purified biaryl product was dissolved in 10 mL of 1:1 trifluoroacetic acid/CH$_2$Cl$_2$ and stirred at rt for 2 h. The solvents were then removed under reduced pressure and the resulting oil was redissolved in 5 mL of toluene and reconcentrated to remove residual TFA. The crude acid (25 mg, 0.047 mmol) was then dissolved in 1 mL of DMF and 10 mL of N-methylmorpholine (0.094 mmol) and 42 mg (0.062 mmol) HATU were added and the reaction solution was stirred at rt for 45 min. Gaseous ammonia was then bubbled in at a gentle rate for about 1 minute and the solution was stirred for an additional 1 min. The reaction solution was then diluted with 10 mL of water and extracted 3× with 30 mL of ethyl acetate. The combined organic layers were dried and concentrated under reduced pressure to a solid which was purified by reversed phase HPLC to provide 3.5 mg (10%) of the compound of Example 30 as its trifluoroacetic acid salt. MS (M+H)$^+$=523.

Example 31

(2R,3S)N1-[(3S)-hexahydro-1-(3-(4-trifluoromethylphenyl)pyrid-5-ylmethyl)-2-oxo-1H-azepin-3-yl]-2-(2-methylpropyl)-3-(propyl)-butanediamide

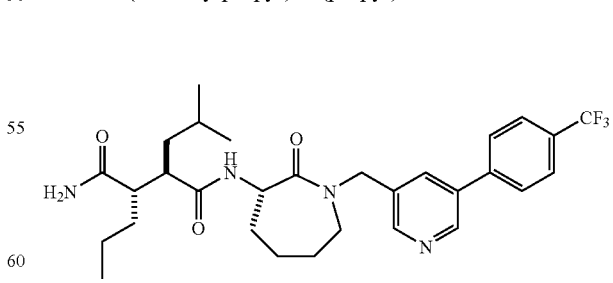

The general procedure reported for the compound of Example 30 was followed using 4-trifluoromethylphenyl boronic acid. Purification by HPLC afforded 6.0 mg of the desired product from as its trifluoroacetic acid salt. MS (M+Na)$^+$=583.

Example 32

(2R,3S)N1-[(3S)-hexahydro-1-(3-(3-chloro-4-fluorophenyl)pyrid-5-ylmethyl)-2-oxo-1H-azepin-3-yl]-2-(2-methylpropyl)-3-(propyl)-butanediamide

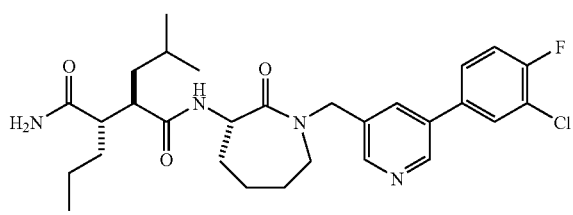

Amide 35 (0.30 g, 0.54 mmol) was dissolved in 3 mL of DMF and 123 mg (0.70 mmol) of 4-methoxyphenyl boronic acid was added, followed by 44 mg (0.0543 mmol) of bis(diphenylphosphinoferrocene) palladim (II) dichloride and 1.0 mL (7.18 mmol) of triethylamine. The reaction solution was heated to 80° C. for 24 h and then allowed to cool to rt. The reaction solution was diluted with 10 mL of water and extracted 2× with 50 mL of ethyl acetate. The combined organic layers were dried and concentrated and the resulting oil was purified by chromatography eluting with 20 to 100% ethyl acetate in hexanes as a solvent to provide 140 mg (50%) of biaryl product. MS (M+Na)$^+$=624.

The general procedure reported for the compound of Example 30 was then followed to provide the amide. Purification by chromatography eluting with 20 to 100% ethyl acetate in hexanes afforded 45 mg of the desired product of Example 32 as its trifluoroacetic acid salt. MS (M+Na)$^+$=567.

Example 33

(2R,3S)N1-[(3S)-hexahydro-1-(3-phenoxybenzyl)-2-oxo-1H-azepin-3-yl]-N4-(butyl)-2-(2-methylpropyl)-3-(propyl)-butanediamide

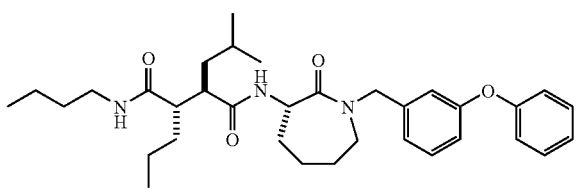

The general procedure reported for Scheme 8 was followed using butylamine. Analysis by $^1$HNMR integration relative to an internal standard revealed a yield of 100% of the desired product. MS (M+Na)$^+$=586.

Example 34

(2R,3S)N1-[(3S)-hexahydro-1-(3-phenoxybenzyl)-2-oxo-1H-azepin-3-yl]-N4-(2-furylmethyl)-2-(2-methylpropyl)-3-(propyl)-butanediamide

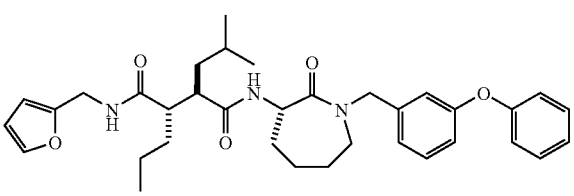

The general procedure reported for Scheme 8 was followed using 2-furylmethylamine. Analysis by $^1$HNMR integration relative to an internal standard revealed a yield of 75% of the desired product. MS (M+Na)$^+$=610.

Example 35

(2R,3S)N1-[(3S)-hexahydro-1-(3-phenoxybenzyl)-2-oxo-1H-azepin-3-yl]-N4-(cyclopentyl)-2-(2-methylpropyl)-3-(propyl)-butanediamide

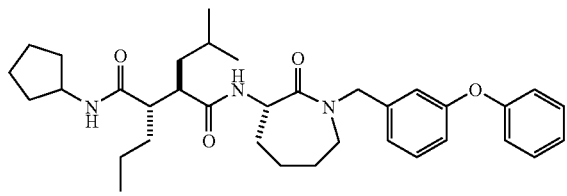

The general procedure reported for Scheme 8 was followed using cyclopentylamine. Analysis by $^1$HNMR integration relative to an internal standard revealed a yield of 42% of the desired product. MS (M+Na)$^+$=598.

Example 36

(2R,3S)N1-[(3S)-hexahydro-1-(3-phenoxybenzyl)-2-oxo-1H-azepin-3-yl]-N4-(cinnamyl)-2-(2-methylpropyl)-3-(propyl)-butanediamide

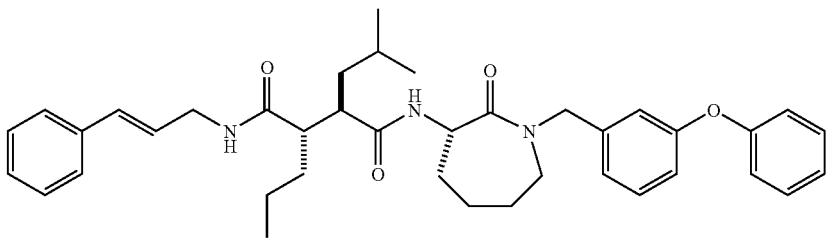

107

The general procedure reported for Scheme 8 was followed using cinnamylamine. Analysis by ¹HNMR integration relative to an internal standard revealed a yield of 100% of the desired product. MS (M+Na)⁺=646.

Example 37

(2R,3S)N1-[(3S)-hexahydro-1-(benzophenon-3-yl)-2-oxo-1H-azepin-3-yl]-2-(2-methylpropyl)-3-(allyl)-butanediamide

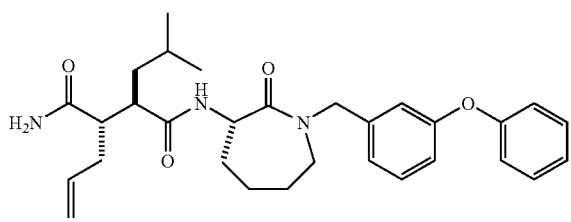

3-Bromomethylbenzophenone. A solution of 3-methylbenzophenone (20 g, 102 mmol) dissolved in 40 mL of 1,2-dibromoethane was heated to reflux. Over a period of about 3 hours a solution of 105 mmol of bromine dissolved in 6 mL of 1,2-dibromoethane was added to the refluxing solution. After the addition was complete the solution was allowed to cool to rt and diluted with 100 mL of dichloromethane. The organic layer was extracted with 1×25 mL of 1 N HCl, 2×15 mL of NaHCO₃ Solution, and 2×25 ML of brine. The organic layers were dried over magnesium sulfate and concentrated in vacuo. The residue was then distilled to afford the product, 16.5 g (60%) as an oil that solidified upon standing, b.p. 160° C. at 300 mTorr. ¹H NMR analysis shows that the product contains approximately 7% of the dibromide.

3-(1,1-dimethylethylcarbomethoxy-N-(benzophenone-3-yl-methyl)caprolactam. Diisopropylamine (4.2 mL, 30 mmol) was dissolved in 25 mL of THF and chilled to −78° C. To the solution was added 10 mL of 2.5M n-butyllithium in hexanes and the solution was warmed to 0° C. and allowed to stir for 10 min. A solution of Boc-protected aminocaprolactam 1a (5.0 grams, 22 mmol) dissolved in 25 mL of THF was then added and the reaction solution was stirred for 1 h at 0° C. Solid 3-bromomethyl-benzophenone was then added and the reaction solution was allowed to warm to rt and stir overnight. The reaction solution was diluted with water and extracted into ethyl acetate (100 mL). The organic layer was rinsed with 2×25 mL of 1 N HCl, 2×25 mL of saturated NaHCO₃ and 2×25 mL of brine, dried over magnesium sulfate, and dried in vacuo. Chromatography eluting with a gradient of 30% to 40% ethyl acetate in hexanes afforded the pure benzophenone-substituted caprolactam derivative (7.4 g, 80%). MS (M+Na)⁺=445.

The compound of Example 10 was synthesized in a manner analagous to the synthesis of the compound of Example 8 using succinate 9 and the benzophenone-substituted caprolactam derivative. The compound was purified by crystallization from ethyl acetate to afford 0.26 g of crystals. MS (M+Na)+=540.

Example 38

(2R,3S)N1-[(3S)-hexahydro-1-(benzophenon-3-yl)-2-oxo-1H-azepin-3-yl]-2-(2-methylpropyl)-3-(propyl)-butanediamide

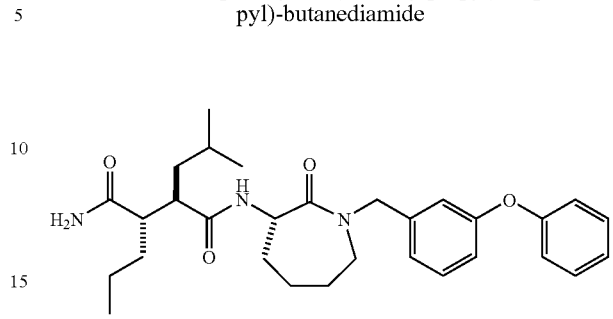

The compound of Example 11 was synthesized in a manner analagous to the synthesis of the compound of Example 8 using succinate 10 and the benzophenone-substituted caprolactam derivative. The compound was purified by crystallization from ethyl acetate to afford 0.25 g of crystals. MS (M+Na)+=542.

Example 39

(2R,3S)N1-[(3S)-hexahydro-1-(4-(4-trifluoromethylphenyl)benzyl)-2-oxo-1H-azepin-3-yl]-2-(2-methylpropyl)-3-(propyl)-butanediamide

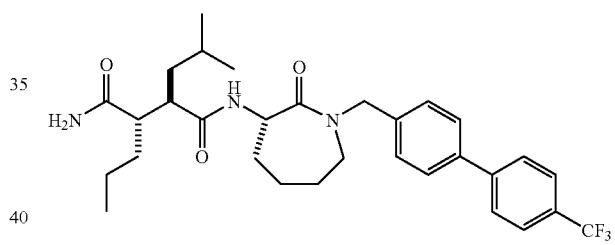

(39-a) 3-(1,1-dimethylethylcarbomethoxy-N-(4-bromophenylmethyl)caprolactam. The title compound was synthesized in a manner analagous to the preparation of 3-(1,1-dimethylethylcarbomethoxy-N-(benzophenone-3-yl-methyl)caprolactam in Example 10 but using 4-bromobenzyl bromide as the alkylaing agent. The compound was purified by chromatography eluting with 5-20% ethyl acetate in hexanes as eluent to provide 7.0 g (70%) of the title compound as a solid. MS (M+Na)+=419.

(39-b) 3-(1,1-dimethylethylcarbomethoxy-N-(4,-(4'-trifluoromethylphenyl)phenylmethyl)caprolactam. To a solution of 3-(1,1-dimethylethylcarbomethoxy-N-(4-bromophenylmethyl)caprolactam (0.5 g, 1.26 mmol) dissolved in 10 mL of toluene was added 263 mg (1.38 mmol) of 4-trifluoromethylphenyl boronic acid, 1 mL of methanol, and 1 mL of a 2M solution of potassium carbonate. The solution was degassed by nitrogen bubbling for 5 min, and then 33 mg of tris(dibenzylideneacetone)dipalladium (0) chloroform adduct and 66 mg of triphenylphosphine was added. The solution was heated to reflux for 16 h and then allowed to cool and diluted with 20 mL of water. The aqueous layer was extracted 3× with 25 mL of ethyla acetate and concentrated. The resulting oil was purified by chromatography eluting with 20% ethyl acetate in hexanes to afford 0.47 g (81%) of an oil which crystallized on standing.

(39-d) The compound 39-d was synthesized in a manner analagous to the synthesis of the compound of Example 8 using succinate 10 (280 mg, 1.04 mmol) and 3-(1,1-dimethylethylcarbomethoxy-N-(4,-(4'-trifluoromethylphenyl)-phenylmethyl)caprolactam. The compound was purified by chromatography eluting with 20-100% ethyl acetate in hexanes to afford 40 mg of a white powder. MS (M+H)+=560.

Example 40

(2S,3R)N1-[(3S)-hexahydro-1-(3-(2-tetrazolylphenyl)benzyl)-2-oxo-1H-azepin-3-yl]-2-(propyl)-3-(2-methylpropyl)-butanediamide

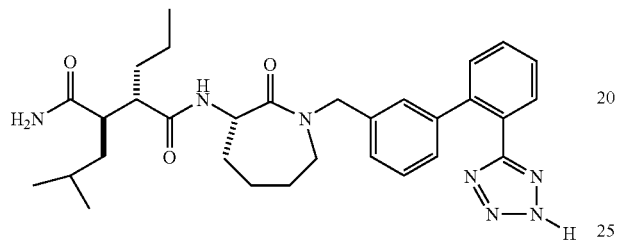

(40-a) The compound of Example 40 was synthesized in a manner analogous to the synthesis of the compound of Example 39, but using the substituted acid 28 of Scheme 6 (50 mg, 0.10 mmol) and o-((N-trityl)-tetrazole)phenylboronic acid under the conditions for the formation of the compound (39-b). The desired biaryl acid was isolated as an impure mixture (134 mg) and used directly in the next step.

(40-b) The acid 40-a (134 mg, impure mixture) was converted to the amide under the conditions reported for the compound of Example 8. The crude amide was then dissolved in 2 mL of 10% trifluoroacetic acid in methanol and allowed to stir at rt for 30 min. The solvents were removed and the residue was purified by chromatography eluting with 10% methanol in ethyl acetate to provide 40 mg (71%, 2 steps) of the compound of Example 40 as a sticky powder. MS (M+Na)+=582.

Example 41

(2S,3R)N1-[(3S)-hexahydro-1-(3-phenoxybenzyl)-2-oxo-1H-azepin-3-yl]-2-(propyl)-3-(2-methylpropyl)-butanediamide

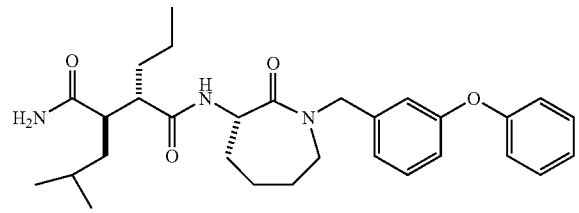

(41-a) The compound of Example 41 is formed by coupling Succinate 23 (480 mg, 1.21 mmol) with the substituted caprolactam TFA salt 2c under the conditions reported for the synthesis of the compound of Example 8. The crude fluorenylmethyl ester was used in the next step with out further purification. MS (M+Na)+=709.

(41-b) The crude fluorenylmethyl ester is dissolved in 2 mL of a 50% solution of piperidine in $CH_2Cl_2$ and stirred for 3 h at rt. A 10 mL portion of 1N HCl was then added and the mixture was extracted 3× with 10 mL of ethyl acetate. The crude acid was used in the next step with out further purification. MS (M+H)+=509.

The compound of Example 41 was then prepared using the acid 41-b under the conditions reported for compound of Example 28. The compound was purified by chromatography eluting with 5% methanol in $CH_2Cl_2$ to afford 120 mg (19%, 3 steps) of a white powder. MS (M+H)+=508.

Example 42

(2S,3R)N1-[1,3-dihydro-1-(3-phenoxybenzyl)-2-oxo-5-(phenyl)-2H-1,4-benzodiazepin-3-yl]-2-(2-methylpropyl)-3-(allyl)-butanediamide

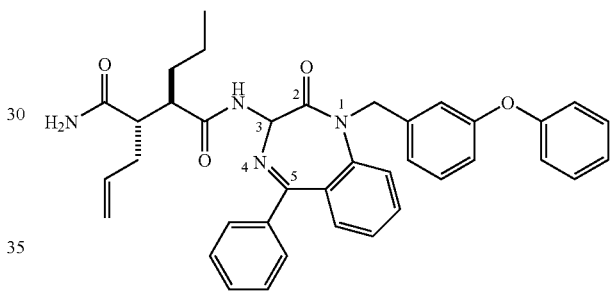

3-Phenoxybenzyl iodide: To a solution of 3-phenoxybenzyl chloride (10.0 g, 45.7 mmol) in 200 ml acetone was added sodium iodide (7.6 g, 507 mmol). The mixture was stirred at temperature overnight. The mixture was diluted with 300 ml hexane and the organic layer was washed twice with 5% sodium bicarbonate, once with brine and then dried over $MgSO_4$. Evaporation of the filtrate gave a light yellow oil. The product was used in next step without purification. $^1$H NMR ($CDCl_3$) 4.4 (s,2H), 6.8-7.4 (m, 9H).

Synthesis of Example 42

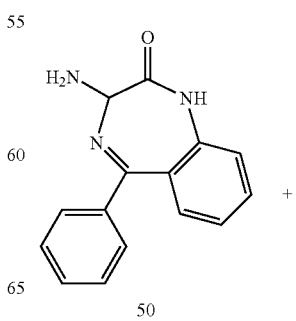

50

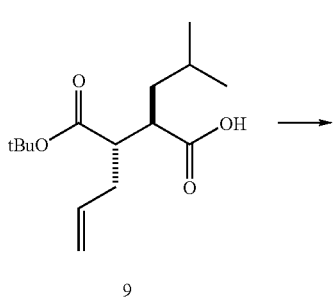

9

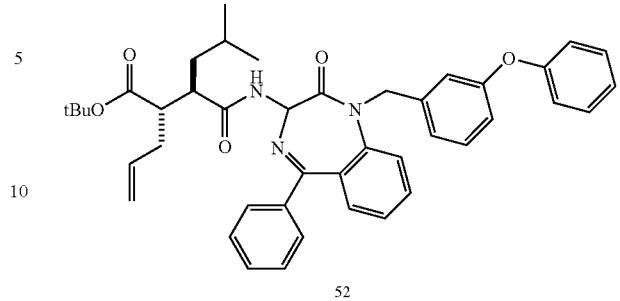

52

To a solution of benzodiazepine 51 (440 mg, 0.875 mmol) in DMF (20 ml) at 0 degrees was added NaH (45 mg, 1.12 mmol). The mixture was stirred at 0 degrees for 1.5 hr and then a solution of 3-phenoxylbenzyl iodide (330 mg, 1.06 mmol) in 10 ml DMF was added dropwise. The reaction mixture was allowed to warm to room temperature and stirred overnight. TLC using hexanes:EtOAc 6:4 (product Rf=0.31) indicated that the reaction was complete. The reaction mixture was quenched with water, and the solvent was evaporated under high vacuum, which provided a viscous yellow oil. The product benzodiazepine 52 was dissolved in ethyl acetate, which was washed with water (2×), brine and then dried over MgSO$_4$.

Evaporation of solvent gave 600 mg of benzodiazepine 52 as a yellow oil which was not further purified. M+H=686.3, M+Na=708.3. $^1$H NMR (CDCl$_3$) 0.8-1.0 (m, 6H), 1.0-1.3 (m, 1H), 1.4-1.5 (d, 9H), 1.5-1.9 (2H), 2.2-2.7 (4H), 4.6-4.8 (d,1H), 4.9-5.2 (m, 2H), 5.6-5.9 (m, 3H), 6.6-7.6 (m, 18H).

A solution of benzodiazepine 52 in 40 ml of TFA/CH$_2$Cl$_2$ (1:1) was stirred overnight at room temperature then evaporated to dryness. Repeated addition of toluene and evaporation provided 560 mg. of 53 as a yellow solid. (M−H=629.1)

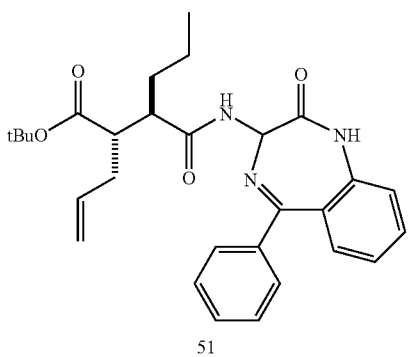

51

To a solution of benzodiazepine 50 (910 mg, 3.63 mmol), succinate 9 (980 mg, 3.63 mmol), hydroxybenzotriazole (980 mg., 7.25 mmol) and EDC (870 mg, 4.54 mmol) in 100 ml CH$_2$Cl$_2$ at 0 degrees was added triethylamine (0.76 ml, 5.45 mmol). The reaction mixture was washed with saturated sodium bicarbonate solution, 1.0N HCl, brine and dried over MgSO$_4$. Evaporation of the organic layer and purification by column chromatography on silica gel with hexane-ethyl acetate (7:3) gave 610 mg of benzodiazepine 51 as a white solid. M+H=504.37. $^1$H NMR (CDCl$_3$) 0.8-1.0 (m, 6H), 1.0-1.2 (m, 1H), 1.4-1.5 (d, 9H), 1.6-1.9 (m, 2H), 2.2-2.8 (m, 4H), 4.9-5.2 (m, 2H), 5.6 (dd, 1H), 5.6-6.0 (m, 1H), 7.0-7.6 (m, 9H).

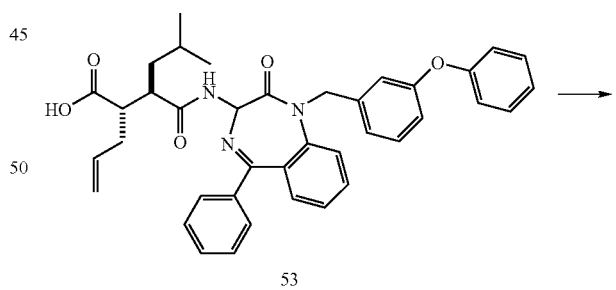

53

Example 42

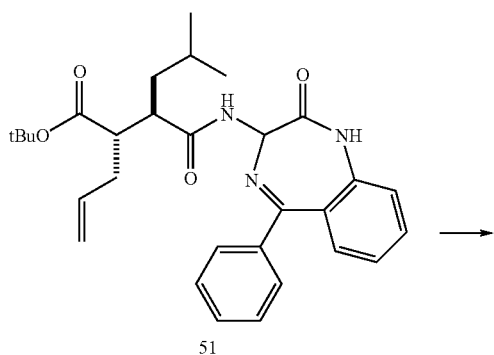

51

To a solution of benzodiazepine 53 and HATU (410 mg, 1.08 mmol) in 30 ml DMF was added diisopropylethylamine (0.6 ml, 3.44 mmol) at 0 degrees. After 10 minutes, ammonia gas was bubbled through the solution for two minutes, and the reaction mixture was allowed to warm to room temperature and stirred overnight. Addition of water and solvent evaporation under high vacuum provided a yellow solid. The solid was taken up in ethyl acetate-water (1:1), and the organic layer was washed with water (2×), brine and then dried over MgSO$_4$. Evaporation of solvent gave a light yellow solid. Chromatographic purification on silica gel using CH$_2$Cl$_2$:methanol (10:0.5) gave 256 mg of Example 42. M+H=629.2 HNMR (CDCl$_3$) 0.8-1.0 (m, 6H), 1.2-1.4 (m, 1H), 1.6-2.0 (m, 2H), 2.2-2.8(4H), 4.6-4.8 (m, 1H), 5.0-0.2(m, 2H), 5.6-5.9 (m, 3H), 6.2-7.8 (m, 18H).

Example 43

(2R) N1-[(3S)-hexahydro-1-(3-phenoxybenzyl)-2-oxo-1H-azepin-3-yl]-2-(2-methylpropyl)-butanediamide

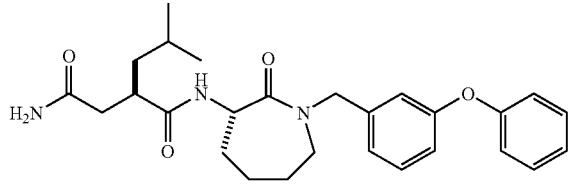

Step (43a): The compound of Step (43a) is formed by coupling succinate 7 (115 mg, 0.5 mmol) with the substituted caprolactam TFA salt (212 mg, 0.5 mmol) from Step (2c) of Example 2 under the conditions reported for the synthesis of the compound of Example 8. The crude tert-butyl ester was taken on without further purification.

Step (43b): The compound of Step (43b) is formed by dissolving the crude product from Step (43a) in 5 mL of a 1:1 solution of TFA/CH$_2$Cl$_2$ and stirring at room temperature for 2 hours. Concentration followed by reconcentration twice from 10 mL of toluene provides the crude acid which was taken on with no further purification.

Step (43c): The title compound, Example 43, was prepared using the acid from Step (43b) under the conditions reported for the compound of Example 7. The compound was purified by chromatography eluting with 5% methanol in CH$_2$Cl$_2$ to afford 50 mg (21%, 3 steps) of a white powder. MS (M+Na)$^+$=488.

Utility

Aβ production has been implicated in the pathology of Alzheimer's Disease (AD). The compounds of the present invention have utility for the prevention and treatment of AD by inhibiting Aβ production. Methods of treatment target formation of Aβ production through the enzymes involved in the proteolytic processing of β-amyloid precursor protein. Compounds that inhibit b or g secretase activity, either directly or indirectly, control the production of Aβ. Such inhibition of β or γ secretases reduces production of Aβ, and is expected to reduce or prevent the neurological disorders associated with Aβ protein, such as Alzheimer's Disease.

Cellular screening methods for inhibitors of Aβ production, testing methods for the in vivo suppression of Aβ production, and assays for the detection of secretase activity are known in the art and have been disclosed in numerous publications, including PCT publication number WO 98/22493, EPO publication number 0652009, U.S. Pat. Nos. 5,703,129 and 5,593,846; all hereby incorporated by reference.

The compounds of the present invention have utility for the prevention and treatment of disorders involving Aβ production, such as cerebrovascular disorders.

Compounds of the present invention have been shown to inhibit Aβ production, as determined by the secretase inhibition assay described below.

Compounds of the present invention have been shown to inhibit Aβ production, utilizing the C-terminus b amyloid precursor protein accumulation assay described below.

Compounds of Formula (I) are expected to possess γ-secretase inhibitory activity. The γ-secretase inhibitory activity of the compounds of the present invention is demonstrated using assays for such activity, for Example, using the assay described below. Compounds of the present invention have been shown to inhibit the activity of γ-secretase, as determined by the Aβ immunoprecipitation assay.

Compounds provided by this invention should also be useful as standards and reagents in determining the ability of a potential pharmaceutical to inhibit Aβ production. These would be provided in commercial kits comprising a compound of this invention.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar, "nm" denotes nanometer, "SDS" denotes sodium dodecyl sulfate, and "DMSO" denotes dimethyl sulfoxide, and "EDTA" denotes ethylenediaminetetraacetato.

A compound is considered to be active if it has an IC$_{50}$ or K$_i$ value of less than about 100 μM for the inhibition of Aβ production or inhibition of proteolytic activity leading to Aβ production. Compounds, as demonstrated by use of the invention, have demonstrated IC$_{50}$ values, for the inhibition of Aβ production, of less than about 100 μM. Preferably compounds, as demonstrated by use of the invention, demonstrate IC$_{50}$ values, for the inhibition of Aβ production, of less than about 1 μM. More preferably compounds, as demonstrated by use of the invention, demonstrate IC$_{50}$ values, for the inhibition of Aβ production, of less than about 100 nM. Even more preferably compounds, as demonstrated by use of the invention, demonstrate IC$_{50}$ values, for the inhibition of Aβ production, of less than about 50 nM.

β Amyloid Precursor Protein Accumulation Assay (βAPPA Assay)

An assay to evaluate the accumulation of Aβ protein was developed to detect potential inhibitors of secretases. The assay uses the N 9 cell line, characterized for expression of exogenous APP by immunoblotting and immunoprecipitation.

The effect of test compounds on the accumulation of Aβ in the conditioned medium is tested by immunoprecipitation. N 9 cells are grown to confluency in 6-well plates and washed twice with 1×Hank's buffered salt solution. The cells are starved in methionine/cysteine deficient media for 30 min., followed by replacement with fresh deficient media containing 150 uCi Tran35S-LABEL™ (ICN). Test compounds dissolved in DMSO (final concentration 1%) are added, over a range of 1 picomolar to 100 micromolar, together with the addition of the fresh media containing Tran35S-LABEL™. The cells are incubated for 4 h at 37° C. in a tissue culture incubator.

At the end of the incubation period, the conditioned medium is harvested and pre-cleared by the addition of 5 μl normal mouse serum and 50 μl of protein A Sepharose (Pharmacia), mixed by end-over-end rotation for 30 minutes at 4°C, followed by a brief centrifugation in a microfuge. The supernatant is then harvested and transferred to fresh tubes containing 5 ug of a monoclonal antibody (examples of antibodies include but are not limited by, clone 1101.1, directed against an internal peptide sequence in Aβ; or 6E10 from Senetek; or 4G8 from Senetek; additionally polyclonals from rabbit antihuman Aβ from Boehringer Mannheim) and 50 µl protein A Sepharose. After incubation overnight at 4°C, the samples are washed three times with high salt washing buffer (50 mM Tris, pH 7.5, 500 mM NaCl, 5 mM EDTA, 0.5% Nonidet P-40), three times with low salt wash buffer (50 mM Tris, pH 7.5, 150 mM NaCl, 5 mM EDTA, 0.5% Nonidet P-40), and three times with 10 mM Tris, pH 7.5. The pellet after the last wash is resuspended in SDS sample buffer (Laemmli U.K. Cleavage of structural proteins during the assembly of the head of bacteriphage T4. Nature 227, 680-5, 1970.) and boiled for 3 minutes. The supernatant is then fractionated on either 10-20% Tris/Tricine SDS gels or on 16.5% Tris/Tricine SDS gels. The gels are dried and exposed to X-ray film or analyzed by phosphorimaging. The resulting image is analyzed for the presence of Aβ polypeptides. The steady-state level of Aβ in the presence of a test compound is compared to wells treated with DMSO (1%) alone. A typical test compound in this assay blocks Aβ accumulation in the conditioned medium, and is considered active with an $IC_{50}$ less than 100 µM.

C-Terminus β-Amyloid Precursor Protein Accumulation Assay (CTF Assay)

The effect of test compounds on the accumulation of C-terminal fragments is determined by immunoprecipitation of APP and fragments thereof from cell lysates. N 9 cells are metabolically labeled, as above, with media containing Tran35S-LABEL™, in the presence or absence of test compounds. At the end of the incubation period, the conditioned medium are harvested and cells lysed in RIPA buffer (10 mM Tris, pH 8.0 containing 1% Triton X-100, 1% deoxycholate, 0.1% SDS, 150 mM NaCl, 0.125% $NaN_3$). Again, lysates are precleared with 5 ul normal rabbit serum/50 ul protein A Sepharose, followed by the addition of BC-1 antiserum (15 µl) and 50 µl protein A Sepharose for 16 hours at 4°C. The immunoprecipitates are washed as above, bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound in this assay stimulates C-terminal fragment accumulation in the cell lysates, and is considered active with an $IC_{50}$ less than 100 µM.

Accumulation-Release Assay

This immunoprecipitation assay is specific for g secretase activity (i.e., proteolytic activity required to generate the C-terminal end of Aβ either by direct cleavage or generating a C-terminal extended species which is subsequently further proteolyzed). N 9 cells are pulse labeled with media containing Tran35S-LABEL™ in the presence of a reported g secretase inhibitor (MDL 28170; Higaki J, Quon D, Zhong Z, Cordell B. Inhibition of beta-amyloid formation identifies proteolytic precursors and subcellular site of catabolism. Neuron 14, 651-659, 1995) for 1 h, followed by washing to remove $^{35}S$ radiolabel and MDL 28170. The media is replaced and test compounds are added over a dose range (for example 0.1 nM to 100 uM). The cells are chased for increasing periods of times and Aβ is isolated from the conditioned medium and C-terminal fragments from cell lysates (see accumulation assay above). The activity of test compounds are characterized by whether a stabilization of C-terminal fragments is observed and whether Aβ is generated from these accumulated precursor. A typical test compound in this assay prevents the generation of Aβ out of accumulated C-terminal fragments and is considered active with an $IC_{50}$ less than 100 µM.

Dosage and Formulation

The compounds determined from the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds determined from the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this invention can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds determined from the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds determined from the present invention may be administered in a single daily dose, or the total daily dosage may be administered in divided doses of two, three, or four times daily.

The compounds identified using the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds determined from the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds determined from the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

The Tables below provide representative Examples of compounds of Formula (I) of the present invention.

TABLE 1

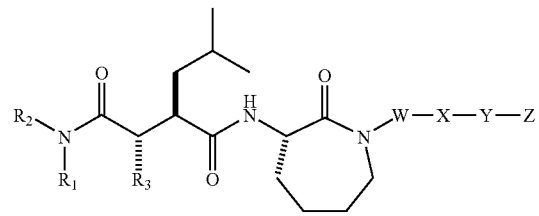

| Ex # | R¹ | R² | R³ | Z—Y—X—W |
|---|---|---|---|---|
| 1 | H | OH | propyl | 3,3-diphenylpropyl |
| 2 | H | OH | propyl | 3-phenoxybenzyl |
| 3 | H | OH | propyl | phenyl |
| 4 | H | CH₃ | propyl | 3-phenoxybenzyl |
| 5 | CH₃ | OCH₃ | propyl | 3-phenoxybenzyl |
| 6 | H | OCH₃ | propyl | 3-phenoxybenzyl |
| 7 | H | H | propyl | 3-phenoxybenzyl |
| 7A | H | NH₂ | propyl | 3-phenoxybenzyl |
| 8 | H | H | allyl | 3-phenoxybenzyl |
| 9 | H | OH | allyl | 3-phenoxybenzyl |
| 10 | H | OH | propyl | 3-(2,4-dichlorophenyl)-benzyl |
| 11 | H | OH | propyl | 3-(4-fluorophenyl)-benzyl |
| 12 | H | OH | propyl | 3-(4-methylphenyl)-benzyl |
| 13 | H | OH | propyl | 3-(4-methoxyphenyl)-benzyl |
| 14 | H | OH | propyl | 3-(3-methyphenyl)-benzyl |
| 15 | H | OH | propyl | 3-(3-chloro-4-fluorophenyl)-benzyl |
| 16 | H | OH | propyl | 3-(4-trifluoromethyl-phenyl)benzyl |
| 17 | H | OH | propyl | 3-(3-methoxyphenyl)-benzyl |
| 18 | H | OH | propyl | 3-(3-fluorophenyl)-benzyl |
| 19 | H | OH | propyl | 3-(2-methoxyphenyl)-benzyl |
| 20 | H | OH | propyl | 3-(2-naphthyl)benzyl |
| 21 | H | H | propyl | 3-(4-methoxyphenyl)-benzyl |
| 22 | H | H | propyl | 3-(3-fluorophenyl)-benzyl |
| 23 | H | H | propyl | 3-(4-F₃C-phenyl)benzyl |
| 24 | H | H | propyl | 3-(2,4-Cl₂-phenyl)benzyl |
| 25 | H | H | propyl | 3-(4-H₃C-phenyl)-benzyl |
| 26 | H | H | propyl | 3-(4-H₃CO-phenyl)-benzyl |
| 27 | H | H | propyl | 3-(3-Cl,4-F-phenyl)-benzyl |
| 28 | H | H | propyl | 3-(3-H₃CO-phenyl)-benzyl |
| 29 | H | H | propyl | 3-(2-H₃CO-phenyl)-benzyl |
| 30 | H | H | propyl | 3-(4-H₃CO-phenyl)-pyrid-5-ylmethyl |
| 31 | H | H | propyl | 3-(4-F₃C-phenyl)-pyrid-5-ylmethyl |
| 32 | H | H | propyl | 3-(3-Cl,4-F-phenyl)-pyrid-5-ylmethyl |
| 33 | H | n-butyl | propyl | 3-phenoxybenzyl |
| 34 | H | 2-furyl-methyl | propyl | 3-phenoxybenzyl |
| 35 | H | C₅H₉ | propyl | 3-phenoxybenzyl |
| 36 | H | cinnamyl | propyl | 3-phenoxybenzyl |
| 37 | H | H | allyl | benzophenone-3-yl-methyl |
| 38 | H | H | propyl | benzophenone-3-yl-methyl |
| 39 | H | H | propyl | 4-(4-F₃C-phenyl)benzyl |

TABLE 1-continued

![structure]

| Ex # | R¹ | R² | R³ | Z—Y—X—W |
|------|----|----|----|---------|
| 40*  | H  | H  | i-butyl<br>R⁵ = propyl | 3-(2-tetrazolyl-phenyl)-benzyl |
| 41*  | H  | H  | i-butyl<br>R⁵ = propyl | 3-phenoxybenzyl |
| 43   | H  | H  | H  | 3-phenoxybenzyl |

Table 2 demonstrates representative compounds envisaged within the scope of the present invention. Each formulae at the start of Table 2 are intended to be paired with each entry in the table which follows.

For example the compound (2R,3S)N1-[(3S)-hexahydro-1-(3-(3,4-dimethoxyphenyl)benzyl)-2-oxo-1H-azepin-3-yl]-2-(2-methylpropyl)-3-(allyl)-butanediamide is represented by Example #139-A-j, which comprises the core A, succinate j, and entry #139.

For example the compound (2R,3S)N1-[6,7-dihydro-5-(3-(3,4-dimethoxyphenyl)benzyl)-6-oxo-5H-dibenz[b,d]azepin-7-yl]-2-(2-methylpropyl)-3-(allyl)-butanediamide is represented by Example #139-B-j, which comprises the core B, succinate j, and entry #139.

For example the compound (2R,3S)N1-[1,3,4,5-tetrahydro-1-(3,4-dimethoxyphenyl)benzyl)-2-oxo-5-(phenyl)-2H-1,5-benzodiazepin-3-yl]-2-(2-methylpropyl)-3-(butyl)-butanediamide, is represented by Example #139-C-ab, which comprises the core C, succinate ab, and entry #139.

TABLE 2

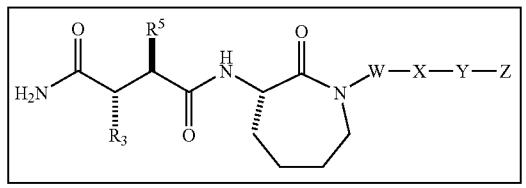

A

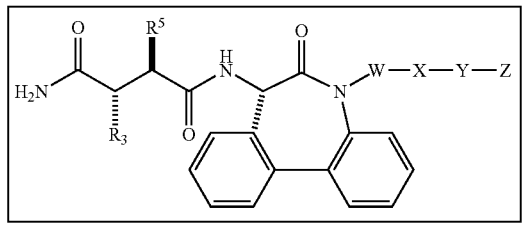

B

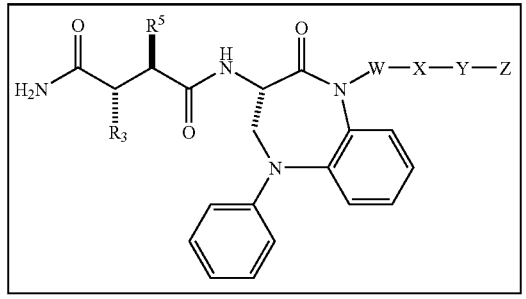

C

TABLE 2-continued
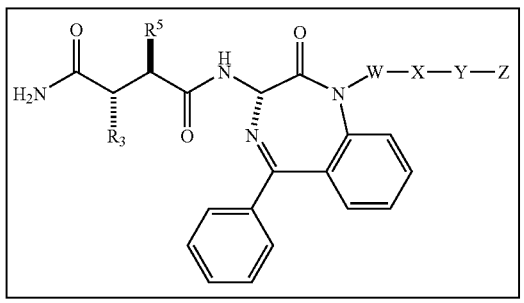
D
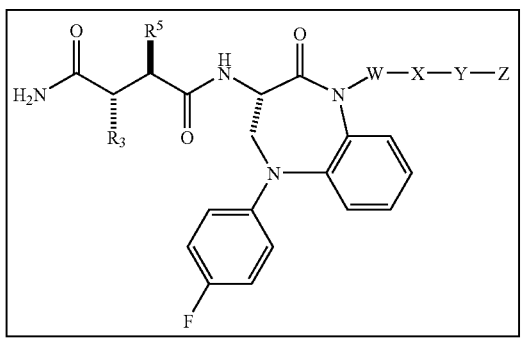
E
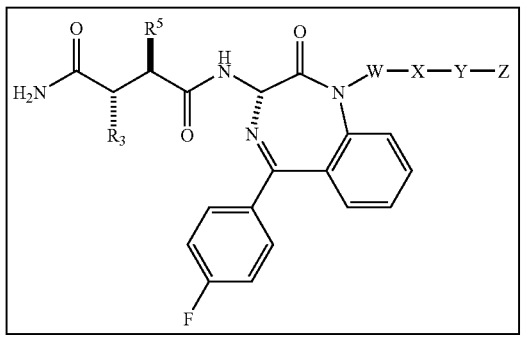
F
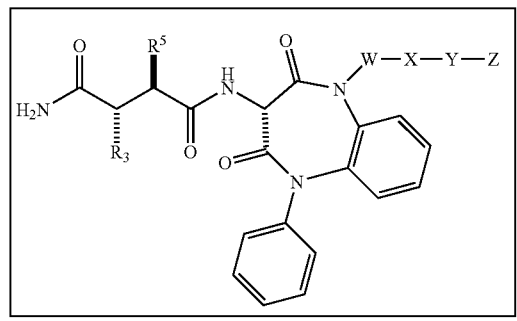
G

TABLE 2-continued

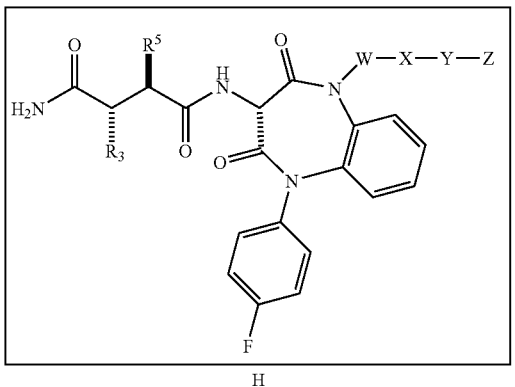

H

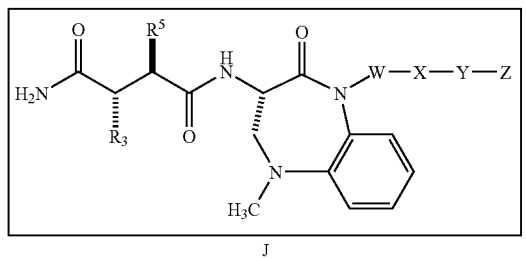

J

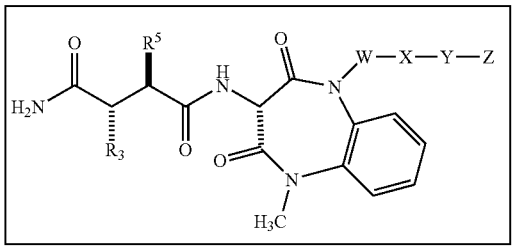

K

| Ex # | W | X | Y | Z |
|---|---|---|---|---|
| 100 | —CH$_2$— | phen-1,3-diyl | bond | phenyl |
| 101 | —CH$_2$— | phen-1,3-diyl | bond | 3,3-diphenylmethyl |
| 102 | —CH$_2$— | phen-1,3-diyl | bond | 2-F-phenyl |
| 103 | —CH$_2$— | phen-1,3-diyl | bond | 3-F-phenyl |
| 104 | —CH$_2$— | phen-1,3-diyl | bond | 4-F-phenyl |
| 105 | —CH$_2$— | phen-1,3-diyl | bond | 2-Cl-phenyl |
| 106 | —CH$_2$— | phen-1,3-diyl | bond | 3-Cl-phenyl |
| 107 | —CH$_2$— | phen-1,3-diyl | bond | 4-Cl-phenyl |
| 108 | —CH$_2$— | phen-1,3-diyl | bond | 2-Me-phenyl |
| 109 | —CH$_2$— | phen-1,3-diyl | bond | 3-Me-phenyl |
| 110 | —CH$_2$— | phen-1,3-diyl | bond | 4-Me-phenyl |
| 111 | —CH$_2$— | phen-1,3-diyl | bond | 2-MeO-phenyl |
| 112 | —CH$_2$— | phen-1,3-diyl | bond | 3-MeO-phenyl |
| 113 | —CH$_2$— | phen-1,3-diyl | bond | 4-MeO-phenyl |
| 114 | —CH$_2$— | phen-1,3-diyl | bond | 2-MeS-phenyl |
| 115 | —CH$_2$— | phen-1,3-diyl | bond | 3-MeS-phenyl |
| 116 | —CH$_2$— | phen-1,3-diyl | bond | 4-MeS-phenyl |
| 117 | —CH$_2$— | phen-1,3-diyl | bond | 2-F$_3$C-phenyl |
| 118 | —CH$_2$— | phen-1,3-diyl | bond | 3-F$_3$C-phenyl |
| 119 | —CH$_2$— | phen-1,3-diyl | bond | 4-F$_3$C-phenyl |
| 120 | —CH$_2$— | phen-1,3-diyl | bond | 2,3-diF-phenyl |
| 121 | —CH$_2$— | phen-1,3-diyl | bond | 2,4-diF-phenyl |
| 122 | —CH$_2$— | phen-1,3-diyl | bond | 2,5-diF-phenyl |
| 123 | —CH$_2$— | phen-1,3-diyl | bond | 2,6-diF-phenyl |
| 124 | —CH$_2$— | phen-1,3-diyl | bond | 3,4-diF-phenyl |
| 125 | —CH$_2$— | phen-1,3-diyl | bond | 3,5-diF-phenyl |
| 126 | —CH$_2$— | phen-1,3-diyl | bond | 2,3-diCl-phenyl |
| 127 | —CH$_2$— | phen-1,3-diyl | bond | 2,4-diCl-phenyl |
| 128 | —CH$_2$— | phen-1,3-diyl | bond | 2,5-diCl-phenyl |

TABLE 2-continued

| | | | | |
|---|---|---|---|---|
| 129 | —CH$_2$— | phen-1,3-diyl | bond | 2,6-diCl-phenyl |
| 130 | —CH$_2$— | phen-1,3-diyl | bond | 3,4-diCl-phenyl |
| 131 | —CH$_2$— | phen-1,3-diyl | bond | 3,5-diCl-phenyl |
| 132 | —CH$_2$— | phen-1,3-diyl | bond | 2-Cl-3-F-phenyl |
| 133 | —CH$_2$— | phen-1,3-diyl | bond | 2-Cl-4-F-phenyl |
| 134 | —CH$_2$— | phen-1,3-diyl | bond | 2-Cl-5-F-phenyl |
| 135 | —CH$_2$— | phen-1,3-diyl | bond | 3-Cl-4-F-phenyl |
| 136 | —CH$_2$— | phen-1,3-diyl | bond | 3-Cl-5-F-phenyl |
| 137 | —CH$_2$— | phen-1,3-diyl | bond | 4-Cl-2-F-phenyl |
| 138 | —CH$_2$— | phen-1,3-diyl | bond | 4-Cl-3-F-phenyl |
| 139 | —CH$_2$— | phen-1,3-diyl | bond | 2,3-diMeO-phenyl |
| 140 | —CH$_2$— | phen-1,3-diyl | bond | 2,4-diMeO-phenyl |
| 141 | —CH$_2$— | phen-1,3-diyl | bond | 2,5-diMeO-phenyl |
| 142 | —CH$_2$— | phen-1,3-diyl | bond | 2,6-diMeO-phenyl |
| 143 | —CH$_2$— | phen-1,3-diyl | bond | 3,4-diMeO-phenyl |
| 144 | —CH$_2$— | phen-1,3-diyl | bond | 3,5-diMeO-phenyl |
| 145 | —CH$_2$— | phen-1,3-diyl | bond | cyclopropyl |
| 146 | —CH$_2$— | phen-1,3-diyl | bond | cyclobutyl |
| 147 | —CH$_2$— | phen-1,3-diyl | bond | cyclopentyl |
| 148 | —CH$_2$— | phen-1,3-diyl | bond | cyclohexyl |
| 149 | —CH$_2$— | phen-1,3-diyl | bond | 2-furanyl |
| 150 | —CH$_2$— | phen-1,3-diyl | bond | 2-thienyl |
| 151 | —CH$_2$— | phen-1,3-diyl | bond | 2-imidazolyl |
| 152 | —CH$_2$— | phen-1,3-diyl | bond | 2-pyridyl |
| 153 | —CH$_2$— | phen-1,3-diyl | bond | 3-pyridyl |
| 154 | —CH$_2$— | phen-1,3-diyl | bond | 4-pyridyl |
| 155 | —CH$_2$— | phen-1,3-diyl | bond | N-morpholinyl |
| 156 | —CH$_2$— | phen-1,3-diyl | bond | N-piperidinyl |
| 157 | —CH$_2$— | phen-1,3-diyl | bond | 3-Me-2-pyridyl |
| 158 | —CH$_2$— | phen-1,3-diyl | bond | 4-Me-2-pyridyl |
| 159 | —CH$_2$— | phen-1,3-diyl | bond | 1-indolyl |
| 160 | —CH$_2$— | phen-1,3-diyl | bond | 2-benzothienyl |
| 161 | —CH$_2$— | phen-1,3-diyl | bond | 2-benzofuranyl |
| 162 | —CH$_2$— | phen-1,3-diyl | bond | 1-benzimidazole |
| 163 | —CH$_2$— | phen-1,3-diyl | bond | 2-naphthyl |
| 164 | —CH$_2$— | pyridin-3,5-diyl | bond | phenyl |
| 165 | —CH$_2$— | pyridin-3,5-diyl | bond | 3,3-diphenylmethyl |
| 166 | —CH$_2$— | pyridin-3,5-diyl | bond | 2-F-phenyl |
| 167 | —CH$_2$— | pyridin-3,5-diyl | bond | 3-F-phenyl |
| 168 | —CH$_2$— | pyridin-3,5-diyl | bond | 4-F-phenyl |
| 169 | —CH$_2$— | pyridin-3,5-diyl | bond | 2-Cl-phenyl |
| 170 | —CH$_2$— | pyridin-3,5-diyl | bond | 3-Cl-phenyl |
| 171 | —CH$_2$— | pyridin-3,5-diyl | bond | 4-Cl-phenyl |
| 172 | —CH$_2$— | pyridin-3,5-diyl | bond | 2-Me-phenyl |
| 173 | —CH$_2$— | pyridin-3,5-diyl | bond | 3-Me-phenyl |
| 174 | —CH$_2$— | pyridin-3,5-diyl | bond | 4-Me-phenyl |
| 175 | —CH$_2$— | pyridin-3,5-diyl | bond | 2-MeO-phenyl |
| 176 | —CH$_2$— | pyridin-3,5-diyl | bond | 3-MeO-phenyl |
| 177 | —CH$_2$— | pyridin-3,5-diyl | bond | 4-MeO-phenyl |
| 178 | —CH$_2$— | pyridin-3,5-diyl | bond | 2-MeS-phenyl |
| 179 | —CH$_2$— | pyridin-3,5-diyl | bond | 3-MeS-phenyl |
| 180 | —CH$_2$— | pyridin-3,5-diyl | bond | 4-MeS-phenyl |
| 181 | —CH$_2$— | pyridin-3,5-diyl | bond | 2-F$_3$C-phenyl |
| 182 | —CH$_2$— | pyridin-3,5-diyl | bond | 3-F$_3$C-phenyl |
| 183 | —CH$_2$— | pyridin-3,5-diyl | bond | 4-F$_3$C-phenyl |
| 184 | —CH$_2$— | pyridin-3,5-diyl | bond | 2,3-diF-phenyl |
| 185 | —CH$_2$— | pyridin-3,5-diyl | bond | 2,4-diF-phenyl |
| 186 | —CH$_2$— | pyridin-3,5-diyl | bond | 2,5-diF-phenyl |
| 187 | —CH$_2$— | pyridin-3,5-diyl | bond | 2,6-diF-phenyl |
| 188 | —CH$_2$— | pyridin-3,5-diyl | bond | 3,4-diF-phenyl |
| 189 | —CH$_2$— | pyridin-3,5-diyl | bond | 3,5-diF-phenyl |
| 190 | —CH$_2$— | pyridin-3,5-diyl | bond | 2,3-diCl-phenyl |
| 191 | —CH$_2$— | pyridin-3,5-diyl | bond | 2,4-diCl-phenyl |
| 192 | —CH$_2$— | pyridin-3,5-diyl | bond | 2,5-diCl-phenyl |
| 193 | —CH$_2$— | pyridin-3,5-diyl | bond | 2,6-diCl-phenyl |
| 194 | —CH$_2$— | pyridin-3,5-diyl | bond | 3,4-diCl-phenyl |
| 195 | —CH$_2$— | pyridin-3,5-diyl | bond | 3,5-diCl-phenyl |
| 196 | —CH$_2$— | pyridin-3,5-diyl | bond | 2-Cl-3-F-phenyl |
| 197 | —CH$_2$— | pyridin-3,5-diyl | bond | 2-Cl-4-F-phenyl |
| 198 | —CH$_2$— | pyridin-3,5-diyl | bond | 2-Cl-5-F-phenyl |
| 199 | —CH$_2$— | pyridin-3,5-diyl | bond | 3-Cl-4-F-phenyl |
| 200 | —CH$_2$— | pyridin-3,5-diyl | bond | 3-Cl-5-F-phenyl |
| 201 | —CH$_2$— | pyridin-3,5-diyl | bond | 4-Cl-2-F-phenyl |
| 202 | —CH$_2$— | pyridin-3,5-diyl | bond | 4-Cl-3-F-phenyl |
| 203 | —CH$_2$— | pyridin-3,5-diyl | bond | 2,3-diMeO-phenyl |
| 204 | —CH$_2$— | pyridin-3,5-diyl | bond | 2,4-diMeO-phenyl |
| 205 | —CH$_2$— | pyridin-3,5-diyl | bond | 2,5-diMeO-phenyl |
| 206 | —CH$_2$— | pyridin-3,5-diyl | bond | 2,6-diMeO-phenyl |

TABLE 2-continued

| | | | | |
|---|---|---|---|---|
| 207 | —CH₂— | pyridin-3,5-diyl | bond | 3,4-diMeO-phenyl |
| 208 | —CH₂— | pyridin-3,5-diyl | bond | 3,5-diMeO-phenyl |
| 209 | —CH₂— | pyridin-3,5-diyl | bond | cyclopropyl |
| 210 | —CH₂— | pyridin-3,5-diyl | bond | cyclobutyl |
| 211 | —CH₂— | pyridin-3,5-diyl | bond | cyclopentyl |
| 212 | —CH₂— | pyridin-3,5-diyl | bond | cyclohexyl |
| 213 | —CH₂— | pyridin-3,5-diyl | bond | 2-furanyl |
| 214 | —CH₂— | pyridin-3,5-diyl | bond | 2-thienyl |
| 215 | —CH₂— | pyridin-3,5-diyl | bond | 2-imidazolyl |
| 216 | —CH₂— | pyridin-3,5-diyl | bond | 2-pyridyl |
| 217 | —CH₂— | pyridin-3,5-diyl | bond | 3-pyridyl |
| 218 | —CH₂— | pyridin-3,5-diyl | bond | 4-pyridyl |
| 219 | —CH₂— | pyridin-3,5-diyl | bond | N-morpholinyl |
| 220 | —CH₂— | pyridin-3,5-diyl | bond | N-piperidinyl |
| 221 | —CH₂— | pyridin-3,5-diyl | bond | 3-Me-2-pyridyl |
| 222 | —CH₂— | pyridin-3,5-diyl | bond | 4-Me-2-pyridyl |
| 223 | —CH₂— | pyridin-3,5-diyl | bond | 1-indolyl |
| 224 | —CH₂— | pyridin-3,5-diyl | bond | 2-benzothienyl |
| 225 | —CH₂— | pyridin-3,5-diyl | bond | 2-benzofuranyl |
| 226 | —CH₂— | pyridin-3,5-diyl | bond | 1-benzimidazole |
| 227 | —CH₂— | pyridin-3,5-diyl | bond | 2-naphthyl |
| 228 | —CH₂— | pyridin-2,6-diyl | bond | phenyl |
| 229 | —CH₂— | pyridin-2,6-diyl | bond | 3,3-diphenylmethyl |
| 230 | —CH₂— | pyridin-2,6-diyl | bond | 2-F-phenyl |
| 231 | —CH₂— | pyridin-2,6-diyl | bond | 3-F-phenyl |
| 232 | —CH₂— | pyridin-2,6-diyl | bond | 4-F-phenyl |
| 233 | —CH₂— | pyridin-2,6-diyl | bond | 2-Cl-phenyl |
| 234 | —CH₂— | pyridin-2,6-diyl | bond | 3-Cl-phenyl |
| 235 | —CH₂— | pyridin-2,6-diyl | bond | 4-Cl-phenyl |
| 236 | —CH₂— | pyridin-2,6-diyl | bond | 2-Me-phenyl |
| 237 | —CH₂— | pyridin-2,6-diyl | bond | 3-Me-phenyl |
| 238 | —CH₂— | pyridin-2,6-diyl | bond | 4-Me-phenyl |
| 239 | —CH₂— | pyridin-2,6-diyl | bond | 2-MeO-phenyl |
| 240 | —CH₂— | pyridin-2,6-diyl | bond | 3-MeO-phenyl |
| 241 | —CH₂— | pyridin-2,6-diyl | bond | 4-MeO-phenyl |
| 242 | —CH₂— | pyridin-2,6-diyl | bond | 2-MeS-phenyl |
| 243 | —CH₂— | pyridin-2,6-diyl | bond | 3-MeS-phenyl |
| 244 | —CH₂— | pyridin-2,6-diyl | bond | 4-MeS-phenyl |
| 245 | —CH₂— | pyridin-2,6-diyl | bond | 2-F₃C-phenyl |
| 246 | —CH₂— | pyridin-2,6-diyl | bond | 3-F₃C-phenyl |
| 247 | —CH₂— | pyridin-2,6-diyl | bond | 4-F₃C-phenyl |
| 248 | —CH₂— | pyridin-2,6-diyl | bond | 2,3-diF-phenyl |
| 249 | —CH₂— | pyridin-2,6-diyl | bond | 2,4-diF-phenyl |
| 250 | —CH₂— | pyridin-2,6-diyl | bond | 2,5-diF-phenyl |
| 251 | —CH₂— | pyridin-2,6-diyl | bond | 2,6-diF-phenyl |
| 252 | —CH₂— | pyridin-2,6-diyl | bond | 3,4-diF-phenyl |
| 253 | —CH₂— | pyridin-2,6-diyl | bond | 3,5-diF-phenyl |
| 254 | —CH₂— | pyridin-2,6-diyl | bond | 2,3-diCl-phenyl |
| 255 | —CH₂— | pyridin-2,6-diyl | bond | 2,4-diCl-phenyl |
| 256 | —CH₂— | pyridin-2,6-diyl | bond | 2,5-diCl-phenyl |
| 257 | —CH₂— | pyridin-2,6-diyl | bond | 2,6-diCl-phenyl |
| 258 | —CH₂— | pyridin-2,6-diyl | bond | 3,4-diCl-phenyl |
| 259 | —CH₂— | pyridin-2,6-diyl | bond | 3,5-diCl-phenyl |
| 260 | —CH₂— | pyridin-2,6-diyl | bond | 2-Cl-3-F-phenyl |
| 261 | —CH₂— | pyridin-2,6-diyl | bond | 2-Cl-4-F-phenyl |
| 262 | —CH₂— | pyridin-2,6-diyl | bond | 2-Cl-5-F-phenyl |
| 263 | —CH₂— | pyridin-2,6-diyl | bond | 3-Cl-4-F-phenyl |
| 264 | —CH₂— | pyridin-2,6-diyl | bond | 3-Cl-5-F-phenyl |
| 265 | —CH₂— | pyridin-2,6-diyl | bond | 4-Cl-2-F-phenyl |
| 266 | —CH₂— | pyridin-2,6-diyl | bond | 4-Cl-3-F-phenyl |
| 267 | —CH₂— | pyridin-2,6-diyl | bond | 2,3-diMeO-phenyl |
| 268 | —CH₂— | pyridin-2,6-diyl | bond | 2,4-diMeO-phenyl |
| 269 | —CH₂— | pyridin-2,6-diyl | bond | 2,5-diMeO-phenyl |
| 270 | —CH₂— | pyridin-2,6-diyl | bond | 2,6-diMeO-phenyl |
| 271 | —CH₂— | pyridin-2,6-diyl | bond | 3,4-diMeO-phenyl |
| 272 | —CH₂— | pyridin-2,6-diyl | bond | 3,5-diMeQ-phenyl |
| 273 | —CH₂— | pyridin-2,6-diyl | bond | cyclopropyl |
| 274 | —CH₂— | pyridin-2,6-diyl | bond | cyclobutyl |
| 275 | —CH₂— | pyridin-2,6-diyl | bond | cyclopentyl |
| 276 | —CH₂— | pyridin-2,6-diyl | bond | cyclohexyl |
| 277 | —CH₂— | pyridin-2,6-diyl | bond | 2-furanyl |
| 278 | —CH₂— | pyridin-2,6-diyl | bond | 2-thienyl |
| 279 | —CH₂— | pyridin-2,6-diyl | bond | 2-imidazolyl |
| 280 | —CH₂— | pyridin-2,6-diyl | bond | 2-pyridyl |
| 281 | —CH₂— | pyridin-2,6-diyl | bond | 3-pyridyl |
| 282 | —CH₂— | pyridin-2,6-diyl | bond | 4-pyridyl |
| 283 | —CH₂— | pyridin-2,6-diyl | bond | N-morpholinyl |
| 284 | —CH₂— | pyridin-2,6-diyl | bond | N-piperidinyl |

TABLE 2-continued

| | | | | |
|---|---|---|---|---|
| 285 | —CH$_2$— | pyridin-2,6-diyl | bond | 3-Me-2-pyridyl |
| 286 | —CH$_2$— | pyridin-2,6-diyl | bond | 4-Me-2-pyridyl |
| 287 | —CH$_2$— | pyridin-2,6-diyl | bond | 1-indolyl |
| 288 | —CH$_2$— | pyridin-2,6-diyl | bond | 2-benzothienyl |
| 289 | —CH$_2$— | pyridin-2,6-diyl | bond | 2-benzofuranyl |
| 290 | —CH$_2$— | pyridin-2,6-diyl | bond | 1-benzimidazole |
| 291 | —CH$_2$— | pyridin-2,6-diyl | bond | 2-naphthyl |
| 292 | —CH$_2$— | pyridin-2,4-diyl | bond | phenyl |
| 293 | —CH$_2$— | pyridin-2,4-diyl | bond | 3,3-diphenylmethyl |
| 294 | —CH$_2$— | pyridin-2,4-diyl | bond | 2-F-phenyl |
| 295 | —CH$_2$— | pyridin-2,4-diyl | bond | 3-F-phenyl |
| 296 | —CH$_2$— | pyridin-2,4-diyl | bond | 4-F-phenyl |
| 297 | —CH$_2$— | pyridin-2,4-diyl | bond | 2-Cl-phenyl |
| 298 | —CH$_2$— | pyridin-2,4-diyl | bond | 3-Cl-phenyl |
| 299 | —CH$_2$— | pyridin-2,4-diyl | bond | 4-Cl-phenyl |
| 300 | —CH$_2$— | pyridin-2,4-diyl | bond | 2-Me-phenyl |
| 301 | —CH$_2$— | pyridin-2,4-diyl | bond | 3-Me-phenyl |
| 302 | —CH$_2$— | pyridin-2,4-diyl | bond | 4-Me-phenyl |
| 303 | —CH$_2$— | pyridin-2,4-diyl | bond | 2-MeO-phenyl |
| 304 | —CH$_2$— | pyridin-2,4-diyl | bond | 3-MeO-phenyl |
| 305 | —CH$_2$— | pyridin-2,4-diyl | bond | 4-MeO-phenyl |
| 306 | —CH$_2$— | pyridin-2,4-diyl | bond | 2-MeS-phenyl |
| 307 | —CH$_2$— | pyridin-2,4-diyl | bond | 3-MeS-phenyl |
| 308 | —CH$_2$— | pyridin-2,4-diyl | bond | 4-MeS-phenyl |
| 309 | —CH$_2$— | pyridin-2,4-diyl | bond | 2-F$_3$C-phenyl |
| 310 | —CH$_2$— | pyridin-2,4-diyl | bond | 3-F$_3$C-phenyl |
| 311 | —CH$_2$— | pyridin-2,4-diyl | bond | 4-F$_3$C-phenyl |
| 312 | —CH$_2$— | pyridin-2,4-diyl | bond | 2,3-diF-phenyl |
| 313 | —CH$_2$— | pyridin-2,4-diyl | bond | 2,4-diF-phenyl |
| 314 | —CH$_2$— | pyridin-2,4-diyl | bond | 2,5-diF-phenyl |
| 315 | —CH$_2$— | pyridin-2,4-diyl | bond | 2,6-diF-phenyl |
| 316 | —CH$_2$— | pyridin-2,4-diyl | bond | 3,4-diF-phenyl |
| 317 | —CH$_2$— | pyridin-2,4-diyl | bond | 3,5-diF-phenyl |
| 318 | —CH$_2$— | pyridin-2,4-diyl | bond | 2,3-diCl-phenyl |
| 319 | —CH$_2$— | pyridin-2,4-diyl | bond | 2,4-diCl-phenyl |
| 320 | —CH$_2$— | pyridin-2,4-diyl | bond | 2,5-diCl-phenyl |
| 321 | —CH$_2$— | pyridin-2,4-diyl | bond | 2,6-diCl-phenyl |
| 322 | —CH$_2$— | pyridin-2,4-diyl | bond | 3,4-diCl-phenyl |
| 323 | —CH$_2$— | pyridin-2,4-diyl | bond | 3,5-diCl-phenyl |
| 324 | —CH$_2$— | pyridin-2,4-diyl | bond | 2-Cl-3-F-phenyl |
| 325 | —CH$_2$— | pyridin-2,4-diyl | bond | 2-Cl-4-F-phenyl |
| 326 | —CH$_2$— | pyridin-2,4-diyl | bond | 2-Cl-5-F-phenyl |
| 327 | —CH$_2$— | pyridin-2,4-diyl | bond | 3-Cl-4-F-phenyl |
| 328 | —CH$_2$— | pyridin-2,4-diyl | bond | 3-Cl-5-F-phenyl |
| 329 | —CH$_2$— | pyridin-2,4-diyl | bond | 4-Cl-2-F-phenyl |
| 330 | —CH$_2$— | pyridin-2,4-diyl | bond | 4-Cl-3-F-phenyl |
| 331 | —CH$_2$— | pyridin-2,4-diyl | bond | 2,3-diMeO-phenyl |
| 332 | —CH$_2$— | pyridin-2,4-diyl | bond | 2,4-diMeO-phenyl |
| 333 | —CH$_2$— | pyridin-2,4-diyl | bond | 2,5-diMeO-phenyl |
| 334 | —CH$_2$— | pyridin-2,4-diyl | bond | 2,6-diMeO-phenyl |
| 335 | —CH$_2$— | pyridin-2,4-diyl | bond | 3,4-diMeO-phenyl |
| 336 | —CH$_2$— | pyridin-2,4-diyl | bond | 3,5-diMeO-phenyl |
| 337 | —CH$_2$— | pyridin-2,4-diyl | bond | cyclopropyl |
| 338 | —CH$_2$— | pyridin-2,4-diyl | bond | cyclobutyl |
| 339 | —CH$_2$— | pyridin-2,4-diyl | bond | cyclopentyl |
| 340 | —CH$_2$— | pyridin-2,4-diyl | bond | cyclohexyl |
| 341 | —CH$_2$— | pyridin-2,4-diyl | bond | 2-furanyl |
| 342 | —CH$_2$— | pyridin-2,4-diyl | bond | 2-thienyl |
| 343 | —CH$_2$— | pyridin-2,4-diyl | bond | 2-imidazolyl |
| 344 | —CH$_2$— | pyridin-2,4-diyl | bond | 2-pyridyl |
| 345 | —CH$_2$— | pyridin-2,4-diyl | bond | 3-pyridyl |
| 346 | —CH$_2$— | pyridin-2,4-diyl | bond | 4-pyridyl |
| 347 | —CH$_2$— | pyridin-2,4-diyl | bond | N-morpholinyl |
| 348 | —CH$_2$— | pyridin-2,4-diyl | bond | N-piperidinyl |
| 349 | —CH$_2$— | pyridin-2,4-diyl | bond | 3-Me-2-pyridyl |
| 350 | —CH$_2$— | pyridin-2,4-diyl | bond | 4-Me-2-pyridyl |
| 351 | —CH$_2$— | pyridin-2,4-diyl | bond | 1-indolyl |
| 352 | —CH$_2$— | pyridin-2,4-diyl | bond | 2-benzothienyl |
| 353 | —CH$_2$— | pyridin-2,4-diyl | bond | 2-benzofuranyl |
| 354 | —CH$_2$— | pyridin-2,4-diyl | bond | 1-benzimidazole |
| 355 | —CH$_2$— | pyridin-2,4-diyl | bond | 2-naphthyl |
| 356 | —CH$_2$— | pyridin-4,2-diyl | bond | phenyl |
| 357 | —CH$_2$— | pyridin-4,2-diyl | bond | 3,3-diphenylmethyl |
| 358 | —CH$_2$— | pyridin-4,2-diyl | bond | 2-F-phenyl |
| 359 | —CH$_2$— | pyridin-4,2-diyl | bond | 3-F-phenyl |
| 360 | —CH$_2$— | pyridin-4,2-diyl | bond | 4-F-phenyl |
| 361 | —CH$_2$— | pyridin-4,2-diyl | bond | 2-Cl-phenyl |

TABLE 2-continued

| | | | | |
|---|---|---|---|---|
| 362 | —CH$_2$— | pyridin-4,2-diyl | bond | 3-Cl-phenyl |
| 363 | —CH$_2$— | pyridin-4,2-diyl | bond | 4-Cl-phenyl |
| 364 | —CH$_2$— | pyridin-4,2-diyl | bond | 2-Me-phenyl |
| 365 | —CH$_2$— | pyridin-4,2-diyl | bond | 3-Me-phenyl |
| 366 | —CH$_2$— | pyridin-4,2-diyl | bond | 4-Me-phenyl |
| 367 | —CH$_2$— | pyridin-4,2-diyl | bond | 2-MeO-phenyl |
| 368 | —CH$_2$— | pyridin-4,2-diyl | bond | 3-MeO-phenyl |
| 369 | —CH$_2$— | pyridin-4,2-diyl | bond | 4-MeO-phenyl |
| 370 | —CH$_2$— | pyridin-4,2-diyl | bond | 2-MeS-phenyl |
| 371 | —CH$_2$— | pyridin-4,2-diyl | bond | 3-MeS-phenyl |
| 372 | —CH$_2$— | pyridin-4,2-diyl | bond | 4-MeS-phenyl |
| 373 | —CH$_2$— | pyridin-4,2-diyl | bond | 2-F$_3$C-phenyl |
| 374 | —CH$_2$— | pyridin-4,2-diyl | bond | 3-F$_3$C-phenyl |
| 375 | —CH$_2$— | pyridin-4,2-diyl | bond | 4-F$_3$C-phenyl |
| 376 | —CH$_2$— | pyridin-4,2-diyl | bond | 2,3-diF-phenyl |
| 377 | —CH$_2$— | pyridin-4,2-diyl | bond | 2,4-diF-phenyl |
| 378 | —CH$_2$— | pyridin-4,2-diyl | bond | 2,5-diF-phenyl |
| 379 | —CH$_2$— | pyridin-4,2-diyl | bond | 2,6-diF-phenyl |
| 380 | —CH$_2$— | pyridin-4,2-diyl | bond | 3,4-diF-phenyl |
| 381 | —CH$_2$— | pyridin-4,2-diyl | bond | 3,5-diF-phenyl |
| 382 | —CH$_2$— | pyridin-4,2-diyl | bond | 2,3-diCl-phenyl |
| 383 | —CH$_2$— | pyridin-4,2-diyl | bond | 2,4-diCl-phenyl |
| 384 | —CH$_2$— | pyridin-4,2-diyl | bond | 2,5-diCl-phenyl |
| 385 | —CH$_2$— | pyridin-4,2-diyl | bond | 2,6-diCl-phenyl |
| 386 | —CH$_2$— | pyridin-4,2-diyl | bond | 3,4-diCl-phenyl |
| 387 | —CH$_2$— | pyridin-4,2-diyl | bond | 3,5-diCl-phenyl |
| 388 | —CH$_2$— | pyridin-4,2-diyl | bond | 2-Cl-3-F-phenyl |
| 389 | —CH$_2$— | pyridin-4,2-diyl | bond | 2-Cl-4-F-phenyl |
| 390 | —CH$_2$— | pyridin-4,2-diyl | bond | 2-Cl-5-F-phenyl |
| 391 | —CH$_2$— | pyridin-4,2-diyl | bond | 3-Cl-4-F-phenyl |
| 392 | —CH$_2$— | pyridin-4,2-diyl | bond | 3-Cl-5-F-phenyl |
| 393 | —CH$_2$— | pyridin-4,2-diyl | bond | 4-Cl-2-F-phenyl |
| 394 | —CH$_2$— | pyridin-4,2-diyl | bond | 4-Cl-3-F-phenyl |
| 395 | —CH$_2$— | pyridin-4,2-diyl | bond | 2,3-diMeO-phenyl |
| 396 | —CH$_2$— | pyridin-4,2-diyl | bond | 2,4-diMeO-phenyl |
| 397 | —CH$_2$— | pyridin-4,2-diyl | bond | 2,5-diMeO-phenyl |
| 398 | —CH$_2$— | pyridin-4,2-diyl | bond | 2,6-diMeO-phenyl |
| 399 | —CH$_2$— | pyridin-4,2-diyl | bond | 3,4-diMeO-phenyl |
| 400 | —CH$_2$— | pyridin-4,2-diyl | bond | 3,5-diMeO-phenyl |
| 401 | —CH$_2$— | pyridin-4,2-diyl | bond | cyclopropyl |
| 402 | —CH$_2$— | pyridin-4,2-diyl | bond | cyclobutyl |
| 403 | —CH$_2$— | pyridin-4,2-diyl | bond | cyclopentyl |
| 404 | —CH$_2$— | pyridin-4,2-diyl | bond | cyclohexyl |
| 405 | —CH$_2$— | pyridin-4,2-diyl | bond | 2-furanyl |
| 406 | —CH$_2$— | pyridin-4,2-diyl | bond | 2-thienyl |
| 407 | —CH$_2$— | pyridin-4,2-diyl | bond | 2-imidazolyl |
| 408 | —CH$_2$— | pyridin-4,2-diyl | bond | 2-pyridyl |
| 409 | —CH$_2$— | pyridin-4,2-diyl | bond | 3-pyridyl |
| 410 | —CH$_2$— | pyridin-4,2-diyl | bond | 4-pyridyl |
| 411 | —CH$_2$— | pyridin-4,2-diyl | bond | N-morpholinyl |
| 412 | —CH$_2$— | pyridin-4,2-diyl | bond | N-piperidinyl |
| 413 | —CH$_2$— | pyridin-4,2-diyl | bond | 3-Me-2-pyridyl |
| 414 | —CH$_2$— | pyridin-4,2-diyl | bond | 4-Me-2-pyridyl |
| 415 | —CH$_2$— | pyridin-4,2-diyl | bond | 1-indolyl |
| 416 | —CH$_2$— | pyridin-4,2-diyl | bond | 2-benzothienyl |
| 417 | —CH$_2$— | pyridin-4,2-diyl | bond | 2-benzofuranyl |
| 418 | —CH$_2$— | pyridin-4,2-diyl | bond | 1-benzimidazole |
| 419 | —CH$_2$— | pyridin-4,2-diyl | bond | 2-naphthyl |
| 420 | —CH$_2$— | piperidin-1,3-diyl | bond | phenyl |
| 421 | —CH$_2$— | piperidin-1,3-diyl | bond | 3,3-diphenylmethyl |
| 422 | —CH$_2$— | piperidin-1,3-diyl | bond | 2-F-phenyl |
| 423 | —CH$_2$— | piperidin-1,3-diyl | bond | 3-F-phenyl |
| 424 | —CH$_2$— | piperidin-1,3-diyl | bond | 4-F-phenyl |
| 425 | —CH$_2$— | piperidin-1,3-diyl | bond | 2-Cl-phenyl |
| 426 | —CH$_2$— | piperidin-1,3-diyl | bond | 3-Cl-phenyl |
| 427 | —CH$_2$— | piperidin-1,3-diyl | bond | 4-Cl-phenyl |
| 428 | —CH$_2$— | piperidin-1,3-diyl | bond | 2-Me-phenyl |
| 429 | —CH$_2$— | piperidin-1,3-diyl | bond | 3-Me-phenyl |

TABLE 2-continued

| | | | | |
|---|---|---|---|---|
| 430 | —CH$_2$— | piperidin-1,3-diyl | bond | 4-Me-phenyl |
| 431 | —CH$_2$— | piperidin-1,3-diyl | bond | 2-MeO-phenyl |
| 432 | —CH$_2$— | piperidin-1,3-diyl | bond | 3-MeO-phenyl |
| 433 | —CH$_2$— | piperidin-1,3-diyl | bond | 4-MeO-phenyl |
| 434 | —CH$_2$— | piperidin-1,3-diyl | bond | 2-MeS-phenyl |
| 435 | —CH$_2$— | piperidin-1,3-diyl | bond | 3-MeS-phenyl |
| 436 | —CH$_2$— | piperidin-1,3-diyl | bond | 4-MeS-phenyl |
| 437 | —CH$_2$— | piperidin-1,3-diyl | bond | 2-F$_3$C-phenyl |
| 438 | —CH$_2$— | piperidin-1,3-diyl | bond | 3-F$_3$C-phenyl |
| 439 | —CH$_2$— | piperidin-1,3-diyl | bond | 4-F$_3$C-phenyl |
| 440 | —CH$_2$— | piperidin-1,3-diyl | bond | 2,3-diF-phenyl |
| 441 | —CH$_2$— | piperidin-1,3-diyl | bond | 2,4-diF-phenyl |
| 442 | —CH$_2$— | piperidin-1,3-diyl | bond | 2,5-diF-phenyl |
| 443 | —CH$_2$— | piperidin-1,3-diyl | bond | 2,6-diF-phenyl |
| 444 | —CH$_2$— | piperidin-1,3-diyl | bond | 3,4-diF-phenyl |
| 445 | —CH$_2$— | piperidin-1,3-diyl | bond | 3,5-diF-phenyl |
| 446 | —CH$_2$— | piperidin-1,3-diyl | bond | 2,3-diCl-phenyl |
| 447 | —CH$_2$— | piperidin-1,3-diyl | bond | 2,4-diCl-phenyl |
| 448 | —CH$_2$— | piperidin-1,3-diyl | bond | 2,5-diCl-phenyl |
| 449 | —CH$_2$— | piperidin-1,3-diyl | bond | 2,6-diCl-phenyl |
| 450 | —CH$_2$— | piperidin-1,3-diyl | bond | 3,4-diCl-phenyl |
| 451 | —CH$_2$— | piperidin-1,3-diyl | bond | 3,5-diCl-phenyl |
| 452 | —CH$_2$— | piperidin-1,3-diyl | bond | 2-Cl-3-F-phenyl |
| 453 | —CH$_2$— | piperidin-1,3-diyl | bond | 2-Cl-4-F-phenyl |
| 454 | —CH$_2$— | piperidin-1,3-diyl | bond | 2-Cl-5-F-phenyl |
| 455 | —CH$_2$— | piperidin-1,3-diyl | bond | 3-Cl-4-F-phenyl |
| 456 | —CH$_2$— | piperidin-1,3-diyl | bond | 3-Cl-5-F-phenyl |
| 457 | —CH$_2$— | piperidin-1,3-diyl | bond | 4-Cl-2-F-phenyl |
| 458 | —CH$_2$— | piperidin-1,3-diyl | bond | 4-Cl-3-F-phenyl |
| 459 | —CH$_2$— | piperidin-1,3-diyl | bond | 2,3-diMeO-phenyl |
| 460 | —CH$_2$— | piperidin-1,3-diyl | bond | 2,4-diMeO-phenyl |
| 461 | —CH$_2$— | piperidin-1,3-diyl | bond | 2,5-diMeO-phenyl |
| 462 | —CH$_2$— | piperidin-1,3-diyl | bond | 2,6-diMeO-phenyl |
| 463 | —CH$_2$— | piperidin-1,3-diyl | bond | 3,4-diMeO-phenyl |
| 464 | —CH$_2$— | piperidin-1,3-diyl | bond | 3,5-diMeO-phenyl |
| 465 | —CH$_2$— | piperidin-1,3-diyl | bond | cyclopropyl |
| 466 | —CH$_2$— | piperidin-1,3-diyl | bond | cyclobutyl |
| 467 | —CH$_2$— | piperidin-1,3-diyl | bond | cyclopentyl |
| 468 | —CH$_2$— | piperidin-1,3-diyl | bond | cyclohexyl |

TABLE 2-continued

| | | | | |
|---|---|---|---|---|
| 469 | —CH$_2$— | piperidin-1,3-diyl | bond | 2-furanyl |
| 470 | —CH$_2$— | piperidin-1,3-diyl | bond | 2-thienyl |
| 471 | —CH$_2$— | piperidin-1,3-diyl | bond | 2-imidazolyl |
| 472 | —CH$_2$— | piperidin-1,3-diyl | bond | 2-pyridyl |
| 473 | —CH$_2$— | piperidin-1,3-diyl | bond | 3-pyridyl |
| 474 | —CH$_2$— | piperidin-1,3-diyl | bond | 4-pyridyl |
| 475 | —CH$_2$— | piperidin-1,3-diyl | bond | N-morpholinyl |
| 476 | —CH$_2$— | piperidin-1,3-diyl | bond | N-piperidinyl |
| 477 | —CH$_2$— | piperidin-1,3-diyl | bond | 3-Me-2-pyridyl |
| 478 | —CH$_2$— | piperidin-1,3-diyl | bond | 4-Me-2-pyridyl |
| 479 | —CH$_2$— | piperidin-1,3-diyl | bond | 1-indolyl |
| 480 | —CH$_2$— | piperidin-1,3-diyl | bond | 2-benzothienyl |
| 481 | —CH$_2$— | piperidin-1,3-diyl | bond | 2-benzofuranyl |
| 482 | —CH$_2$— | piperidin-1,3-diyl | bond | 1-benzimidazole |
| 483 | —CH$_2$— | piperidin-1,3-diyl | bond | 2-naphthyl |
| 484 | —CH$_2$— | piperidin-3,1-diyl | bond | phenyl |
| 485 | —CH$_2$— | piperidin-3,1-diyl | bond | 3,3-diphenylmethyl |
| 486 | —CH$_2$— | piperidin-3,1-diyl | bond | 2-F-phenyl |
| 487 | —CH$_2$— | piperidin-3,1-diyl | bond | 3-F-phenyl |
| 488 | —CH$_2$— | piperidin-3,1-diyl | bond | 4-F-phenyl |
| 489 | —CH$_2$— | piperidin-3,1-diyl | bond | 2-Cl-phenyl |
| 490 | —CH$_2$— | piperidin-3,1-diyl | bond | 3-Cl-phenyl |
| 491 | —CH$_2$— | piperidin-3,1-diyl | bond | 4-Cl-phenyl |
| 492 | —CH$_2$— | piperidin-3,1-diyl | bond | 2-Me-phenyl |
| 493 | —CH$_2$— | piperidin-3,1-diyl | bond | 3-Me-phenyl |
| 494 | —CH$_2$— | piperidin-3,1-diyl | bond | 4-Me-phenyl |
| 495 | —CH$_2$— | piperidin-3,1-diyl | bond | 2-MeO-phenyl |
| 496 | —CH$_2$— | piperidin-3,1-diyl | bond | 3-MeO-phenyl |
| 497 | —CH$_2$— | piperidin-3,1-diyl | bond | 4-MeO-phenyl |
| 498 | —CH$_2$— | piperidin-3,1-diyl | bond | 2-MeS-phenyl |
| 499 | —CH$_2$— | piperidin-3,1-diyl | bond | 3-MeS-phenyl |
| 500 | —CH$_2$— | piperidin-3,1-diyl | bond | 4-MeS-phenyl |
| 501 | —CH$_2$— | piperidin-3,1-diyl | bond | 2-F$_3$C-phenyl |
| 502 | —CH$_2$— | piperidin-3,1-diyl | bond | 3-F$_3$C-phenyl |
| 503 | —CH$_2$— | piperidin-3,1-diyl | bond | 4-F$_3$C-phenyl |
| 504 | —CH$_2$— | piperidin-3,1-diyl | bond | 2,3-diF-phenyl |
| 505 | —CH$_2$— | piperidin-3,1-diyl | bond | 2,4-diF-phenyl |
| 506 | —CH$_2$— | piperidin-3,1-diyl | bond | 2,5-diF-phenyl |
| 507 | —CH$_2$— | piperidin-3,1-diyl | bond | 2,6-diF-phenyl |

TABLE 2-continued

| | | | | |
|---|---|---|---|---|
| 508 | —CH$_2$— | piperidin-3,1-diyl | bond | 3,4-diF-phenyl |
| 509 | —CH$_2$— | piperidin-3,1-diyl | bond | 3,5-diF-phenyl |
| 510 | —CH$_2$— | piperidin-3,1-diyl | bond | 2,3-diCl-phenyl |
| 511 | —CH$_2$— | piperidin-3,1-diyl | bond | 2,4-diCl-phenyl |
| 512 | —CH$_2$— | piperidin-3,1-diyl | bond | 2,5-diCl-phenyl |
| 513 | —CH$_2$— | piperidin-3,1-diyl | bond | 2,6-diCl-phenyl |
| 514 | —CH$_2$— | piperidin-3,1-diyl | bond | 3,4-diCl-phenyl |
| 515 | —CH$_2$— | piperidin-3,1-diyl | bond | 3,5-diCl-phenyl |
| 516 | —CH$_2$— | piperidin-3,1-diyl | bond | 2-Cl-3-F-phenyl |
| 517 | —CH$_2$— | piperidin-3,1-diyl | bond | 2-Cl-4-F-phenyl |
| 518 | —CH$_2$— | piperidin-3,1-diyl | bond | 2-Cl-5-F-phenyl |
| 519 | —CH$_2$— | piperidin-3,1-diyl | bond | 3-Cl-4-F-phenyl |
| 520 | —CH$_2$— | piperidin-3,1-diyl | bond | 3-Cl-5-F-phenyl |
| 521 | —CH$_2$— | piperidin-3,1-diyl | bond | 4-Cl-2-F-phenyl |
| 522 | —CH$_2$— | piperidin-3,1-diyl | bond | 4-Cl-3-F-phenyl |
| 523 | —CH$_2$— | piperidin-3,1-diyl | bond | 2,3-diMeO-phenyl |
| 524 | —CH$_2$— | piperidin-3,1-diyl | bond | 2,4-diMeO-phenyl |
| 525 | —CH$_2$— | piperidin-3,1-diyl | bond | 2,5-diMeO-phenyl |
| 526 | —CH$_2$— | piperidin-3,1-diyl | bond | 2,6-diMeO-phenyl |
| 527 | —CH$_2$— | piperidin-311-diyl | bond | 3,4-diMeO-phenyl |
| 528 | —CH$_2$— | piperidin-3,1-diyl | bond | 3,5-diMeO-phenyl |
| 529 | —CH$_2$— | piperidin-3,1-diyl | bond | cyclopropyl |
| 530 | —CH$_2$— | piperidin-3,1-diyl | bond | cyclobutyl |
| 531 | —CH$_2$— | piperidin-3,1-diyl | bond | cyclopentyl |
| 532 | —CH$_2$— | piperidin-3,1-diyl | bond | cyclohexyl |
| 533 | —CH$_2$— | piperidin-3,1-diyl | bond | 2-furanyl |
| 534 | —CH$_2$— | piperidin-3,1-diyl | bond | 2-thienyl |
| 535 | —CH$_2$— | piperidin-3,1-diyl | bond | 2-imidazolyl |
| 536 | —CH$_2$— | piperidin-3,1-diyl | bond | 2-pyridyl |
| 537 | —CH$_2$— | piperidin-3,1-diyl | bond | 3-pyridyl |
| 538 | —CH$_2$— | piperidin-3,1-diyl | bond | 4-pyridyl |
| 539 | —CH$_2$— | piperidin-3,1-diyl | bond | N-morpholinyl |
| 540 | —CH$_2$— | piperidin-3,1-diyl | bond | N-piperidinyl |
| 541 | —CH$_2$— | piperidin-3,1-diyl | bond | 3-Me-2-pyridyl |
| 542 | —CH$_2$— | piperidin-3,1-diyl | bond | 4-Me-2-pyridyl |
| 543 | —CH$_2$— | piperidin-3,1-diyl | bond | 1-indolyl |
| 544 | —CH$_2$— | piperidin-3,1-diyl | bond | 2-benzothienyl |
| 545 | —CH$_2$— | piperidin-3,1-diyl | bond | 2-benzofuranyl |
| 546 | —CH$_2$— | piperidin-3,1-diyl | bond | 1-benzimidazole |

TABLE 2-continued

| | | | | |
|---|---|---|---|---|
| 547 | —CH₂— | piperidin-3,1-diyl | bond | 2-naphthyl |
| 548 | —CH₂— | cyclohex-1,3-diyl | bond | phenyl |
| 549 | —CH₂— | cyclohex-1,3-diyl | bond | 3,3-diphenylmethyl |
| 550 | —CH₂— | cyclohex-1,3-diyl | bond | 2-F-phenyl |
| 551 | —CH₂— | cyclohex-1,3-diyl | bond | 3-F-phenyl |
| 552 | —CH₂— | cyclohex-1,3-diyl | bond | 4-F-phenyl |
| 553 | —CH₂— | cyclohex-1,3-diyl | bond | 2-Cl-phenyl |
| 554 | —CH₂— | cyclohex-1,3-diyl | bond | 3-Cl-phenyl |
| 555 | —CH₂— | cyclohex-1,3-diyl | bond | 4-Cl-phenyl |
| 556 | —CH₂— | cyclohex-1,3-diyl | bond | 2-Me-phenyl |
| 557 | —CH₂— | cyclohex-1,3-diyl | bond | 3-Me-phenyl |
| 558 | —CH₂— | cyclohex-1,3-diyl | bond | 4-Me-phenyl |
| 559 | —CH₂— | cyclohex-1,3-diyl | bond | 2-MeO-phenyl |
| 560 | —CH₂— | cyclohex-1,3-diyl | bond | 3-MeO-phenyl |
| 561 | —CH₂— | cyclohex-1,3-diyl | bond | 4-MeO-phenyl |
| 562 | —CH₂— | cyclohex-1,3-diyl | bond | 2-MeS-phenyl |
| 563 | —CH₂— | cyclohex-1,3-diyl | bond | 3-MeS-phenyl |
| 564 | —CH₂— | cyclohex-1,3-diyl | bond | 4-MeS-phenyl |
| 565 | —CH₂— | cyclohex-1,3-diyl | bond | 2-F₃C-phenyl |
| 566 | —CH₂— | cyclohex-1,3-diyl | bond | 3-F₃C-phenyl |
| 567 | —CH₂— | cyclohex-1,3-diyl | bond | 4-F₃C-phenyl |
| 568 | —CH₂— | cyclohex-1,3-diyl | bond | 2,3-diF-phenyl |
| 569 | —CH₂— | cyclohex-1,3-diyl | bond | 2,4-diF-phenyl |
| 570 | —CH₂— | cyclohex-1,3-diyl | bond | 2,5-diF-phenyl |
| 571 | —CH₂— | cyclohex-1,3-diyl | bond | 2,6-diF-phenyl |
| 572 | —CH₂— | cyclohex-1,3-diyl | bond | 3,4-diF-phenyl |
| 573 | —CH₂— | cyclohex-1,3-diyl | bond | 3,5-diF-phenyl |
| 574 | —CH₂— | cyclohex-1,3-diyl | bond | 2,3-diCl-phenyl |
| 575 | —CH₂— | cyclohex-1,3-diyl | bond | 2,4-diCl-phenyl |
| 576 | —CH₂— | cyclohex-1,3-diyl | bond | 2,5-diCl-phenyl |
| 577 | —CH₂— | cyclohex-1,3-diyl | bond | 2,6-diCl-phenyl |
| 578 | —CH₂— | cyclohex-1,3-diyl | bond | 3,4-diCl-phenyl |
| 579 | —CH₂— | cyclohex-1,3-diyl | bond | 3,5-diCl-phenyl |
| 580 | —CH₂— | cyclohex-1,3-diyl | bond | 2-Cl-3-F-phenyl |
| 581 | —CH₂— | cyclohex-1,3-diyl | bond | 2-Cl-4-F-phenyl |
| 582 | —CH₂— | cyclohex-1,3-diyl | bond | 2-Cl-5-F-phenyl |
| 583 | —CH₂— | cyclohex-1,3-diyl | bond | 3-Cl-4-F-phenyl |
| 584 | —CH₂— | cyclohex-1,3-diyl | bond | 3-Cl-5-F-phenyl |
| 585 | —CH₂— | cyclohex-1,3-diyl | bond | 4-Cl-2-F-phenyl |
| 586 | —CH₂— | cyclohex-1,3-diyl | bond | 4-Cl-3-F-phenyl |
| 587 | —CH₂— | cyclohex-1,3-diyl | bond | 2,3-diMeO-phenyl |
| 588 | —CH₂— | cyclohex-1,3-diyl | bond | 2,4-diMeO-phenyl |
| 589 | —CH₂— | cyclohex-1,3-diyl | bond | 2,5-diMeO-phenyl |
| 590 | —CH₂— | cyclohex-1,3-diyl | bond | 2,6-diMeO-phenyl |
| 591 | —CH₂— | cyclohex-1,3-diyl | bond | 3,4-diMeO-phenyl |
| 592 | —CH₂— | cyclohex-1,3-diyl | bond | 3,5-diMeO-phenyl |
| 593 | —CH₂— | cyclohex-1,3-diyl | bond | cyclopropyl |
| 594 | —CH₂— | cyclohex-1,3-diyl | bond | cyclobutyl |
| 595 | —CH₂— | cyclohex-1,3-diyl | bond | cyclopentyl |
| 596 | —CH₂— | cyclohex-1,3-diyl | bond | cyclohexyl |
| 597 | —CH₂— | cyclohex-1,3-diyl | bond | 2-furanyl |
| 598 | —CH₂— | cyclohex-1,3-diyl | bond | 2-thienyl |
| 599 | —CH₂— | cyclohex-1,3-diyl | bond | 2-imidazolyl |
| 600 | —CH₂— | cyclohex-1,3-diyl | bond | 2-pyridyl |
| 601 | —CH₂— | cyclohex-1,3-diyl | bond | 3-pyridyl |
| 602 | —CH₂— | cyclohex-1,3-diyl | bond | 4-pyridyl |
| 603 | —CH₂— | cyclohex-1,3-diyl | bond | N-morpholinyl |
| 604 | —CH₂— | cyclohex-1,3-diyl | bond | N-piperidinyl |
| 605 | —CH₂— | cyclohex-1,3-diyl | bond | 3-Me-2-pyridyl |
| 606 | —CH₂— | cyclohex-1,3-diyl | bond | 4-Me-2-pyridyl |
| 607 | —CH₂— | cyclohex-1,3-diyl | bond | 1-indolyl |
| 608 | —CH₂— | cyclohex-1,3-diyl | bond | 2-benzothienyl |
| 609 | —CH₂— | cyclohex-1,3-diyl | bond | 2-benzofuranyl |
| 610 | —CH₂— | cyclohex-1,3-diyl | bond | l-benzimidazole |
| 611 | —CH₂— | cyclohex-1,3-diyl | bond | 2-naphthyl |
| 612 | —CH₂— | cyclopropan-1,2-diyl | bond | phenyl |
| 613 | —CH₂— | Cyclopropan-1,2-diyl | bond | 3,3-diphenylmethyl |
| 614 | —CH₂— | cyclopropan-1,2 diyl | bond | 2-F-phenyl |
| 615 | —CH₂— | cyclopropan-1,2 diyl | bond | 3-F-phenyl |
| 616 | —CH₂— | ciclopropan-1,2-diyl | bond | 4-F-phenyl |
| 617 | —CH₂— | cyclopropan-1,2-diyl | bond | 2-Cl-phenyl |

TABLE 2-continued

| | | | | |
|---|---|---|---|---|
| 618 | —CH$_2$— | cyclopropan-1,2-diyl | bond | 3-Cl-phenyl |
| 619 | —CH$_2$— | cyclopropan-1,2-diyl | bond | 4-Cl-phenyl |
| 620 | —CH$_2$— | cyclopropan-1,2-diyl | bond | 2-Me-phenyl |
| 621 | —CH$_2$— | cyclopropan-1,2-diyl | bond | 3-Me-phenyl |
| 622 | —CH$_2$— | cyclopropan-1,2-diyl | bond | 4-Me-phenyl |
| 623 | —CH$_2$— | cyclopropan-1,2-diyl | bond | 2-MeO-phenyl |
| 624 | —CH$_2$— | cyclopropan-1,2-diyl | bond | 3-MeO-phenyl |
| 625 | —CH$_2$— | cyclopropan-1,2-diyl | bond | 4-MeO-phenyl |
| 626 | —CH$_2$— | cyclopropan-1,2-diyl | bond | 2-MeS-phenyl |
| 627 | —CH$_2$— | cyclopropan-1,2-diyl | bond | 3-MeS-phenyl |
| 628 | —CH$_2$— | cyclopropan-1,2-diyl | bond | 4-MeS-phenyl |
| 629 | —CH$_2$— | cyclopropan-1,2-diyl | bond | 2-F$_3$C-phenyl |
| 630 | —CH$_2$— | cyclopropan-1,2-diyl | bond | 3-F$_3$C-phenyl |
| 631 | —CH$_2$— | cyclopropan-1,2-diyl | bond | 4-F$_3$C-phenyl |
| 632 | —CH$_2$— | cyclopropan-1,2-diyl | bond | 2,3-diF-phenyl |
| 633 | —CH$_2$— | cyclopropan-1,2-diyl | bond | 2,4-diF-phenyl |
| 634 | —CH$_2$— | cyclopropan-1,2-diyl | bond | 2,5-diF-phenyl |
| 635 | —CH$_2$— | cyclopropan-1,2-diyl | bond | 2,6-diF-phenyl |
| 636 | —CH$_2$— | cyclopropan-1,2-diyl | bond | 3,4-diF-phenyl |
| 637 | —CH$_2$— | cyclopropan-1,2-diyl | bond | 3,5-diF-phenyl |
| 638 | —CH$_2$— | cyclopropan-1,2-diyl | bond | 2,3-diCl-phenyl |
| 639 | —CH$_2$— | cyclopropan-1,2-diyl | bond | 2,4-diCl-phenyl |
| 640 | —CH$_2$— | cyclopropan-1,2-diyl | bond | 2,5-diCl-phenyl |
| 641 | —CH$_2$— | cyclopropan-1,2-diyl | bond | 2,6-diCl-phenyl |
| 642 | —CH$_2$— | cyclopropan-1,2-diyl | bond | 3,4-diCl-phenyl |
| 643 | —CH$_2$— | cyclopropan-1,2-diyl | bond | 3,5-diCl-phenyl |
| 644 | —CH$_2$— | cyclopropan-1,2-diyl | bond | 2-Cl-3-F-phenyl |
| 645 | —CH$_2$— | cyclopropan-1,2-diyl | bond | 2-Cl-4-F-phenyl |
| 646 | —CH$_2$— | cyclopropan-1,2-diyl | bond | 2-Cl-5-F-phenyl |
| 647 | —CH$_2$— | cyclopropan-1,2-diyl | bond | 3-Cl-4-F-phenyl |
| 648 | —CH$_2$— | cyclopropan-1,2-diyl | bond | 3-Cl-5-F-phenyl |
| 649 | —CH$_2$— | cyclopropan-1,2-diyl | bond | 4-Cl-2-F-phenyl |
| 650 | —CH$_2$— | cyclopropan-1,2-diyl | bond | 4-Cl-3-F-phenyl |
| 651 | —CH$_2$— | cyclopropan-1,2-diyl | bond | 2,3-diMeO-phenyl |
| 652 | —CH$_2$— | cyclopropan-1,2-diyl | bond | 2,4-diMeO-phenyl |
| 653 | —CH$_2$— | cyclopropan-1,2-diyl | bond | 2,5-diMeO-phenyl |
| 654 | —CH$_2$— | cyclopropan-1,2-diyl | bond | 2,6-diMeO-phenyl |
| 655 | —CH$_2$— | cyclopropan-1,2-diyl | bond | 3,4-diMeO-phenyl |
| 656 | —CH$_2$— | cyclopropan-1,2-diyl | bond | 3,5-diMeO-phenyl |

TABLE 2-continued

| | | | | |
|---|---|---|---|---|
| 657 | —CH$_2$— | cyclopropan-1,2-diyl | bond | cyclopropyl |
| 658 | —CH$_2$— | cyclopropan-1,2-diyl | bond | cyclobutyl |
| 659 | —CH$_2$— | cyclopropan-1,2-diyl | bond | cyclopentyl |
| 660 | —CH$_2$— | cyclopropan-1,2-diyl | bond | cyclohexyl |
| 661 | —CH$_2$— | cyclopropan-1,2-diyl | bond | 2-furanyl |
| 662 | —CH$_2$— | cyclopropan-1,2-diyl | bond | 2-thienyl |
| 663 | —CH$_2$— | cyclopropan-1,2-diyl | bond | 2-imidazolyl |
| 664 | —CH$_2$— | cyclopropan-1,2-diyl | bond | 2-pyridyl |
| 665 | —CH$_2$— | cyclopropan-1,2-diyl | bond | 3-pyridyl |
| 666 | —CH$_2$— | cyclopropan-1,2-diyl | bond | 4-pyridyl |
| 667 | —CH$_2$— | cyclopropan-1,2-diyl | bond | N-morpholinyl |
| 668 | —CH$_2$— | cyclopropan-1,2-diyl | bond | N-piperidinyl |
| 669 | —CH$_2$— | cyclopropan-1,2-diyl | bond | 3-Me-2-pyridyl |
| 670 | —CH$_2$— | cyclopropan-1,2-diyl | bond | 4-Me-2-pyridyl |
| 671 | —CH$_2$— | cyclopropan-1,2-diyl | bond | 1-indolyl |
| 672 | —CH$_2$— | cyclopropan-1,2-diyl | bond | 2-benzothienyl |
| 673 | —CH$_2$— | cyclopropan-1,2-diyl | bond | 2-benzofuranyl |
| 674 | —CH$_2$— | cyclopropan-1,2-diyl | bond | 1-benzimidazole |
| 675 | —CH$_2$— | cyclopropan-1,2-diyl | bond | 2-naphthyl |
| 676 | —CH$_2$— | cyclopentan-1,3-diyl | bond | phenyl |
| 677 | —CH$_2$— | cyclopentan-1,3-diyl | bond | 3,3-diphenylmethyl |
| 678 | —CH$_2$— | cyclopentan-1,3-diyl | bond | 2-F-phenyl |
| 679 | —CH$_2$— | cyclopentan-1,3-diyl | bond | 3-F-phenyl |
| 680 | —CH$_2$— | cyclopentan-1,3-diyl | bond | 4-F-phenyl |
| 681 | —CH$_2$— | cyclopentan-1,3-diyl | bond | 2-Cl-phenyl |
| 682 | —CH$_2$— | cyclopentan-1,3-diyl | bond | 3-Cl-phenyl |
| 683 | —CH$_2$— | cyclopentan-1,3-diyl | bond | 4-Cl-phenyl |
| 684 | —CH$_2$— | cyclopentan-1,3-diyl | bond | 2-Me-phenyl |
| 685 | —CH$_2$— | cyclopentan-1,3-diyl | bond | 3-Me-phenyl |
| 686 | —CH$_2$— | cyclopentan-1,3-diyl | bond | 4-Me-phenyl |
| 687 | —CH$_2$— | cyclopentan-1,3-diyl | bond | 2-MeO-phenyl |
| 688 | —CH$_2$— | cyclopentan-1,3-diyl | bond | 3-MeO-phenyl |
| 689 | —CH$_2$— | cyclopentan-1,3-diyl | bond | 4-MeO-phenyl |
| 690 | —CH$_2$— | cyclopentan-1,3-diyl | bond | 2-MeS-phenyl |
| 691 | —CH$_2$— | cyclopentan-1,3-diyl | bond | 3-MeS-phenyl |
| 692 | —CH$_2$— | cyclopentan-1,3-diyl | bond | 4-MeS-phenyl |
| 693 | —CH$_2$— | cyclopentan-1,3-diyl | bond | 2-F$_3$C-phenyl |
| 694 | —CH$_2$— | cyclopentan-1,3-diyl | bond | 3-F$_3$C-phenyl |
| 695 | —CH$_2$— | cyclopentan-1,3-diyl | bond | 4-F$_3$C-phenyl |

TABLE 2-continued

| | | | | |
|---|---|---|---|---|
| 696 | —CH$_2$— | cyclopentan-1,3-diyl | bond | 2,3-diF-phenyl |
| 697 | —CH$_2$— | cyclopentan-1,3-diyl | bond | 2,4-diF-phenyl |
| 698 | —CH$_2$— | cyclopentan-1,3-diyl | bond | 2,5-diF-phenyl |
| 699 | —CH$_2$— | cyclopentan-1,3-diyl | bond | 2,6-diF-phenyl |
| 700 | —CH$_2$— | cyclopentan-1,3-diyl | bond | 3,4-diF-phenyl |
| 701 | —CH$_2$— | cyclopentan-1,3-diyl | bond | 3,5-diF-phenyl |
| 702 | —CH$_2$— | cyclopentan-1,3-diyl | bond | 2,3-diCl-phenyl |
| 703 | —CH$_2$— | cyclopentan-1,3-diyl | bond | 2,4-diCl-phenyl |
| 704 | —CH$_2$— | cyclopentan-1,3-diyl | bond | 2,5-diCl-phenyl |
| 705 | —CH$_2$— | cyclopentan-1,3-diyl | bond | 2,6-diCl-phenyl |
| 706 | —CH$_2$— | cyclopentan-1,3-diyl | bond | 3,4-diCl-phenyl |
| 707 | —CH$_2$— | cyclopentan-1,3-diyl | bond | 3,5-diCl-phenyl |
| 708 | —CH$_2$— | cyclopentan-1,3-diyl | bond | 2-Cl-3-F-phenyl |
| 709 | —CH$_2$— | cyclopentan-1,3-diyl | bond | 2-Cl-4-F-phenyl |
| 710 | —CH$_2$— | cyclopentan-1,3-diyl | bond | 2-Cl-5-F-phenyl |
| 711 | —CH$_2$— | cyclopentan-1,3-diyl | bond | 3-Cl-4-F-phenyl |
| 712 | —CH$_2$— | cyclopentan-1,3-diyl | bond | 3-Cl-5-F-phenyl |
| 713 | —CH$_2$— | cyclopentan-1,3-diyl | bond | 4-Cl-2-F-phenyl |
| 714 | —CH$_2$— | cyclopentan-1,3-diyl | bond | 4-Cl-3-F-phenyl |
| 715 | —CH$_2$— | cyclopentan-1,3-diyl | bond | 2,3-diMeO-phenyl |
| 716 | —CH$_2$— | cyclopentan-1,3-diyl | bond | 2,4-diMeO-phenyl |
| 717 | —CH$_2$— | cyclopentan-1,3-diyl | bond | 2,5-diMeO-phenyl |
| 718 | —CH$_2$— | cyclopentan-1,3-diyl | bond | 2,6-diMeO-phenyl |
| 719 | —CH$_2$— | cyclopentan-1,3-diyl | bond | 3,4-diMeO-phenyl |
| 720 | —CH$_2$— | cyclopentan-1,3-diyl | bond | 3,5-diMeO-phenyl |
| 721 | —CH$_2$— | cyclopentan-1,3-diyl | bond | cyclopropyl |
| 722 | —CH$_2$— | cyclopentan-1,3-diyl | bond | cyclobutyl |
| 723 | —CH$_2$— | cyclopentan-1,3-diyl | bond | cyclopentyl |
| 724 | —CH$_2$— | cyclopentan-1,3-diyl | bond | cyclohexyl |
| 725 | —CH$_2$— | cyclopentan-1,3-diyl | bond | 2-furanyl |
| 726 | —CH$_2$— | cyclopentan-1,3-diyl | bond | 2-thienyl |
| 727 | —CH$_2$— | cyclopentan-1,3-diyl | bond | 2-imidazolyl |
| 728 | —CH$_2$— | cyclopentan-1,3-diyl | bond | 2-pyridyl |
| 729 | —CH$_2$— | cyclopentan-1,3-diyl | bond | 3-pyridyl |
| 730 | —CH$_2$— | cyclopentan-1,3-diyl | bond | 4-pyridyl |
| 731 | —CH$_2$— | cyclopentan-1,3-diyl | bond | N-morpholinyl |
| 732 | —CH$_2$— | cyclopentan-1,3-diyl | bond | N-piperidinyl |
| 733 | —CH$_2$— | cyclopentan-1,3-diyl | bond | 3-Me-2-pyridyl |
| 734 | —CH$_2$— | cyclopentan-1,3-diyl | bond | 4-Me-2-pyridyl |

TABLE 2-continued

| | | | | |
|---|---|---|---|---|
| 735 | —CH$_2$— | cyclopentan-1,3-diyl | bond | 1-indolyl |
| 736 | —CH$_2$— | cyclopentan-1,3-diyl | bond | 2-benzothienyl |
| 737 | —CH$_2$— | cyclopentan-1,3-diyl | bond | 2-benzofuranyl |
| 738 | —CH$_2$— | cyclopentan-1,3-diyl | bond | 1-benzimidazole |
| 739 | —CH$_2$— | cyclopentan-1,3-diyl | bond | 2-naphthyl |
| 740 | —CH$_2$— | phen-1,3-diyl | —O— | phenyl |
| 741 | —CH$_2$— | phen-1,3-diyl | —O— | 3,3-diphenylmethyl |
| 742 | —CH$_2$— | phen-1,3-diyl | —O— | 2-F-phenyl |
| 743 | —CH$_2$— | phen-1,3-diyl | —O— | 3-F-phenyl |
| 744 | —CH$_2$— | phen-1,3-diyl | —O— | 4-F-phenyl |
| 745 | —CH$_2$— | phen-1,3-diyl | —O— | 2-Cl-phenyl |
| 746 | —CH$_2$— | phen-1,3-diyl | —O— | 3-Cl-phenyl |
| 747 | —CH$_2$— | phen-1,3-diyl | —O— | 4-Cl-phenyl |
| 748 | —CH$_2$— | phen-1,3-diyl | —O— | 2-Me-phenyl |
| 749 | —CH$_2$— | phen-1,3-diyl | —O— | 3-Me-phenyl |
| 750 | —CH$_2$— | phen-1,3-diyl | —O— | 4-Me-phenyl |
| 751 | —CH$_2$— | phen-1,3-diyl | —O— | 2-MeO-phenyl |
| 752 | —CH$_2$— | phen-1,3-diyl | —O— | 3-MeO-phenyl |
| 753 | —CH$_2$— | phen-1,3-diyl | —O— | 4-MeO-phenyl |
| 754 | —CH$_2$— | phen-1,3-diyl | —O— | 2-MeS-phenyl |
| 755 | —CH$_2$— | phen-1,3-diyl | —O— | 3-MeS-phenyl |
| 756 | —CH$_2$— | phen-1,3-diyl | —O— | 4-MeS-phenyl |
| 757 | —CH$_2$— | phen-1,3-diyl | —O— | 2-F$_3$C-phenyl |
| 758 | —CH$_2$— | phen-1,3-diyl | —O— | 3-F$_3$C-phenyl |
| 759 | —CH$_2$— | phen-1,3-diyl | —O— | 4-F$_3$C-phenyl |
| 760 | —CH$_2$— | phen-1,3-diyl | —O— | 2,3-diF-phenyl |
| 761 | —CH$_2$— | phen-1,3-diyl | —O— | 2,4-diF-phenyl |
| 762 | —CH$_2$— | phen-1,3-diyl | —O— | 2,5-diF-phenyl |
| 763 | —CH$_2$— | phen-1,3-diyl | —O— | 2,6-diF-phenyl |
| 764 | —CH$_2$— | phen-1,3-diyl | —O— | 3 4-diF-phenyl |
| 765 | —CH$_2$— | phen-1,3-diyl | —O— | 3,5-diF-phenyl |
| 766 | —CH$_2$— | phen-1,3-diyl | —O— | 2,3-diCl-phenyl |
| 767 | —CH$_2$— | phen-1,3-diyl | —O— | 2,4-diCl-phenyl |
| 768 | —CH$_2$— | phen-1,3-diyl | —O— | 2,5-diCl-phenyl |
| 769 | —CH$_2$— | phen-1,3-diyl | —O— | 2,6-diCl-phenyl |
| 770 | —CH$_2$— | phen-1,3-diyl | —O— | 3,4-diCl-phenyl |
| 771 | —CH$_2$— | phen-1,3-diyl | —O— | 3,5-diCl-phenyl |
| 772 | —CH$_2$— | phen-1,3-diyl | —O— | 2-Cl-3-F-phenyl |
| 773 | —CH$_2$— | phen-1,3-diyl | —O— | 2-Cl-4-F-phenyl |
| 774 | —CH$_2$— | phen-1,3-diyl | —O— | 2-Cl-5-F-phenyl |
| 775 | —CH$_2$— | phen-1,3-diyl | —O— | 3-Cl-4-F-phenyl |
| 776 | —CH$_2$— | phen-1,3-diyl | —O— | 3-Cl-5-F-phenyl |
| 777 | —CH$_2$— | phen-1,3-diyl | —O— | 4-Cl-2-F-phenyl |
| 778 | —CH$_2$— | phen-1,3-diyl | —O— | 4-Cl-3-F-phenyl |
| 779 | —CH$_2$— | phen-1,3-diyl | —O— | 2,3-diMeo-phenyl |
| 780 | —CH$_2$— | phen-1,3-diyl | —O— | 2,4-diMeo-phenyl |
| 781 | —CH$_2$— | phen-1,3-diyl | —O— | 2,5-diMeo-phenyl |
| 782 | —CH$_2$— | phen-1,3-diyl | —O— | 2,6-diMeo-phenyl |
| 783 | —CH$_2$— | phen-1,3-diyl | —O— | 3,4-diMeo-phenyl |
| 784 | —CH$_2$— | phen-1,3-diyl | —O— | 3,5-diMeo-phenyl |
| 785 | —CH$_2$— | phen-1,3-diyl | —O— | cyclopropyl |
| 786 | —CH$_2$— | phen-1,3-diyl | —O— | cyclobutyl |
| 787 | —CH$_2$— | phen-1,3-diyl | —O— | cyclopentyl |
| 788 | —CH$_2$— | phen-1,3-diyl | —O— | cyclohexyl |
| 789 | —CH$_2$— | phen-1,3-diyl | —O— | 2-furanyl |
| 790 | —CH$_2$— | phen-1,3-diyl | —O— | 2-thienyl |
| 791 | —CH$_2$— | phen-1,3-diyl | CH$_2$CH$_2$ | 2-imidazolyl |
| 792 | —CH$_2$— | phen-1,3-diyl | —O— | 2-pyridyl |
| 793 | —CH$_2$— | phen-1,3-diyl | —O— | 3-pyridyl |
| 794 | —CH$_2$— | phen-1,3-diyl | —O— | 4-pyridyl |
| 795 | —CH$_2$— | phen-1,3-diyl | CH$_2$CH$_2$ | N-morpholinyl |
| 796 | —CH$_2$— | phen-1,3-diyl | CH$_2$CH$_2$ | N-piperidinyl |
| 797 | —CH$_2$— | phen-1,3-diyl | —O— | 3-Me-2-pyridyl |
| 798 | —CH$_2$— | phen-1,3-diyl | —O— | 4-Me-2-pyridyl |
| 799 | —CH$_2$— | phen-1,3-diyl | CH$_2$CH$_2$ | 1-indolyl |
| 800 | —CH$_2$— | phen-1,3-diyl | —O— | 2-benzothienyl |
| 801 | —CH$_2$— | phen-1,3-diyl | —O— | 2-benzofuranyl |
| 802 | —CH$_2$— | phen-1,3-diyl | CH$_2$CH$_2$ | 1-benzimidazole |
| 803 | —CH$_2$— | phen-1,3-diyl | —O— | 2-naphthyl |
| 804 | —CH$_2$— | pyridin-3,5-diyl | —O— | phenyl |
| 805 | —CH$_2$— | pyridin-3,5-diyl | —O— | 3,3-diphenylmethyl |
| 806 | —CH$_2$— | pyridin-3,5-diyl | —O— | 2-F-phenyl |

TABLE 2-continued

| | | | | |
|---|---|---|---|---|
| 807 | —CH$_2$— | pyridin-3,5-diyl | —O— | 3-F-phenyl |
| 808 | —CH$_2$— | pyridin-3,5-diyl | —O— | 4-F-phenyl |
| 809 | —CH$_2$— | pyridin-3,5-diyl | —O— | 2-Cl-phenyl |
| 810 | —CH$_2$— | pyridin-3,5-diyl | —O— | 3-Cl-phenyl |
| 811 | —CH$_2$— | pyridin-3,5-diyl | —O— | 4-Cl-phenyl |
| 812 | —CH$_2$— | pyridin-3,5-diyl | —O— | 2-Me-phenyl |
| 813 | —CH$_2$— | pyridin-3,5-diyl | —O— | 3-Me-phenyl |
| 814 | —CH$_2$— | pyridin-3,5-diyl | —O— | 4-Me-phenyl |
| 815 | —CH$_2$— | pyridin-3,5-diyl | —O— | 2-MeO-phenyl |
| 816 | —CH$_2$— | pyridin-3,5-diyl | —O— | 3-MeO-phenyl |
| 817 | —CH$_2$— | pyridin-3,5-diyl | —O— | 4-MeO-phenyl |
| 818 | —CH$_2$— | pyridin-3,5-diyl | —O— | 2-MeS-phenyl |
| 819 | —CH$_2$— | pyridin-3,5-diyl | —O— | 3-MeS-phenyl |
| 820 | —CH$_2$— | pyridin-3,5-diyl | —O— | 4-MeS-phenyl |
| 821 | —CH$_2$— | pyridin-3,5-diyl | —O— | 2-F$_3$C-phenyl |
| 822 | —CH$_2$— | pyridin-3,5-diyl | —O— | 3-F$_3$C-phenyl |
| 823 | —CH$_2$— | pyridin-3,5-diyl | —O— | 4-F$_3$C-phenyl |
| 824 | —CH$_2$— | pyridin-3,5-diyl | —O— | 2,3-diF-phenyl |
| 825 | —CH$_2$— | pyridin-3,5-diyl | —O— | 2,4-diF-phenyl |
| 826 | —CH$_2$— | pyridin-3,5-diyl | —O— | 2,5-diF-phenyl |
| 827 | —CH$_2$— | pyridin-3,5-diyl | —O— | 2,6-diF-phenyl |
| 828 | —CH$_2$— | pyridin-3,5-diyl | —O— | 3,4-diF-phenyl |
| 829 | —CH$_2$— | pyridin-3,5-diyl | —O— | 3,5-diF-phenyl |
| 830 | —CH$_2$— | pyridin-3,5-diyl | —O— | 2,3-diCl-phenyl |
| 831 | —CH$_2$— | pyridin-3,5-diyl | —O— | 2,4-diCl-phenyl |
| 832 | —CH$_2$— | pyridin-3,5-diyl | —O— | 2,5-diCl-phenyl |
| 833 | —CH$_2$— | pyridin-3,5-diyl | —O— | 2,6-diCl-phenyl |
| 834 | —CH$_2$— | pyridin-3,5-diyl | —O— | 3,4-diCl-phenyl |
| 835 | —CH$_2$— | pyridin-3,5-diyl | —O— | 3,5-diCl-phenyl |
| 836 | —CH$_2$— | pyridin-3,5-diyl | —O— | 2-Cl-3-F-phenyl |
| 837 | —CH$_2$— | pyridin-3,5-diyl | —O— | 2-Cl-4-F-phenyl |
| 838 | —CH$_2$— | pyridin-3,5-diyl | —O— | 2-Cl-5-F-phenyl |
| 839 | —CH$_2$— | pyridin-3,5-diyl | —O— | 3-Cl-4-F-phenyl |
| 840 | —CH$_2$— | pyridin-3,5-diyl | —O— | 3-Cl-5-F-phenyl |
| 841 | —CH$_2$— | pyridin-3,5-diyl | —O— | 4-Cl-2-F-phenyl |
| 842 | —CH$_2$— | pyridin-3,5-diyl | —O— | 4-Cl-3-F-phenyl |
| 843 | —CH$_2$— | pyridin-3,5-diyl | —O— | 2,3-diMeO-phenyl |
| 844 | —CH$_2$— | pyridin-3,5-diyl | —O— | 2,4-diMeO-phenyl |
| 845 | —CH$_2$— | pyridin-3,5-diyl | —O— | 2,5-diMeO-phenyl |
| 846 | —CH$_2$— | pyridin-3,5-diyl | —O— | 2,6-diMeO-phenyl |
| 847 | —CH$_2$— | pyridin-3,5-diyl | —O— | 3,4-diMeO-phenyl |
| 848 | —CH$_2$— | pyridin-3,5-diyl | —O— | 3,5-diMeO-phenyl |
| 849 | —CH$_2$— | pyridin-3,5-diyl | —O— | cyclopropyl |
| 850 | —CH$_2$— | pyridin-3,5-diyl | —O— | cyclobutyl |
| 851 | —CH$_2$— | pyridin-3,5-diyl | —O— | cyclopentyl |
| 852 | —CH$_2$— | pyridin-3,5-diyl | —O— | cyclohexyl |
| 853 | —CH$_2$— | pyridin-3,5-diyl | —O— | 2-furanyl |
| 854 | —CH$_2$— | pyridin-3,5-diyl | —O— | 2-thienyl |
| 855 | —CH$_2$— | pyridin-3,5-diyl | CH$_2$CH$_2$ | 2-imidazolyl |
| 856 | —CH$_2$— | pyridin-3,5-diyl | —O— | 2-pyridyl |
| 857 | —CH$_2$— | pyridin-3,5-diyl | —O— | 3-pyridyl |
| 858 | —CH$_2$— | pyridin-3,5-diyl | —O— | 4-pyridyl |
| 859 | —CH$_2$— | pyridin-3,5-diyl | CH$_2$CH$_2$ | N-morpholinyl |
| 860 | —CH$_2$— | pyridin-3,5-diyl | CH$_2$CH$_2$ | N-piperidinyl |
| 861 | —CH$_2$— | pyridin-3,5-diyl | —O— | 3-Me-2-pyridyl |
| 862 | —CH$_2$— | pyridin-3,5-diyl | —O— | 4-Me-2-pyridyl |
| 863 | —CH$_2$— | pyridin-3,5-diyl | CH$_2$CH$_2$ | 1-indolyl |
| 864 | —CH$_2$— | pyridin-3,5-diyl | —O— | 2-benzothienyl |
| 865 | —CH$_2$— | pyridin-3,5-diyl | —O— | 2-benzofuranyl |
| 866 | —CH$_2$— | pyridin-3,5-diyl | CH$_2$CH$_2$ | 1-benzimidazole |
| 867 | —CH$_2$— | pyridin-3,5-diyl | —O— | 2-naphthyl |
| 868 | —CH$_2$— | pyridin-2,6-diyl | —O— | phenyl |
| 869 | —CH$_2$— | pyridin-2,6-diyl | —O— | 3,3-diphenylmethyl |
| 870 | —CH$_2$— | pyridin-2,6-diyl | —O— | 2-F-phenyl |
| 871 | —CH$_2$— | pyridin-2,6-diyl | —O— | 3-F-phenyl |
| 872 | —CH$_2$— | pyridin-2,6-diyl | —O— | 4-F-phenyl |
| 873 | —CH$_2$— | pyridin-2,6-diyl | —O— | 2-Cl-phenyl |
| 874 | —CH$_2$— | pyridin-2,6-diyl | —O— | 3-Cl-phenyl |
| 875 | —CH$_2$— | pyridin-2,6-diyl | —O— | 4-Cl-phenyl |
| 876 | —CH$_2$— | pyridin-2,6-diyl | —O— | 2-Me-phenyl |
| 877 | —CH$_2$— | pyridin-2,6-diyl | —O— | 3-Me-phenyl |
| 878 | —CH$_2$— | pyridin-2,6-diyl | —O— | 4-Me-phenyl |
| 879 | —CH$_2$— | pyridin-2,6-diyl | —O— | 2-MeO-phenyl |
| 880 | —CH$_2$— | pyridin-2,6-diyl | —O— | 3-MeO-phenyl |
| 881 | —CH$_2$— | pyridin-2,6-diyl | —O— | 4-MeO-phenyl |
| 882 | —CH$_2$— | pyridin-2,6-diyl | —O— | 2-MeS-phenyl |
| 883 | —CH$_2$— | pyridin-2,6-diyl | —O— | 3-MeS-phenyl |
| 884 | —CH$_2$— | pyridin-2,6-diyl | —O— | 4-MeS-phenyl |

TABLE 2-continued

| | | | | |
|---|---|---|---|---|
| 885 | —CH$_2$— | pyridin-2,6-diyl | —O— | 2-F$_3$C-phenyl |
| 886 | —CH$_2$— | pyridin-2,6-diyl | —O— | 3-F$_3$C-phenyl |
| 887 | —CH$_2$— | pyridin-2,6-diyl | —O— | 4-F$_3$C-phenyl |
| 888 | —CH$_2$— | pyridin-2,6-diyl | —O— | 2,3-diF-phenyl |
| 889 | —CH$_2$— | pyridin-2,6-diyl | —O— | 2,4-diF-phenyl |
| 890 | —CH$_2$— | pyridin-2,6-diyl | —O— | 2,5-diF-phenyl |
| 891 | —CH$_2$— | pyridin-2,6-diyl | —O— | 2,6-diF-phenyl |
| 892 | —CH$_2$— | pyridin-2,6-diyl | —O— | 3,4-diF-phenyl |
| 893 | —CH$_2$— | pyridin-2,6-diyl | —O— | 3,5-diF-phenyl |
| 894 | —CH$_2$— | pyridin-2,6-diyl | —O— | 2,3-diCl-phenyl |
| 895 | —CH$_2$— | pyridin-2,6-diyl | —O— | 2,4-diCl-phenyl |
| 896 | —CH$_2$— | pyridin-2,6-diyl | —O— | 2,5-diCl-phenyl |
| 897 | —CH$_2$— | pyridin-2,6-diyl | —O— | 2,6-diCl-phenyl |
| 898 | —CH$_2$— | pyridin-2,6-diyl | —O— | 3,4-diCl-phenyl |
| 899 | —CH$_2$— | pyridin-2,6-diyl | —O— | 3,5-diCl-phenyl |
| 900 | —CH$_2$— | pyridin-2,6-diyl | —O— | 2-Cl-3-F-phenyl |
| 901 | —CH$_2$— | pyridin-2,6-diyl | —O— | 2-Cl-4-F-phenyl |
| 902 | —CH$_2$— | pyridin-2,6-diyl | —O— | 2-Cl-5-F-phenyl |
| 903 | —CH$_2$— | pyridin-2,6-diyl | —O— | 3-Cl-4-F-phenyl |
| 904 | —CH$_2$— | pyridin-2,6-diyl | —O— | 3-Cl-5-F-phenyl |
| 905 | —CH$_2$— | pyridin-2,6-diyl | —O— | 4-Cl-2-F-phenyl |
| 906 | —CH$_2$— | pyridin-2,6-diyl | —O— | 4-Cl-3-F-phenyl |
| 907 | —CH$_2$— | pyridin-2,6-diyl | —O— | 2,3-diMeO-phenyl |
| 908 | —CH$_2$— | pyridin-2,6-diyl | —O— | 2,4-diMeO-phenyl |
| 909 | —CH$_2$— | pyridin-2,6-diyl | —O— | 2,5-diMeO-phenyl |
| 910 | —CH$_2$— | pyridin-2,6-diyl | —O— | 2,6-diMeO-phenyl |
| 911 | —CH$_2$— | pyridin-2,6-diyl | —O— | 3,4-diMeO-phenyl |
| 912 | —CH$_2$— | pyridin-2,6-diyl | —O— | 3,5-diMeO-phenyl |
| 913 | —CH$_2$— | pyridin-2,6-diyl | —O— | cyclopropyl |
| 914 | —CH$_2$— | pyridin-2,6-diyl | —O— | cyclobutyl |
| 915 | —CH$_2$— | pyridin-2,6-diyl | —O— | cyclopentyl |
| 916 | —CH$_2$— | pyridin-2,6-diyl | —O— | cyclohexyl |
| 917 | —CH$_2$— | pyridin-2,6-diyl | —O— | 2-furanyl |
| 918 | —CH$_2$— | pyridin-2,6-diyl | —O— | 2-thienyl |
| 919 | —CH$_2$— | pyridin-2,6-diyl | CH$_2$CH$_2$ | 2-imidazolyl |
| 920 | —CH$_2$— | pyridin-2,6-diyl | —O— | 2-pyridyl |
| 921 | —CH$_2$— | pyridin-2,6-diyl | —O— | 3-pyridyl |
| 922 | —CH$_2$— | pyridin-2,6-diyl | —O— | 4-pyridyl |
| 923 | —CH$_2$— | pyridin-2,6-diyl | CH$_2$CH$_2$ | N-morpholinyl |
| 924 | —CH$_2$— | pyridin-2,6-diyl | CH$_2$CH$_2$ | N-piperidinyl |
| 925 | —CH$_2$— | pyridin-2,6-diyl | —O— | 3-Me-2-pyridyl |
| 926 | —CH$_2$— | pyridin-2,6-diyl | —O— | 4-Me-2-pyridyl |
| 927 | —CH$_2$— | pyridin-2,6-diyl | CH$_2$CH$_2$ | 1-indolyl |
| 928 | —CH$_2$— | pyridin-2,6-diyl | —O— | 2-benzothienyl |
| 929 | —CH$_2$— | pyridin-2,6-diyl | —O— | 2-benzofuranyl |
| 930 | —CH$_2$— | pyridin-2,6-diyl | CH$_2$CH$_2$ | 1-benzimidazole |
| 931 | —CH$_2$— | pyridin-2,6-diyl | —O— | 2-naphthyl |
| 932 | —CH$_2$— | pyridin-2,4-diyl | —O— | phenyl |
| 933 | —CH$_2$— | pyridin-2,4-diyl | —O— | 3,3-diphenylmethyl |
| 934 | —CH$_2$— | pyridin-2,4-diyl | —O— | 2-F-phenyl |
| 935 | —CH$_2$— | pyridin-2,4-diyl | —O— | 3-F-phenyl |
| 936 | —CH$_2$— | pyridin-2,4-diyl | —O— | 4-F-phenyl |
| 937 | —CH$_2$— | pyridin-2,4-diyl | —O— | 2-Cl-phenyl |
| 938 | —CH$_2$— | pyridin-2,4-diyl | —O— | 3-Cl-phenyl |
| 939 | —CH$_2$— | pyridin-2,4-diyl | —O— | 4-Cl-phenyl |
| 940 | —CH$_2$— | pyridin-2,4-diyl | —O— | 2-Me-phenyl |
| 941 | —CH$_2$— | pyridin-2,4-diyl | —O— | 3-Me-phenyl |
| 942 | —CH$_2$— | pyridin-2,4-diyl | —O— | 4-Me-phenyl |
| 943 | —CH$_2$— | pyridin-2,4-diyl | —O— | 2-MeO-phenyl |
| 944 | —CH$_2$— | pyridin-2,4-diyl | —O— | 3-MeO-phenyl |
| 945 | —CH$_2$— | pyridin-2,4-diyl | —O— | 4-MeO-phenyl |
| 946 | —CH$_2$— | pyridin-2,4-diyl | —O— | 2-MeS-phenyl |
| 947 | —CH$_2$— | pyridin-2,4-diyl | —O— | 3-MeS-phenyl |
| 948 | —CH$_2$— | pyridin-2,4-diyl | —O— | 4-MeS-phenyl |
| 949 | —CH$_2$— | pyridin-2,4-diyl | —O— | 2-F$_3$C-phenyl |
| 950 | —CH$_2$— | pyridin-2,4-diyl | —O— | 3-F$_3$C-phenyl |
| 951 | —CH$_2$— | pyridin-2,4-diyl | —O— | 4-F$_3$C-phenyl |
| 952 | —CH$_2$— | pyridin-2,4-diyl | —O— | 2,3-diF-phenyl |
| 953 | —CH$_2$— | pyridin-2,4-diyl | —O— | 2,4-diF-phenyl |
| 954 | —CH$_2$— | pyridin-2,4-diyl | —O— | 2,5-diF-phenyl |
| 955 | —CH$_2$— | pyridin-2,4-diyl | —O— | 2,6-diF-phenyl |
| 956 | —CH$_2$— | pyridin-2,4-diyl | —O— | 3,4-diF-phenyl |
| 957 | —CH$_2$— | pyridin-2,4-diyl | —O— | 3,5-diF-phenyl |
| 958 | —CH$_2$— | pyridin-2,4-diyl | —O— | 2,3-diCl-phenyl |
| 959 | —CH$_2$— | pyridin-2,4-diyl | —O— | 2,4-diCl-phenyl |
| 960 | —CH$_2$— | pyridin-2,4-diyl | —O— | 2,5-diCl-phenyl |
| 961 | —CH$_2$— | pyridin-2,4-diyl | —O— | 2,6-diCl-phenyl |
| 962 | —CH$_2$— | pyridin-2,4-diyl | —O— | 3,4-diCl-phenyl |

TABLE 2-continued

| | | | | |
|---|---|---|---|---|
| 963 | —CH$_2$— | pyridin-2,4-diyl | —O— | 3,5-diCl-phenyl |
| 964 | —CH$_2$— | pyridin-2,4-diyl | —O— | 2-Cl-3-F-phenyl |
| 965 | —CH$_2$— | pyridin-2,4-diyl | —O— | 2-Cl-4-F-phenyl |
| 966 | —CH$_2$— | pyridin-2,4-diyl | —O— | 2-Cl-5-F-phenyl |
| 967 | —CH$_2$— | pyridin-2,4-diyl | —O— | 3-Cl-4-F-phenyl |
| 968 | —CH$_2$— | pyridin-2,4-diyl | —O— | 3-Cl-5-F-phenyl |
| 969 | —CH$_2$— | pyridin-2,4-diyl | —O— | 4-Cl-2-F-phenyl |
| 970 | —CH$_2$— | pyridin-2,4-diyl | —O— | 4-Cl-3-F-phenyl |
| 971 | —CH$_2$— | pyridin-2,4-diyl | —O— | 2,3-diMeO-phenyl |
| 972 | —CH$_2$— | pyridin-2,4-diyl | —O— | 2,4-diMeO-phenyl |
| 973 | —CH$_2$— | pyridin-2,4-diyl | —O— | 2,5-diMeO-phenyl |
| 974 | —CH$_2$— | pyridin-2,4-diyl | —O— | 2,6-diMeO-phenyl |
| 975 | —CH$_2$— | pyridin-2,4-diyl | —O— | 3,4-diMeO-phenyl |
| 976 | —CH$_2$— | pyridin-2,4-diyl | —O— | 3,5-diMeO-phenyl |
| 977 | —CH$_2$— | pyridin-2,4-diyl | —O— | cyclopropyl |
| 978 | —CH$_2$— | pyridin-2,4-diyl | —O— | cyclobutyl |
| 979 | —CH$_2$— | pyridin-2,4-diyl | —O— | cyclopentyl |
| 980 | —CH$_2$— | pyridin-2,4-diyl | —O— | cyclohexyl |
| 981 | —CH$_2$— | pyridin-2,4-diyl | —O— | 2-furanyl |
| 982 | —CH$_2$— | pyridin-2,4-diyl | —O— | 2-thienyl |
| 983 | —CH$_2$— | pyridin-2,4-diyl | CH$_2$CH$_2$ | 2-imidazolyl |
| 984 | —CH$_2$— | pyridin-2,4-diyl | —O— | 2-pyridyl |
| 985 | —CH$_2$— | pyridin-2,4-diyl | —O— | 3-pyridyl |
| 986 | —CH$_2$— | pyridin-2,4-diyl | —O— | 4-pyridyl |
| 987 | —CH$_2$— | pyridin-2,4-diyl | CH$_2$CH$_2$ | N-morpholinyl |
| 988 | —CH$_2$— | pyridin-2,4-diyl | CH$_2$CH$_2$ | N-piperidinyl |
| 989 | —CH$_2$— | pyridin-2,4-diyl | —O— | 3-Me-2-pyridyl |
| 990 | —CH$_2$— | pyridin-2,4-diyl | —O— | 4-Me-2-pyridyl |
| 991 | —CH$_2$— | pyridin-2,4-diyl | CH$_2$CH$_2$ | 1-indolyl |
| 992 | —CH$_2$— | pyridin-2,4-diyl | —O— | 2-benzothienyl |
| 993 | —CH$_2$— | pyridin-2,4-diyl | —O— | 2-benzofuranyl |
| 994 | —CH$_2$— | pyridin-2,4-diyl | CH$_2$CH$_2$ | 1-benzimidazole |
| 995 | —CH$_2$— | pyridin-2,4-diyl | —O— | 2-naphthyl |
| 996 | —CH$_2$— | pyridin-4,2-diyl | —O— | phenyl |
| 997 | —CH$_2$— | pyridin-4,2-diyl | —O— | 3,3-diphenylmethyl |
| 998 | —CH$_2$— | pyridin-4,2-diyl | —O— | 2-F-phenyl |
| 999 | —CH$_2$— | pyridin-4,2-diyl | —O— | 3-F-phenyl |
| 1000 | —CH$_2$— | pyridin-4,2-diyl | —O— | 4-F-phenyl |
| 1001 | —CH$_2$— | pyridin-4,2-diyl | —O— | 2-Cl-phenyl |
| 1002 | —CH$_2$— | pyridin-4,2-diyl | —O— | 3-Cl-phenyl |
| 1003 | —CH$_2$— | pyridin-4,2-diyl | —O— | 4-Cl-phenyl |
| 1004 | —CH$_2$— | pyridin-4,2-diyl | —O— | 2-Me-phenyl |
| 1005 | —CH$_2$— | pyridin-4,2-diyl | —O— | 3-Me-phenyl |
| 1006 | —CH$_2$— | pyridin-4,2-diyl | —O— | 4-Me-phenyl |
| 1007 | —CH$_2$— | pyridin-4,2-diyl | —O— | 2-MeO-phenyl |
| 1008 | —CH$_2$— | pyridin-4,2-diyl | —O— | 3-MeO-phenyl |
| 1009 | —CH$_2$— | pyridin-4,2-diyl | —O— | 4-MeO-phenyl |
| 1010 | —CH$_2$— | pyridin-4,2-diyl | —O— | 2-MeS-phenyl |
| 1011 | —CH$_2$— | pyridin-4,2-diyl | —O— | 3-MeS-phenyl |
| 1012 | —CH$_2$— | pyridin-4,2-diyl | —O— | 4-MeS-phenyl |
| 1013 | —CH$_2$— | pyridin-4,2-diyl | —O— | 2-F$_3$C-phenyl |
| 1014 | —CH$_2$— | pyridin-4,2-diyl | —O— | 3-F$_3$C-phenyl |
| 1015 | —CH$_2$— | pyridin-4,2-diyl | —O— | 4-F$_3$C-phenyl |
| 1016 | —CH$_2$— | pyridin-4,2-diyl | —O— | 2,3-diF-phenyl |
| 1017 | —CH$_2$— | pyridin-4,2-diyl | —O— | 2,4-diF-phenyl |
| 1018 | —CH$_2$— | pyridin-4,2-diyl | —O— | 2,5-diF-phenyl |
| 1019 | —CH$_2$— | pyridin-4,2-diyl | —O— | 2,6-diF-phenyl |
| 1020 | —CH$_2$— | pyridin-4,2-diyl | —O— | 3,4-diF-phenyl |
| 1021 | —CH$_2$— | pyridin-4,2-diyl | —O— | 3,5-diF-phenyl |
| 1022 | —CH$_2$— | pyridin-4,2-diyl | —O— | 2,3-diCl-phenyl |
| 1023 | —CH$_2$— | pyridin-4,2-diyl | —O— | 2,4-diCl-phenyl |
| 1024 | —CH$_2$— | pyridin-4,2-diyl | —O— | 2,5-diCl-phenyl |
| 1025 | —CH$_2$— | pyridin-4,2-diyl | —O— | 2,6-diCl-phenyl |
| 1026 | —CH$_2$— | pyridin-4,2-diyl | —O— | 3,4-diCl-phenyl |
| 1027 | —CH$_2$— | pyridin-4,2-diyl | —O— | 3,5-diCl-phenyl |
| 1028 | —CH$_2$— | pyridin-4,2-diyl | —O— | 2-Cl-3-F-phenyl |
| 1029 | —CH$_2$— | pyridin-4,2-diyl | —O— | 2-Cl-4-F-phenyl |
| 1030 | —CH$_2$— | pyridin-4,2-diyl | —O— | 2-Cl-5-F-phenyl |
| 1031 | —CH$_2$— | pyridin-4,2-diyl | —O— | 3-Cl-4-F-phenyl |
| 1032 | —CH$_2$— | pyridin-4,2-diyl | —O— | 3-Cl-5-F-phenyl |
| 1033 | —CH$_2$— | pyridin-4,2-diyl | —O— | 4-Cl-2-F-phenyl |
| 1034 | —CH$_2$— | pyridin-4,2-diyl | —O— | 4-Cl-3-F-phenyl |
| 1035 | —CH$_2$— | pyridin-4,2-diyl | —O— | 2,3-diMeO-phenyl |
| 1036 | —CH$_2$— | pyridin-4,2-diyl | —O— | 2,4-diMeO-phenyl |
| 1037 | —CH$_2$— | pyridin-4,2-diyl | —O— | 2,5-diMeO-phenyl |
| 1038 | —CH$_2$— | pyridin-4,2-diyl | —O— | 2,6-diMeO-phenyl |
| 1039 | —CH$_2$— | pyridin-4,2-diyl | —O— | 3,4-diMeO-phenyl |
| 1040 | —CH$_2$— | pyridin-4,2-diyl | —O— | 3,5-diMeO-phenyl |

TABLE 2-continued

| | | | | |
|---|---|---|---|---|
| 1041 | —CH$_2$— | pyridin-4,2-diyl | —O— | cyclopropyl |
| 1042 | —CH$_2$— | pyridin-4,2-diyl | —O— | cyclobutyl |
| 1043 | —CH$_2$— | pyridin-4,2-diyl | —O— | cyclopentyl |
| 1044 | —CH$_2$— | pyridin-4,2-diyl | —O— | cyclohexyl |
| 1045 | —CH$_2$— | pyridin-4,2-diyl | —O— | 2-furanyl |
| 1046 | —CH$_2$— | pyridin-4,2-diyl | —O— | 2-thienyl |
| 1047 | —CH$_2$— | pyridin-4,2-diyl | CH$_2$CH$_2$ | 2-imidazolyl |
| 1048 | —CH$_2$— | pyridin-4,2-diyl | —O— | 2-pyridyl |
| 1049 | —CH$_2$— | pyridin-4,2-diyl | —O— | 3-pyridyl |
| 1050 | —CH$_2$— | pyridin-4,2-diyl | —O— | 4-pyridyl |
| 1051 | —CH$_2$— | pyridin-4,2-diyl | CH$_2$CH$_2$ | N-morpholinyl |
| 1052 | —CH$_2$— | pyridin-4,2-diyl | CH$_2$CH$_2$ | N-piperidinyl |
| 1053 | —CH$_2$— | pyridin-4,2-diyl | —O— | 3-Me-2-pyridyl |
| 1054 | —CH$_2$— | pyridin-4,2-diyl | —O— | 4-Me-2-pyridyl |
| 1055 | —CH$_2$— | pyridin-4,2-diyl | CH$_2$CH$_2$ | 1-indolyl |
| 1056 | —CH$_2$— | pyridin-4,2-diyl | —O— | 2-benzothienyl |
| 1057 | —CH$_2$— | pyridin-4,2-diyl | —O— | 2-benzofuranyl |
| 1058 | —CH$_2$— | pyridin-4,2-diyl | CH$_2$CH$_2$ | 1-benzimidazole |
| 1059 | —CH$_2$— | pyridin-4,2-diyl | —O— | 2-naphthyl |
| 1060 | —CH$_2$— | piperidin-1,3-diyl | —O— | phenyl |
| 1061 | —CH$_2$— | piperidin-1,3-diyl | —O— | 3,3-diphenylmethyl |
| 1062 | —CH$_2$— | piperidin-1,3 diyl | —O— | 2-F-phenyl |
| 1063 | —CH$_2$— | piperidin-1,3-diyl | —O— | 3-F-phenyl |
| 1064 | —CH$_2$— | piperidin-1,3-diyl | —O— | 4-F-phenyl |
| 1065 | —CH$_2$— | piperidin-1,3-diyl | —O— | 2-Cl-phenyl |
| 1066 | —CH$_2$— | piperidin-1,3-diyl | —O— | 3-Cl-phenyl |
| 1067 | —CH$_2$— | piperidin-1,3-diyl | —O— | 4-Cl-phenyl |
| 1068 | —CH$_2$— | piperidin-1,3-diyl | —O— | 2-Me-phenyl |
| 1069 | —CH$_2$— | piperidin-1,3-diyl | —O— | 3-Me-phenyl |
| 1070 | —CH$_2$— | piperidin-1,3-diyl | —O— | 4-Me-phenyl |
| 1071 | —CH$_2$— | piperidin-1,3-diyl | —O— | 2-MeO-phenyl |
| 1072 | —CH$_2$— | piperidin-1,3-diyl | —O— | 3-MeO-phenyl |
| 1073 | —CH$_2$— | piperidin-1,3-diyl | —O— | 4-MeO-phenyl |
| 1074 | —CH$_2$— | piperidin-1,3-diyl | —O— | 2-MeS-phenyl |
| 1075 | —CH$_2$— | piperidin-1,3-diyl | —O— | 3-MeS-phenyl |
| 1076 | —CH$_2$— | piperidin-1,3-diyl | —O— | 4-MeS-phenyl |
| 1077 | —CH$_2$— | piperidin-1,3-diyl | —O— | 2-F$_3$C-phenyl |
| 1078 | —CH$_2$— | piperidin-1,3-diyl | —O— | 3-F$_3$C-phenyl |
| 1079 | —CH$_2$— | piperidin-1,3-diyl | —O— | 4-F$_3$C-phenyl |
| 1080 | —CH$_2$— | piperidin-1,3-diyl | —O— | 2,3-diF-phenyl |
| 1081 | —CH$_2$— | piperidin-1,3-diyl | —O— | 2,4-diF-phenyl |
| 1082 | —CH$_2$— | piperidin-1,3-diyl | —O— | 2,5-diF-phenyl |
| 1083 | —CH$_2$— | piperidin-1,3-diyl | —O— | 2,6-diF-phenyl |
| 1084 | —CH$_2$— | piperidin-1,3-diyl | —O— | 3,4-diF-phenyl |
| 1085 | —CH$_2$— | piperidin-1,3-diyl | —O— | 3,5-diF-phenyl |
| 1086 | —CH$_2$— | piperidin-1,3-diyl | —O— | 2,3-diCl-phenyl |
| 1087 | —CH$_2$— | piperidin-1,3-diyl | —O— | 2,4-diCl-phenyl |
| 1088 | —CH$_2$— | piperidin-1,3-diyl | —O— | 2,5-diCl-phenyl |
| 1089 | —CH$_2$— | piperidin-1,3-diyl | —O— | 2,6-diCl-phenyl |

TABLE 2-continued

| | | | | |
|---|---|---|---|---|
| 1090 | —CH$_2$— | piperidin-1,3-diyl | —O— | 3,4-diCl-phenyl |
| 1091 | —CH$_2$— | piperidin-1,3-diyl | —O— | 3,5-diCl-phenyl |
| 1092 | —CH$_2$— | piperidin-1,3-diyl | —O— | 2-Cl-3-F-phenyl |
| 1093 | —CH$_2$— | piperidin-1,3-diyl | —O— | 2-Cl-4-F-phenyl |
| 1094 | —CH$_2$— | piperidin-1,3-diyl | —O— | 2-Cl-5-F-phenyl |
| 1095 | —CH$_2$— | piperidin-1,3-diyl | —O— | 3-Cl-4-F-phenyl |
| 1096 | —CH$_2$— | piperidin-1,3-diyl | —O— | 3-Cl-5-F-phenyl |
| 1097 | —CH$_2$— | piperidin-1,3-diyl | —O— | 4-Cl-2-F-phenyl |
| 1098 | —CH$_2$— | piperidin-1,3-diyl | —O— | 4-Cl-3-F-phenyl |
| 1099 | —CH$_2$— | piperidin-1,3-diyl | —O— | 2,3-diMeO-phenyl |
| 1100 | —CH$_2$— | piperidin-1,3-diyl | —O— | 2,4-diMeO-phenyl |
| 1101 | —CH$_2$— | piperidin-1,3-diyl | —O— | 2,5-diMeO-phenyl |
| 1102 | —CH$_2$— | piperidin-1,3-diyl | —O— | 2,6-diMeO-phenyl |
| 1103 | —CH$_2$— | piperidin-1,3-diyl | —O— | 3,4-diMeO-phenyl |
| 1104 | —CH$_2$— | piperidin-1,3-diyl | —O— | 3,5-diMeO-phenyl |
| 1105 | —CH$_2$— | piperidin-1,3-diyl | —O— | Cyclopropyl |
| 1106 | —CH$_2$— | piperidin-1,3-diyl | —O— | Cyclobutyl |
| 1107 | —CH$_2$— | piperidin-1,3-diyl | —O— | Cyclopentyl |
| 1108 | —CH$_2$— | piperidin-1,3-diyl | —O— | Cyclohexyl |
| 1109 | —CH$_2$— | piperidin-1,3-diyl | —O— | 2-furanyl |
| 1110 | —CH$_2$— | piperidin-1,3-diyl | —O— | 2-thienyl |
| 1111 | —CH$_2$— | piperidin-1,3-diyl | CH$_2$CH$_2$ | 2-imidazolyl |
| 1112 | —CH$_2$— | piperidin-1,3-diyl | —O— | 2-pyridyl |
| 1113 | —CH$_2$— | piperidin-1,3-diyl | —O— | 3-pyridyl |
| 1114 | —CH$_2$— | piperidin-1,3-diyl | —O— | 4-pyridyl |
| 1115 | —CH$_2$— | piperidin-1,3-diyl | CH$_2$CH$_2$ | N-morpholinyl |
| 1116 | —CH$_2$— | piperidin-1,3-diyl | CH$_2$CH$_2$ | N-piperidinyl |
| 1117 | —CH$_2$— | piperidin-1,3-diyl | —O— | 3-Me-2-pyridyl |
| 1118 | —CH$_2$— | piperidin-1,3-diyl | —O— | 4-Me-2-pyridyl |
| 1119 | —CH$_2$— | piperidin-1,3-diyl | CH$_2$CH$_2$ | 1-indolyl |
| 1120 | —CH$_2$— | piperidin-1,3-diyl | —O— | 2-benzothienyl |
| 1121 | —CH$_2$— | piperidin-1,3-diyl | —O— | 2-berizofuranyl |
| 1122 | —CH$_2$— | piperidin-1,3-diyl | CH$_2$CH$_2$ | 1-benzimidazole |
| 1123 | —CH$_2$— | piperidin-1,3-diyl | —O— | 2-naphthyl |
| 1124 | —CH$_2$— | piperidin-3,1-diyl | —O— | Phenyl |
| 1125 | —CH$_2$— | piperidin-3,1-diyl | —O— | 3,3-diphenylmethyl |
| 1126 | —CH$_2$— | piperidin-3,1-diyl | —O— | 2-F-phenyl |
| 1127 | —CH$_2$— | piperidin-3,1-diyl | —O— | 3-F-phenyl |
| 1128 | —CH$_2$— | piperidin-3,1-diyl | —O— | 4-F-phenyl |

TABLE 2-continued

| | | | | |
|---|---|---|---|---|
| 1129 | —CH$_2$— | piperidin-3,1-diyl | —O— | 2-Cl-phenyl |
| 1130 | —CH$_2$— | piperidin-3,1-diyl | —O— | 3-Cl-phenyl |
| 1131 | —CH$_2$— | piperidin-3,1-diyl | —O— | 4-Cl-phenyl |
| 1132 | —CH$_2$— | piperidin-3,1-diyl | —O— | 2-Me-phenyl |
| 1133 | —CH$_2$— | piperidin-3,1-diyl | —O— | 3-Me-phenyl |
| 1134 | —CH$_2$— | piperidin-3,1-diyl | —O— | 4-Me-phenyl |
| 1135 | —CH$_2$— | piperidin-3,1-diyl | —O— | 2-MeO-phenyl |
| 1136 | —CH$_2$— | piperidin-3,1-diyl | —O— | 3-MeO-phenyl |
| 1137 | —CH$_2$— | piperidin-3,1-diyl | —O— | 4-MeO-phenyl |
| 1138 | —CH$_2$— | piperidin-3,1-diyl | —O— | 2-MeS-phenyl |
| 1139 | —CH$_2$— | piperidin-3,1-diyl | —O— | 3-MeS-phenyl |
| 1140 | —CH$_2$— | piperidin-3,1-diyl | —O— | 4-MeS-phenyl |
| 1141 | —CH$_2$— | piperidin-3,1-diyl | —O— | 2-F$_3$C-phenyl |
| 1142 | —CH$_2$— | piperidin-3,1-diyl | —O— | 3-F$_3$C-phenyl |
| 1143 | —CH$_2$— | piperidin-3,1-diyl | —O— | 4-F$_3$C-phenyl |
| 1144 | —CH$_2$— | piperidin-3,1-diyl | —O— | 2,3-diF-phenyl |
| 1145 | —CH$_2$— | piperidin-3,1-diyl | —O— | 2,4-diF-phenyl |
| 1146 | —CH$_2$— | piperidin-3,1-diyl | —O— | 2,5-diF-phenyl |
| 1147 | —CH$_2$— | piperidin-3,1-diyl | —O— | 2,6-diF-phenyl |
| 1148 | —CH$_2$— | piperidin-3,1-diyl | —O— | 3,4-diF-phenyl |
| 1149 | —CH$_2$— | piperidin-3,1-diyl | —O— | 3,5-diF-phenyl |
| 1150 | —CH$_2$— | piperidin-3,1-diyl | —O— | 2,3-diCl-phenyl |
| 1151 | —CH$_2$— | piperidin-3,1-diyl | —O— | 2,4-diCl-phenyl |
| 1152 | —CH$_2$— | piperidin-3,1-diyl | —O— | 2,5-diCl-phenyl |
| 1153 | —CH$_2$— | piperidin-3,1-diyl | —O— | 2,6-diCl-phenyl |
| 1154 | —CH$_2$— | piperidin-3,1-diyl | —O— | 3,4-diCl-phenyl |
| 1155 | —CH$_2$— | piperidin-3,1-diyl | —O— | 3,5-diCl-phenyl |
| 1156 | —CH$_2$— | piperidin-3,1-diyl | —O— | 2-Cl-3-F-phenyl |
| 1157 | —CH$_2$— | piperidin-3,1-diyl | —O— | 2-Cl-4-F-phenyl |
| 1158 | —CH$_2$— | piperidin-3,1-diyl | —O— | 2-Cl-5-F-phenyl |
| 1159 | —CH$_2$— | piperidin-3,1-diyl | —O— | 3-Cl-4-F-phenyl |
| 1160 | —CH$_2$— | piperidin-3,1-diyl | —O— | 3-Cl-5-F-phenyl |
| 1161 | —CH$_2$— | piperidin-3,1-diyl | —O— | 4-Cl-2-F-phenyl |
| 1162 | —CH$_2$— | piperidin-3,1-diyl | —O— | 4-Cl-3-F-phenyl |
| 1163 | —CH$_2$— | piperidin-3,1-diyl | —O— | 2,3-diMeO-phenyl |
| 1164 | —CH$_2$— | piperidin-3,1-diyl | —O— | 2,4-diMeO-phenyl |
| 1165 | —CH$_2$— | piperidin-3,1-diyl | —O— | 2,5-diMeO-phenyl |
| 1166 | —CH$_2$— | piperidin-3,1-diyl | —O— | 2,6-diMeO-phenyl |
| 1167 | —CH$_2$— | piperidin-3,1-diyl | —O— | 3 4-diMeO-phenyl |

TABLE 2-continued

| | | | | |
|---|---|---|---|---|
| 1168 | —CH$_2$— | piperidin-3,1-diyl | —O— | 3,5-diMeO-phenyl |
| 1169 | —CH$_2$— | piperidin-3,1-diyl | —O— | Cyclopropyl |
| 1170 | —CH$_2$— | piperidin-3,1-diyl | —O— | Cyclobutyl |
| 1171 | —CH$_2$— | piperidin-3,1-diyl | —O— | Cyclopentyl |
| 1172 | —CH$_2$— | piperidin-3,1-diyl | —O— | Cyclohexyl |
| 1173 | —CH$_2$— | piperidin-3,1-diyl | —O— | 2-furanyl |
| 1174 | —CH$_2$— | piperidin-3,1-diyl | —O— | 2-thienyl |
| 1175 | —CH$_2$— | piperidin-3,1-diyl | CH$_2$CH$_2$ | 2-imidazolyl |
| 1176 | —CH$_2$— | piperidin-3,1-diyl | —O— | 2-pyridyl |
| 1177 | —CH$_2$— | piperidin-3,1-diyl | —O— | 3-pyridyl |
| 1178 | —CH$_2$— | piperidin-3,1-diyl | —O— | 4-pyridyl |
| 1179 | —CH$_2$— | piperidin-3,1-diyl | CH$_2$CH$_2$ | N-morpholinyl |
| 1180 | —CH$_2$— | piperidin-3,1-diyl | CH$_2$CH$_2$ | N-piperidinyl |
| 1181 | —CH$_2$— | piperidin-3,1-diyl | —O— | 3-Me-2-pyridyl |
| 1182 | —CH$_2$— | piperidin-3,1-diyl | —O— | 4-Me-2-pyridyl |
| 1183 | —CH$_2$— | piperidin-3,1-diyl | CH$_2$CH$_2$ | 1-indolyl |
| 1184 | —CH$_2$— | piperidin-3,1-diyl | —O— | 2-benzothienyl |
| 1185 | —CH$_2$— | piperidin-3,1-diyl | —O— | 2-benzofuranyl |
| 1186 | —CH$_2$— | piperidin-3,1-diyl | CH$_2$CH$_2$ | 1-benzimidazole |
| 1187 | —CH$_2$— | piperidin-3,1-diyl | —O— | 2-naphthyl |
| 1188 | —CH$_2$— | cyclohex-1,3-diyl | —O— | phenyl |
| 1189 | —CH$_2$— | cyclohex-1,3-diyl | —O— | 3,3-diphenylmethyl |
| 1190 | —CH$_2$— | cyclohex-1,3-diyl | —O— | 2-F-phenyl |
| 1191 | —CH$_2$— | cyclohex-1,3-diyl | —O— | 3-F-phenyl |
| 1192 | —CH$_2$— | cyclohex-1,3-diyl | —O— | 4-F-phenyl |
| 1193 | —CH$_2$— | cyclohex-1,3-diyl | —O— | 2-Cl-phenyl |
| 1194 | —CH$_2$— | cyclohex-1,3-diyl | —O— | 3-Cl-phenyl |
| 1195 | —CH$_2$— | cyclohex-1,3-diyl | —O— | 4-Cl-phenyl |
| 1196 | —CH$_2$— | cyclohex-1,3-diyl | —O— | 2-Me-phenyl |
| 1197 | —CH$_2$— | cyclohex-1,3-diyl | —O— | 3-Me-phenyl |
| 1198 | —CH$_2$— | cyclohex-1,3-diyl | —O— | 4-Me-phenyl |
| 1199 | —CH$_2$— | cyclohex-1,3-diyl | —O— | 2-MeO-phenyl |
| 1200 | —CH$_2$— | cyclohex-1,3-diyl | —O— | 3-MeO-phenyl |
| 1201 | —CH$_2$— | cyclohex-1,3-diyl | —O— | 4-MeO-phenyl |
| 1202 | —CH$_2$— | cyclohex-1,3-diyl | —O— | 2-MeS-phenyl |
| 1203 | —CH$_2$— | cyclohex-1,3-diyl | —O— | 3-MeS-phenyl |
| 1204 | —CH$_2$— | cyclohex-1,3-diyl | —O— | 4-MeS-phenyl |
| 1205 | —CH$_2$— | cyclohex-1,3-diyl | —O— | 2-F$_3$C-phenyl |
| 1206 | —CH$_2$— | cyclohex-1,3-diyl | —O— | 3-F$_3$C-phenyl |
| 1207 | —CH$_2$— | cyclohex-1,3-diyl | —O— | 4-F$_3$C-phenyl |
| 1208 | —CH$_2$— | cyclohex-1,3-diyl | —O— | 2,3-diF-phenyl |
| 1209 | —CH$_2$— | cyclohex-1,3-diyl | —O— | 2,4-diF-phenyl |
| 1210 | —CH$_2$— | cyclohex-1,3-diyl | —O— | 2,5-diF-phenyl |
| 1211 | —CH$_2$— | cyclohex-1,3-diyl | —O— | 2,6-diF-phenyl |
| 1212 | —CH$_2$— | cyclohex-1,3-diyl | —O— | 3,4-diF-phenyl |
| 1213 | —CH$_2$— | cyclohex-1,3-diyl | —O— | 3,5-diF-phenyl |
| 1214 | —CH$_2$— | cyclohex-1,3-diyl | —O— | 2,3-diCl-phenyl |
| 1215 | —CH$_2$— | cyclohex-1,3-diyl | —O— | 2,4-diCl-phenyl |
| 1216 | —CH$_2$— | cyclohex-1,3-diyl | —O— | 2,5-diCl-phenyl |
| 1217 | —CH$_2$— | cyclohex-1,3-diyl | —O— | 2,6-diCl-phenyl |
| 1218 | —CH$_2$— | cyclohex-1,3-diyl | —O— | 3,4-diCl-phenyl |
| 1219 | —CH$_2$— | cyclohex-1,3-diyl | —O— | 3,5-diCl-phenyl |
| 1220 | —CH$_2$— | cyclohex-1,3-diyl | —O— | 2-Cl-3-F-phenyl |
| 1221 | —CH$_2$— | cyclohex-1,3-diyl | —O— | 2-Cl-4-F-phenyl |
| 1222 | —CH$_2$— | cyclohex-1,3-diyl | —O— | 2-Cl-5-F-phenyl |
| 1223 | —CH$_2$— | cyclohex-1,3-diyl | —O— | 3-Cl-4-F-phenyl |
| 1224 | —CH$_2$— | cyclohex-1,3-diyl | —O— | 3-Cl-5-F-phenyl |
| 1225 | —CH$_2$— | cyclohex-1,3-diyl | —O— | 4-Cl-2-F-phenyl |

TABLE 2-continued

| | | | | |
|---|---|---|---|---|
| 1226 | —CH$_2$— | cyclohex-1,3-diyl | —O— | 4-Cl-3-F-phenyl |
| 1227 | —CH$_2$— | cyclohex-1,3-diyl | —O— | 2,3-diMeO-phenyl |
| 1228 | —CH$_2$— | cyclohex-1,3-diyl | —O— | 2,4-diMeO-phenyl |
| 1229 | —CH$_2$— | cyclohex-1,3-diyl | —O— | 2,5-diMeO-phenyl |
| 1230 | —CH$_2$— | cyclohex-1,3-diyl | —O— | 2,6-diMeO-phenyl |
| 1231 | —CH$_2$— | cyclohex-1,3-diyl | —O— | 3,4-diMeO-phenyl |
| 1232 | —CH$_2$— | cyclohex-1,3-diyl | —O— | 3,5-diMeO-phenyl |
| 1233 | —CH$_2$— | cyclohex-1,3-diyl | —O— | Cyclopropyl |
| 1234 | —CH$_2$— | cyclohex-1,3-diyl | —O— | Cyclobutyl |
| 1235 | —CH$_2$— | cyclohex-1,3-diyl | —O— | Cyclopentyl |
| 1236 | —CH$_2$— | cyclohex-1,3-diyl | —O— | Cyclohexyl |
| 1237 | —CH$_2$— | cyclohex-1,3-diyl | —O— | 2-furanyl |
| 1238 | —CH$_2$— | cyclohex-1,3-diyl | —O— | 2-thienyl |
| 1239 | —CH$_2$— | cyclohex-1,3-diyl | CH$_2$CH$_2$ | 2-imidazolyl |
| 1240 | —CH$_2$— | cyclohex-1,3-diyl | —O— | 2-pyridyl |
| 1241 | —CH$_2$— | cyclohex-1,3-diyl | —O— | 3-pyridyl |
| 1242 | —CH$_2$— | cyclohex-1,3-diyl | —O— | 4-pyridyl |
| 1243 | —CH$_2$— | cyclohex-1,3-diyl | CH$_2$CH$_2$ | N-morpholinyl |
| 1244 | —CH$_2$— | cyclohex-1,3-diyl | CH$_2$CH$_2$ | N-piperidinyl |
| 1245 | —CH$_2$— | cyclohex-1,3-diyl | —O— | 3-Me-2-pyridyl |
| 1246 | —CH$_2$— | cyclohex-1,3-diyl | —O— | 4-Me-2-pyridyl |
| 1247 | —CH$_2$— | cyclohex-1,3-diyl | CH$_2$CH$_2$ | 1-indolyl |
| 1248 | —CH$_2$— | cyclohex-1,3-diyl | —O— | 2-benzothienyl |
| 1249 | —CH$_2$— | cyclohex-1,3-diyl | —O— | 2-benzofuranyl |
| 1250 | —CH$_2$— | cyclohex-1,3-diyl | CH$_2$CH$_2$ | i-benzimidazole |
| 1251 | —CH$_2$— | cyclohex-1,3-diyl | —O— | 2-naphthyl |
| 1252 | —CH$_2$— | cyclopropan-1,2-diyl | —O— | phenyl |
| 1253 | —CH$_2$— | cyclopropan-1,2-diyl | —O— | 3,3-diphenylmethyl |
| 1254 | —CH$_2$— | cyclopropan-1,2-diyl | —O— | 2-F-phenyl |
| 1255 | —CH$_2$— | cyclopropan-1,2-diyl | —O— | 3-F-phenyl |
| 1256 | —CH$_2$— | cyclopropan-1,2-diyl | —O— | 4-F-phenyl |
| 1257 | —CH$_2$— | cyclopropan-1,2-diyl | —O— | 2-Cl-phenyl |
| 1258 | —CH$_2$— | cyclopropan-1,2-diyl | —O— | 3-Cl-phenyl |
| 1259 | —CH$_2$— | cyclopropan-1,2-diyl | —O— | 4-Cl-phenyl |
| 1260 | —CH$_2$— | cyclopropan-1,2-diyl | —O— | 2-Me-phenyl |
| 1261 | —CH$_2$— | cyclopropan-1,2-diyl | —O— | 3-Me-phenyl |
| 1262 | —CH$_2$— | cyclopropan-1,2-diyl | —O— | 4-Me-phenyl |
| 1263 | —CH$_2$— | cyclopropan-1,2-diyl | —O— | 2-MeO-phenyl |
| 1264 | —CH$_2$— | cyclopropan-1,2-diyl | —O— | 3-MeO-phenyl |
| 1265 | —CH$_2$— | cyclopropan-1,2-diyl | —O— | 4-MeO-phenyl |
| 1266 | —CH$_2$— | cyclopropan-1,2-diyl | —O— | 2-MeS-phenyl |
| 1267 | —CH$_2$— | cyclopropan-1,2-diyl | —O— | 3-MeS-phenyl |
| 1268 | —CH$_2$— | cyclopropan-1,2-diyl | —O— | 4-MeS-phenyl |
| 1269 | —CH$_2$— | cyclopropan-1,2-diyl | —O— | 2-F$_3$C-phenyl |
| 1270 | —CH$_2$— | cyclopropan-1,2-diyl | —O— | 3-F$_3$C-phenyl |
| 1271 | —CH$_2$— | cyclopropan-1,2-diyl | —O— | 4-F$_3$C-phenyl |
| 1272 | —CH$_2$— | cyclopropan-1,2-diyl | —O— | 2,3-diF-phenyl |
| 1273 | —CH$_2$— | cyclopropan-1,2-diyl | —O— | 2,4-diF-phenyl |
| 1274 | —CH$_2$— | cyclopropan-1,2-diyl | —O— | 2,5-diF-phenyl |
| 1275 | —CH$_2$— | cyclopropan-1,2-diyl | —O— | 2,6-diF-phenyl |
| 1276 | —CH$_2$— | cyclopropan-1,2-diyl | —O— | 3,4-diF-phenyl |
| 1277 | —CH$_2$— | cyclopropan-1,2-diyl | —O— | 3,5-diF-phenyl |

TABLE 2-continued

| | | | | |
|---|---|---|---|---|
| 1278 | —CH$_2$— | cyclopropan-1,2-diyl | —O— | 2,3-diCl-phenyl |
| 1279 | —CH$_2$— | cyclopropan-1,2-diyl | —O— | 2,4-diCl-phenyl |
| 1280 | —CH$_2$— | cyclopropan-1,2-diyl | —O— | 2,5-diCl-phenyl |
| 1281 | —CH$_2$— | cyclopropan-1,2-diyl | —O— | 2,6-diCl-phenyl |
| 1282 | —CH$_2$— | cyclopropan-1,2-diyl | —O— | 3,4-diCl-phenyl |
| 1283 | —CH$_2$— | cyclopropan-1,2-diyl | —O— | 3,5-diCl-phenyl |
| 1284 | —CH$_2$— | cyclopropan-1,2-diyl | —O— | 2-Cl-3-F-phenyl |
| 1285 | —CH$_2$— | cyclopropan-1,2-diyl | —O— | 2-Cl-4-F-phenyl |
| 1286 | —CH$_2$— | cyclopropan-1,2-diyl | —O— | 2-Cl-5-F-phenyl |
| 1287 | —CH$_2$— | cyclopropan-1,2-diyl | —O— | 3-Cl-4-F-phenyl |
| 1288 | —CH$_2$— | cyclopropan-1,2-diyl | —O— | 3-Cl-5-F-phenyl |
| 1289 | —CH$_2$— | cyclopropan-1,2-diyl | —O— | 4-Cl-2-F-phenyl |
| 1290 | —CH$_2$— | cyclopropan-1,2-diyl | —O— | 4-Cl-3-F-phenyl |
| 1291 | —CH$_2$— | cyclopropan-1,2-diyl | —O— | 2,3-diMeO-phenyl |
| 1292 | —CH$_2$— | cyclopropan-1,2-diyl | —O— | 2,4-diMeO-phenyl |
| 1293 | —CH$_2$— | cyclopropan-1,2-diyl | —O— | 2,5-diMeO-phenyl |
| 1294 | —CH$_2$— | cyclopropan-1,2-diyl | —O— | 2,6-diMeO-phenyl |
| 1295 | —CH$_2$— | cyclopropan-1,2-diyl | —O— | 3,4-diMeO-phenyl |
| 1296 | —CH$_2$— | cyclopropan-1,2-diyl | —O— | 3,5-diMeO-phenyl |
| 1297 | —CH$_2$— | cyclopropan-1,2-diyl | —O— | Cyclopropyl |
| 1298 | —CH$_2$— | cyclopropan-1,2-diyl | —O— | Cyclobutyl |
| 1299 | —CH$_2$— | cyclopropan-1,2-diyl | —O— | Cyclopentyl |
| 1300 | —CH$_2$— | cyclopropan-1,2-diyl | —O— | Cyclohexyl |
| 1301 | —CH$_2$— | cyclopropan-1,2-diyl | —O— | 2-furanyl |
| 1302 | —CH$_2$— | cyclopropan-1,2-diyl | —O— | 2-thienyl |
| 1303 | —CH$_2$— | cyclopropan-1,2-diyl | CH$_2$CH$_2$ | 2-imidazolyl |
| 1304 | —CH$_2$— | cyclopropan-1,2-diyl | —O— | 2-pyridyl |
| 1305 | —CH$_2$— | cyclopropan-1,2-diyl | —O— | 3-pyridyl |
| 1306 | —CH$_2$— | cyclopropan-1,2-diyl | —O— | 4-pyridyl |
| 1307 | —CH$_2$— | cyclopropan-1,2-diyl | CH$_2$CH$_2$ | N-morpholinyl |
| 1308 | —CH$_2$— | cyclopropan-1,2-diyl | CH$_2$CH$_2$ | N-piperidinyl |
| 1309 | —CH$_2$— | cyclopropan-1,2-diyl | —O— | 3-Me-2-pyridyl |
| 1310 | —CH$_2$— | cyclopropan-1,2-diyl | —O— | 4-Me-2-pyridyl |
| 1311 | —CH$_2$— | cyclopropan-1,2-diyl | CH$_2$CH$_2$ | 1-indolyl |
| 1312 | —CH$_2$— | cyclopropan-1,2-diyl | —O— | 2-benzothienyl |
| 1313 | —CH$_2$— | cyclopropan-1,2-diyl | —O— | 2-benzofuranyl |
| 1314 | —CH$_2$— | cyclopropan-1,2-diyl | CH$_2$CH$_2$ | 1-benzimidazole |
| 1315 | —CH$_2$— | cyclopropan-1,2-diyl | —O— | 2-naphthyl |
| 1316 | —CH$_2$— | cyclopentan-1,3-diyl | —O— | phenyl |

TABLE 2-continued

| | | | | |
|---|---|---|---|---|
| 1317 | —CH$_2$— | cyclopentan-1,3-diyl | —O— | 3,3-diphenylmethyl |
| 1318 | —CH$_2$— | cyclopentan-1,3-diyl | —O— | 2-F-phenyl |
| 1319 | —CH$_2$— | cyclopentan-1,3-diyl | —O— | 3-F-phenyl |
| 1320 | —CH$_2$— | cyclopentan-1,3-diyl | —O— | 4-F-phenyl |
| 1321 | —CH$_2$— | cyclopentan-1,3-diyl | —O— | 2-Cl-phenyl |
| 1322 | —CH$_2$— | cyclopentan-1,3-diyl | —O— | 3-Cl-phenyl |
| 1323 | —CH$_2$— | cyclopentan-1,3-diyl | —O— | 4-Cl-phenyl |
| 1324 | —CH$_2$— | cyclopentan-1,3-diyl | —O— | 2-Me-phenyl |
| 1325 | —CH$_2$— | cyclopentan-1,3-diyl | —O— | 3-Me-phenyl |
| 1326 | —CH$_2$— | cyclopentan-1,3-diyl | —O— | 4-Me-phenyl |
| 1327 | —CH$_2$— | cyclopentan-1,3-diyl | —O— | 2-MeO-phenyl |
| 1328 | —CH$_2$— | cyclopentan-1,3-diyl | —O— | 3-MeO-phenyl |
| 1329 | —CH$_2$— | cyclopentan-1,3-diyl | —O— | 4-MeO-phenyl |
| 1330 | —CH$_2$— | cyclopentan-1,3-diyl | —O— | 2-MeS-phenyl |
| 1331 | —CH$_2$— | cyclopentan-1,3-diyl | —O— | 3-MeS-phenyl |
| 1332 | —CH$_2$— | cyclopentan-1,3-diyl | —O— | 4-MeS-phenyl |
| 1333 | —CH$_2$— | cyclopentan-1,3-diyl | —O— | 2-F$_3$C-phenyl |
| 1334 | —CH$_2$— | cyclopentan-1,3-diyl | —O— | 3-F$_3$C-phenyl |
| 1335 | —CH$_2$— | cyclopentan-1,3-diyl | —O— | 4-F$_3$C-phenyl |
| 1336 | —CH$_2$— | cyclopentan-1,3-diyl | —O— | 2,3-diF-phenyl |
| 1337 | —CH$_2$— | cyclopentan-1,3-diyl | —O— | 2,4-diF-phenyl |
| 1338 | —CH$_2$— | cyclopentan-1,3-diyl | —O— | 2,5-diF-phenyl |
| 1339 | —CH$_2$— | cyclopentan-1,3-diyl | —O— | 2,6-diF-phenyl |
| 1340 | —CH$_2$— | cyclopentan-1,3-diyl | —O— | 3,4-diF-phenyl |
| 1341 | —CH$_2$— | cyclopentan-1,3-diyl | —O— | 3,5-diF-phenyl |
| 1342 | —CH$_2$— | cyclopentan-1,3-diyl | —O— | 2,3-diCl-phenyl |
| 1343 | —CH$_2$— | cyclopentan-1,3-diyl | —O— | 2,4-diCl-phenyl |
| 1344 | —CH$_2$— | cyclopentan-1,3-diyl | —O— | 2,5-diCl-phenyl |
| 1345 | —CH$_2$— | cyclopentan-1,3-diyl | —O— | 2,6-diCl-phenyl |
| 1346 | —CH$_2$— | cyclopentan-1,3-diyl | —O— | 3,4-diCl-phenyl |
| 1347 | —CH$_2$— | cyclopentan-1,3-diyl | —O— | 3,5-diCl-phenyl |
| 1348 | —CH$_2$— | cyclopentan-1,3-diyl | —O— | 2-Cl-3-F-phenyl |
| 1349 | —CH$_2$— | cyclopentan-1,3-diyl | —O— | 2-Cl-4-F-phenyl |
| 1350 | —CH$_2$— | cyclopentan-1,3-diyl | —O— | 2-Cl-5-F-phenyl |
| 1351 | —CH$_2$— | cyclopentan-1,3-diyl | —O— | 3-Cl-4-F-phenyl |
| 1352 | —CH$_2$— | cyclopentan-1,3-diyl | —O— | 3-Cl-5-F-phenyl |
| 1353 | —CH$_2$— | cyclopentan-1,3-diyl | —O— | 4-Cl-2-F-phenyl |
| 1354 | —CH$_2$— | cyclopentan-1,3-diyl | —O— | 4-Cl-3-F-phenyl |
| 1355 | —CH$_2$— | cyclopentan-1,3-diyl | —O— | 2,3-diMeO-phenyl |

TABLE 2-continued

| | | | | |
|---|---|---|---|---|
| 1356 | —CH$_2$— | cyclopentan-1,3-diyl | —O— | 2,4-diMeO-phenyl |
| 1357 | —CH$_2$— | cyclopentan-1,3-diyl | —O— | 2,5-diMeO-phenyl |
| 1358 | —CH$_2$— | cyclopentan-1,3-diyl | —O— | 2,6-diMeO-phenyl |
| 1359 | —CH$_2$— | cyclopentan-1,3-diyl | —O— | 3,4-diMeO-phenyl |
| 1360 | —CH$_2$— | cyclopentan-1,3-diyl | —O— | 3,5-diMeO-phenyl |
| 1361 | —CH$_2$— | cyclopentan-1,3-diyl | —O— | Cyclopropyl |
| 1362 | —CH$_2$— | cyclopentan-1,3-diyl | —O— | Cyclobutyl |
| 1363 | —CH$_2$— | cyclopentan-1,3-diyl | —O— | Cyclopentyl |
| 1364 | —CH$_2$— | cyclopentan-1,3-diyl | —O— | Cyclohexyl |
| 1365 | —CH$_2$— | cyclopentan-1,3-diyl | —O— | 2-furanyl |
| 1366 | —CH$_2$— | cyclopentan-1,3-diyl | —O— | 2-thienyl |
| 1367 | —CH$_2$— | cyclopentan-1,3-diyl | CH$_2$CH$_2$ | 2-imidazolyl |
| 1368 | —CH$_2$— | cyclopentan-1,3-diyl | —O— | 2-pyridyl |
| 1369 | —CH$_2$— | cyclopentan-1,3-diyl | —O— | 3-pyridyl |
| 1370 | —CH$_2$— | cyclopentan-1,3-diyl | —O— | 4-pyridyl |
| 1371 | —CH$_2$— | cyclopentan-1,3-diyl | CH$_2$CH$_2$ | N-morpholinyl |
| 1372 | —CH$_2$— | cyclopentan-1,3-diyl | CH$_2$CH$_2$ | N-piperidinyl |
| 1373 | —CH$_2$— | cyclopentan-1,3-diyl | —O— | 3-Me-2-pyridyl |
| 1374 | —CH$_2$— | cyclopentan13 diyl | —O— | 4-Me-2-pyridyl |
| 1375 | —CH$_2$— | cyclopentan-1,3-diyl | CH$_2$CH$_2$ | 1-indolyl |
| 1376 | —CH$_2$— | cyclopentan-1,3-diyl | —O— | 2-benzothienyl |
| 1377 | —CH$_2$— | cyclopentan-1,3-diyl | —O— | 2-benzofuranyl |
| 1378 | —CH$_2$— | cyclopentan-1,3-diyl | CH$_2$CH$_2$ | 1-benzimidazole |
| 1379 | —CH$_2$— | cyclopentan-1,3-diyl | —O— | 2-naphthyl |
| 1380 | —CH$_2$— | bond | bond | phenyl |
| 1381 | —CH$_2$— | bond | bond | 3,3-diphenyl |
| 1382 | —CH$_2$— | bond | bond | 2-F-phenyl |
| 1383 | —CH$_2$— | bond | bond | 3-F-phenyl |
| 1384 | —CH$_2$— | bond | bond | 4-F-phenyl |
| 1385 | —CH$_2$— | bond | bond | 2-Cl-phenyl |
| 1386 | —CH$_2$— | bond | bond | 3-Cl-phenyl |
| 1387 | —CH$_2$— | bond | bond | 4-Cl-phenyl |
| 1388 | —CH$_2$— | bond | bond | 2-Me-phenyl |
| 1389 | —CH$_2$— | bond | bond | 3-Me-phenyl |
| 1390 | —CH$_2$— | bond | bond | 4-Me-phenyl |
| 1391 | —CH$_2$— | bond | bond | 2-MeO-phenyl |
| 1392 | —CH$_2$— | bond | bond | 3-MeO-phenyl |
| 1393 | —CH$_2$— | bond | bond | 4-MeO-phenyl |
| 1394 | —CH$_2$— | bond | bond | 2-MeS-phenyl |
| 1395 | —CH$_2$— | bond | bond | 3-MeS-phenyl |
| 1396 | —CH$_2$— | bond | bond | 4-MeS-phenyl |
| 1397 | —CH$_2$— | bond | bond | 2-F$_3$C-phenyl |
| 1398 | —CH$_2$— | bond | bond | 3-F$_3$C-phenyl |
| 1399 | —CH$_2$— | bond | bond | 4-F$_3$C-phenyl |
| 1400 | —CH$_2$— | bond | bond | 2,3-diF-phenyl |
| 1401 | —CH$_2$— | bond | bond | 2,4-diF-phenyl |
| 1402 | —CH$_2$— | bond | bond | 2,5-diF-phenyl |
| 1403 | —CH$_2$— | bond | bond | 2,6-diF-phenyl |
| 1404 | —CH$_2$— | bond | bond | 3,4-diF-phenyl |
| 1405 | —CH$_2$— | bond | bond | 3,5-diF-phenyl |
| 1406 | —CH$_2$— | bond | bond | 2,3-diCl-phenyl |
| 1407 | —CH$_2$— | bond | bond | 2,4-diCl-phenyl |
| 1408 | —CH$_2$— | bond | bond | 2,5-diCl-phenyl |
| 1409 | —CH$_2$— | bond | bond | 2,6-diCl-phenyl |
| 1410 | —CH$_2$— | bond | bond | 3,4-diCl-phenyl |

TABLE 2-continued

| | | | | |
|---|---|---|---|---|
| 1411 | —CH$_2$— | bond | bond | 3,5-diCl-phenyl |
| 1412 | —CH$_2$— | bond | bond | 2-Cl-3-F-phenyl |
| 1413 | —CH$_2$— | bond | bond | 2-Cl-4-F-phenyl |
| 1414 | —CH$_2$— | bond | bond | 2-Cl-5-F-phenyl |
| 1415 | —CH$_2$— | bond | bond | 3-Cl-4-F-phenyl |
| 1416 | —CH$_2$— | bond | bond | 3-Cl-5-F-phenyl |
| 1417 | —CH$_2$— | bond | bond | 4-Cl-2-F-phenyl |
| 1418 | —CH$_2$— | bond | bond | 4-Cl-3-F-phenyl |
| 1419 | —CH$_2$— | bond | bond | 2,3-diMeO-phenyl |
| 1420 | —CH$_2$— | bond | bond | 2,4-diMeO-phenyl |
| 1421 | —CH$_2$— | bond | bond | 2,5-diMeO-phenyl |
| 1422 | —CH$_2$— | bond | bond | 2,6-diMeO-phenyl |
| 1423 | —CH$_2$— | bond | bond | 3,4-diMeO-phenyl |
| 1424 | —CH$_2$— | bond | bond | 3,5-diMeO-phenyl |
| 1425 | —CH$_2$— | bond | bond | cyclopropyl |
| 1426 | —CH$_2$— | bond | bond | cyclobutyl |
| 1427 | —CH$_2$— | bond | bond | cyclopentyl |
| 1428 | —CH$_2$— | bond | bond | cyclohexyl |
| 1429 | —CH$_2$— | bond | bond | 2-furanyl |
| 1430 | —CH$_2$— | bond | bond | 2-thienyl |
| 1431 | —CH$_2$— | bond | bond | 2-imidazolyl |
| 1432 | —CH$_2$— | bond | bond | 2-pyridyl |
| 1433 | —CH$_2$— | bond | bond | 3-pyridyl |
| 1434 | —CH$_2$— | bond | bond | 4-pyridyl |
| 1435 | —CH$_2$— | bond | bond | N-morpholinyl |
| 1436 | —CH$_2$— | bond | bond | N-piperidinyl |
| 1437 | —CH$_2$— | bond | bond | 3-Me-2-pyridyl |
| 1438 | —CH$_2$— | bond | bond | 4-Me-2-pyridyl |
| 1439 | —CH$_2$— | bond | bond | 1-indolyl |
| 1440 | —CH$_2$— | bond | bond | 2-benzothienyl |
| 1441 | —CH$_2$— | bond | bond | 2-benzofuranyl |
| 1442 | —CH$_2$— | bond | bond | 1-benzimidazole |
| 1443 | —CH$_2$— | bond | bond | 2-naphthyl |
| 1444 | —CH$_2$CH$_2$— | bond | bond | phenyl |
| 1445 | —CH$_2$CH$_2$— | bond | bond | 3,3-diphenyl |
| 1446 | —CH$_2$CH$_2$— | bond | bond | 2-F-phenyl |
| 1447 | —CH$_2$CH$_2$— | bond | bond | 3-F-phenyl |
| 1448 | —CH$_2$CH$_2$— | bond | bond | 4-F-phenyl |
| 1449 | —CH$_2$CH$_2$— | bond | bond | 2-Cl-phenyl |
| 1450 | —CH$_2$CH$_2$— | bond | bond | 3-Cl-phenyl |
| 1451 | —CH$_2$CH$_2$— | bond | bond | 4-Cl-phenyl |
| 1452 | —CH$_2$CH$_2$— | bond | bond | 2-Me-phenyl |
| 1453 | —CH$_2$CH$_2$— | bond | bond | 3-Me-phenyl |
| 1454 | —CH$_2$CH$_2$— | bond | bond | 4-Me-phenyl |
| 1455 | —CH$_2$CH$_2$— | bond | bond | 2-MeO-phenyl |
| 1456 | —CH$_2$CH$_2$— | bond | bond | 3-MeO-phenyl |
| 1457 | —CH$_2$CH$_2$— | bond | bond | 4-MeO-phenyl |
| 1458 | —CH$_2$CH$_2$— | bond | bond | 2-MeS-phenyl |
| 1459 | —CH$_2$CH$_2$— | bond | bond | 3-MeS-phenyl |
| 1460 | —CH$_2$CH$_2$— | bond | bond | 4-MeS-phenyl |
| 1461 | —CH$_2$CH$_2$— | bond | bond | 2-F$_3$C-phenyl |
| 1462 | —CH$_2$CH$_2$— | bond | bond | 3-F$_3$C-phenyl |
| 1463 | —CH$_2$CH$_2$— | bond | bond | 4-F$_3$C-phenyl |
| 1464 | —CH$_2$CH$_2$— | bond | bond | 2,3-diF-phenyl |
| 1465 | —CH$_2$CH$_2$— | bond | bond | 2,4-diF-phenyl |
| 1466 | —CH$_2$CH$_2$— | bond | bond | 2,5-diF-phenyl |
| 1467 | —CH$_2$CH$_2$— | bond | bond | 2,6-diF-phenyl |
| 1468 | —CH$_2$CH$_2$— | bond | bond | 3,4-diF-phenyl |
| 1469 | —CH$_2$CH$_2$— | bond | bond | 3,5-diF-phenyl |
| 1470 | —CH$_2$CH$_2$— | bond | bond | 2,3-diCl-phenyl |
| 1471 | —CH$_2$CH$_2$— | bond | bond | 2,4-diCl-phenyl |
| 1472 | —CH$_2$CH$_2$— | bond | bond | 2,5-diCl-phenyl |
| 1473 | —CH$_2$CH$_2$— | bond | bond | 2,6-diCl-phenyl |
| 1474 | —CH$_2$CH$_2$— | bond | bond | 3,4-diCl-phenyl |
| 1475 | —CH$_2$CH$_2$— | bond | bond | 3,5-diCl-phenyl |
| 1476 | —CH$_2$CH$_2$— | bond | bond | 2-Cl-3-F-phenyl |
| 1477 | —CH$_2$CH$_2$— | bond | bond | 2-Cl-4-F-phenyl |
| 1478 | —CH$_2$CH$_2$— | bond | bond | 2-Cl-5-F-phenyl |
| 1479 | —CH$_2$CH$_2$— | bond | bond | 3-Cl-4-F-phenyl |
| 1480 | —CH$_2$CH$_2$— | bond | bond | 3-Cl-5-F-phenyl |
| 1481 | —CH$_2$CH$_2$— | bond | bond | 4-Cl-2-F-phenyl |
| 1482 | —CH$_2$CH$_2$— | bond | bond | 4-Cl-3-F-phenyl |
| 1483 | —CH$_2$CH$_2$— | bond | bond | 2,3-diMeO-phenyl |
| 1484 | —CH$_2$CH$_2$— | bond | bond | 2,4-diMeO-phenyl |
| 1485 | —CH$_2$CH$_2$— | bond | bond | 2,5-diMeO-phenyl |
| 1486 | —CH$_2$CH$_2$— | bond | bond | 2,6-diMeO-phenyl |
| 1487 | —CH$_2$CH$_2$— | bond | bond | 3,4-diMeO-phenyl |
| 1488 | —CH$_2$CH$_2$— | bond | bond | 3,5-diMeO-phenyl |
| 1489 | —CH$_2$CH$_2$— | bond | bond | cyclopropyl |

TABLE 2-continued

| | | | | |
|---|---|---|---|---|
| 1490 | —CH$_2$CH$_2$— | bond | bond | cyclobutyl |
| 1491 | —CH$_2$CH$_2$— | bond | bond | cyclopentyl |
| 1492 | —CH$_2$CH$_2$— | bond | bond | cyclohexyl |
| 1493 | —CH$_2$CH$_2$— | bond | bond | 2-furanyl |
| 1494 | —CH$_2$CH$_2$— | bond | bond | 2-thienyl |
| 1495 | —CH$_2$CH$_2$— | bond | bond | 2-imidazolyl |
| 1496 | —CH$_2$CH$_2$— | bond | bond | 2-pyridyl |
| 1497 | —CH$_2$CH$_2$— | bond | bond | 3-pyridyl |
| 1498 | —CH$_2$CH$_2$— | bond | bond | 4-pyridyl |
| 1499 | —CH$_2$CH$_2$— | bond | bond | N-morpholinyl |
| 1500 | —CH$_2$CH$_2$— | bond | bond | N-piperidinyl |
| 1501 | —CH$_2$CH$_2$— | bond | bond | 3-Me-2-pyridyl |
| 1502 | —CH$_2$CH$_2$— | bond | bond | 4-Me-2-pyridyl |
| 1503 | —CH$_2$CH$_2$— | bond | bond | 1-indolyl |
| 1504 | —CH$_2$CH$_2$— | bond | bond | 2-benzothienyl |
| 1505 | —CH$_2$CH$_2$— | bond | bond | 2-benzofuranyl |
| 1506 | —CH$_2$CH$_2$— | bond | bond | 1-benzimidazole |
| 1507 | —CH$_2$CH$_2$— | bond | bond | 2-naphthyl |
| 1508 | —CH$_2$CH$_2$CH$_2$— | bond | bond | phenyl |
| 1509 | —CH$_2$CH$_2$CH$_2$— | bond | bond | 3,3-diphenyl |
| 1510 | —CH$_2$CH$_2$CH$_2$— | bond | bond | 2-F-phenyl |
| 1511 | —CH$_2$CH$_2$CH$_2$— | bond | bond | 3-F-phenyl |
| 1512 | —CH$_2$CH$_2$CH$_2$— | bond | bond | 4-F-phenyl |
| 1513 | —CH$_2$CH$_2$CH$_2$— | bond | bond | 2-Cl-phenyl |
| 1514 | —CH$_2$CH$_2$CH$_2$— | bond | bond | 3-Cl-phenyl |
| 1515 | —CH$_2$CH$_2$CH$_2$— | bond | bond | 4-Cl-phenyl |
| 1516 | —CH$_2$CH$_2$CH$_2$— | bond | bond | 2-Me-phenyl |
| 1517 | —CH$_2$CH$_2$CH$_2$— | bond | bond | 3-Me-phenyl |
| 1518 | —CH$_2$CH$_2$CH$_2$— | bond | bond | 4-Me-phenyl |
| 1519 | —CH$_2$CH$_2$CH$_2$— | bond | bond | 2-MeO-phenyl |
| 1520 | —CH$_2$CH$_2$CH$_2$— | bond | bond | 3-MeO-phenyl |
| 1521 | —CH$_2$CH$_2$CH$_2$— | bond | bond | 4-MeO-phenyl |
| 1522 | —CH$_2$CH$_2$CH$_2$— | bond | bond | 2-MeS-phenyl |
| 1523 | —CH$_2$CH$_2$CH$_2$— | bond | bond | 3-MeS-phenyl |
| 1524 | —CH$_2$CH$_2$CH$_2$— | bond | bond | 4-MeS-phenyl |
| 1525 | —CH$_2$CH$_2$CH$_2$— | bond | bond | 2-F$_3$C-phenyl |
| 1526 | —CH$_2$CH$_2$CH$_2$— | bond | bond | 3-F$_3$C-phenyl |
| 1527 | —CH$_2$CH$_2$CH$_2$— | bond | bond | 4-F$_3$C-phenyl |
| 1528 | —CH$_2$CH$_2$CH$_2$— | bond | bond | 2,3-diF-phenyl |
| 1529 | —CH$_2$CH$_2$CH$_2$— | bond | bond | 2,4-diF-phenyl |
| 1530 | —CH$_2$CH$_2$CH$_2$— | bond | bond | 2,5-diF-phenyl |
| 1531 | —CH$_2$CH$_2$CH$_2$— | bond | bond | 2,6-diF-phenyl |
| 1532 | —CH$_2$CH$_2$CH$_2$— | bond | bond | 3,4-diF-phenyl |
| 1533 | —CH$_2$CH$_2$CH$_2$— | bond | bond | 3,5-diF-phenyl |
| 1534 | —CH$_2$CH$_2$CH$_2$— | bond | bond | 2,3-diCl-phenyl |
| 1535 | —CH$_2$CH$_2$CH$_2$— | bond | bond | 2,4-diCl-phenyl |
| 1536 | —CH$_2$CH$_2$CH$_2$— | bond | bond | 2,5-diCl-phenyl |
| 1537 | —CH$_2$CH$_2$CH$_2$— | bond | bond | 2,6-diCl-phenyl |
| 1538 | —CH$_2$CH$_2$CH$_2$— | bond | bond | 3,4-diCl-phenyl |
| 1539 | —CH$_2$CH$_2$CH$_2$— | bond | bond | 3,5-diCl-phenyl |
| 1540 | —CH$_2$CH$_2$CH$_2$— | bond | bond | 2-Cl-3-F-phenyl |
| 1541 | —CH$_2$CH$_2$CH$_2$— | bond | bond | 2-Cl-4-F-phenyl |
| 1542 | —CH$_2$CH$_2$CH$_2$— | bond | bond | 2-Cl-5-F-phenyl |
| 1543 | —CH$_2$CH$_2$CH$_2$— | bond | bond | 3-Cl-4-F-phenyl |
| 1544 | —CH$_2$CH$_2$CH$_2$— | bond | bond | 3-Cl-5-F-phenyl |
| 1545 | —CH$_2$CH$_2$CH$_2$— | bond | bond | 4-Cl-2-F-phenyl |
| 1546 | —CH$_2$CH$_2$CH$_2$— | bond | bond | 4-Cl-3-F-phenyl |
| 1547 | —CH$_2$CH$_2$CH$_2$— | bond | bond | 2,3-diMeO-phenyl |
| 1548 | —CH$_2$CH$_2$CH$_2$— | bond | bond | 2,4-diMeO-phenyl |
| 1549 | —CH$_2$CH$_2$CH$_2$— | bond | bond | 2,5-diMeO-phenyl |
| 1550 | —CH$_2$CH$_2$CH$_2$— | bond | bond | 2,6-diMeO-phenyl |
| 1551 | —CH$_2$CH$_2$CH$_2$— | bond | bond | 3,4-diMeO-phenyl |
| 1552 | —CH$_2$CH$_2$CH$_2$— | bond | bond | 3,5-diMeO-phenyl |
| 1553 | —CH$_2$CH$_2$CH$_2$— | bond | bond | cyclopropyl |
| 1554 | —CH$_2$CH$_2$CH$_2$— | bond | bond | cyclobutyl |
| 1555 | —CH$_2$CH$_2$CH$_2$— | bond | bond | cyclopentyl |
| 1556 | —CH$_2$CH$_2$CH$_2$— | bond | bond | cyclohexyl |
| 1557 | —CH$_2$CH$_2$CH$_2$— | bond | bond | 2-furanyl |
| 1558 | —CH$_2$CH$_2$CH$_2$— | bond | bond | 2-thienyl |
| 1559 | —CH$_2$CH$_2$CH$_2$— | bond | bond | 2-imidazolyl |
| 1560 | —CH$_2$CH$_2$CH$_2$— | bond | bond | 2-pyridyl |
| 1561 | —CH$_2$CH$_2$CH$_2$— | bond | bond | 3-pyridyl |
| 1562 | —CH$_2$CH$_2$CH$_2$— | bond | bond | 4-pyridyl |
| 1563 | —CH$_2$CH$_2$CH$_2$— | bond | bond | N-morpholinyl |
| 1564 | —CH$_2$CH$_2$CH$_2$— | bond | bond | N-piperidinyl |
| 1565 | —CH$_2$CH$_2$CH$_2$— | bond | bond | 3-Me-2-pyridyl |
| 1566 | —CH$_2$CH$_2$CH$_2$— | bond | bond | 4-Me-2-pyridyl |
| 1567 | —CH$_2$CH$_2$CH$_2$— | bond | bond | 1-indolyl |
| 1568 | —CH$_2$CH$_2$CH$_2$— | bond | bond | 2-benzothienyl |

TABLE 2-continued

| | | | | |
|---|---|---|---|---|
| 1569 | —CH$_2$CH$_2$CH$_2$— | bond | bond | 2-benzofuranyl |
| 1570 | —CH$_2$CH$_2$CH$_2$— | bond | bond | 1-benzimidazole |
| 1571 | —CH$_2$CH$_2$CH$_2$— | bond | bond | 2-naphthyl |
| 1572 | —CH$_2$CH$_2$— | bond | —O— | phenyl |
| 1573 | —CH$_2$CH$_2$— | bond | —O— | 3,3-diphenylmethyl |
| 1574 | —CH$_2$CH$_2$— | bond | —O— | 2-F-phenyl |
| 1575 | —CH$_2$CH$_2$— | bond | —O— | 3-F-phenyl |
| 1576 | —CH$_2$CH$_2$— | bond | —O— | 4-F-phenyl |
| 1577 | —CH$_2$CH$_2$— | bond | —O— | 2-Cl-phenyl |
| 1578 | —CH$_2$CH$_2$— | bond | —O— | 3-Cl-phenyl |
| 1579 | —CH$_2$CH$_2$— | bond | —O— | 4-Cl-phenyl |
| 1580 | —CH$_2$CH$_2$— | bond | —O— | 2-Me-phenyl |
| 1581 | —CH$_2$CH$_2$— | bond | —O— | 3-Me-phenyl |
| 1582 | —CH$_2$CH$_2$— | bond | —O— | 4-Me-phenyl |
| 1583 | —CH$_2$CH$_2$— | bond | —O— | 2-MeO-phenyl |
| 1584 | —CH$_2$CH$_2$— | bond | —O— | 3-MeO-phenyl |
| 1585 | —CH$_2$CH$_2$— | bond | —O— | 4-MeO-phenyl |
| 1586 | —CH$_2$CH$_2$— | bond | —O— | 2-MeS-phenyl |
| 1587 | —CH$_2$CH$_2$— | bond | —O— | 3-MeS-phenyl |
| 1588 | —CH$_2$CH$_2$— | bond | —O— | 4-MeS-phenyl |
| 1589 | —CH$_2$CH$_2$— | bond | —O— | 2-F$_3$C-phenyl |
| 1590 | —CH$_2$CH$_2$— | bond | —O— | 3-F$_3$C-phenyl |
| 1591 | —CH$_2$CH$_2$— | bond | —O— | 4-F$_3$C-phenyl |
| 1592 | —CH$_2$CH$_2$— | bond | —O— | 2,3-diF-phenyl |
| 1593 | —CH$_2$CH$_2$— | bond | —O— | 2,4-diF-phenyl |
| 1594 | —CH$_2$CH$_2$— | bond | —O— | 2,5-diF-phenyl |
| 1595 | —CH$_2$CH$_2$— | bond | —O— | 2,6-diF-phenyl |
| 1596 | —CH$_2$CH$_2$— | bond | —O— | 3,4-diF-phenyl |
| 1597 | —CH$_2$CH$_2$— | bond | —O— | 3,5-diF-phenyl |
| 1598 | —CH$_2$CH$_2$— | bond | —O— | 2,3-diCl-phenyl |
| 1599 | —CH$_2$CH$_2$— | bond | —O— | 2,4-diCl-phenyl |
| 1600 | —CH$_2$CH$_2$— | bond | —O— | 2,5-diCl-phenyl |
| 1601 | —CH$_2$CH$_2$— | bond | —O— | 2,6-diCl-phenyl |
| 1602 | —CH$_2$CH$_2$— | bond | —O— | 3,4-diCl-phenyl |
| 1603 | —CH$_2$CH$_2$— | bond | —O— | 3,5-diCl-phenyl |
| 1604 | —CH$_2$CH$_2$— | bond | —O— | 2-Cl-3-F-phenyl |
| 1605 | —CH$_2$CH$_2$— | bond | —O— | 2-Cl-4-F-phenyl |
| 1606 | —CH$_2$CH$_2$— | bond | —O— | 2-Cl-5-F-phenyl |
| 1607 | —CH$_2$CH$_2$— | bond | —O— | 3-Cl-4-F-phenyl |
| 1608 | —CH$_2$CH$_2$— | bond | —O— | 3-Cl-5-F-phenyl |
| 1609 | —CH$_2$CH$_2$— | bond | —O— | 4-Cl-2-F-phenyl |
| 1610 | —CH$_2$CH$_2$— | bond | —O— | 4-Cl-3-F-phenyl |
| 1611 | —CH$_2$CH$_2$— | bond | —O— | 2,3-diMeO-phenyl |
| 1612 | —CH$_2$CH$_2$— | bond | —O— | 2,4-diMeO-phenyl |
| 1613 | —CH$_2$CH$_2$— | bond | —O— | 2,5-diMeO-phenyl |
| 1614 | —CH$_2$CH$_2$— | bond | —O— | 2,6-diMeO-phenyl |
| 1615 | —CH$_2$CH$_2$— | bond | —O— | 3,4-diMeO-phenyl |
| 1616 | —CH$_2$CH$_2$— | bond | —O— | 3,5-diMeO-phenyl |
| 1617 | —CH$_2$CH$_2$— | bond | —O— | cyclopropyl |
| 1618 | —CH$_2$CH$_2$— | bond | —O— | cyclobutyl |
| 1619 | —CH$_2$CH$_2$— | bond | —O— | cyclopentyl |
| 1620 | —CH$_2$CH$_2$— | bond | —O— | cyclohexyl |
| 1621 | —CH$_2$CH$_2$— | bond | —O— | 2-furanyl |
| 1622 | —CH$_2$CH$_2$— | bond | —O— | 2-thienyl |
| 1623 | —CH$_2$CH$_2$— | bond | —O— | 2-pyridyl |
| 1624 | —CH$_2$CH$_2$— | bond | —O— | 3-pyridyl |
| 1625 | —CH$_2$CH$_2$— | bond | —O— | 4-pyridyl |
| 1626 | —CH$_2$CH$_2$— | bond | —O— | 3-Me-2-pyridyl |
| 1627 | —CH$_2$CH$_2$— | bond | —O— | 4-Me-2-pyridyl |
| 1628 | —CH$_2$CH$_2$— | bond | —O— | 2-benzothienyl |
| 1629 | —CH$_2$CH$_2$— | bond | —O— | 2-benzofuranyl |
| 1630 | —CH$_2$CH$_2$— | bond | —O— | 2-naphthyl |
| 1631 | —CH$_2$CH$_2$CH$_2$— | bond | —O— | phenyl |
| 1632 | —CH$_2$CH$_2$CH$_2$— | bond | —O— | 3,3-diphenylmethyl |
| 1633 | —CH$_2$CH$_2$CH$_2$— | bond | —O— | 2-F-phenyl |
| 1634 | —CH$_2$CH$_2$CH$_2$— | bond | —O— | 3-F-phenyl |
| 1635 | —CH$_2$CH$_2$CH$_2$— | bond | —O— | 4-F-phenyl |
| 1636 | —CH$_2$CH$_2$CH$_2$— | bond | —O— | 2-Cl-phenyl |
| 1637 | —CH$_2$CH$_2$CH$_2$— | bond | —O— | 3-Cl-phenyl |
| 1638 | —CH$_2$CH$_2$CH$_2$— | bond | —O— | 4-Cl-phenyl |
| 1639 | —CH$_2$CH$_2$CH$_2$— | bond | —O— | 2-Me-phenyl |
| 1640 | —CH$_2$CH$_2$CH$_2$— | bond | —O— | 3-Me-phenyl |
| 1641 | —CH$_2$CH$_2$CH$_2$— | bond | —O— | 4-Me-phenyl |
| 1642 | —CH$_2$CH$_2$CH$_2$— | bond | —O— | 2-MeO-phenyl |
| 1643 | —CH$_2$CH$_2$CH$_2$— | bond | —O— | 3-MeO-phenyl |
| 1644 | —CH$_2$CH$_2$CH$_2$— | bond | —O— | 4-MeO-phenyl |
| 1645 | —CH$_2$CH$_2$CH$_2$— | bond | —O— | 2-MeS-phenyl |

TABLE 2-continued

| | | | | |
|---|---|---|---|---|
| 1646 | —CH₂CH₂CH₂— | bond | —O— | 3-MeS-phenyl |
| 1647 | —CH₂CH₂CH₂— | bond | —O— | 4-MeS-phenyl |
| 1648 | —CH₂CH₂CH₂— | bond | —O— | 2-F₃C-phenyl |
| 1649 | —CH₂CH₂CH₂— | bond | —O— | 3-F₃C-phenyl |
| 1650 | —CH₂CH₂CH₂— | bond | —O— | 4-F₃C-phenyl |
| 1651 | —CH₂CH₂CH₂— | bond | —O— | 2,3-diF-phenyl |
| 1652 | —CH₂CH₂CH₂— | bond | —O— | 2,4-diF-phenyl |
| 1653 | —CH₂CH₂CH₂— | bond | —O— | 2,5-diF-phenyl |
| 1654 | —CH₂CH₂CH₂— | bond | —O— | 2,6-diF-phenyl |
| 1655 | —CH₂CH₂CH₂— | bond | —O— | 3,4-diF-phenyl |
| 1656 | —CH₂CH₂CH₂— | bond | —O— | 3,5-diF-phenyl |
| 1657 | —CH₂CH₂CH₂— | bond | —O— | 2,3-diCl-phenyl |
| 1658 | —CH₂CH₂CH₂— | bond | —O— | 2,4-diCl-phenyl |
| 1659 | —CH₂CH₂CH₂— | bond | —O— | 2,5-diCl-phenyl |
| 1660 | —CH₂CH₂CH₂— | bond | —O— | 2,6-diCl-phenyl |
| 1661 | —CH₂CH₂CH₂— | bond | —O— | 3,4-diCl-phenyl |
| 1662 | —CH₂CH₂CH₂— | bond | —O— | 3,5-diCl-phenyl |
| 1663 | —CH₂CH₂CH₂— | bond | —O— | 2-Cl-3-F-phenyl |
| 1664 | —CH₂CH₂CH₂— | bond | —O— | 2-Cl-4-F-phenyl |
| 1665 | —CH₂CH₂CH₂— | bond | —O— | 2-Cl-5-F-phenyl |
| 1666 | —CH₂CH₂CH₂— | bond | —O— | 3-Cl-4-F-phenyl |
| 1667 | —CH₂CH₂CH₂— | bond | —O— | 3-Cl-5-F-phenyl |
| 1668 | —CH₂CH₂CH₂— | bond | —O— | 4-Cl-2-F-phenyl |
| 1669 | —CH₂CH₂CH₂— | bond | —O— | 4-Cl-3-F-phenyl |
| 1670 | —CH₂CH₂CH₂— | bond | —O— | 2,3-diMeO-phenyl |
| 1671 | —CH₂CH₂CH₂— | bond | —O— | 2,4-diMeO-phenyl |
| 1672 | —CH₂CH₂CH₂— | bond | —O— | 2,5-diMeO-phenyl |
| 1673 | —CH₂CH₂CH₂— | bond | —O— | 2,6-diMeO-phenyl |
| 1674 | —CH₂CH₂CH₂— | bond | —O— | 3,4-diMeO-phenyl |
| 1675 | —CH₂CH₂CH₂— | bond | —O— | 3,5-diMeO-phenyl |
| 1676 | —CH₂CH₂CH₂— | bond | —O— | cyclopropyl |
| 1677 | —CH₂CH₂CH₂— | bond | —O— | cyclobutyl |
| 1678 | —CH₂CH₂CH₂— | bond | —O— | cyclopentyl |
| 1679 | —CH₂CH₂CH₂— | bond | —O— | cyclohexyl |
| 1680 | —CH₂CH₂CH₂— | bond | —O— | 2-furanyl |
| 1681 | —CH₂CH₂CH₂— | bond | —O— | 2-thienyl |
| 1682 | —CH₂CH₂CH₂— | bond | —O— | 2-pyridyl |
| 1683 | —CH₂CH₂CH₂— | bond | —O— | 3-pyridyl |
| 1684 | —CH₂CH₂CH₂— | bond | —O— | 4-pyridyl |
| 1685 | —CH₂CH₂CH₂— | bond | —O— | 3-Me-2-pyridyl |
| 1686 | —CH₂CH₂CH₂— | bond | —O— | 4-Me-2-pyridyl |
| 1687 | —CH₂CH₂CH₂— | bond | —O— | 2-benzothienyl |
| 1688 | —CH₂CH₂CH₂— | bond | —O— | 2-benzofuranyl |
| 1689 | —CH₂CH₂CH₂— | bond | —O— | 2-naphthyl | wherein R³ and R⁵ are:

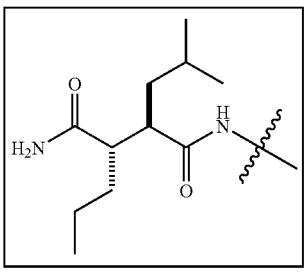

a

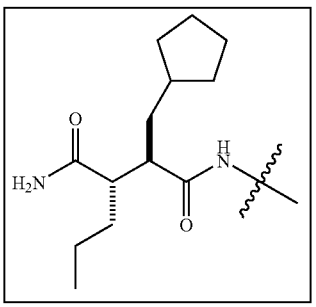

b

TABLE 2-continued
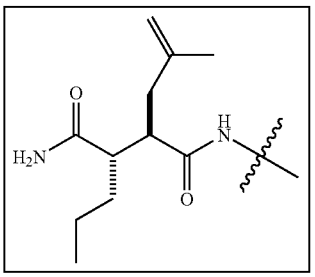
c
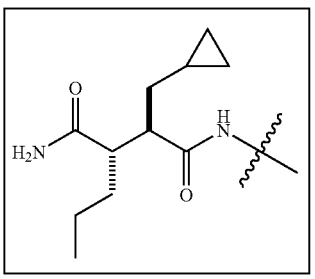
d
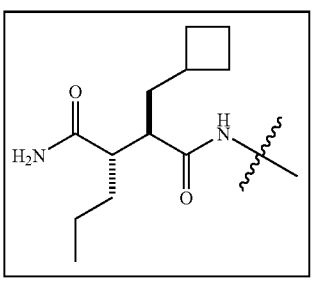
e
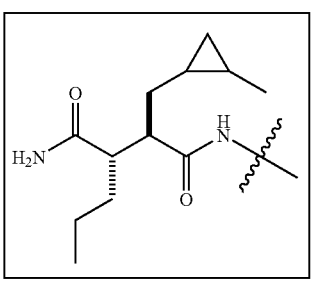
f
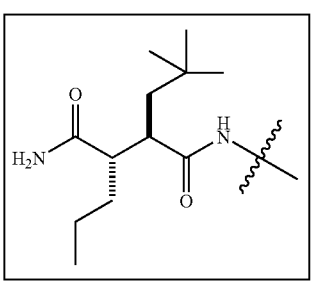
g TABLE 2-continued
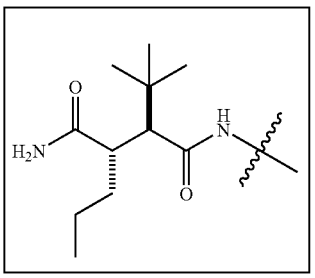
h
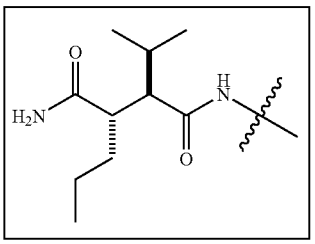
i
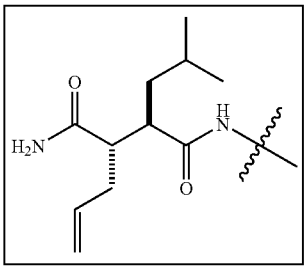
j
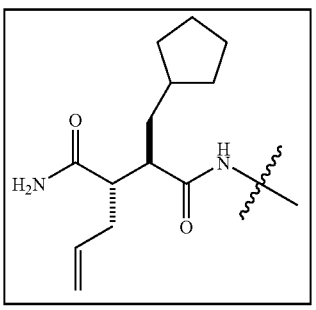
k
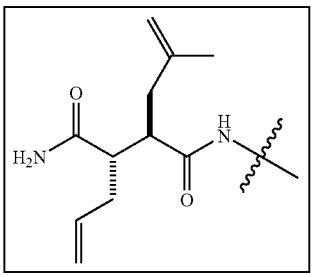
l TABLE 2-continued
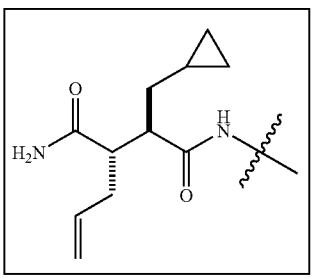
m
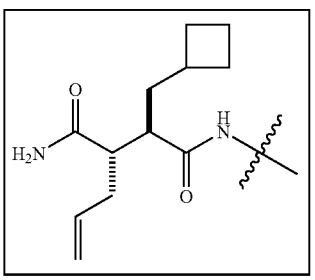
n
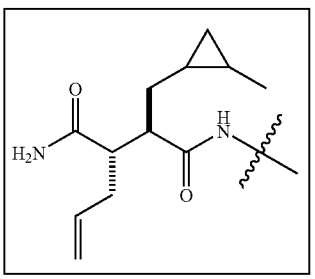
o
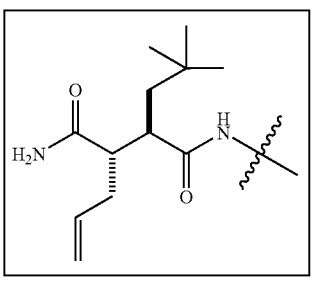
p
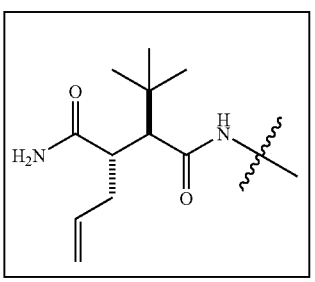
q TABLE 2-continued
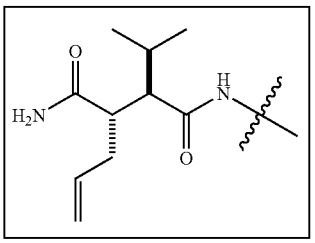
r
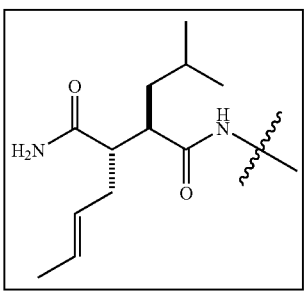
s
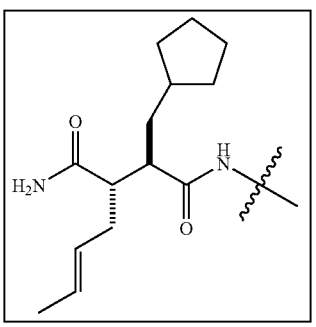
t
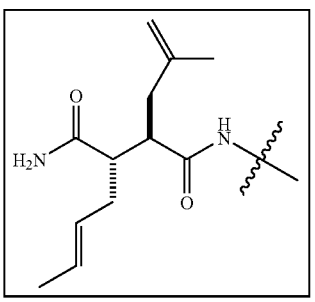
u
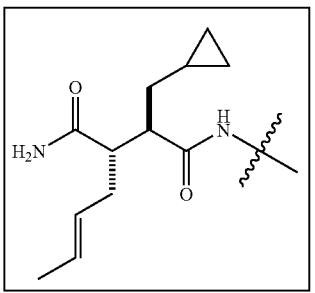
v TABLE 2-continued
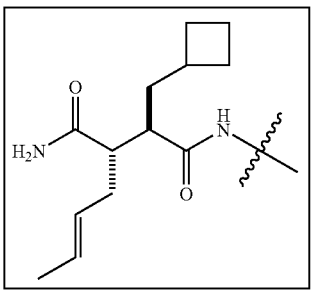
w
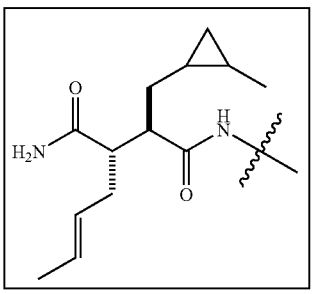
x
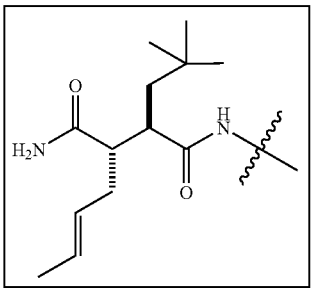
y
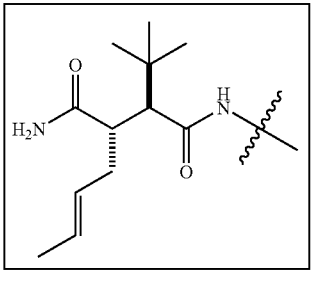
z
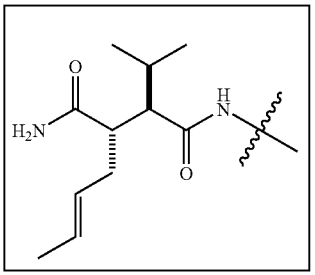
aa TABLE 2-continued
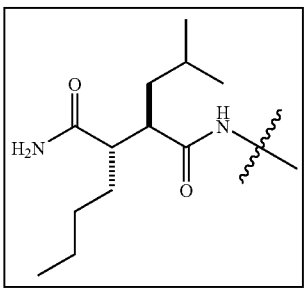
ab
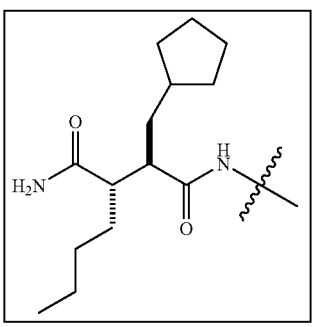
ac
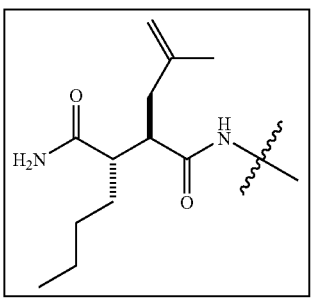
ad
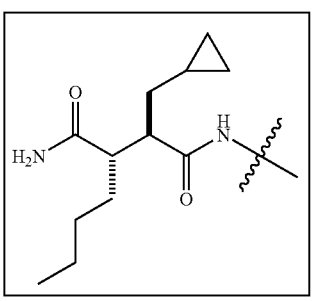
ae
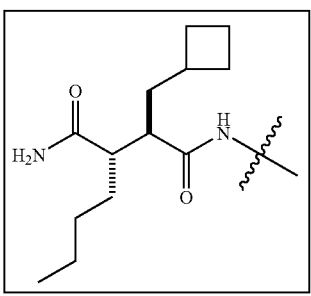
af TABLE 2-continued
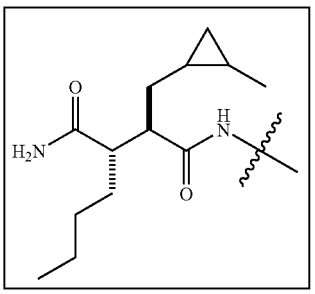
ag
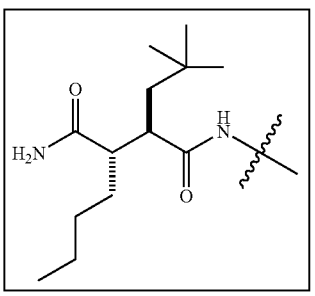
ah
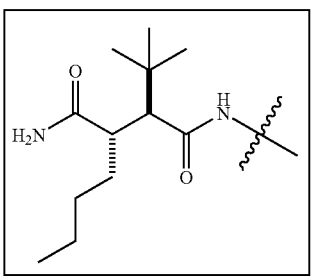
ai
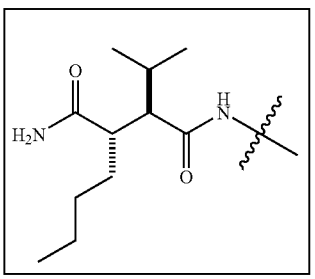
aj
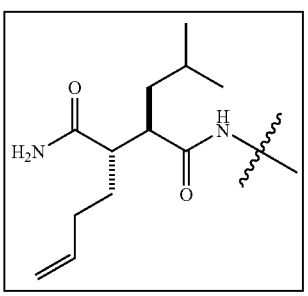
ak TABLE 2-continued
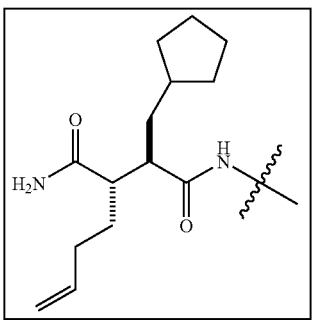
al
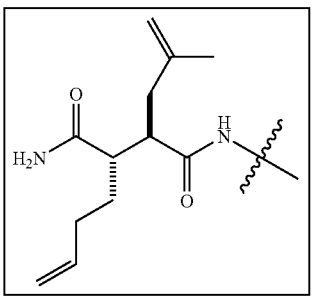
am
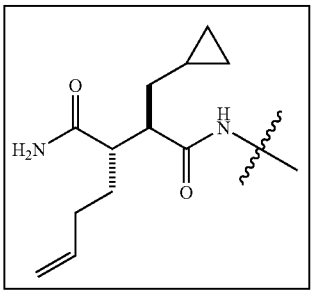
an
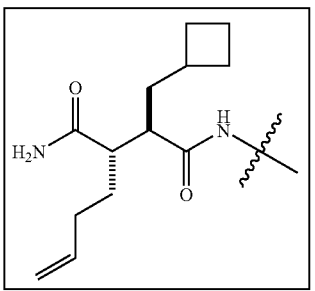
ao
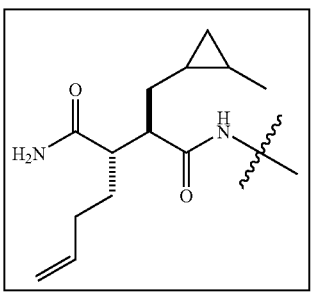
ap TABLE 2-continued
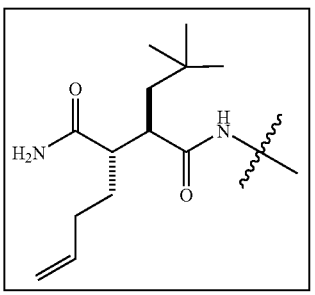
aq
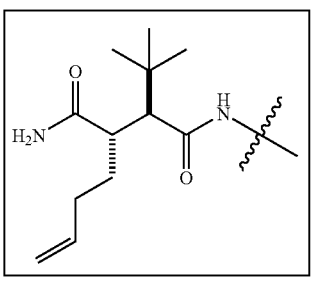
ar
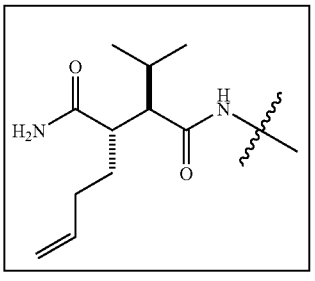
as
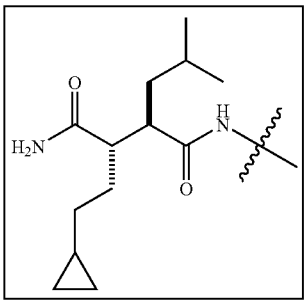
at
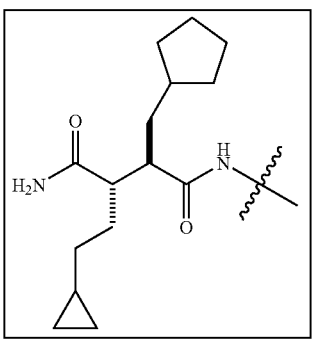
au TABLE 2-continued
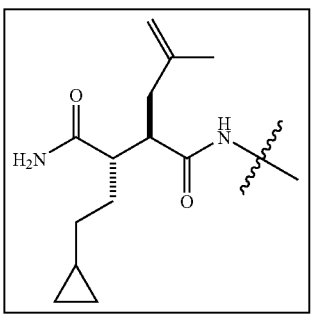
av
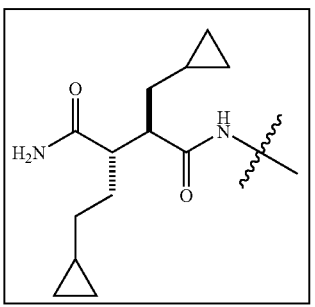
aw
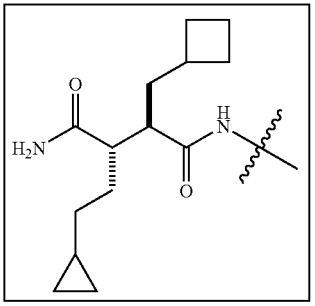
ax
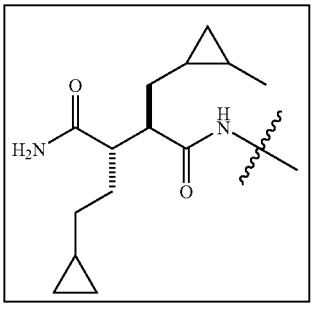
ay
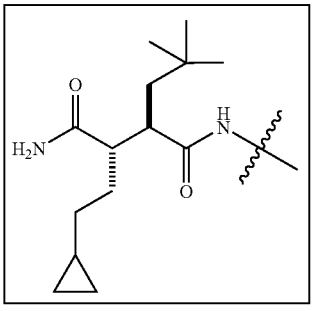
az TABLE 2-continued
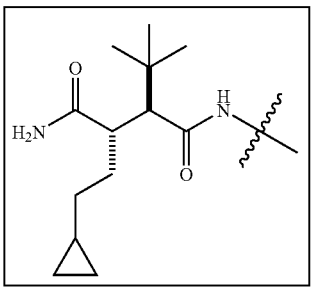
ba
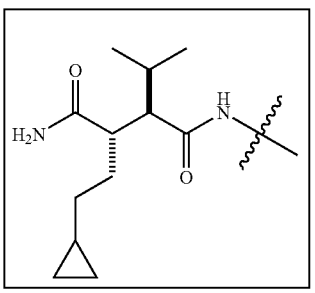
bb
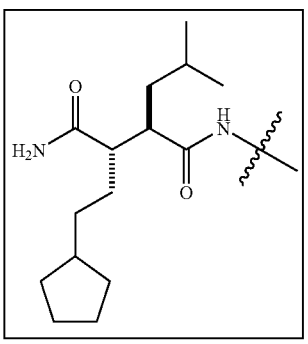
bc
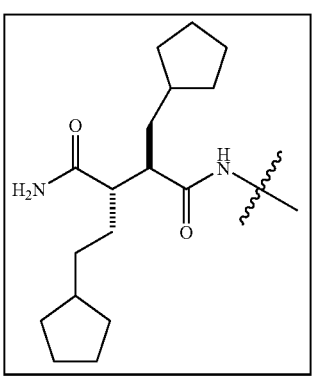
bd TABLE 2-continued
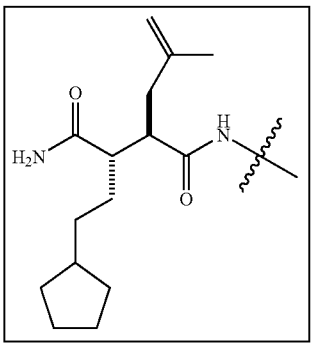
be
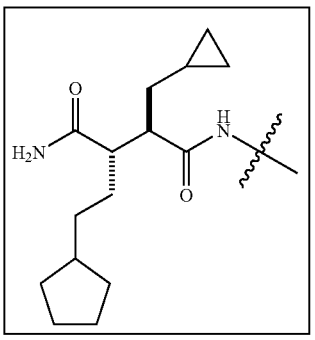
bf
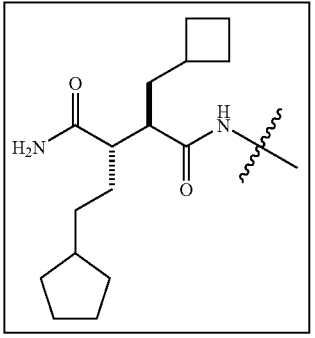
bg
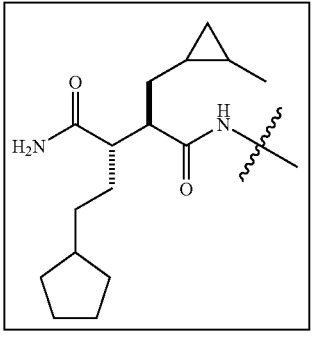
bh TABLE 2-continued
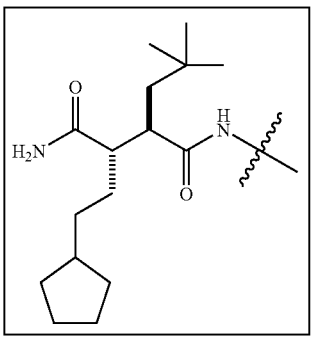
bi
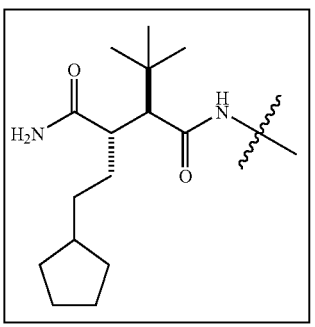
bj
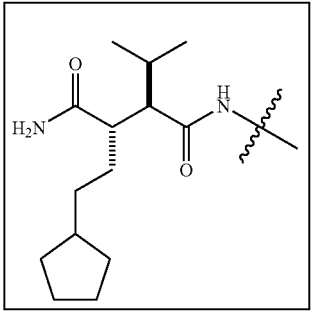
bk
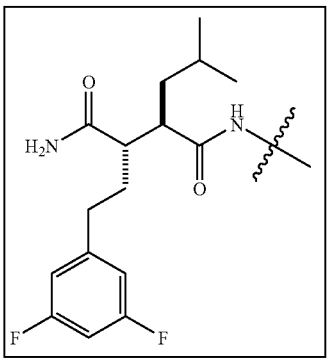
bl TABLE 2-continued
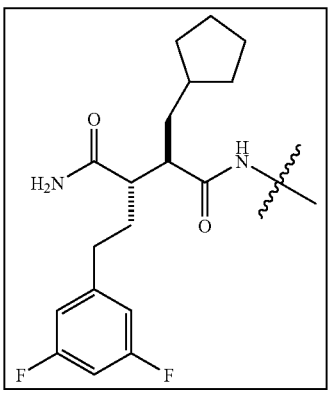
bm
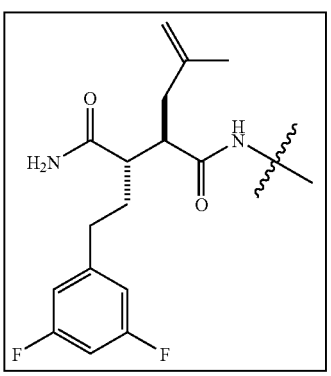
bn
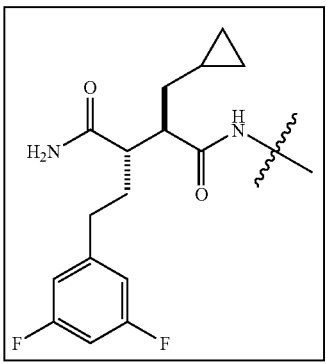
bo
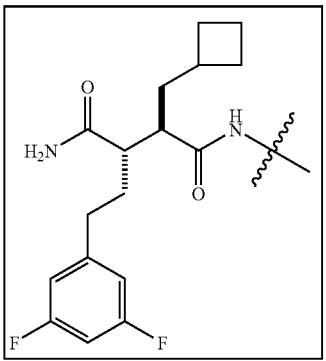
bp TABLE 2-continued
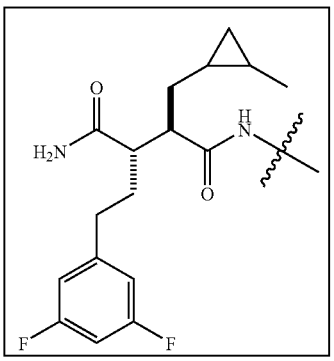
bq
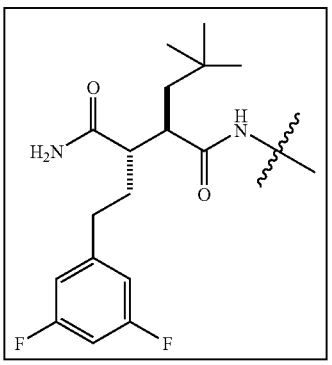
br
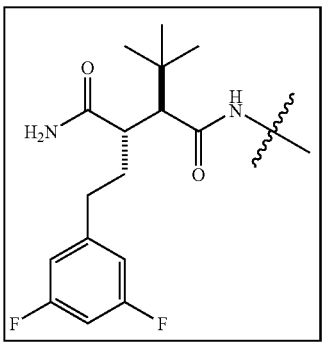
bs
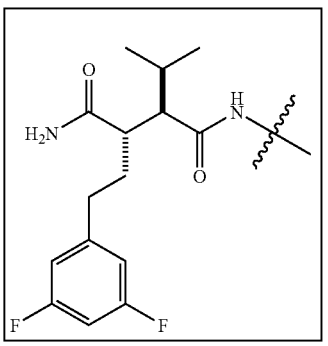
bt

What is claimed is:

1. A compound of Formula (Id):

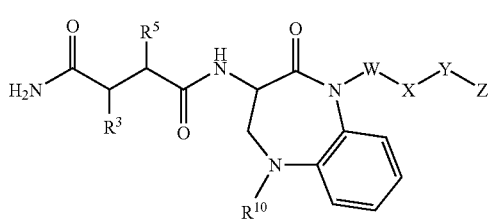

or a pharmaceutically acceptable salt thereof, wherein:

R³ is —CH₃, —CH₂CH₃, —CH₂CH₂CH₃, —CH₂CH₂CH₂CH₃, —CH₂(CH₃)₂, —CH(CH₃)CH₂CH₃, —CH₂CH(CH₃)₂, —CH₂C(CH₃)₃, —CF₃, —CH₂CF₃, —CH₂CH₂CF₃, —CH₂CH₂CH₂CF₃, —CH=CH₂, —CH₂CH=CH₂, —CH₂C(CH₃)=CH₂, —CH₂CH=C(CH₃)₂, —CH₂CH₂CH=CH₂, —CH₂CH₂C(CH₃)=CH₂, —CH₂CH₂CH=C(CH₃)₂, cis-CH₂CH=CH(CH₃), cis-CH₂CH₂CH=CH(CH₃), trans-CH₂CH=CH(CH₃), trans-CH₂CH₂CH=CH(CH₃);
—C≡CH, —CH₂C≡CH, —CH₂C≡C(CH₃), cyclopropyl-CH₂—, cyclobutyl-CH₂—, cyclopentyl-CH₂—, cyclohexyl-CH₂—, cyclopropyl-CH₂CH₂—, cyclobutyl-CH₂CH₂—, cyclopentyl-CH₂CH₂—, cyclohexyl-CH₂CH₂—, phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂—, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, phenyl-CH₂CH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, or R⁵ is —CH₃, —CH₂CH₃, —CH₂CH₂CH₃, —CH₂(CH₃)₂, —CH₂CH₂CH₂CH₃, —CH(CH₃)CH₂CH₃, —CH₂CH(CH₃)₂, —CH₂C(CH₃)₃, —CH₂CH₂CH₂CH₂CH₃, —CH(CH₃)CH₂CH₂CH₃, —CH₂CH(CH₃)CH₂CH₃, —CH₂CH₂CH(CH₃)₂, —CH(CH₂CH₃)₂, —CF₃, —CH₂CF₃, —CH₂CH₂CF₃, —CH₂CH₂CH₂CF₃, —CH₂CH₂CH₂CH₂CF₃, —CH=CH₂, —CH₂CH=CH₂, —CH=CHCH₃, cis-CH₂CH=CH(CH₃), trans-CH₂CH=CH(CH₃), trans-CH₂CH=CH(C₆H₅), —CH₂CH=C(CH₃)₂, cis-CH₂CH=CHCH₂CH₃, trans-CH₂CH=CHCH₂CH₃, cis-CH₂CH₂CH=CH(CH₃), trans-CH₂CH₂CH=CH(CH₃), trans-CH₂CH=CHCH₂(C₆H₅),
—C≡CH, —CH₂C≡CH, —CH₂C≡C(CH₃), —CH₂C≡C(C₆H₅)—CH₂CH₂C≡CH, —CH₂CH₂C≡C(CH₃), —CH₂CH₂C≡C(C₆H₅)—CH₂CH₂CH₂C≡CH, —CH₂CH₂CH₂C≡C(CH₃), —CH₂CH₂CH₂C≡C(C₆H₅)
cyclopropyl-CH₂—, cyclobutyl-CH₂—, cyclopentyl-CH₂—, cyclohexyl-CH₂—, (2-CH₃-cyclopropyl)CH₂—, (3-CH₃-cyclobutyl)CH₂—, cyclopropyl-CH₂CH₂—, cyclobutyl-CH₂CH₂—, cyclopentyl-CH₂CH₂—, cyclohexyl-CH₂CH₂—, (2-CH₃-cyclopropyl)CH₂CH₂—, (3-CH₃-cyclobutyl)CH₂CH₂—, phenyl-CH₂—, (2-F-phenyl)CH₂—, (3-F-phenyl)CH₂—, (4-F-phenyl)CH₂—, furanyl-CH₂—, thienyl-CH₂—, pyridyl-CH₂—, 1-imidazolyl-CH₂—, oxazolyl-CH₂—, isoxazolyl-CH₂—, phenyl-CH₂CH₂—, (2-F-phenyl)CH₂CH₂—, (3-F-phenyl)CH₂CH₂—, (4-F-phenyl)CH₂CH₂—, furanyl-CH₂CH₂—, thienyl-CH₂CH₂—, pyridyl-CH₂CH₂—, 1-imidazolyl-CH₂CH₂—, oxazolyl-CH₂CH₂—, isoxazolyl-CH₂CH₂—, W is a bond, —CH₂—, or —CH(CH₃)—;
X is a bond;

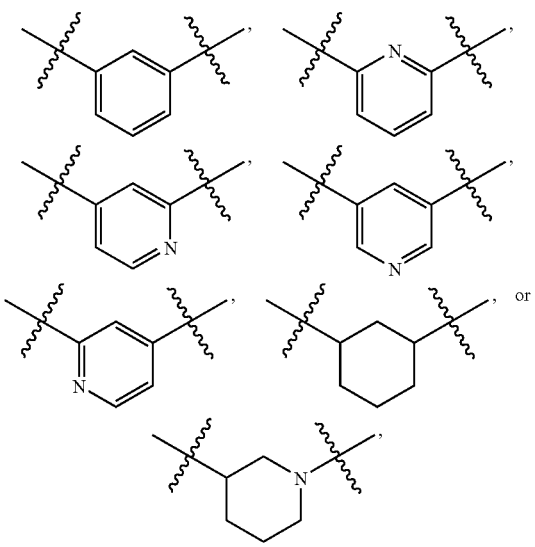

Y is a bond, —CH₂—V—, —V—, or —V—CH₂—;
V is a bond, —C(=O)—, —O—, —S—, —S(=O)—, —S(=O)₂—, —NH—, or —N(CH₃)—,
Z is phenyl 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino,N-piperinyl, phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂—, (4-Cl-phenyl)CH₂—, (2,3-diFphenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, (2-MeO-phenyl)CH$_2$—, (3-MeO-phenyl)CH$_2$—, (4-MeO-phenyl)CH$_2$—, (2-Me-phenyl)CH$_2$—, (3-Me-phenyl)CH$_2$—, (4-Me-phenyl)CH$_2$—, (2-MeS-phenyl)CH$_2$—, (3-MeS-phenyl)CH$_2$—, 4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, (cyclopropyl)CH$_2$—, (cyclobutyl)CH$_2$—, (cyclopentyl)CH$_2$—, (cyclohexyl)CH$_2$—, (morpholino)CH$_2$—, (N-pipridinyl)CH$_2$—, phenyl-CH$_2$CH$_2$—, (phenyl)$_2$CHCH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, (3-Cl-4-F-phenyl)CH$_2$CH$_2$—, (2-MeO-phenyl)CH$_2$CH$_2$—, (3-MeO-phenyl)CH$_2$CH$_2$—, (4-MeO-phenyl)CH$_2$CH$_2$—, (2-Me-phenyl)CH$_2$CH$_2$—, (3Me-phenyl)CH$_2$CH$_2$—, (4-Me-phenyl)CH$_2$CH$_2$—, (2-MeS-phenyl)CH$_2$CH$_2$—, (3-MeS-phenyl)CH$_2$CH$_2$—, (4-MeS-phenyl)CH$_2$CH$_2$—, (2-CF$_3$O-phenyl)CH$_2$CH$_2$—, (3-CF$_3$O-phenyl)CH$_2$CH$_2$—, (4-CF$_3$O-phenyl)CH$_2$CH$_2$—, (furanyl)CH$_2$CH$_2$—, (thienyl)CH$_2$CH$_2$—, (pyridyl)CH$_2$CH$_2$—, (2-Me-pyridyl)CH$_2$CH$_2$—, (3-Me-pyridyl)CH$_2$CH$_2$—, (4-Me-pyridyl)CH$_2$CH$_2$—, (imidazolyl)CH$_2$CH$_2$—, (oxazolyl)CH$_2$CH$_2$—, (isoxazolyl)CH$_2$CH$_2$—, (benzimidazolyl)CH$_2$CH$_2$—, (cyclopropyl)CH$_2$CH$_2$—, (cyclobutyl)CH$_2$CH$_2$—, (cyclopentyl)CH$_2$CH$_2$—, (cyclohexyl)CH$_2$CH$_2$—, (morpholino)CH$_2$CH$_2$—, (N-pipridinyl)CH$_2$CH$_2$—, and $R^{10}$ is H, methyl, ethyl, phenyl, benzyl, phenethyl, 4-F-phenyl, (4-F-phenyl)CH$_2$—, (4-F-phenyl)CH$_2$CH$_2$—, 4-Cl-phenyl, (4-Cl-phenyl)CH$_2$—, (4-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 4-CF$_3$-phenyl, (4-CF$_3$-phenyl)CH$_2$—, or (4-CF$_3$-phenyl)CH$_2$CH$_2$—.

2. A compound of Formula (Id) according to claim 1:

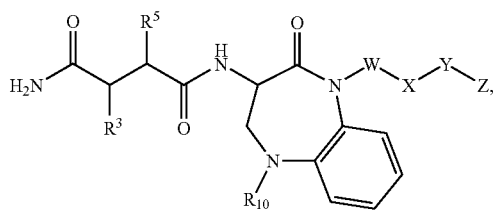

or a pharmaceutically acceptable salt thereof, wherein:

$R^3$ is —CH$_3$, —CH$_2$CH$_3$, —CH$_2$CH$_2$CH$_3$, —CH$_2$CH$_2$CH$_2$CH$_3$, —CH$_2$(CH$_3$)$_2$, —CH(CH$_3$)CH$_2$CH$_3$, —CH$_2$CH(CH$_3$)$_2$, —CH$_2$C(CH$_3$)$_3$, —CF$_3$, —CH$_2$CF$_3$, —CH$_2$CH$_2$CF$_3$, —CH$_2$CH$_2$CH$_2$CF$_3$, —CH═CH$_2$, —CH$_2$CH═CH$_2$, —CH$_2$C(CH$_3$)═CH$_2$, —CH$_2$CH═C(CH$_3$)$_2$, —CH$_2$CH$_2$CH═CH$_2$, —CH$_2$CH$_2$C(CH$_3$)═CH$_2$, —CH$_2$CH$_2$CH═C(CH$_3$)$_2$, cis-CH$_2$CH═CH(CH$_3$), cis-CH$_2$CH$_2$CH═CH(CH$_3$), trans-CH$_2$CH═CH(CH$_3$), trans-CH$_2$CH$_2$CH═CH(CH$_3$);

—C≡CH, —CH$_2$C≡CH, —CH$_2$C≡C(CH$_3$), cyclopropyl-CH$_2$—, cyclobutyl-CH$_2$—, cyclopentyl-CH$_2$—, cyclohexyl-CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, phenyl-CH$_2$CH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, or $R^5$ is —CH$_3$, —CH$_2$CH$_3$, —CH$_2$CH$_2$CH$_3$, —CH$_2$(CH$_3$)$_2$, —CH$_2$CH$_2$CH$_2$CH$_3$, —CH(CH$_3$)CH$_2$CH$_3$, —CH$_2$CH(CH$_3$)$_2$, —CH$_2$C(CH$_3$)$_3$, —CH$_2$CH$_2$CH$_2$CH$_2$CH$_3$, —CH(CH$_3$)CH$_2$CH$_2$CH$_3$, —CH$_2$CH(CH$_3$)CH$_2$CH$_3$, —CH$_2$CH$_2$CH(CH$_3$)$_2$, —CH(CH$_2$CH$_3$)$_2$, —CF$_3$, —CH$_2$CF$_3$, —CH$_2$CH$_2$CF$_3$, —CH$_2$CH$_2$CH$_2$CF$_3$, —CH$_2$CH$_2$CH$_2$CH$_2$CF$_3$, —CH═CH$_2$, —CH$_2$CH═CH$_2$, —CH═CHCH$_3$, cis-CH$_2$CH═CH(CH$_3$), trans-CH$_2$CH═CH(CH$_3$), trans-CH$_2$CH═CH(C$_6$H$_5$), —CH$_2$CH═C(CH$_3$)$_2$, cis-CH$_2$CH═CHCH$_2$CH$_3$, trans-CH$_2$CH═CHCH$_2$CH$_3$, cis-CH$_2$CH$_2$CH═CH(CH$_3$), trans-CH$_2$CH$_2$CH═CH(CH$_3$), trans-CH$_2$CH═CHCH$_2$(C$_6$H$_5$), —C≡CH, —CH$_2$C≡CH, —CH$_2$C≡C(CH$_3$), —CH$_2$C≡C(C$_6$H$_5$)—CH$_2$CH$_2$C≡CH, —CH$_2$CH$_2$C≡C(CH$_3$), —CH$_2$CH$_2$C≡C(C$_6$H$_5$)—CH$_2$CH$_2$CH$_2$C≡CH, —CH$_2$CH$_2$CH$_2$C≡C(CH$_3$), —CH$_2$CH$_2$CH$_2$C≡C(C$_6$H$_5$)

cyclopropyl-CH$_2$—, cyclobutyl-CH$_2$—, cyclopentyl-CH$_2$—, cyclohexyl-CH$_2$—, (2-CH$_3$-cyclopropyl)CH$_2$—, (3-CH$_3$-cyclobutyl)CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, (2-CH$_3$-cyclopropyl)CH$_2$CH$_2$—, (3-CH$_3$-cyclobutyl)CH$_2$CH$_2$—, phenyl-CH$_2$—, (2-F-phenyl)CH$_2$—, (3-F-phenyl)CH$_2$—, (4-F-phenyl)CH$_2$—, furanyl-CH$_2$—, thienyl-CH$_2$—, pyridyl-CH$_2$—, 1-imidazolyl-CH$_2$—, oxazolyl-CH$_2$—, isoxazolyl-CH$_2$—, phenyl-CH$_2$CH$_2$—, (2-F-phenyl)CH$_2$CH$_2$—, (3-F-phenyl)CH$_2$CH$_2$—, (4-F-phenyl)CH$_2$CH$_2$—, furanyl-CH$_2$CH$_2$—, thienyl-CH$_2$CH$_2$—, pyridyl-CH$_2$CH$_2$—, 1-imidazolyl-CH$_2$CH$_2$—, oxazolyl-CH$_2$CH$_2$—, isoxazolyl-CH$_2$CH$_2$—, W is a bond, —CH$_2$—, or —CH(CH$_3$)—;

X is a bond;

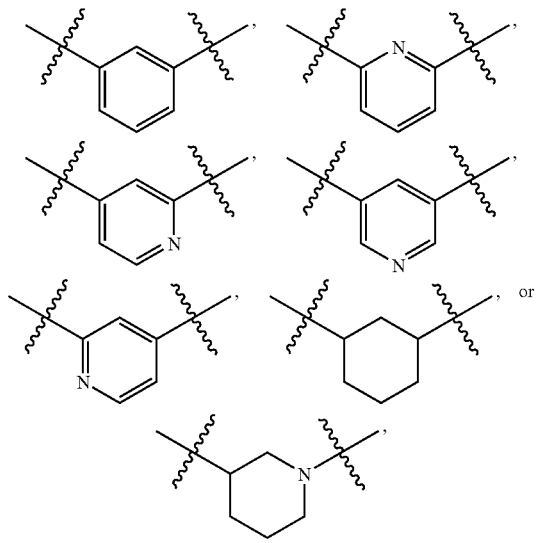

Y is a bond, —CH$_2$—V—, —V—, or —V—CH$_2$—;

V is a bond, —C(=O)—, —O—, —S—, —S(=O)—, —S(=O)$_2$—, —NH—, or —N(CH$_3$)—, and

Z is phenyl 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, (2-MeO-phenyl)CH$_2$—, (3-MeO-phenyl)CH$_2$—, (4-MeO-phenyl)CH$_2$—, (2-Me-phenyl)CH$_2$—, (3-Me-phenyl)CH$_2$—, (4-Me-phenyl)CH$_2$—, (2-MeS-phenyl)CH$_2$—, (3-MeS-phenyl)CH$_2$—, 4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, (cyclopropyl)CH$_2$—, (cyclobutyl)CH$_2$—, (cyclopentyl)CH$_2$—, (cyclohexyl)CH$_2$—, (morpholino)CH$_2$—, (N-pipridinyl)CH$_2$—, phenyl-CH$_2$CH$_2$—, (phenyl)$_2$CHCH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, (3-Cl-4-F-phenyl)CH$_2$CH$_2$—, (2-MeO-phenyl)CH$_2$CH$_2$—, (3-MeO-phenyl)CH$_2$CH$_2$—, (4-MeO-phenyl)CH$_2$CH$_2$—, (2-Me-phenyl)CH$_2$CH$_2$—, (3-Me-phenyl)CH$_2$CH$_2$—, (4-Me-phenyl)CH$_2$CH$_2$—, (2-MeS-phenyl)CH$_2$CH$_2$—, (3-MeS-phenyl)CH$_2$CH$_2$—, (4-MeS-phenyl)CH$_2$CH$_2$—, (2-CF$_3$O-phenyl)CH$_2$CH$_2$—, (3-CF$_3$O-phenyl)CH$_2$CH$_2$—, (4-CF$_3$O-phenyl)CH$_2$CH$_2$—, (furanyl)CH$_2$CH$_2$—, (thienyl)CH$_2$CH$_2$—, (pyridyl)CH$_2$CH$_2$—, (2-Me-pyridyl)CH$_2$CH$_2$—, (3-Me-pyridyl)CH$_2$CH$_2$—, (4-Me-pyridyl)CH$_2$CH$_2$—, (imidazolyl)CH$_2$CH$_2$—, (oxazolyl)CH$_2$CH$_2$—, (isoxazolyl)CH$_2$CH$_2$—, (benzimidazolyl)CH$_2$CH$_2$—, (cyclopropyl)CH$_2$CH$_2$—, (cyclobutyl)CH$_2$CH$_2$—, (cyclopentyl)CH$_2$CH$_2$—, (cyclohexyl)CH$_2$CH$_2$—, (morpholino)CH$_2$CH$_2$—, (N-pipridinyl)CH$_2$CH$_2$—.

3. A compound of Formula (Id) according to claim 1:

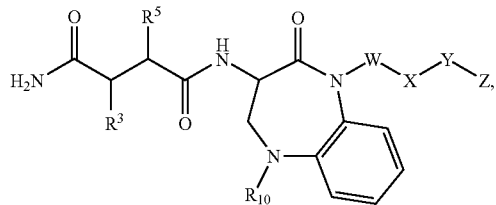

or a pharmaceutically acceptable salt thereof, wherein:

$R^3$ is —CH$_3$, —CH$_2$CH$_3$, —CH$_2$CH$_2$CH$_3$, —CH$_2$CH$_2$CH$_2$CH$_3$, —CH$_2$(CH$_3$)$_2$, —CH(CH$_3$)CH$_2$CH$_3$, —CH$_2$CH(CH$_3$)$_2$, —CH$_2$C(CH$_3$)$_3$, —CF$_3$, —CH$_2$CF$_3$, —CH$_2$CH$_2$CF$_3$, —CH$_2$CH$_2$CH$_2$CF$_3$, —CH=CH$_2$, —CH$_2$CH=CH$_2$, —CH$_2$C(CH$_3$)=CH$_2$, —CH$_2$CH=C(CH$_3$)$_2$, —CH$_2$CH$_2$CH=CH$_2$, —CH$_2$CH$_2$C(CH$_3$)=CH$_2$, —CH$_2$CH$_2$CH=C(CH$_3$)$_2$, cis-CH$_2$CH=CH(CH$_3$), cis-CH$_2$CH$_2$CH=CH(CH$_3$), trans-CH$_2$CH=CH(CH$_3$), trans-CH$_2$CH$_2$CH=CH(CH$_3$);

—C≡CH, —CH$_2$C≡CH, —CH$_2$C≡C(CH$_3$), cyclopropyl-CH$_2$—, cyclobutyl-CH$_2$—, cyclopentyl-CH$_2$—, cyclohexyl-CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4- diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, phenyl-CH$_2$CH$_2$—,
(2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, or R$^5$ is —CH$_3$, —CH$_2$CH$_3$, —CH$_2$CH$_2$CH$_3$, —CH$_2$(CH$_3$)$_2$, —CH$_2$CH$_2$CH$_2$CH$_3$, —CH(CH$_3$)CH$_2$CH$_3$, —CH$_2$CH(CH$_3$)$_2$, —CH$_2$C(CH$_3$)$_3$, —CH$_2$CH$_2$CH$_2$CH$_2$CH$_3$, —CH(CH$_3$)CH$_2$CH$_2$CH$_3$, —CH$_2$CH(CH$_3$)CH$_2$CH$_3$, —CH$_2$CH$_2$CH(CH$_3$)$_2$, —CH(CH$_2$CH$_3$)$_2$, —CF$_3$, —CH$_2$CF$_3$, —CH$_2$CH$_2$CF$_3$, —CH$_2$CH$_2$CH$_2$CF$_3$, —CH$_2$CH$_2$CH$_2$CH$_2$CF$_3$, —CH═CH$_2$, —CH$_2$CH═CH$_2$, —CH═CHCH$_3$, cis-CH$_2$CH═CH(CH$_3$), trans-CH$_2$CH═CH(CH$_3$), trans-CH$_2$CH═CH(C$_6$H$_5$), —CH$_2$CH═C(CH$_3$)$_2$, cis-CH$_2$CH═CHCH$_2$CH$_3$, trans-CH$_2$CH═CHCH$_2$CH$_3$, cis-CH$_2$CH$_2$CH═CH(CH$_3$), trans-CH$_2$CH$_2$CH═CH(CH$_3$), trans-CH$_2$CH═CHCH$_2$(C$_6$H$_5$), —C≡CH, —CH$_2$C≡CH, —CH$_2$C≡C(CH$_3$), —CH$_2$C≡C(C$_6$H$_5$)—CH$_2$CH$_2$C≡CH, —CH$_2$CH$_2$C≡C(CH$_3$), —CH$_2$CH$_2$C≡C(C$_6$H$_5$)—CH$_2$CH$_2$CH$_2$C≡CH, —CH$_2$CH$_2$CH$_2$C≡C(CH$_3$), —CH$_2$CH$_2$CH$_2$C≡C(C$_6$H$_5$)

cyclopropyl-CH$_2$—, cyclobutyl-CH$_2$—, cyclopentyl-CH$_2$—, cyclohexyl-CH$_2$—, (2-CH$_3$-cyclopropyl)CH$_2$—, (3-CH$_3$-cyclobutyl)CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, (2-CH$_3$-cyclopropyl)CH$_2$CH$_2$—, (3-CH$_3$-cyclobutyl)CH$_2$CH$_2$—, phenyl-CH$_2$—, (2-F-phenyl)CH$_2$—, (3-F-phenyl)CH$_2$—, (4-F-phenyl)CH$_2$—, furanyl-CH$_2$—, thienyl-CH$_2$—, pyridyl-CH$_2$—, 1-imidazolyl-CH$_2$—, oxazolyl-CH$_2$—, isoxazolyl-CH$_2$—, phenyl-CH$_2$CH$_2$—, (2-F-phenyl)CH$_2$CH$_2$—, (3-F-phenyl)CH$_2$CH$_2$—,
(4-F-phenyl)CH$_2$CH$_2$—, furanyl-CH$_2$CH$_2$—, thienyl-CH$_2$CH$_2$—, pyridyl-CH$_2$CH$_2$—, 1-imidazolyl-CH$_2$CH$_2$—, oxazolyl-CH$_2$CH$_2$—, isoxazolyl-CH$_2$CH$_2$—, W is a bond, —CH$_2$—, or —CH(CH$_3$)—;
X is a bond;

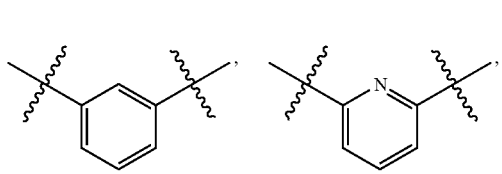

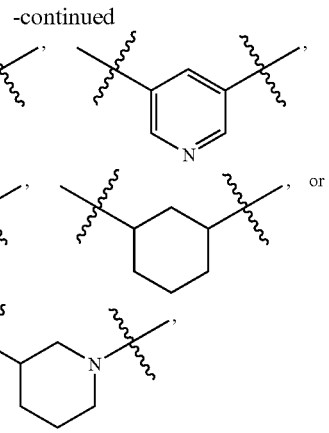

Y is a bond, —CH$_2$—V—, —V—, or —V—CH$_2$—;
V is a bond, —C(═O)—, —O—, —S—, —S(═O)—, —S(═O)$_2$—, —NH—, or —N(CH$_3$)—, and
Z is phenyl 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino,N-piperinyl,
phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, (2-MeO-phenyl)CH$_2$—, (3-MeO-phenyl)CH$_2$—, (4-MeO-phenyl)CH$_2$—, (2-Me-phenyl)CH$_2$—, (3-Me-phenyl)CH$_2$—, (4-Me-phenyl)CH$_2$—, (2-MeS-phenyl)CH$_2$—, (3-MeS-phenyl)CH$_2$—, 4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, (cyclopropyl)CH$_2$—, (cyclobutyl)CH$_2$—, (cyclopentyl)CH$_2$—, (cyclohexyl)CH$_2$—, (morpholino)CH$_2$—, (N-pipridinyl)CH$_2$—, phenyl-CH$_2$CH$_2$—, (phenyl)$_2$CHCH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)

CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, (3-Cl-4-F-phenyl)CH₂CH₂—, (2-MeO-phenyl)CH₂CH₂—, (3-MeO-phenyl)CH₂CH₂—, (4-MeO-phenyl)CH₂CH₂—, (2-Me-phenyl)CH₂CH₂—, (3-Me-phenyl)CH₂CH₂—, (4-Me-phenyl)CH₂CH₂—, (2-MeS-phenyl)CH₂CH₂—, (3-MeS-phenyl)CH₂CH₂—, (4-MeS-phenyl)CH₂CH₂—, (2-CF₃O-phenyl)CH₂CH₂—, (3-CF₃O-phenyl)CH₂CH₂—, (4-CF₃O-phenyl)CH₂CH₂—, (furanyl)CH₂CH₂—, (thienyl)CH₂CH₂—, (pyridyl)CH₂CH₂—, (2-Me-pyridyl)CH₂CH₂—, (3-Me-pyridyl)CH₂CH₂—, (4-Me-pyridyl)CH₂CH₂—, (imidazolyl)CH₂CH₂—, (oxazolyl)CH₂CH₂—, (isoxazolyl)CH₂CH₂—, (benzimidazolyl)CH₂CH₂—, (cyclopropyl)CH₂CH₂—, (cyclobutyl)CH₂CH₂—, (cyclopentyl)CH₂CH₂—, (cyclohexyl)CH₂CH₂—, (morpholino)CH₂CH₂—, (N-piperidinyl)CH₂CH₂—.

4. A compound of Formula (Id) according to claim 1:

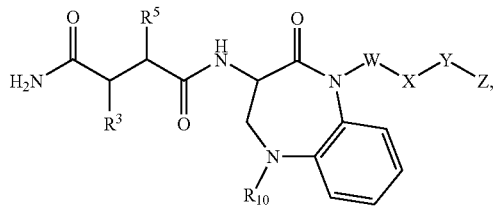

or a pharmaceutically acceptable salt thereof, wherein:

$R^3$ is —CH₃, —CH₂CH₃, —CH₂CH₂CH₃, —CH₂CH₂CH₂CH₃, —CH₂(CH₃)₂, —CH(CH₃)CH₂CH₃, —CH₂CH(CH₃)₂, —CH₂C(CH₃)₃, —CF₃, —CH₂CF₃, —CH₂CH₂CF₃, —CH₂CH₂CH₂CF₃, —CH=CH₂, —CH₂CH=CH₂, —CH₂C(CH₃)=CH₂, —CH₂CH=C(CH₃)₂, —CH₂CH₂CH=CH₂, —CH₂CH₂C(CH₃)=CH₂, —CH₂CH₂CH=C(CH₃)₂, cis-CH₂CH=CH(CH₃), cis-CH₂CH₂CH=CH(CH₃), trans-CH₂CH=CH(CH₃), trans-CH₂CH₂CH=CH(CH₃);

—C≡CH, —CH₂C≡CH, —CH₂C≡C(CH₃), cyclopropyl-CH₂—, cyclobutyl-CH₂—, cyclopentyl-CH₂—, cyclohexyl-CH₂—, cyclopropyl-CH₂CH₂—, cyclobutyl-CH₂CH₂—, cyclopentyl-CH₂CH₂—, cyclohexyl-CH₂CH₂—, phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂—, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, phenyl-CH₂CH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, or $R^5$ is —CH₃, —CH₂CH₃, —CH₂CH₂CH₃, —CH₂(CH₃)₂, —CH₂CH₂CH₂CH₃, —CH(CH₃)CH₂CH₃, —CH₂CH(CH₃)₂, —CH₂C(CH₃)₃, —CH₂CH₂CH₂CH₃, —CH(CH₃)CH₂CH₃, —CH₂CH(CH₃)CH₂CH₃, —CH₂CH₂CH(CH₃)₂, —CH(CH₂CH₃)₂, —CF₃, —CH₂CF₃, —CH₂CH₂CF₃, —CH₂CH₂CH₂CF₃, —CH₂CH₂CH₂CH₂CF₃, —CH=CH₂, —CH₂CH=CH₂, —CH=CHCH₃, cis-CH₂CH=CH(CH₃), trans-CH₂CH=CH(CH₃), trans-CH₂CH=CH(C₆H₅), —CH₂CH=C(CH₃)₂, cis-CH₂CH=CHCH₂CH₃, trans-CH₂CH=CHCH₂CH₃, cis-CH₂CH₂CH=CH(CH₃), trans-CH₂CH₂CH=CH(CH₃), trans-CH₂CH=CHCH₂(C₆H₅), —C≡CH, —CH₂C≡CH, —CH₂C≡C(CH₃), —CH₂C≡C(C₆H₅)—CH₂CH₂C≡CH, —CH₂CH₂C≡C(CH₃), —CH₂CH₂C≡C(C₆H₅)—CH₂CH₂CH₂C≡CH, —CH₂CH₂CH₂C≡C(CH₃), —CH₂CH₂CH₂C≡C(C₆H₅)

cyclopropyl-CH₂—, cyclobutyl-CH₂—, cyclopentyl-CH₂—, cyclohexyl-CH₂—, (2-CH₃-cyclopropyl)CH₂—, (3-CH₃-cyclobutyl)CH₂—, cyclopropyl-CH₂CH₂—, cyclobutyl-CH₂CH₂—, cyclopentyl-CH₂CH₂—, cyclohexyl-CH₂CH₂—, (2-CH₃-cyclopropyl)CH₂CH₂—, (3-CH₃-cyclobutyl)CH₂CH₂—, phenyl-CH₂—, (2-F-phenyl)CH₂—, (3-F-phenyl)CH₂—, (4-F-phenyl)CH₂—, furanyl-CH₂—, thienyl-CH₂—, pyridyl-CH₂—, 1-imidazolyl-CH₂—, oxazolyl-CH₂—, isoxazolyl-CH₂—, phenyl-CH₂CH₂—, (2-F-phenyl)CH₂CH₂—, (3-F-phenyl)CH₂CH₂—, (4-F-phenyl)CH₂CH₂—, furanyl-CH₂CH₂—, thienyl-CH₂CH₂—, pyridyl-CH₂CH₂—, 1-imidazolyl-CH₂CH₂—, oxazolyl-CH₂CH₂—, isoxazolyl-CH₂CH₂—, W is a bond, —CH₂—, or —CH(CH₃)—;

X is a bond;

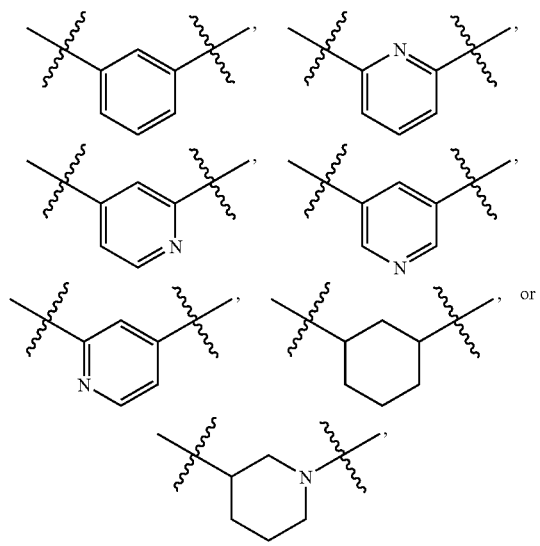

Y is a bond, —CH$_2$—V—, —V—, or —V—CH$_2$—;

V is a bond, —C(=O)—, —O—, —S—, —S(=O)—, —S(=O)$_2$—, —NH—, or —N(CH$_3$)—, and

Z is phenyl 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino,N-piperinyl, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, (2-MeO-phenyl)CH$_2$—, (3-MeO-phenyl)CH$_2$—,(4-MeO-phenyl)CH$_2$—, (2-Me-phenyl)CH$_2$—, (3-Me-phenyl)CH$_2$—, (4-Me-phenyl)CH$_2$—, (2-MeS-phenyl)CH$_2$—, (3-MeS-phenyl)CH$_2$—, 4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, (cyclopropyl)CH$_2$—, (cyclobutyl)CH$_2$—, (cyclopentyl)CH$_2$—, (cyclohexyl)CH$_2$—, (morpholino)CH$_2$—, (N-pipridinyl)CH$_2$—, phenyl-CH$_2$CH$_2$—, (phenyl)$_2$CHCH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, (3-Cl-4-F-phenyl)CH$_2$CH$_2$—, (2-MeO-phenyl)CH$_2$CH$_2$—, (3-MeO-phenyl)CH$_2$CH$_2$—, (4-MeO-phenyl)CH$_2$CH$_2$—, (2-Me-phenyl)CH$_2$CH$_2$—, (3-Me-phenyl)CH$_2$CH$_2$—, (4-Me-phenyl)CH$_2$CH$_2$—, (2-MeS-phenyl)CH$_2$CH$_2$—, (3-MeS-phenyl)CH$_2$CH$_2$—, (4-MeS-phenyl)CH$_2$CH$_2$—, (2-CF$_3$O-phenyl)CH$_2$CH$_2$—, (3-CF$_3$O-phenyl)CH$_2$CH$_2$—, (4-CF$_3$O-phenyl)CH$_2$CH$_2$—, (furanyl)CH$_2$CH$_2$—, (thienyl)CH$_2$CH$_2$—, (pyridyl)CH$_2$CH$_2$—, (2-Me-pyridyl)CH$_2$CH$_2$—, (3-Me-pyridyl)CH$_2$CH$_2$—, (4-Me-pyridyl)CH$_2$CH$_2$—, (imidazolyl)CH$_2$CH$_2$—, (oxazolyl)CH$_2$CH$_2$—, (isoxazolyl)CH$_2$CH$_2$—, (benzimidazolyl)CH$_2$CH$_2$—, (cyclopropyl)CH$_2$CH$_2$—, (cyclobutyl)CH$_2$CH$_2$—, (cyclopentyl)CH$_2$CH$_2$—, (cyclohexyl)CH$_2$CH$_2$—, (morpholino)CH$_2$CH$_2$—, (N-pipridinyl)CH$_2$CH$_2$—.

5. A compound according to claim 1, or a pharmaceutically acceptable salt form thereof, selected from the group consisting of:

(2R,3S)N1-[1,3,4,5-tetrahydro-1-(3-phenoxybenzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-(4-ethoxyphenyl)benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(2-methylpropyl)-3-(allyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(2-methylpropyl)-3-(butyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclopropylmethyl)-3-(propyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclopropylmethyl)-3-(allyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclopropylmethyl)-3-(butyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclobutylmethyl)-3-(propyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclobutylmethyl)-3-(allyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclobutylmethyl)-3-(butyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclopentylmethyl)-3-(propyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-(2-naphthyl)benzyl)-2-oxo-5-(phenyl)-2H-1,5-benzodiazepin-3-yl]-2-(cyclopentylmethyl)-3-(allyl)-butanediamide;

(2R,3S)N1-[1,3,4,5-tetrahydro-1-(3-phenoxybenzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(3-(4-methoxyphenyl)benzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(3-(4-trifluoromethylphenyl)benzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(3-(4-methylphenyl)benzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(3-(2,4-dichlorophenyl)benzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(3-(3-chloro-4-fluorophenyl)benzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(benzophenon-3-yl)-2-oxo-5-(phenyl)-2H-1,5-benzodiazepin-3-yl]-2-(cyclopentylmethyl)-3-(butyl)-butanediamide; and (2R,3S)N1-[1,3,4,5-tetrahydro-1-(3-(2-naphthyl)benzyl)-2-oxo-5-(phenyl)-2H-1,5-benzodiazepin-3-yl]-2-(cyclopentylmethyl)-3-(butyl)-butanediamide;

(2R,3S)N1-[1,3,4,5-tetrahydro-1-(benzyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(phenethyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-((4-fluorophenyl)methyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(cyclopropylmethyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(cyclobutylmethyl)-2-oxo-5-(phenyl)-2H-1,5-benzodiazepin-3-yl]-2-(2-methylpropyl)-3-(propyl)-butanediamide;

(2R,3S)N1-[1,3,4,5-tetrahydro-1-(cyclopentylmethyl)-2-oxo-5-(phenyl)-2H-1,5-benzodiazepin-3-yl]-2-(2-methylpropyl)-3-(propyl)-butanediamide;
(2R,3S)N1-[1,3,4,5-tetrahydro-1-(cyclohexylmethyl)-2-oxo-5-(phenyl)-2H-1,5-benzodiazepin-3-yl]-2-(2-methylpropyl)-3-(propyl)-butanediamide;
(2R,3S)N1-[1,3,4,5-tetrahydro-1-(cyclopropylethyl)-2-oxo-5-(phenyl)-2H-1,5-benzodiazepin-3-yl]-2-(2-methylpropyl)-3-(propyl)-butanediamide;
(2R,3S)N1-[1,3,4,5-tetrahydro-1-(cyclobutylethyl)-2-oxo-5-(phenyl)-2H-1,5-benzodiazepin-3-yl]-2-(2-methylpropyl)-3-(propyl)-butanediamide;
(2R,3S)N1-[1,3,4,5-tetrahydro-1-(cyclopentylethyl)-2-oxo-5-(phenyl)-2H-1,5-benzodiazepin-3-yl]-2-(2-methylpropyl)-3-(propyl)-butanediamide;
(2R,3S)N1-[1,3,4,5-tetrahydro-1-(cyclohexylethyl)-2-oxo-5-(phenyl)-2H-1,5-benzodiazepin-3-yl]-2-(2-methylpropyl)-3-(propyl)-butanediamide;
(2R,3S)N1-[1,3,4,5-tetrahydro-1-(benzyl)-2-oxo-5-(phenyl)-2H-1,5-benzodiazepin-3-yl]-2-(2-methylpropyl)-3-(allyl)-butanediamide;
(2R,3S)N1-[1,3,4,5-tetrahydro-1-(phenethyl)-2-oxo-5-(phenyl)-2H-1,5-benzodiazepin-3-yl]-2-(2-methylpropyl)-3-(allyl)-butanediamide;
(2R,3S)N1-[1,3,4,5-tetrahydro-1-((4-fluorophenyl)methyl)-2-oxo-5-(phenyl)-2H-1,5-benzodiazepin-3-yl]-2-(2-methylpropyl)-3-(allyl)-butanediamide;
(2R,3S)N1-[1,3,4,5-tetrahydro-1-(cyclopropylmethyl)-2-oxo-5-(phenyl)-2H-1,5-benzodiazepin-3-yl]-2-(2-methylpropyl)-3-(allyl)-butanediamide;
(2R,3S)N1-[1,3,4,5-tetrahydro-1-(cyclobutylmethyl)-2-oxo-5-(phenyl)-2H-1,5-benzodiazepin-3-yl]-2-(2-methylpropyl)-3-(allyl)-butanediamide;
(2R,3S)N1-[1,3,4,5-tetrahydro-1-(cyclopentylmethyl)-2-oxo-5-(phenyl)-2H-1,5-benzodiazepin-3-yl]-2-(2-methylpropyl)-3-(allyl)-butanediamide;
(2R,3S)N1-[1,3,4,5-tetrahydro-1-(cyclohexylmethyl)-2-oxo-5-(phenyl)-2H-1,5-benzodiazepin-3-yl]-2-(2-methylpropyl)-3-(allyl)-butanediamide;
(2R,3S)N1-[1,3,4,5-tetrahydro-1-(cyclopropylethyl)-2-oxo-5-(phenyl)-2H-1,5-benzodiazepin-3-yl]-2-(2-methylpropyl)-3-(allyl)-butanediamide;
(2R,3S)N1-[1,3,4,5-tetrahydro-1-(cyclobutylethyl)-2-oxo-5-(phenyl)-2H-1,5-benzodiazepin-3-yl]-2-(2-methylpropyl)-3-(allyl)-butanediamide;
(2R,3S)N1-[1,3,4,5-tetrahydro-1-(cyclopentylethyl)-2-oxo-5-(phenyl)-2H-1,5-benzodiazepin-3-yl]-2-(2-methylpropyl)-3-(allyl)-butanediamide;
(2R,3S)N1-[1,3,4,5-tetrahydro-1-(cyclohexylethyl)-2-oxo-5-(phenyl)-2H-1,5-benzodiazepin-3-yl]-2-(2-methylpropyl)-3-(allyl)-butanediamide;
(2R,3S)N1-[1,3,4,5-tetrahydro-1-(benzyl)-2-oxo-5-(phenyl)-2H-1,5-benzodiazepin-3-yl]-2-(2-methylpropyl)-3-(butyl)-butanediamide;
(2R,3S)N1-[1,3,4,5-tetrahydro-1-(phenethyl)-2-oxo-5-(phenyl)-2H-1,5-benzodiazepin-3-yl]-2-(2-methylpropyl)-3-(butyl)-butanediamide;
(2R,3S)N1-[1,3,4,5-tetrahydro-1-((4-fluorophenyl)methyl)-2-oxo-5-(phenyl)-2H-1,5-benzodiazepin-3-yl]-2-(2-methylpropyl)-3-(butyl)-butanediamide;
(2R,3S)N1-[1,3,4,5-tetrahydro-1-(cyclopropylmethyl)-2-oxo-5-(phenyl)-2H-1,5-benzodiazepin-3-yl]-2-(2-methylpropyl)-3-(butyl)-butanediamide;
(2R,3S)N1-[1,3,4,5-tetrahydro-1-(cyclobutylmethyl)-2-oxo-5-(phenyl)-2H-1,5-benzodiazepin-3-yl]-2-(2-methylpropyl)-3-(butyl)-butanediamide;
(2R,3S)N1-[1,3,4,5-tetrahydro-1-(cyclopentylmethyl)-2-oxo-5-(phenyl)-2H-1,5-benzodiazepin-3-yl]-2-(2-methylpropyl)-3-(butyl)-butanediamide;
(2R,3S)N1-[1,3,4,5-tetrahydro-1-(cyclohexylmethyl)-2-oxo-5-(phenyl)-2H-1,5-benzodiazepin-3-yl]-2-(2-methylpropyl)-3-(butyl)-butanediamide;
(2R,3S)N1-[1,3,4,5-tetrahydro-1-(cyclopropylethyl)-2-oxo-5-(phenyl)-2H-1,5-benzodiazepin-3-yl]-2-(2-methylpropyl)-3-(butyl)-butanediamide;
(2R,3S)N1-[1,3,4,5-tetrahydro-1-(cyclobutylethyl)-2-oxo-5-(phenyl)-2H-1,5-benzodiazepin-3-yl]-2-(2-methylpropyl)-3-(butyl)-butanediamide;
(2R,3S)N1-[1,3,4,5-tetrahydro-1-(cyclopentylethyl)-2-oxo-5-(phenyl)-2H-1,5-benzodiazepin-3-yl]-2-(2-methylpropyl)-3-(butyl)-butanediamide; and
(2R,3S)N1-[1,3,4,5-tetrahydro-1-(cyclohexylethyl)-2-oxo-5-(phenyl)-2H-1,5-benzodiazepin-3-yl]-2-(2-methylpropyl)-3-(butyl)-butanediamide.

6. A pharmaceutical composition comprising a compound of claim 5 or a pharmaceutically acceptable salt thereof, and a pharmaceutically acceptable carrier.

7. A method for the treatment of Alzheimer's Disease comprising administering to a host in need of such treatment a therapeutically effective amount of a compound of claim 5 or a pharmaceutically acceptable salt thereof.

8. A method for the treatment of Alzheimer's Disease comprising administering to a host in need of such treatment a therapeutically effective amount of a compound,
(2R,3S)N1-[1,3,4,5-tetrahydro-1-(3,4-dimethoxyphenyl)benzyl)-2-oxo-5-(phenyl)-2H-1,5-benzodiazepin-3-yl]-2-(2-methylpropyl)-3-(butyl)-butanediamide, or a pharmaceutically acceptable salt thereof.

9. A pharmaceutical composition comprising a compound,
(2R,3S)N1-[1,3,4,5-tetrahydro-1-(3,4-dimethoxyphenyl)benzyl)-2-oxo-5-(phenyl)-2H-1,5-benzodiazepin-3-yl]-2-(2-methylpropyl)-3-(butyl)-butanediamide,
or a pharmaceutically acceptable salt thereof and a pharmaceutically acceptable carrier.

* * * * *